US007638600B2

(12) United States Patent
Fischetti et al.

(10) Patent No.: US 7,638,600 B2

(45) Date of Patent: Dec. 29, 2009

(54) **LYTIC ENZYMES AND SPORE SURFACE ANTIGEN FOR DETECTION AND TREATMENT OF *BACILLUS ANTHRACIS* BACTERIA AND SPORES**

(75) Inventors: Vincent A. Fischetti, West Hempstead, NY (US); Raymond Schuch, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 10/593,545

(22) PCT Filed: Mar. 23, 2005

(86) PCT No.: PCT/US2005/009928

§ 371 (c)(1),
(2), (4) Date: Jul. 16, 2007

(87) PCT Pub. No.: WO2005/089527

PCT Pub. Date: Sep. 29, 2005

(65) Prior Publication Data

US 2007/0254321 A1 Nov. 1, 2007

Related U.S. Application Data

(60) Provisional application No. 60/555,916, filed on Mar. 24, 2004.

(51) Int. Cl.
*C07K 14/00* (2006.01)
*A61K 38/00* (2006.01)

(52) U.S. Cl. .......................................... 530/350; 514/2

(58) Field of Classification Search ....................... None
See application file for complete search history.

(56) References Cited

OTHER PUBLICATIONS

Schuch et al.,"A bacteriolytic agent that detects and kills *Bacillus anthracis*", Nature 418: 884-889 Aug. 22, 2002.*

* cited by examiner

*Primary Examiner*—Anand U Desai
(74) *Attorney, Agent, or Firm*—Brinks Hofer Gilson & Lione

(57) ABSTRACT

Novel bacteriophages of *Bacillus anthracis*, the nucleic acids of its genome, nucleic acids comprising nucleotide sequences of open reading frames (ORFs) of its genome, and polypeptides encoded by the nucleic acids, are described. Therapeutic and diagnostic compositions, methods and kits related thereto are also provided.

15 Claims, 37 Drawing Sheets

FIGURE 1A: Polynucleotide Sequence of Phage Gamma (γ) (SEQ ID NO:1)

CTCAACTTCGCAGAAAAATCCGTTTTTGCATATTTTTTTAAGGGGGTGTAATCATGGCTGGAAGAAATAAACAACCACTC
TCTGTTATACAGGGAAAAGGTAGATCAAATCACATTACAAAAAGTGAGAAAAACAGACGAGAAAAACAAGAAGAAGCATT
GCGGGGGCATACTGATAAAATTGAAGCTCCTTCTTATTTGACTGCAGCACAAAAAAAGGAATTCGATACTTTAGCTGCTG
AATTAGTCAGATTGAAAATTTTCAGTAACTTAGATGTTGACAGTTTAGCAAGGTACGTTGATTCTAAAGACCAATATATA
AAAATGGTTCGTCTGCTAAGAAAAACAAAACCTTCAGATGACTTTAAATTGTATTCTCAAATGCAAAGAAGTAAAAATCT
TTTATTCAATGAATGCCGTTCTTCAGCTAGTGATTTAGGTTTGACCATTACATCCCGCTTAAAATTAGTTATTCCAGAAG
TAGATACTTCACAACAAAAGCAAAGTGAAGCGCAAAAGCGTTTTGGTGATCGTATATGAACTGGATAATGGAACGGGTTT
TTGCATATTGCGAGGACATTTTAAACGGCAAGATAAATAGTTGTAAAAAACATCGTTGGGCCATTGAACGATTTATAAGG
GATTATGAGGAGTGTCAAAGTGAAGACAGTCCTTTTTATTTTGATGGAGAGATAGCGGAGGATTTTTACTGGTTTGCAAA
GGAATTTAAGCACGTTGAAGGGATTTTGGCAGGTGAATCCGTAGAATTAACTGATTTTCAATTGTTTCTAGCGGCTAATA
TTTTCGGATTCAAAAAGAAAATAAATGGAGCAAGGCGATTTAGAAAGGTTTTTATTCAGTTAGCGCGTAAAAATGCTAAA
TCTCAGTTTCTTGCTATTGTAGCAGCTTTTTGTACATTTCTTGGAGACGAAAAACAACGGGCTTATATTGCTGGATGGAC
AAGAGACCAATCATCTGAAGTTTATGAAGCTGTAAAAACAGGGATTAGTTCTAGTGAATTGTTAGAAGGTAAATGGAAAG
AGGCTTATAGTACCATTGAAATATTTAAGAATGGTTCAGTTGTCGTTCCACTTTCAAAAGAAGCTAGAAAAACTGGTGAT
GGTAAAAACCCGTCTCTTGGAATTGTCGATGAATATCATGCACATGAAACTGATGAAATTTATGACGTTTTATCGTCTGG
TATGGTGGCAAGGAAAGAGCCGTTAATGTTTATCATAACAACAGCTGGTTTCGACTTATCAAGACCTTGTTATAGAGAGT
ATGAGTATGTCAGTGACATCTTAGACCCGTCAAAAAATGTAGAAAACGATGATTATTTCGTTATGATCTGTGAATTGGAA
AAGAACGATGATATCAAAGATGAGTCGAATTGGATAAAAGCAAACCCAATCGTAGCTACATATGAAGAAGGTTTGGAAGG
TATACGTTCAGATTTGAAGGTTGCTCTTGATAGACCTGAAAAGATGAGGGCTTTTTTAACCAAAAACATGAATATTTGGG
TCGATAAAAAGGACAACGGATACATGGATATGTCAAAATGGCAAAAATGCGAAGTAGATACCTTTGATTTTTCAGGTGCG
ACTCTTTGGATAGGTGGCGACTTATCAATGACAACAGATTTAACTAGTGTCGGTTGGGTTGGAATGGACGATGAAGGTGA
TTTTATTGTTGGACAACATTCATTTATGCCTGAAGCACGTTTGAAAGAAAAGATGGCCATAGATAAGGTGCGTTATGATT
TATGGGCCGAACAAGGGTATTTAACTTTAACGCCTGGTGAAATGGTTGATTATACAATTGTTGAGTCTTGGATAGAAAAC
TTTTCAAAAGACAAAGAAATTCAAGAGTTTGATTACGATAAATGGAATGCGTTACATCTAGCACAAAATTTAGAGAATAA
AGGGTTCGTTTGTGTAGAAATCCCTCAAAGGATTGCTAATTTATCCATTCCGACTAAAAATTTTCGAGAAAAAGTATACG
AAAAGAAAGTTAAACATAATGGAGATCCAGTCCTTTTTTGGGCGCTTAATAATGCTGTTGTTAAAATGGATGATCAGGAA
AACATTATGATTTCGAAAAAAATAAGTAAAAATCGTATTGATCCAGCAGCAGCGGTCTTAAATGCATTTTCTAGGGCTAT
GTATGGAGCAAGTGTCAGGTTTGATGTATCTGAATTTGCAAATAAAGACTTTCTAGGCAAGTTATGGAACTAGGGAGGGG
GTGAACATGTGAAGATAGTGGATTCTGTTAAAAAGTTCTTTAATTTTGAAAAACGCCAAACGTCGCAGGTAATAGAGTTG
AATAAAGACGATGAAAAATTATTAGAATGGCTAGGGATTTCTCCAAGTACTATTAGCGTTAAAGGAAAAAATGCTTTAAA
AGTTGCTACAGTCTTTGCTTGTATCAAAATACTATCTGAATCCGTATCAAAGTTACCGTTGAAAATTTATCAGGAAGATG
AATATGGAATCCAACGCGGTACAAAGCATTATCTCAACAATTTACTGAGACTAAGGCCTAACCCGTATATGTCCAGTATG
AACTTTTTCGGATCATTAGAAGCTCAAAAAAATTTATATGGCAATAGCTACGCTAACATAGAGTTTGATAGAAAAGGTAA
AGTCCAAGCGTTATGGCCGATAGATGCTTCTAAAGTGACAGTATACATTGATGACGTTGGTTTATTAAATTCCAAAACTA
AAATGTGGTATGTAGTAAATACGGGTGGACAACAAAGAGTGTTAAAGCCAGAAGAGATACTGCACTTTAAAAACGGAATA
ACTCTTGATGGTCTTGTCGGTGTTCCTACAATGGAATATTTAAAGTCTACATTAGAAAATTCAGCTTCAGCTGATAAATT
CATAAATAATTTTTACAAACAAGGGTTACAGGTAAAGGGATTAGTTCAATATGTCGGTGATTTAAATGAAGATGCGAAAA
AGGTTTTCCGAGAAAATTTCGAATCAATGTCTAGCGGTCTTCAAAATAGCCATCGTATTGCATTAATGCCAGTAGGATAT
CAATTTCAACCTATTTCATTAAATATGTCAGATGCTCAATTTCTCGAAAATACCGAACTTACTATTAGGCAAATCGCTAC
TGCATTCGGCATTAAAATGCATCAATTAAATGATTTGAGTAAAGCGACTTTAAATAATATTGAGCAGCAGCAACAACAAT
TCTATACCGATACATTACAAGCGACTTTAACAATGTATGAGCAAGAAATGACGTATAAGCTATTTTTAGACAGTGAGTTG
GATAAGGGGTTTTATTCAAAATTCAATGTAGACGCTATTTTAAGAGCGGATATCAAAACGAGATATGAAGCTTACAGAAC
GGGTATTCAAGGCGGTTTCCTTAAACCTAACGAAGCTAGAAGTAAAGAAGATTTACCACCAGAAGCTGGTGGGGATCGTT
TACTTGTTAATGGAAATATGTTGCCGATTGATATGGCTGGACAGGCATATTTGAAGGGAGGTGATACTAATGGAGAAGTC
AGCAAAGAAGGAAATGAAGGAAATTAGAGCTTTGCCAATGACTATTGAAGTCCGTGAAGTTAATGAGGACGAGGGAAAAC
GAACAATTTCGGGATCGATAAAATATAACAATGAAAGTGCCGAAATGCGTGACTGGTGGGGCGATACTTTCGTAGAAGAG
ATTGCTGAGGGAGCTTTTGATGAAAGTTTAAAAGTTCGTGATGTTGTAGGTTTATGGTCTCACGACACATCTCAAGTATT
AGGAAATACTAAAAGTAAAACTTTACGAATCGAAAATGACAAGAAAGAATTACGATTTGAATTAGATATTCCTAATACAA
CTGTTGGGAATGACGCATGGGAATTAATTAAGCGTGGAGATGTTGATGGAGTTTCTTTTGGGATGAAGGTTACAAAAGAC
AAATGGTCATCGGAAGAACGTGAAAATGGAAAGCTTTATAAGCGTTCGATTTTAAATGCTGAACTATATGAAATATCACC
GGTTGCATTCCCTGCATATCCAACGAATGAAGTAAGTGTACGTTCATTGGATGATTTTAAAGCTGGAGAAAAGCGAGTAG
CTGATGAGTTTAGGAAAAGAAAACTACAAATCGAACTAGAGCTTATATAAGGCTCTTTTTTTATTGATAAATTTAAGGAG
TGATTTGAATGTCAAAAGAATTACGTGAATTATTAGCTAAGTTAGAAGGGAAAAAGGAAGAAGTACGCTCTCTTATGGGA
GAAGATAAAGTGGCAGAAGCAGAACAAATGATGGAAGAAGTGCGATCACTTCAGAAAAAAATTGATTTACAACGCTCATT
AGATGAAGCAGAAACGGAAGAACGAAATAATGGAAGAGAAGTTGAAACACGTAATGTAGATGGTGAAATGGAATACCGCG

FIGURE 1A CONTINUED

ATGTGTTTATGAAAGCATTACGCAATAAACCATTAAATGCTGAAGAACGTGAATTTCTTGAGGATGATTTAGAACAACGT
GCCATGTCAGGATTAACTGGGGAAGATGGAGGACTTGTCATCCCTCAAGATATTCAAACGCAAATCAATGAATTAGCTCG
TTCATTTGATGCGCTTGAGCAATATGTAACTGTTGAACCAGTGCGTACACGTTCAGGATCACGAGTATTAGAGAAAAATT
CAGATATGATTCCGTTTGCTGAAATCACTGAAATGGGTGAAATTCCAGAAACTGATAATCCGAAATTTTCAAATGTACAA
TATGCAGTGAAGGACAGAGCAGGTATTTTACCGTTATCTCGTTCATTACTTCAAGATAGTGATCAAAACATCCTAAAGTA
TGTGACTAAATGGCTAGGTAAGAAATCTAAAGTTACACGTAATGTGTTAATCTTGGGCGTAATTGAAAAGTTAACAAAAC
AAGCAATCAAATCTCTGGATGATATTAAAGATGTATTAAATGTTAAATTAGACCCAGCGATTTCTCCGAATGCGATTTTA
CTTACAAACCAAGATGGATTTAATTATTTAGACAAATTAAAAGATAAAGACGGAAAATATATTTTACAGTCAGATCCAAC
GCAAAAAAACAAAAAACTATTTGCTGGTACTAATCCAGTCGTTGTTGTTTCGAATCGTTTCTTAAAATCAAAGGGAACTA
CAGCTAAAAAAGCGCCACTTATTATTGGTGATTTAAAAGAAGCTATTGTTTTATTTAAACGTGAAGATATGGAACTGGCT
TCTACAGATGTAGGTGGTAAAGCATTCACTCGTAATACATTAGATTTACGCGCAATTCAACGTGATGATGTGCAAATGTG
GGATAATGAAGCAGCAGTTTACGGAGAAATCGATTTAAGCGCTCCTGTTGAACAACCTCAAGGGTAAACTAAGGAGGCAT
TTGAATGCTTGTTACCTTAGAAGAAGCTAAAGAATGGATTCGAGTGGACGGAGACGATGACCCAACTATCACTATGTTAA
TTAAAGCGGCTGAATTATATATTTACAAAGCAACTGGCAAAACATTTACTCAAACAAATGAAGATGCTAAGTTGCTTTGT
TTATTTCTGGTGGCTGATTGGTACGGAAATCGACTACTTGTAGGTGAAAAAGCCAGTGAAAAAATCAGAACCATTGTTCA
GAGTATGATATTACAGCTCCAATATGCTTCAGAGCCTCAGGAGGAAAGAAAATGAATCCTGCAAAATTAGATAAACGGCT
TACATTTCAAGTAAAAGATGAAAATGCAAAAGGGCCTGACGGTGATCCGATAGATGGATATAAAGATGCTTTTACCGTAT
GGGGCTCTTTTGTTTATTTAAAGGGAAGGAAATACTTTGAGGCAGCAGCTGCTAATAGTGAGGTTCAAGGAGAAACAGAA
ATCAGAAATCGGGATGATGTAAGTGCAGATATGAAAATTAAGTACAAAAACGTGATTTATGATATTGTTTCCGTTATTCC
AACTCAAGATCATACTTTATTAATCATGTGGAAACGTGGTGAAATGAATGGCTGATGGTATAGATTTAGATTTATTAGGA
TTTGATCGTTTAGTTACTGAATTAGACCAAATGGGGTTACGGGGAGAGAAAATTGAAGATAAAGCTCTTGCAGCTGGTGG
TGAACCTATTCGTAAAGCCATTGCAGAACGAGCGCCAAGAAGCCCAAGCCCCAAAAAACGATCTAAAAGTGAACCGTGGC
GTACAGGGCAACATGGTGCAGACCAGATAAAAGTAACAAAAGCTAAACTTGAAGGTGGAATAAAAACAGTAAAAATAGGT
CTTAATAAAGCGGATCGTTCCCCGTGGTTCTATTTAAAGTTCCATGAATGGGGTACATCCAAAATGCCAGCACATCCATT
TATAGAGCCGGGTTTTAATGCTTCAAAAGCGGAAGCTGTACGTGCTATGACAGATATTTTAAAGAACGAAATGAGGTTGG
ATTTGTGATAAATTTAAGACCTGATATTTTACAAGCTCTTGAGAATGATCAAGAGCTTGTTTCATTGTTGGGTGGGAAAC
GAATTTATTACCGTAAAGCAAAGAAGGCAGAAGAGTTTCCGCGAATTACGTATTTTGAATTAGACAATAGGCCAGATGGA
TTTGCAGATAATCAAGAGATTGAAAGTGAAATCTTGTTTCAAGTTGATGTTTGGGCAAAGAGTAGTACAACAGCAATCCA
TCAAAAAGTGAATGAAATCATGAAAAGAATTGGTTTCTCACGCTATGCGGTTGCTGATTTATATGAAGAGGATACACAAA
TATTTCATTATGCGATGAGATTCGCAAAAGGAGTGGAATTATAAATGGCTGGAGAAGTTGTAAGAATTAGTTCAACGGTT
GGTGTAGACAACCTTGTATATGCGAAAGTTTTACAAGATGATTCGTCTGCTATTAAATATACAGATGTAAAGAAAATGGA
AGGTGCTGTAAAGGTTAAATTAACTAAAAAAGTAGCTTCTGAGGTTATGTGGAGCGATAACAGAAAATCAGAGATTGCAG
AATCTGATGGCGAAACTGAAGTGGAGATTGAGGTTCGAGGACTTTCACTTTCTACAAAGGCTGACATTGAAGGGTTTCCA
GAAGTAAAAGATGGCGTTTTAGATGAGAAACGTGAAGGTGAGAAACCATATTTAGCTATTGGTTTCCGATTCTTAAAAGC
TAATGATAAGTATCGATATGTTTGGTTATTAAAAGGGAAACTTTCACAAGAGGAAGAAGAAGCTGAAACGAAAAAAGACA
AACCGAACTTCCAAACAACAAAATTGAAAGGTTCCTTTATTGAACGTGATTTTGATGATAGAACGAAATTTACAGCAGAT
GAAGATGAACCAACGTTCACAAAATTAGTTGGAGATAATTGGTTTAATAAAGTATATGAAAAACCAGTGACACAACCACC
AGCAGGAAAGTAAGAGGGAGCAAAAGCTCTCTCTTTTTTATTAAATTTAGGAGGGAAAAACTATGAAATTAACATTAATG
ATTAATAAAGAAAAACAAACTTTTAATATGCCAGAATTTATTCCAGCCCGCCTTATTCGTCAGGCTCCTGAACTTGCTGA
AATTCCAAACAATCCTGGTCCAGAAGATATGGATAAAATGGTTCAATTCGTAGTGAAAGTTTATGATGGTCAATTTACAT
TAGATCAGTATTGGGATGGTGTTGATGCCCGTAAATTCTTATCGACAACTTCAGATGTAATTAACGCAATTATAAATGAA
ACAGTGGAAGCAGCAGGGGGTAGTACTGAATCAGGAGAAGAAGAAAACCCAAACGCATAGAGGGAGGAGGGCTAACGTTC
AGTGAGTTTATGGACGAGCTCTACCTCTCTTTATTGCGACAAGGGTACAAACACCATCACATTGATAATGAGATGGATAT
TTGGCATTATTTGAGACTTAATCGAAAAATGCATGAAAACGGAAATGAAAATTACGAAGGCTCCAATTCAAATGAAATAG
AAGTGCCAGCGGAAAACATTATTTAACGAGGGAGGTGAGACTATGGCGAATGAAATAAATAATCTAGTCGTTAGACTTTC
CCTTGATAACGTAAATTTCAGACAAGGTATCTCGAATTCAGGTCGTGCAGTCAGGACGTTACAGAATGAATTGAAATCTG
TAAGTACAGGAATGGGCGGTTTTGCTAACGCTAGTCAGCAAACACAAGCGAAAATGAATACACTCAGTAGGCTCATTGAT
GCGCAAAAAGAGAAAGTTAAAGCGTTACGACAAGCCTATGATCAAAATAAGGCTAAATTAGGTGAAAATGATGCAGCAAC
CCAGCGATATGCTTCGCAAGTTAATAAGGCAGTTGCTGATTTAAATAGATTTGAAAATGAATTAAAGCAAGTAAACCGTC
AAGCTGAACAAAAAGGGATGGATAAGTTAAACAACTCTTTAAAATCCCTACAAGCTGAATTTCAGTCTATTACAACAGGT
ATGGGCGGTTTTTCTAATGCGACAGAACAAACAAGGGCTAAAGTAGATGTTTTATCCCGTATGGTAGATAAACAAAAAGA
GAAGATTAGGGAACTTCAACAAGCCTATAATCGTGCTAAAACAGAAGAAGGCGAAGCGAGTCAATCAGCACAAAGATACG
CTGAACAAATTCATCGGGCAACAGCTGAACTGAATCGATTTGAAACTGGATTACAGCAGTCAAATCGTGAATTAGAACAG
CAAGGGAATCGCCTATTGAACTTCGGAAATCGCATGGAGACATTAGGTAATCATTTGCAAAATGCCGGAATGCAGATCGG
CATGGTATTTGGTGGTATGACTTACGCAATAGGTCGGGGCTTAAAATCAGCAATCACTGAATCAATGAATTTTGAGCAAC
AGATGGCCAATGTAAAAGCTGTTTCTGGATCTACTGGAGCAGAAATGAAAAAGTTAAGTGAATTGGCTGTTAATATGGGA
GAAACAACAAAATACTCCAGTGTTCAAGCAGGTCAAGGTATCGAGGAATTAATAAAGGCTGGTGTTAGCTTACAAGATAT

FIGURE 1A CONTINUED

TATTAACGGCGGATTGGCAGGTGCCCTTAACTTAGCGACGGCAGGGGAATTAGAGTTAGGTGAAGCAGCCGAAATTGCTT
CCACAGCTCTGAATGCATTTAAAGCAGACCATCTTTCAGTTGCGGATGCAGCCAATATTTTATCTGGTGCAGCCAATGCT
TCCGCAACTGATGTAAGAGAGTTAAAATATGGACTTTCAGCTTCATCAGCAGTAGCAGCGGGAGCCGGAATGACGTTTAA
GGATACAGCTACAACTTTAGCGGTATTTGCACAAAATGGTCTTAAGGGATCAGATGCAGGTACATCTTTAAAAACAATGT
TAATGAGGTTAAATCCTTCAACAAAAGAAGCATATAACAAAATGAGAGATTTAGGACTTATTACTTATAATGCACAGGCA
GGTTTTGATTTCTTAGTTAAAAACGGTATTCAACCAGCTTCCAGAAATGTAGGGGATATAGAAGTAGCTTTAGAACAATA
TGTAATGAAAACAGAAGGTGTAACGAAATGGAATGATAAATGTGATACAACGTTTCGCGAATTAGCAACAAGTTCGGCAT
TTTTATCATCAAAATTCTATGATCAACAGGGGCATATTCAAAGTCTAGAAAATATTTCAGGTACACTTCATGAATCGATG
AAAGATTTAACAGACCAACAACGAAGTATGGCTCTGGAAACATTATTTGGTTCCGATGCTGTACGTGGTGCGACTATCTT
GTTTAAAGAAGGCGCCAAAGGTGTCAATGAAATGTGGGATTCCATGTCAAAGGTTACAGCAGCTGATGTAGCAGCGACCA
AAATTGATACTTTAAAGGGACGACTTACATTACTAGATTCAGCGTTTTCCACAATGAAAAAGACAATTGGTGATGCACTA
GCTCCAGTAGTTAGTGTTTTTGTTGCTGGTTTACAAAAACTTGTTGATGGATTCAACTCTTTACCTGGACCAGTACAAAA
GGCAATAGCAATTACAGGTGGTATCGTCCTTGCTTTAACAGCTGTGGCTACAGCAATAGGTGTGGTTTTAGCAGCGTTTG
GAATGATTGCTTCAGGAATTGGTTCTTTATCTCTTGCTTTAGCATCAGTCGGTGGGATTGCTGGAATTGCGGCTGGAGCA
GTTGGATTCTTAGGAAGCGCGCTTGCGGTTTTAACAGGGCCAATTGGTCTAGTAGCAGCGGCTCTTATCGGAACTGGTGT
TGTTGCATATAAAGCATATCAAAAAGCGACTGAAGACAGTATCGCATCAGTAGACCGCTTTGCTACAAATACAGAAGGGA
AAGTAAGCTCCTCAACAAAGAAGGTTCTTGGCGAGTATTTCAAGCTGTCCGATGGTATTAGACAAAAGTTAACTGAAATT
AGATTGAACCATGAAGTAATAACAGAAGAACAGTCGCAAAAGTTGATTGGTCAATATGACAAATTAGCTAATACAATCAT
TGAAAAAACCAACGCAAGGCAGCAAAAAGAAATTGAAGGGCTTAAAAAGTTCTTTGCTGATTCGTATGTATTAACCGCTG
AAGAAGAGAACAAACGAATCGAACAGTTAAATCAGCACTATGAACAAGAAAAGCTAAAAACGCAAGAAAAAGAAAATAAA
ATTAAAGAGATCTTACAAACAGCGGCTAGAGAAAACAGAGAATTAACGACATCCGAACGTATCTCTTTACAAGCATTGCA
GGATGAAATGGACAGAGTTGCTGTTGAGCATATGTCTAAAAATCAAATGGAGCAGAAGGTTATTCTTGAAAATATGCGTG
TGCAGGCTAGTGAAATTTCAGCTAGACAGGCAGCGGAAGTTGTAGAGAATAGCGCCAAAGCAAGAGATAAAGTTATTGAA
GATGCGAAAAAGACCCGTGATGAAAAAATTGCAGAGGCGATTCGCCAACGTGATGAAAATAAAACAATCACTGCTGATGA
AGCGAACGCAATCATTGCAGAGGCAAAACGTCAATATGATAGTACAGTTTCTACAGCTCGAGATAAACATAAAGAAATTG
TGAGTGAAGCAAAAGCGCAAGCTGGTGAACATGCAAATCAGGTAGATTGGGAAACTGGCCAAGTAAAATCGAAATATCAA
GCTATGAAAGACGATGTTATTCGAAAAATGAAAGAAATGTGGTCGGACGTTACCAACAAATATGAAGATATGAAAAACTC
TGCAAGCAACAAAGTAGAGGAGATAAAAAATACAGTTTCAAGAAAATTTGAAGAGCAGAAAAAAGCTGTTACTGATAAGA
TGTCAGAAATAAAAAGTAGTATTGAAGATAAGTGGAATACAGTTGAAAAGTTTTTCAGTTCTATAAATTTACGTTCCATC
GGTAAATCAATCATAGAAGGGCTTGGCAAGGGAATAGATGACGCTTCAGGAGGTCTGTTTAGTAAGGCTGCGGAAATTGC
AAGTGATATTAAGAAGACTATTTCTGGAGCATTAGAAATTAACAGTCCGTCTAAAGTGATGATTCCAGTCGGTAGCGCAG
TTCCAGAAGGTGTTGGGGTTGGTATGGATAAGGGAAAACGATTTGTTGTGGATGCAGCAAAAAATGTAGTCGGAACTGTT
AAGAAACAAATGGGGAATATGCCATCTGTTTTTGATTTTGGATTCCAAACAAATCAATATAGTATCCCGCAAAATACATT
TAGCGATTTCAGTGGATATATGCAACCGCAATTATCTTATAACAATCCATCTATGGCAAAAACAATATTCCCAAATAGAC
CAGGTGGAGAACAAGAACTGAATTTAACCGTAAACATGACTAATGTTTTAGATGGAAAAGAGCTTGCAAACGGAAGTTAC
ACCTATACTACAAAACTTCAAAATCGTGAACAAAAAAGAAGAGCGGAATTTTAAGGGTGGTGAGCACGTTGGGGAAACTT
AGTTTTACTTTTAATAATATTAGAAAAGATTATATTCAAATGCTAGTTGGAAGAAAACGTCCTTCATGGGCTCCAGTAAA
AAGAAGATTAGTAAGAGTCCCTCATCGCGCAGGGGCTCTTTTACTTAATACAGAAACGGAGGAACGTCGTATTGACGTTC
CTCTTGTTATTAAAGCGAAAAAAGATATGGCAGATTTACAAAAGTTAAAAGAAGATTTAGCGGATTGGTTATATACAGAG
CAACCCGCTGAACTTATTTTTGATGATGAGTTAGACAGGACTTATTTAGCATTAATTGATGGTTCTGTCGATTTGGATGA
AATAGTCAATAGAGGTAGAGGTGTTATTACTTTTGTTTGTCCAATGCCGTATAAATTAGGGAAAACAAATACTCACAAAT
TTACGCAAGAGTGGTCTACAGAAACAACTTCTTATTTTACTAATAAAGGAAGTGTAGAAGCTCCAGCGTTAATTGAAATG
ACGGTGAAAAAACCAAGTACCTTTTTAGATGTATGGTTTGGAGAGTATCCGAATAATCGTGATTATTTCAGAATAGGCTA
CCCTCTGACTGTGGAAGAAACCACGGTACAAGAACGAGAAAGAGTTATGTGGGATGAAATGGCCACTCCTATAGGATGGA
CACCCGTTACTGGACAATTCGATGATATGAAAGGAACAGGGAGTTTTAAATCGCGTGGTGGTTATGCGCTGTATTGTGAA
GATTACGGAAAAGATGTAGGATTCTACGGTGCTATAGCCAAGAAAAACATTCCGGGCGGCCCATTACAAGACTTTGAAAT
GGAGGCATGGATGACTTTAAAGTCTAAAAATATAGGTGAAATGGGTCGTGTTGAAGTTCTTCTTCTAGATGAGGCTAGTA
ATGTGGTAGCCCGCATCAATATGAATGATCTATATGCAACTGCCGAAATTACAAGGGCACATATGAAAATTGGAAATAGC
GGAACACCCAATAGTTTTCGAAAATTAGTTGATACAAGTGGGTATTATTCGAATACATTTAACCAATTTCGAGGGCGTTT
GCGTATCGCTAGGCGGGGGAAGGTGTGGTCTGTATATGTGGCTAAGTTTATAGATGGTACAGAAAAAGATGGCGCTTCGC
TTGTAGAACGTTGGATTGATGAAACAGGAAATCCAATGACAGAACGTAAAATTGCACAAGTTATGATTGCGATTTGCAAG
TGGGATAATCACCAGCCTGTTAATGAAATACAAATTGATGATTTGAAATTTTGGAAGGTAAACAAAGTTCCATCTAATGC
ACAACCATATATCTTTGATACTGGAGATAAAATTGTTATCGATACTGAGAAAAGTCTTGTCACAATCAACGGGAAGAATG
CAATCAATATAAAAGAAATCTTTAGTAATTTTCCTGTCATAATACGTGGTGACAATCGTATCGATATTATGCCGCCAGAT
GTAAACGCAACAATCAGTTATAGGGAGAGATATAGATGAGAACACCAAGCGGGATTTTGCATGTTGTGGATTTTAAAACA
GATCAAATCGTCGCAGCTATCCAACCAGAGGACTATTGGGATGACAAACGGCATTGGGAACTTAAAAATAATGTTGACAT
GTTGGATTTCACCGCATTTGATGGAACAGACCATGCAGTTACCTTACAACAACAGAATCTTGTTTTGAAAGAAGTTCGCG

FIGURE 1A CONTINUED

ATGGAAGAATCGTACCATATGTTATTACAGAGACTGAAAAAAATTCCGATACACGATCTATTACCACATATGCTTCAGGA
GCTTGGATTCAAATTGCGAAATCAGGGATTATAAAACCACAACGGATAGAGAGTAAGACGGTTAATGAGTTTATGGATTT
AGCACTCTTAGGTATGAAGTGGAAACGCGGAATTACTGAATATGCTGGATTTCATACAATGACCATCGATGAATATATTG
ACCCACTCACTTTTTTAAAGAAGATTGCATCTTTATTTAAACTGGAAATTCGATATCGTGTTGAGATTAAAGGTTCAAGA
ATCATCGGTTGGTATGTAGATATGATTCAAAAACGTGGTCATGATACAGGCAAAGAAATAGAATTAGGAAAAGATTTAGT
CGGTGTTACGCGAATTGAACATACACGTAATATTTGCTCTGCTTTAGTTGGATTTGTAAAAGGTGAAGGTGACAAAGTAA
TCACTATTGAAAGCATTAATAAAGGTCTACCCTATATCGTAGATGCAGATGCGTTTCAAAGATGGAATGAACACGGACAA
CATAAATTCGGTTTTTATACACCAGAAACAGAAGAATTAGACATGACTCCAAAACGTTTACTGACGCTTATGGAAATAGA
ATTGAAAAAGCGTGTCAACTCTTCAATTTCTTATGAAGTGGAAGCACAATCTATTGGTCGTATTTTCGGTCTAGAACACG
AATTAATTAACGAAGGCGACACGATTAAAATTAAAGATACAGGGTTTACACCAGAATTATATCTTGAAGCGCGAGTAATA
GCTGGGGATGAATCTTTTACAGATTCAACGCAAGATAAATATGAATTCGGAGATTATCGTGAGATAGTTAATCAAAATGA
GGAATTAAGAAAAATTTATAATAGAATCCTTAGTTCGCTTGGTAATAAACAAGAAATGATAGATCAGCTAGACAGATTAG
TTCAAGAAGCTAACGAAACCGCTAGTAATGCAAAGAAGGAGTCAGAAGCAGCAAAAACACTAGCTGAAAAAGTACAAGAA
AATATTAAAAATAATACCGTTGAAATTATAGAATCTAAGAATCCACCGACAACAGGTCTTAAACCATTTAAAACGCTTTG
GCGTGATATTAGTATCGGAAAGCCTGGTATTTTAAAAATATGGACAGGTACAGCGTGGGAATCGGTTGTACCTGATGTTG
AATCTGTAAAAAAAGAAACATTAGATCAGGTTAATAAAGATATCGCAACCACAAAAACAGAGTTAAATCAAAAGGTTCAA
GAAGCCCAGAACCAAGCGACTGGTCAATTCAATGAAGTGAAAGAGAGTTTACAAGGCGTTAGTCGTACGATTTCTAATGT
TGAGAACAAACAAGGTGAAATCGATAAGAAGATTACTAAGTTTGAACAAGATTCAAGTGGATTTAAAACTTCAATTGAAT
CGTTAACGAAAAAAGATACTGAAATTAGTAATAAATTAAATACAGTTGAGTCTACTGTGGAAGGTACGAAAAAGACGATA
TCTGAGGTACAGCAAACAACTAATGATTTAAAGAAAAAAACTACTGAAATAGAAGAGAAGGCTGGAAAAATCACCGAAAA
ACTTACAAGTTTAGAGACAAGAGAAGTTAATGTTCGAAACTATGTAATTAACTCTGATTTTTCGAATGTTACAAATTCTT
GGATTGGAATTACTAATGCAACTCTTTTTAAATTTGTAGATGTGAATATTTCGGAAGCCTCCGCTATTAAGAAAGGTTTA
CAAATAACAAGTAATAAAGCTTTTGTTTATCAGAAGTTACCCGCAGACGTGTTTAAAAAGAAGAAGGGGATAGCTTCTTG
TTATATAAATGTATCAAGTTTTACACCTGGTACAGATTATCCACGTTTATATATGAGATTCACCTATGACCAAAACGGAA
CAGAAAAACAATATTATGCCATTTTAAAACAACAAGAAGTAACTAATGGATGGATTAGGATTTCTATACCATTTGATACA
ACTGGATATACAGGTGAATTAAAAGAAGTACGTGTAAATATAGCTACCGCTGACACAACTACTATCGATGCAACGTTCAC
TGGAATAATGGTTACATTCGGTGACTTAATTGAATCTTGGAATCTCGCTCCAGAAGATGGAGTAACACAAGGTGTTTTTC
AATCTAAAACAACCGAGATTGAAAAAGTGTGGATGGTGTAAAAACTACTGTAACAAATGTTCAAAATAGCCAAGCTGGA
TTTGAAAAGCGCATGTCTAATGTGGAACAAACAGCAACTGGATTATCTTCTACCGTAAGTAATTTAAACAATGTAGTATC
CGATCAAGGAAAAAAGCTTACTGAAGCAAATACAAAACTCGAACAGCAAGCAACCGCGATTGGAGCAAAAGTTGAGCTTA
AACAAGTAGAGGATTATGTTGCTGGGTTTAAGATTCCTGAGTTGAAACAAACAGTTGATAAAAATAAACAAGATTTATTA
GATGAATTAGCCAATAAGCTTGCAACTGAACAATTTAACCAGAAGATGACTCTGATTGATAACCGTTTCACTATTAATGA
ACAGGGTATCAATGCCGCAGCAAAAAAGACAGAAGTATATACAAAGACGCAAGCAGATGGACAATTTGCTACAGATTCTT
ATGTAAGAGATATGGAGTCGCGCCTGCAGCTAACAGAAAAGGGTGTTAGCATATCTGTAAAAGAAAATGATGTAATCGCA
GCCATTAACATGAGTAAAGAAAACATTAAGTTAAATGCTGCACGAATAGATTTAGTTGGTAAAGTTAATGCGGAGTGGAT
TAAAGCTGGATTGCTGAGCGGTTGCCAAATTAGAACATCAAATACGGATAACTATGTTAGTTTAGATGATCAATTTATAC
GTCTCTATGAAAGAGGAGTTGCTAGAGCATTTCTGGGGCATTACAGAAGATCAGATGGTGCAGTACAACCGACTTTCATC
TTAGGTTCAGATGAAAAGACTAACGCTCCGGAAGGTACTTTGTTTATGTCTCAAGCAGGTGCAGGATGGTCAGGGGCTTA
TGCGAGCATTGGTATTAGCAATGGCATAGTTGATGGTGCAGTCCAAAAGTCTGTGTATTGGGAGTTGCAAAGAAACGGAC
TAAGTGTTCTAAACGCTAATGATTACCATGTTTTTTACGCTGGAAATGGAAATTGGTATTTCAGAAGAGGGAAACCAGGG
TTGTATCAAACTTCGTTAGTCGTTGAAGATAATAGTACAGATTCTGATTTAAGATTACCTAATGTAACTATACGTAATAG
CCGTGCAGCAGGATATACAGGAGTTATTCAATTGAAATCCCCTGTTACTCAAAATGGATGGGGTGCTGTTCAAGGGAATT
TTATGACTCCTTCATTACGGGAGTATAAATCTAATATCCGTGATATTTCTTTTTCCGCCTTAGAAAAAATTAGAAGTCTT
AAAATTAGACAATTTAATTATAAGAATGCTGTAAACGAACTATACCGGATGAGAGAAGAGAAAAGTCCCAATGATCCACC
ATTGACAACAGAAGATATTAAAACATACTACGGTTTAATCGTAGATGAATGTGATGAAATGTTTGTGGATGAAAGTGGGA
AAGGAATTCATTTGTACTCATACGCATCCATTGGAATTAAAGGTTTACAAGAAGTTGATGCAACAGTACAGGAACAGGAG
GTAGAAATAGCAAATCTAAAATCACAAATAGCTAGTCAAGAAGATCGGATAGCACGATTAGAAGAATTATTACTACAACA
ATTAATAAATAAGAAACCAGAGCAGCCATAGGCTGGTCTTTTTATTTTGGCCAAAAAGGAGAGGAAAAGATGGATCGTAT
TGATGTATTACTAAAAGCATTTATAGCTGCGTTTGGTGGCTTCTGTGGGTATTTCTTGGGAGGATGGGATGCAACATTGA
AAATCTTAGTGACAATGGTAGTTATTGATTATTTAACTGGCATGATTGCAGCAGGGTATAACGGAGAATTAAAAAGCAAA
GTTGGTTTCAAAGGCATCGCCAAAAAGGTGGTGCTTTTTCTTTTGGTCGGAGCGGCCGCTCAACTAGACTCGGCACTTGG
AAGCAACAGTGCAATCCGTGAAGCAACAATTTTCTTCTTCATGGGTAATGAATTACTTTCACTCTTAGAAAATGCCGGGC
GAATGGGTATTCCACTCCCACAAGCATTAACAAATGCAGTTGAGATTTTAGGTGGTAAACAAAAACAAGAAGAGAAAAAA
GGAGATGTTCAGTAATGGAAATCCAAAAAAAATTAGTTGATCCAAGTAAGTATGGTACAAAGTGTCCGTATACAATGAAG
CCTAAATATATCACTGTTCACAACACATATAATGATGCTCCAGCTGAAAATGAAGTGAGTTACATGATTAGTAACAATAA
TGAGGTGTCGTTTCATATTGCAGTAGATGACAAGAAAGCGATTCAAGGTATTCCGTTGGAACGTAATGCATGGGCTTGCG
GAGACGGCAATGGTTCGGGGAATCGTCAATCCATTTCTGTAGAAATCTGTTATTCAAAATCAGGAGGAGATAGATACTAT

FIGURE 1A CONTINUED

AAAGCTGAGGATAATGCTGTTGATGTTGTACGACAACTTATGTCTATGTACAATATTCCGATTGAAAATGTTCGAACTCA
TCAATCCTGGTCAGGTAAATATTGTCCGCATAGAATGTTAGCTGAGGGAAGGTGGGAGCATTCATTCAGAAGGTTAAGA
ATGGGAATGTGGCGACTACTTCACCAACAAAACAAAACATCATCCAATCAGGGGCTTTCTCACCGTATGAAACCCCTGAT
GTTATGGGAGCATTAACGTCACTTAAAATGACAGCTGATTTTATCTTACAATCGGATGGATTAACTTATTTTATTTCCAA
ACCGACTTCAGATGCACAACTAAAAGCAATGAAAGAATACCTTGACCGTAAAGGTTGGTGGTATGAAGTTAAATAAAACA
AAAGAATAGTTTTATGAACAAAAATAAGAGCCGTCCTGTTGGGCGGCTTTTTTTATTGCTCAATTACTGTTGCACTAAT
TTTAGGCATTCCTGTTTTATCTTTTTCGTCGTAGGCGCCATAGATTGTTACTATTGATCCTTTAGATATTTTTAATCCGT
TTTTAAGTGTTATTTCATTTTCGTTCGTTTGCACTCCACTTTGGACAATTTGAATAGTGTACATGCCTTTGCCGTCATTT
TCGTTTGTGCTTATGACAAATGAAGGTAATGCTGAAGACTTAAGTAATAAATCTACCGTTCCGGTAGCTTTAAGCCTTTT
TCCTTTTTCGTATTGATCTCCATTTGCCTTAACAAAACTAACTTCTTCAGCATCTTGCTTTATCTTCTTATTTAACTCAT
CCTGAGATGTTAAATCTTTTTTAGTTTCTGGTTGAGATTTGACGTTCGTTTTTTCACTTGATTCACTTTGTTTAGAAGAA
TCACAAGCTGTTAGACCTAACAATAAGGTACTTCCAATGCAAATACTTATAAGTTTTTTATACATTTTCATTCTCCTCCT
CTATCCAAATTTCTTCCATGTGCAATTTTAATTCCTTTGCAATTTTATAGGCTGTAAGAAAGGTAGGTAGCGTCGTGTTA
TTAACGAGTGAACTCATTGTAGTTTGACTAATTCCAATAAGTTTTGAAAACTCCTTTTGACGTATTTCTCTTTCAGCAAA
AATAACACGAAGTTTACATTTTAATCGCACAATATCACCTCTTTAATTATATACAATTCGCATATGGAAATGTGTCCTCC
TTTAATTTAATCAACGAACATTTAGAAAAGTTTAAATGGACAGGCAATATAACTCTTTCTAAGTCATATACCTATATCAA
GACCACGAGGAATACCAAGTGGAACTAAGGACATCAAGAGGGGAGAGGATTACATGCGTTGGCAGTATAATCACTTGAAT
ACAACTCCATATCTTCATCCATCCAAAGAATTATGTTCAATGTACAATGGATCGAGATCAAGAGCAGAGACGGAATCAAT
TTTAAATCACATGAAAAATCATGAAGTTTATGATCGAAAAGAATATAAAGGATATTTCAGTTTGTCACAGGTATTAGAAG
AAGATCTATATGGAGAGGAAGAAGATGTTTTAAACTGGGAAATTCTAATGGATTGTTATGATGTAGTTCTTACAAGAAAA
GGTATTGCATTTCGTGAAAAAGAAGAGGAGGAACAAGCATGACTCTTGCTGGAGAAGCGATTATTATTTGGACGGCAACA
GGGTTGTCAGTAGTTGCAATGAAGGCAGCAGAAAAAATGGGGAAAAGTGTTCCACATTGGCTTCCACGTGTCACTTTGTA
CACAACACTTACAGGCTCGTTTCTATACCTTCTACGTTATGTTCTCGTTTTATTTCTATGAAGGAATACGATGTGGAAAC
TTTTCATTCCTTATGTCATAAGGAGTTTAGCTTGTATGCACGTATTCCTTGAAACAGGGATATATACCCTCTATAAGAGG
GATATAAGGAGTGATTTTATGCTGGAGTTGTTATCAGTACCATTCGCAGGTTTAATTTTCGCCATAGTTGGCGAAAGGCT
CAAAGGAAGAGAGAGTGATCGAAAGAAAATACAAGTTTTTTTGAAGTAAGCGGAATTGCGATACGTAGAGAGGACAAAT
TACAGTATCCAGTTTTTCTTGAACAAAAAGAGGATGACCGAAGTACAACTTATATATATCGGTTGCCTGTAGGAATGCCG
AGTAAAATTATTCAGAAGGTCGAGGATGTTGTCTCTGAAGGGCTAAGTAAACCTGTCCGAATTGATTATGATAATTACAA
GCTAAATATTCGTGTGTTTCATAGGGATATACCGAAAAAATGGTCATGGTCTAAAGGTTTGGTTGCAGAAGGAAGCTGGT
GTGTTCCAATGGGCCAAAGTTTAGAAAAACTTATCTATCATGATTTTGATAAAACACCACATATGACACTAGGTGGTCTG
ACACGGATGGGAAAAACGGTATTTTTAAAAAATGTAGTTACTTCTCTTACTTTAGCACAACCAGAACATATTAATTTATA
CATTATTGATTTAAAAGGGGGCTTGGAGTTTGGGCCGTATAAGAATTTAAAACAGGTAGTTTCTATTGCTGAAAAGCCCG
CAGAAGCTTTTATGATATTAACTAATATCCTCAAGAAGATGGAAGAGAAAATGGAATATATGAAATGTAGACATTATACG
AATGTTGTAGAAACAAATATCAAAGAGCGTTACTTCATAATAGTAGACGAAGGAGCCGAACTTTGCCCAGATAAAAGTAT
GAAAAAAGAACAGCAAAGGTTATTAGGAGCGTGTCAACAAATGCTCTCTCATATAGCGCGCATAGGTGGTGCTTTAGGTT
TTAGATTGATTTTTTGTACACAGTACCCGACAGGGGATACATTACCGCGCCAAGTAAAACAAAATAGTGATGCGAAATTA
GGCTTTAGATTACCGACTCAAACAGCATCAAGTGTTGTTATAGATGAAGCGGGATTAGAAACGATAAAAAGCATTCCCGG
ACGCGCGATTTTCAAAACCGATAGACTTACAGAAATACAAGTGCCTTACATTAGTAATGAGATGATGTGGGAGCATTTAA
AAGGATATGAGGTGGAGAAACATGAGGATGCAAACGCATATGCAAATCAACCGTCAAATGGCGATACTTGCGACGATTAG
AAAGCTACAGTTTGCAACGAGAAGGCATTTAATGAGTATTCATGAAATGGGTGGAATAAGAAATGCAAATCGAATTCTGA
AAGATTTATCTATTTATACAAGTAAGGTAGTTTACAATAAAGAGCATGTATATTATTTAAACCAATCAGGACATAAGTTG
TTTGGCGAAGGGAAAGTTGTACATCATGGTAAAGTTACACACGCTCTTTTACGTAATGAAGCTTGGTTAAATTTATATTG
TCCTGATGATTGGCAAGTAGAAACTGAAATTAAATATATAAAGGATAATAAAAAGAAAAAAATAATTCCAGATGTGAAAT
TTCGTGATGAGGACAGAATACTTCATGCTGTAGAAATAGATCGTACTCAGAAAATGATAGTGAACGATGAAAAATTAAAA
AAATATGAGGAGTTAACGCAGATTTATAAACAGAAGCATAACGGGAAAGTGCCAGTTATTCATTTCTTTACAATCACAAA
ATATAGAGAAAAGAAATTAGAAGAACTGGCAAATAAATATAATGTGTTTGTAAAAGTATATGTAATCGCTACTACTTAAT
GATGAAAAAAAGAGCTGATCATTTTCGAATGATTAGCTCTTTTTTATGTATTGTATTACGTCGTCTATTTTGTAAATTTT
ATTAATTCCTTTTTCTGCAGCAATGGCATTTAAAGCATCAATGATAGCTTCAAGCGAATCAAAACGAACAGCATTAGCAT
TACCATTCACTAAATCACTAATCGTGTTGTATCTTACTTGGGATTCTGTAGATAATTTATTTTTAGTGATCCCCAATTCA
TCTAAAGAATTTCCGAGTGTGAATTTCATTTTATTCTCCTCCGCAGCACTGGTTATCTTGTACTCATTTTACAACATCAA
TCGAAATTAGTAAAACTTTTTTCGTTCAACTATTGACGTTGAATAATTAGAGAGTTATAATTCAACTTAAAAGGAGGAAC
AATTATGAATCGAGTAAATGATTATTTTGGTTTAGAAAGTAAATCAGATTGCATTTGGTTTTATGGTTTCTTCAGTATAT
CTACGATTTTATTTTTAATCGATATGATTATTGCTCTTATATAAGGAGGGGAGAAAATGCTTAGCTCAGCAAACTATACG
CAATATAAAAAATTACAATCATTCCGATCAGTAGAAGAGATGAATGAAGCGATTTGTTCTTTTTTATACAAACATACACA
TGAATTATCCGAATCAGCAATAAAAGTATTGAAATTTCTAGCAAGGCACTCTTGTAAAATCCCAGGTGTCTCTTTCTTGA
AGGTAGGGACAATTGCGGAGGCATTAAATATAAGTGATCGAACTGTTCGCAGGGTACTAAAAGTATTAGAGGATTTTGAA
GTAGTAACTAGACATAAAACAATTCGAACGGAAGGAAAATTACGTGGAGGGAACGGACATAACGTCTATGTCCTTCTAAA

FIGURE 1A CONTINUED

AAAATATAGTGTCACACCGAATGTCCTACCGAAAATGTCACAGCGACAAGATGAAGAAAACCTTACAGAATCAAAGGTTT
CAGATACAAAAACGGACAAGGAAGCTAAACTTTCTGAATCACACCCTCTAGAAGAATTGAAAAGCGAATTAAACGTAAAA
GAAACGTCAGCAAGGGAATCTAAAGAAATCGAATTAGAGGATCTAGATGAAACTTTTACACCAGAAAATGTACCAAGCCA
ATTCAGAGATGTGGTAGCTCCATTCTTCAAATCAGCAGATAAAATTTATAAATTGTATCATCGAGTATTAATAGCTTATA
AACGTTCAAAAATAGACAAGCCTATTGAACAAGTGATAAATCAAGCCATTCAAGCATTCAAAGAAACTGTCTTCGCAGAA
AAAGCAAATAAAATTAGAAGTACTTTTGAAGGTTATTTTTATAGAATTGTTGAAAGTAAATTTGTAATGGAGAGAAGGAA
AGAATGTCGAGGATTATTGTTCGATTGGTTAAATGAATAATATAAAATTGCCCACAGGGAAAAATATATATATAATTTAA
TTATCATATTCTTAGTAAATAAGTGGGTGAAAATTTTGAAATACGCTGTTTATGTACGAGTTTCAACGGATAGAGATGAG
CAAGTTTCATCTGTTGAAAATCAGATTGATATTTGTCGATATTGGTTAGAAAAAAACGGATATGAGTGGGATCCAAATGC
AGTATATTTTGACGATGGTATTTCTGGTACAGCTTGGTTAGAACGTCATGCGATGCAACTAATATTAGAAAAAGCAAGAC
GAAATGAATTGGATACAGTCGTATTTAAATCTATACACCGTTTAGCAAGGGATCTAAGGGATGCCTTAGAAATTAAAGAA
ATTCTAATAGGTCATGGGATACGCTTGGTTACAATTGAAGAAAATTACGATAGTTTATATGAAGGTGGCAATGATATTAA
ATTCGAAATGTTTGCCATGTTTGCTGCACAATTACCTAAAACTATATCTGTATCTGTTTCTGCTGCAATGCAAGCTAAAG
CAAGAAGAGGCGAGTTTATTGGAAAACCGGGATTAGGATACGATGTAATTGACAAGAAACTTGTTATCAATGAAAAGGAA
GCTGAAATTGTAAGGGAAATTTTTGATTTATCCTATAAAGGCTATGGATTTAAGAAAATAGCGAATATCCTAAACGATAA
AGGCACATATACGAAGTTTGGCCAGTTATGGTCGCATACAACTGTAGGGAAGATTTTAAAGAACCAGACGTATAAAGGGA
ATTTGGTCTTAAATAGTTATAAAACAGTAAAAGTAGATGGAAAGAAGAAAAGAGTTTACACTCCGAAAGAGAGATTAACA
ATTATAGAAGACCATTATCCAACAATTGTATCAAAAGAATTATGGAATGCGGTAAATAGCGATAGGGCAAGTAAAAAGAA
AACAAAACAAGATACAAGAAATGAATTTAGAGGAATGATGTTTTGTAAACATTGTGGTGAGCCAATTACAGCTAAGTATT
CAGGTAGATACGCAAAAGGAAGTAAAAAAGAGTGGGTATATATGAAATGCAGTAATTATATTAGATTCAATCGCTGCGTT
AACTTTGACCCGGCTCATTATGATGATATAAGAGAGGCGATTATCTATGGATTGAAGCAGCAAGAAAAAGAACTAGAGAT
ACATTTCAATCCAAAAATGCATCAAAAAAGAAATGATAAATCTACAGAAATTAAGAAGCAAATTAAGTTGTTAAAAGTGA
AAAAAGAGAAGTTGATTGATTTATACGTAGAAGGATTAATCGATAAAGAAATGTTTTCGAAGCGGGATCTTAATTTCGAG
AATGAAATTAAAGAGCAAGAGTTGGCATTACTTAAATTAACAGATCAGAATAAGAGAAATAAAGAAGAGAAAAAAATTAA
AGAAGCTTTTTCAATGCTCGATGAAGAAAAAGATATGCATGAGGTTTTTAAAACTTTAATAAAGAAAATCACACTTAGTA
AGGATAAGTATATCGACATCGAATATACATTTTCTTTATAGTTTTAAAGTTGGTTATTAGTTACTGTGATACTACCTGCA
GTAACACCGATAGCTTGTCCAAGATCATGTTGTGTTAAATTCCGTTCTCTTCGTAATTGACGTAACCGATCTTTAAATTC
CACAATAATCACCTCATAAGTGGTTTGTTAGGATTATTATAATATTTCCTAAAGGGAAAATCAATCCGAGTTATTTCTAA
GAATAATATAAAATATGTGTAAAAATATATCTTGAATTTTCCCTAAGGGAATGTTAAGGTGATTTACAAAGATATAGAAA
GGAGTTACCACATGAAAGTAATTAAAGACGAGACAAAATTAAAAGCTGCATTCAAAAAATCTGGGTATAAGTATCAAGAG
TTAGCTGACGAATTAGAAATATCCTGCAGCTACTGTTACAAGCTAATTAACAATCATAATTACAAAAAGAAAATATCGTA
TAACTTAGCATCCAGAATGGCGCATGTATTAAATGCAAGTGTAGTTGATTTGTTTGAAGAGCAAGTCGATTTTTTTTAAT
ACCAATATTCCCTGAGGGAACATAGGGGTGAGAGGGCCATGTCAGAAATTTATTACAAAGGGTTTATCATCAAGGAAACT
TATGGCGAAAGAAATATCGAAGAAGTGTTTAAAGAAGCATATGAGTCATTTTATGGGGTTGAAGTTAAGGTTGTTAAAAA
GGAATTAGGGACTAAACGCAATAGTGCAGCCAGCTAATCTTTAAACTTCAGTGAGAACATTCAATGAAGTCGATTATAAA
ATGGACAAGCCTGAAAGGAGAGAAATGAATGAAAAACGGGAAAAGGTTGACTAAACGTGAAAAAATGCATCTTAAATCAT
ATAGCTTAAATCCTGATAATTGGTTGGTTTTCAAGAAAGCGGATGGAGAAATGCATTTAGTACACCGTTATACTAGCACA
ACTCGTGTAATTCCAAGTTTATAAGTTTAGGAGGGAATAAGATGGATCAGTTAACAGTAGCAAGTGAATTACGTCTTTTA
GGGAGAAGAAAAGTAGCTGGATATGAATTTACTGGAATCGAGGGAGGATTTGGTGAAGGTAAAAAAGCAATGTTGGTTTT
GGATATAGCTACAATTCATAACCAACCATTAAAAGAAATCAATCGTCGCATTAATGATAATCGCATTCGATTTAAAGATG
GTGTGGATATTGTTGATTTGAAAAGTGGTGGCTTTAACCCACCACAATTATTAAACCTTGGTTTCTCAAATATGCAGATA
GCGAAATCAAATAACATCTACCTTCTATCAGAACGAGGTTACGCAAAACTATTAAAAATTCTCGAAGATGATAAAGCTTG
GGAATTATACGACATATTAGTTGATGAGTACTTCAACATGAGAGAAAAGAATCAAGTGGCTACAGATCCAATGAGTATTT
TAAAACTTACATTCGAAGCATTAGAAGGCCAGCAGCAAGCAATCGAAGAGATAAAGTCGGATGTACAAGACTTGAGAGAA
AATACACCATTATTTGCAATTGAATGTGATGAAATCTCTACAGCTGTAAAACGTCAAGGAGTCATATTGTTAGGTGGAAA
ACAGTCTAATGCCTATCGAAATCGTGGATTAAGAGGGAAAGTTTATCGTGATATCTACAACCAACTATACCGTGAATTCG
GAGTGAAAAGTCACAAAGCAATTAAACGTTGTCACTTAAATGTAGCAGTAAAAATAGTTGAAGAATATACACTTCCAATT
GTATTGAGCGAAGAGATTTCTTTTGTAAATGCACAAATGGATTTTACAGAAATGTAGTTAGTTAAAACATTCTCAACCGG
TTTTTTTCTAAGTTAAAAATTTAAAGAAAAGGTGGAAAAGACAATGGACCAGTTACGTGTTATTGAGGGAGAAAAAGTGG
ATAAGCCAGATTATGTTGAGATATACCTTGGAGCATTTATGAATGCAGTTAATGAGTTAAAGAAACAGGATGAGGAAACG
AGATCATTAAGCAAGGATACGTATAAAAAAGCAATTTTTTATGGAGTTAGATACATTTCAATATCAAAAAATGACAGTTT
GAATTATGACTACCTAATGAATAGATTTCTTTTAATAAGCTATTTAGAAAATTTGATGAAGGTGTTGACGCCTAGGGATT
TTATGACCATATTCCCAATCGATAAAAATTATGATGGCGCTCGTTATGAAATGAAAGATTACTTTTTTACCATGAATGAA
ATTAAAAAAATCGGAATGGATACACCTATTGGAGAGAAAATCATGGAGTTTTTATGGGATTACCAAAACTTTAAAGATAT
AACACTATTTAACTTAGCCTCTGTAAGCATTTTAAATAAATTGCAGAAAATGCAAGGTAAAAAAACGTTAACTGAAGAGT
TTGCCGAGCGATTAGGTATCGATACTTACACGAAGCATAAAGAAAAGGGTGGAAAAGAATATATTACAAATGACCGTACT
GGTGAGATCCAAGAAGTTAAAAAATCTAGACCAAGATATTTAAAACCAGTTCAATGATTGATGTTATTAAGGCTTATAAA

FIGURE 1A CONTINUED

CAAAGAAAGTAACTTGCGCCAACAAGTTACTAAATAAAAATACTTATAAAAATATACTTATTAGAAATATAACATACACA
CTCGATGTATGGAAAGGGTGTTATTATGGCTCTTTTTAGAAAAGTGCATACAGAATTTTGGACAGACGTAAAAGTATCAG
AAGATATGACGCCAGAAGACAAATTGTTTATGGTGTACCTTTTAACTAATCCCCATACAACTCAATTGGGAGTATATGAA
ATCACACCTAAGATGATAGCTTTTGAAATCGGACTATCAATAGAGTCGGCTAGAGCACTATTGGAACGTTTTGAAAACCA
TCATAAATTAATTAAATATAACAAACTGACAAGAGAAATTGCTATAAAAAATTGGGGCAAATACAACCTGAATAGAGGCG
GGAAACCAATTGAAGATTGTCTTAAAAGAGAAATTGATAAAGTGAAAGATTTATCTCTAATAAAATTCATTTTAGAACAT
ACAGATCATGCAGCTTTAAAAAGAAAAATCAATCTTTATGCGGGTTTTGACGATACGTCCCACGATACGTTAGCGATACG
TGACCAAGAAGAAGAAAAAGAACAAAAAAAAGAACAAAAAGAAGAACAAGAAGAAAAAGAAAAAGAAAAAGAAAAACAAA
AAGAAGAAGAAAAAGAACCAGAAGAAGAAAAAACAAGAATAAAATCCAAAGCGTCTTTAAAATCAGACGCAAAGTCCAAT
CCAATACCGTATAAAGATATATTGGATTACTTGAATGAAAAAGCAAATAAAAATTTCAATCCTAAAGCAGAAGGACATAG
AAAGTTAATTCGCGCTAGATGGAATGAGGGGTATAAACTAGAGGACTTTAAAAAAGTTATCGATAACAAAACTACGCAAT
GGTTTGGTAAGAAAAGTTTTGATGGAAAACCACTAGATCAATTTTTAAGACCGAGCACGTTATTTGCACAAAAACATTTT
GACAACTACTTAAATGAAACGGTCAACATATCCAATCAACAACATGGAGATCAGATTGTTATACCTGGATTTAGGGGGA
AATGCCGTTTTAGAAAGGAGTACTAAATGTGAAAAAGATACAAGATTCTTTTGAAAAACTTACTAAGTTAAAATTTGCAG
ATGAACAATGTGATAAGCACACCTTTAATAAACATGGGAAAGAAGTTATTAAATTAGTTAGGAAAATGATTGATGATGCA
GGAACGGTATATTGTCCCCGCTGCATGGTTGAAGAGCAAAATTCAGTTTTATTTCAACAAGCAAATAATCATTATAAAAA
GATTAATAGAGAACGGAAGAAAAATGTACTCTTTCAACACAGCATCATAGAAAATCAATCCATTACAGAATCAAGATTGT
CTACATACAAGACGGATTGTCAAGAAACGAAAGAAAACAAAGAAAAAGCTATAAAAAATTCTTGAACGCATAAAAAACGGT
GAGTTTTTAAATGTATACATTGCAGGGATTCAAGGAGTAGGAAAAAGCCATTTAGCGTATGCGATGCTGTATGAATTAGT
TAAACACTATTGGGTAATATCAGACGGTGAGAAATTAAATGACGAACATGCTTTTAAAAATATGAAAAGCTGCTTATTTG
TAGAGATTGAAAAGCTAATTCGATTAATACAGCACTCTTTTAGAAATATAGAGTCAAAATATACAATGGATTATTGTATC
AGTTTAATGGTAGATGTGGATTTCCTTGTAATCGATGATTTAGGAGCTGAAAGTGGTTCGATGAATCGAAACGGAGAAGC
AAGCGATTTTGTTCATAAAATACTTTATGGTGTTACAAATGGACGGCAAGGAGCAAATAAAACAACAATTACAACTTCAA
ATCTGTCAAGCGCTCAATTATTTCAAAAATACGATCCGAAACTAGCAAGTAGATTGTTAAACGGTGTATCGAAAGATGAA
ACAATTGTTTTTAAAACAACCACTGACAAACGAATTGTAAATTTAGACATTGGATTCTAATAAAGGGGTGCGGAGAAAT
GAAAGAGGTAAAGGGGAAAAACACCAAATTAATGGAAGAATTTGACGTGTTATTAAGACAACTGCTGATTAAATCTAAAA
CAGATGAAAGGGTAAAAAACTTTTTGGATGATCTGTTTGAAATGCTAAGTGATAATAAGCTGCAGTCTGATATTGATTTC
AAAACAGCATTAAATAAGTTAAGAGAAAAGCACTTTCCTAAGTTTGATAAAGGAGAGAGCAAAAATGACTAAAGAAAAGG
GACAAGCTAAGGAAGTAGTTAATGTTCGTGGAATGTCAGATGATGAGTTTATAGAGAAATACGGAAGGCTTGTACATCAT
TGCGTATGGAAAAGATATGCGAAAAAAAAGGCCAGTATAGAGCGTGATACCGGTTTAGATATTGAGGATTTAACACAATT
CGGAATGATCGGTTTGATAAAGGCGCGAGATAATTTTGACCTTGAATTTGGATGTGCGTTTTCAACGTATGCTGTTCCGA
AAATTATTGGGGAAATAGGAAGGGCAATTCGGGATAACCAAAAAATAAAAGTTCAAAGAACCGTATATGGCGTAAAAGGA
AAGATTTTAAATCAACAGTTAGCAGATAAAGAACCAGAAGAAATAGCAGACATTTTGGATGAGTCAGTATCTTTAGTAAA
GACGGCTTTAGAGTATCAACCAAGCACAGATTCACTCAATAAGGTTGTATATGCATCTGGAGCTAATGAAGAACTGACAT
TAGAAAGAATGATAGAGGATACTAAAACGGAAGACATTGAAGAAACAACCATTAATCGAGCTGTGATAAGAGAATTTAAA
GCTGCATTGCCTCCTAAAGAATATATCGTTTTAGATATGCGTTTACAAAATATGACGCAACAAAACATTGCAAATCAAAT
GGGATACAGTCAGGTACAAATTAGCCGTATATTAGCAAAGATTAATCAAAGAGCTGCTCAATTTGGTAAAGAAGGAGGGC
TTCAAGATTGAGTGTTACAAAAGGTGTTTGTATCGATGTAGATCACTCAGATTTGCTACATGAGAAAGTAGAGTACTTTT
TATTCCCTGCTAAACCAAGTCATTACTATGTAAGCAGATTTAATCGTAAAGGAGCGCATTTTGGTTGTTATCAAGCTGAA
AGGTTTCAAATCACGGAAAAGGAAGTATGGACACCAGAACCTCAACCGAATCTGCCTGAGTTGAATACAAGCTTATTCTA
TAGAGCTCAGTTGATTTGGCGAAAAAAGGGGTATAAAGATAAACCACTTAAAGACTACATCGTACAGCCGAGAGGGAAAC
ATTGCTACTTTTGGCATGATCGGGAGCGAAAGAAATTTTGTGGCTGTTTTCCGCTACATTGGTTTACCGATTTTGTACCA
GTTCAAAGTCATCATATAGAAGAAAAAACTAGAGAAGAGGTTAAGTTATTACAACGGCCAGATGGACAACTTGCATTTTT
TTAACGAAAGAAAGTGAATGGGCGTTTTACCCAGTCATCGATTTAAAAAAAGGAGTGTTCGTAATGGATATTAAAAAGTT
ATTTGCAATGCAGAACATTTTGGATAAAAGAGTTTTAGAGTCAAAAAATCTTTCTAGAGGAGAAGTATTCGAATTTAGAA
TACTAGCGTTTTTAGATGAATTAGGCGAATGCATGAAGGAATGGCGAGTATTTAAGTTTTGGAGCGACGATCGTAAACCG
AGAACTAGCATACCTACAGGGGAAATCATAGTACTAGATGATGGTTATGAAGTAGAAGTTTATAAAAACCCTTTACTTGA
GGAATATGTGGACGGACTACATTTTGCAATTGGACTTTGCATAGATTTGAAAACAGAAATTAACTTTCCTGCTTCTATGC
GTTGCGAGACAGTTACAGAGCAATTTTTCGAATTGTATCATCTAGCAATACGATTAAAAGAAGAACCGACAGCATTTAGG
GCAGATGTTCTTTTATCCCATTATCTTGGTTTAGGGGAATTGTTGTGCTTTTCGTTAGAAGAAATTGGACATGAGTACAT
TGAGAAAAACAAAATCAATCATGAACGTCAAAGTAATGGATACTAATACAATTTGAATTTTGTTAAGAAATGAGGGTGAT
TGAAATAAGTTGGTGGGCAATAGCGATCGGTTTATATCTATTGATTGGAGTTGCATTACTTATATGGATAATCGCAACGG
ATAGTTGGGGTTCGTTATTCTTATATCCTGTTTTTGCGGTAGTCATTGTTTTGGGATGGCTTCCATTAATGATAAGAAGC
ATTGTACAAGAGATATCTAAAGCGATTCATAAGTGGAAAAGAAAGCAGAAAACTGAATAGAAGTATTATTTCAGGGAGGG
AGAATAAATGATTTATGAAGTTACAGATTATTGCAGTCAGTGTGATAGAAAAATAGAGAATTGCGATTGCTGTTGTAATA
AGTGTGATGAGTGGTTGCACGATTGTAAATGTAAAGATAAATAAGCAAAAAAGGGGAATGAAAGATATGAAATGGATGTA
CAACCTTGATAGCAATAATGAGATTTGGACAAGCGATAAATTTGAAATGAAAGAAGAAGCTATTCAAGCAGCTTTAAAAG

FIGURE 1A CONTINUED

ATTGGACAGATAAAATGGTAGCGGATAGAGCGGCAGTCGATAATGAATTCCAAATTGGACAATTCAAACAGTATTCTCCA
TGGATCAATGCAGATGTATTGTTGGATGAATTGTATGAACGAGCAACCGATGAATGTGGAGAGGTTGCGGAATATTGGCT
TTCAGGTGTGCCGATGGACGAAGGGGAAAAGCTTCAAGAACAAATTAATAAGGTAGTTACAGAATGGCTAAAAGGAATAA
ATGAGCATCCTAGCTTTGGTTCAATTGAAAATATTGAAACGATAGATGCTAGCAAAATTGAATATAAAGAAAACTAAACA
AAAGCGTTATTTGATAAAAAATAAGAAAGCCCTAGCTTTCTTATTATATGTAAAAAGTCATATGTTTTTTATCTTCTTTA
TAGTACTCTAACCGGTTTTGCAAAGTGCCAGTGTGGAACTCAAACTTATGGCCATCTGGATCTGTAAAGTAAAGAGATCT
TTGGTCTCTCTCATCTCTTTCTCGGCCAGGTAAAATATTAACATCATTTTGAATTAATACTTCTTTTAAATGGTCTAATG
CTTCATTAGTTACAGTGAAAGCCATATGTGTATAAGATTGCTTAATTTCATTTCTTGGTATATCTTCTTCAACATTTAAA
GCAATCCATAATCCATTTAAATCAAAATACGCTAATTTTCTACCTTTTACTAATAATTTTGCTTGAAGTATTTTTTTGAT
AGAATTCAATAGATTTTTCCAAGTTTGATACAGAAAAACAAATATGGTTAATGCCCTGTAGCATAAAAAACGCCCCCTAT
AATTAAATGATTTTCAATATTTTTATATAAAGATTATAAAAGTTTATGCGCGATTTATAAAGGATTACTACAAAATAGTT
ATTTGAATTAAAAAGAGCGCCGTTGGAGAGTGCGGTGCTCTTAGACCAAGAACTATAACAGGGATTAAGGAAAGAATATT
GTATACCAAATTGATAGTAATGCAAGCCATCCAATTGTCAGCGCTATGTATTTTAAAATTTTCATGATTACTCCTTTTAG
GTATAGAGTGCACCAAGCAAGAGGATGTTATTAATTTTTAAACAAAATGCTTATTTAAAAACTAAAGAGGGCTTTTTAAA
GCGCTCCTTAAGAAAAATAAAAAAGAATACCTCATGATACTGTATGTATGTTTTTTTAGGAATGTGAGGATTTAAAACAA
AATCGTTATTTTATAGATCGGAGTGAAATTCAAATGATTGTTAAAGCGACAATAAAACTTGAATTAGATGATTCGCAGAA
AAATTGGGTTTCTTATGTTAGAGAACAAGGTGGAGAAGAAGCGGTATTTCATTATCTGGAAGAAGAAGTGCAGAAGAAAA
TTGAATTAGCTGATTTTGTGGAGATGAAATACAAAAATAAGTAATTTAAACCAAAACGCTATTTTATAAAATAAAACAGC
TAGCGTGATTAGCTAGCTGTCCTGTTAAGAAAAGAAAACGGTGTTTAGCAAATGTTGCTGTTGTAATTGCGAATTACAAC
CATAGTATGAGCAGAAGTAAAAATGTTATGCAAGAAAGTTAAATAAAAACTGCATTTTATTGAAAAGGGGGAATGGATAT
GTCTCTAGTAGGGAATTTAAAGGAACTCCAAGAAAAAGCCATCGATGAAAAGGTATTGGAATTTGCGGAAGAAATGGAAA
TCGTAATAACTAAAAGTGCCGCAAGCGGATATTCAGGTCATAGATATAAGATTCATAATGAAAATCCAAATCGGCATATG
ATGTGTTCAAAAATATTTATAGAAAAGTTACAAGAATTACTGGACGGTGTGAAGGTTGAATTTAAGGAAGAAGAAAAGAA
AAATATTTTAGGCGGATCTTACTACGAACATTACATCCGTTTTAAGTGGAATGACTAATTTCTTATTAAAAATTTTATTT
TGGAGAAAGGGAGTAGAAAGAATGAAAACTTTTAATGTGACTTTTACAGAGTTGAAAATATATGAAGCAGTCATTGAAGC
GGAGTCAGCGGAAAAGATTATTGATGTGATTAAACACTTAAAAAGAACTGAAGATGATTTAGTAGACAAAGGAGTCATCA
TAAACGAAGTTAGTGAGATAAATGTTAGTAAAGAACAAAAGTTCGAATAAATCAACTTCTCAGATTGTTTATTTTGAGAC
GGAAACAACTTTCTGAATATCATAAGACCTTATTAGCGAAAAAACTCTTATTCGAGCGTACAAGCCTGTTATACACGTTG
CACGGAAATTAGAATGAATTTGTTAAGGAAGGAAGTATAAAAATGAGGGCTTGGAAGAAAAAACATGTTAAAAGAGCATT
TTTGAATCGTCAAAAGGAAATTGATAAAGAACGGACTGCTGCAGCTTGGAGAAATATTTTTGTGAAATCAGGAATCATAA
AATAAAAAAGGAAAAGCAACTCGTTGGGGACAAGTCACTTTTCCAGATGGCAATGTAAATCCATTATAGCAAAACATATG
TACAAGCTGTAGCAATAAACAACGAGATATTTTGACACCTATCGACAATTAGAAATGTGGTTGTTGATCTAGAAATATGA
AAGTAGGTGAATCATCATTTGTTTAACTGGCTGAGAGATTACCAAAAGTTAGAAGAAGACATAGCCTATCTGGAATACAA
CTTAGATAAGACAAAAGCTGAATTAAGACGCTGGGTGAGTGGTGATTTGAGAGAAGTACGTTTAACGGCAGAATCTGAAG
GTGCAAAAGTTGAAAACCGCATTGAAGCGATTGAATACGAATTAGCACATAAGATGAACGATATGTATAAATTAAAAAAG
TTAATTAGTAAGTTTAGAGGTTTAGAAAATCAGATACTCAAATTAAAATATGTGGATGGTATGACGTTAGAAGAAATAGC
AGAGGCAGTAAATTATAGTTCTAGTCATATCAAAAAGAAACATGCTGAACTCGTTAGATTAATTAAGTTCGTGGAGCGAG
AAGGTGTCATTTAGGTTCACTCCTAAAATGAATCGAAACGGTTGAAAAAATGATTTATATTGATAGCATACAATTTTAGC
AGAAGGGCAACTGGTGCACGGTTGCTCTTTTTGATTTTGGAGGTTATTAGACGATGGATGTACAAGAGTTGTCGAGACGA
TTAGAAAATCTAGAACATAAAGTGCTTCAGGTAGAAACGAAGGCAGATGTGCTAAACCGAACAGCTATACAAAAAGGCGA
TAAAATAAAAGTGGTGTATCCGCATTTAGGGATACAAGGCGAGTATTTAGTGGAGAAAATTGATAATGGTGTGTTGGAAT
TGGTAGCAGAAGAAACAATGAAAAAAATACAGGAGTGATTAGGATTGAAGAAGTTATCTAAACAAGAGCTAGCAGCTGTA
ATGACACATTGTATTTCAACGCTTGGTGAGCAGATTGTTAATGAGCATATTAATCCCCAGAAGTTGGCGCAAGCAAGTGC
ACTCCATAACGATCTCTTTGATAATACCACTCCTAAAGAACGTAGGGAAGCGACGATCAGTTTACTAGGGAAAGCGATTG
ATGAGTTTTTAGAGAGTAAGGAGTGAGGATATGGGAAAGGGATATTTTAATAAGGCTGTATGTTTAGTGTGTGGTCATCA
AGATAGAGTGAATCATCCATCTAAAAAAGAGTATCAAGAAGTAACGGTTTGTCCGGAATGCAACGGTGCTTTTGTAGATG
TGTGGAAGCTAGGAAAGTACAAACGTAATACACAGTCTAATGAAGAACCTTTATTAACAATTACATTAACAGATATAGAT
GCTAAACCGATAGTTCATTACAAAGGTGAACAGATAGATAGAAAGTTACGTGTTACGTTTGATTGGGAATCTCAATCGAT
TGATAAAATTAATCGGACATACATTCATATTGAACATGTACCAGCCGATAACAAACGTTTAAATACCGAGACCATTCAGC
ATAATCATCCTATTGCAAATAAGGAACAAGTTTAGATGTTGTCCATATTTGTTAATAGGTAAAAGATAAGTGTTTTATCT
GGAAGTTCAAACGTGAATTAAAGAAATTAAAAAAGGAATATGAAAAGGAGAGTCACTGAATGAACGGGTTTAATAAAATT
GTAAACGATATGCAAAATGAACAAGTAGGAAATGCTATGCTAGATTTTGCTTTGGCCGCTAAAATGATGTTCGCTGCCTT
TACACAGTTTAAAGAAGCTGGATTTAACGAAGAGCAGTCATTCGAATTAACACGTGAGATATTAATTGATTCATTAAGTA
AGAATCAATAGATCAATGAGGTGAAAGGGAATGCAAGTATATTGCTCTGAGTGTGATAAAAGTTATGACATGCAGCCGCA
AGTAACACAACTCCCTAATCGTATTGAGAAGTGTTTCTTTATTTGTCCTCATTGTAATCATGAACATATAGCTGCGTACG
TGAATGATAAGATTCGTAAGTATCAAGCAGATATAGCAAAGTGTCATGAGCGGATTAATAAAAAGAATCTTGCTATCGAA
GATGAAATGAAACGATTAAGGAAGAGGTTTGACAGGAGAAAGTGAGAGGTGAAGCGAGTTTGAAAATGCTATTAACAAAG

FIGURE 1A CONTINUED

CATTGGTGTTTAGATAGAAACTGCGGATTTGAAGAGACTTCTCATAAGGTACGTGATGGTTGGAAATGTCCTGATTGTAA
TGGACCAATGGCGTTTCAACAGGTGAATAAGAAAAAAGAAAGCGCCAAGTGATGGTGCTTTTTATTTTGGAGGAGGATGA
AGGATGGAAGGACAGGAGTTAACATTGGAAAAGAAAGACAGTATTTATCTTAGACCAAGATACCCTCATAAGATTGACGC
AAGTAAAATCAAATCCTTAAAAGATGTAATTAAGATTTTAGGATTGATGGATATTCGTTTGGACGACAAGGCGGTCATTG
GTCTAGAACACTTGATTGAAAAGGAGGAAGAATAAAATGGCCAATAACAAATTAATTATTGAAGTAACTGCGGATACAAC
TGAGGCATTAGAAGGAATTAAAGAAGTAACTGAAGCAGCTAATGAATGTGCAGATGCGCTGGACAAATTAGAAAAGATTA
TGGATAAGTTTACAAATCGAAGTGATACAGTGGAACTCTATTGTGAAGGTAAATTGTTATCGAAGTCTACAGTTAATCAT
ACAGCTGATTCAATTCAATGTCGCATAATCAAGGGAGAAGAGCTTGGAGGAAGTGAACGCTGATGAAGAAACCGCTTAGA
CCATGCTGCGAATTTCATTGTTATAATCTCACACGTGAAAGATATTGTGAGGAACATAGATACAAAGAGAAGGAAACGCA
GCAGGATAAGAATAGATACTACGACCGATTCAAACGGGACAAAGAGAGTACGGCTTTCTATAGGTCAAAGGCATGGGAAA
GGTTAAGAGAGCAGGCACTAATGAGAGACAAAGGGTTGTGCCTACATTGTAAGAACAATAGAAAGATTAAAGTTGCAGAT
ATGGTTGACCATATCATTCCAATCAAAGTTGATCCAAGTTTAAAACTCAAATTAGAAAATTTACAATCACTTTGTAATCC
ATGTCACAACAGAAAAACAGCAGAAGACAAAAAGAAATACGGGTAGGGGCGGGTCGAAAAACATTCAGGGCGGTCTGTCC
GTACcgccgcccc FIGURE 1B: Polypeptide Sequences grouped by open reading frames (ORF) of Phage Gamma (γ)

γ phage: Polypeptides Encoded by Polynucleotide Open Reading Frames

Orf1 (SEQ ID NO:3)
MAGRNKQPLSVIQGKGRSNHITKSEKNRREKQEEALRGHTDKIEAPSYLTAAQKKEFDTLAAELVRLKIFS
NLDVDSLARYVDSKDQYIKMVRLLRKTKPSDDFKLYSQMQRSKNLLFNECRSSASDLGLTITSRLKLVIPE
VDTSQQKQSEAQKRFGDRI

Orf2 (SEQ ID NO:5)
MNWIMERVFAYCEDILNGKINSCKKHRWAIERFIRDYEECQSEDSPFYFDGEIAEDFYWFAKEFKHVEGI
LAGESVELTDFQLFLAANIFGFKKKINGARRFRKVFIQLARKNAKSQFLAIVAAFCTFLGDEKQRAYIAG
WTRDQSSEVYEAVKTGISSSELLEGKWKEAYSTIEIFKNGSVVVPLSKEARKTGDGKNPSLGIVDEYHAH
ETDEIYDVLSSGMVARKEPLMFIITTAGFDLSRPCYREYEYVSDILDPSKNVENDDYFVMICELEKNDDI
KDESNWIKANPIVATYEEGLEGIRSDLKVALDRPEKMRAFLTKNMNIWVDKKDNGYMDMSKWQKCEVDTF
DFSGATLWIGGDLSMTTDLTSVGWVGMDDEGDFIVGQHSFMPEARLKEKMAIDKVRYDLWAEQGYLTLTP
GEMVDYTIVESWIENFSKDKEIQEFDYDKWNALHLAQNLENKGFVCVEIPQRIANLSIPTKNFREKVYEK
KVKHNGDPVLFWALNNAVVKMDDQENIMISKKISKNRIDPAAAVLNAFSRAMYGASVRFDVSEFANKDFL
GKLWN

Orf3 (SEQ ID NO:7)
VKIVDSVKKFFNFEKRQTSQVIELNKDDEKLLEWLGISPSTISVKGKNALKVATVFACIKILSESVSKLPL
KIYQEDEYGIQRGTKHYLNNLLRLRPNPYMSSMNFFGSLEAQKNLYGNSYANIEFDRKGKVQALWPIDASK
VTVYIDDVGLLNSKTKMWYVVNTGGQQRVLKPEEILHFKNGITLDGLVGVPTMEYLKSTLENSASADKFIN
NFYKQGLQVKGLVQYVGDLNEDAKKVFRENFESMSSGLQNSHRIALMPVGYQFQPISLNMSDAQFLENTEL
TIRQIATAFGIKMHQLNDLSKATLNNIEQQQQQFYTDTLQATLTMYEQEMTYKLFLDSELDKGFYSKFNVD
AILRADIKTRYEAYRTGIQGGFLKPNEARSKEDLPPEAGGDRLLVNGNMLPIDMAGQAYLKGGDTNGEVSK
EGNEGN

Orf4 (SEQ ID NO:9)
MEKSAKKEMKEIRALPMTIEVREVNEDEGKRTISGSIKYNNESAEMRDWWGDTFVEEIAEGAFDESLKVRD
VVGLWSHDTSQVLGNTKSKTLRIENDKKELRFELDIPNTTVGNDAWELIKRGDVDGVSFGMKVTKDKWSSE
ERENGKLYKRSILNAELYEISPVAFPAYPTNEVSVRSLDDFKAGEKRVADEFRKRKLQIELELI

Orf5 (SEQ ID NO:11)
MSKELRELLAKLEGKKEEVRSLMGEDKVAEAEQMMEEVRSLQKKIDLQRSLDEAETEERNNGREVETRNVD
GEMEYRDVFMKALRNKPLNAEEREFLEDDLEQRAMSGLTGEDGGLVIPQDIQTQINELARSFDALEQYVTV
EPVRTRSGSRVLEKNSDMIPFAEITEMGEIPETDNPKFSNVQYAVKDRAGILPLSRSLLQDSDQNILKYVT
KWLGKKSKVTRNVLILGVIEKLTKQAIKSLDDIKDVLNVKLDPAISPNAILLTNQDGFNYLDKLKDKDGKY
ILQSDPTQKNKKLFAGTNPVVVVSNRFLKSKGTTAKKAPLIIGDLKEAIVLFKREDMELASTDVGGKAFTR
NTLDLRAIQRDDVQMWDNEAAVYGEIDLSAPVEQPQG

Orf6 (SEQ ID NO:13)
MLVTLEEAKEWIRVDGDDDPTITMLIKAAELYIYKATGKTFTQTNEDAKLLCLFLVADWYGNRLLVGEKAS
EKIRTIVQSMILQLQYASEPQEERK

Orf7 (SEQ ID NO:15)
MNPAKLDKRLTFQVKDENAKGPDGDPIDGYKDAFTVWGSFVYLKGRKYFEAAAANSEVQGETEIRNRDDVS
ADMKIKYKNVIYDIVSVIPTQDHTLLIMWKRGEMNG

FIGURE 1B CONTINUED

Orf8 (SEQ ID NO:17)
MKLTLMINKEKQTFNMPEFIPARLIRQAPELAEIPNNPGPEDMDKMVQFVVKVYDGQFTLDQYWDGVDARK
FLSTTSDVINAIINETVEAAGGSTESGEEENPNA

Orf9 (SEQ ID NO:19)
VINLRPDILQALENDQELVSLLGGKRIYYRKAKKAEEFPRITYFELDNRPDGFADNQEIESEILFQVDVWA
KSSTTAIHQKVNEIMKRIGFSRYAVADLYEEDTQIFHYAMRFAKGVEL

Orf10 (SEQ ID NO:21)
MAGEVVRISSTVGVDNLVYAKVLQDDSSAIKYTDVKKMEGAVKVKLTKKVASEVMWSDNRKSEIAESDGET
EVEIEVRGLSLSTKADIEGFPEVKDGVLDEKREGEKPYLAIGFRFLKANDKYRYVWLLKGKLSQEEEEAET
KKDKPNFQTTKLKGSFIERDFDDRTKFTADEDEPTFTKLVGDNWFNKVYEKPVTQPPAGK

Orf11 (SEQ ID NO:23)
MKLTLMINKEKQTFNMPEFIPARLIRQAPELAEIPNNPGPEDMDKMVQFVVKVYDGQFTLDQYWDGVDARK
FLSTTSDVINAIINETVEAAGGSTESGEEENPNA

Orf12 (SEQ ID NO:25)
MDELYLSLLRQGYKHHHIDNEMDIWHYLRLNRKMHENGNENYEGSNSNEIEVPAENII

Orf13 (SEQ ID NO:27)
MANEINNLVVRLSLDNVNFRQGISNSGRAVRTLQNELKSVSTGMGGFANASQQTQAKMNTLSRLIDAQKEK
VKALRQAYDQNKAKLGENDAATQRYASQVNKAVADLNRFENELKQVNRQAEQKGMDKLNNSLKSLQAEFQS
ITTGMGGFSNATEQTRAKVDVLSRMVDKQKEKIRELQQAYNRAKTEEGEASQSAQRYAEQIHRATAELNRF
ETGLQQSNRELEQQGNRLLNFGNRMETLGNHLQNAGMQIGMVFGGMTYAIGRGLKSAITESMNFEQQMANV
KAVSGSTGAEMKKLSELAVNMGETTKYSSVQAGQGIEELIKAGVSLQDIINGGLAGALNLATAGELELGEA
AEIASTALNAFKADHLSVADAANILSGAANASATDVRELKYGLSASSAVAAGAGMTFKDTATTLAVFAQNG
LKGSDAGTSLKTMLMRLNPSTKEAYNKMRDLGLITYNAQAGFDFLVKNGIQPASRNVGDIEVALEQYVMKT
EGVTKWNDKCDTTFRELATSSAFLSSKFYDQQGHIQSLENISGTLHESMKDLTDQQRSMALETLFGSDAVR
GATILFKEGAKGVNEMWDSMSKVTAADVAATKIDTLKGRLTLLDSAFSTMKKTIGDALAPVVSVFVAGLQK
LVDGFNSLPGPVQKAIAITGGIVLALTAVATAIGVVLAAFGMIASGIGSLSLALASVGGIAGIAAGAVGFL
GSALAVLTGPIGLVAAALIGTGVVAYKAYQKATEDSIASVDRFATNTEGKVSSSTKKVLGEYFKLSDGIRQ
KLTEIRLNHEVITEEQSQKLIGQYDKLANTIIEKTNARQQKEIEGLKKFFADSYVLTAEEENKRIEQLNQH
YEQEKLKTQEKENKIKEILQTAARENRELTTSERISLQALQDEMDRVAVEHMSKNQMEQKVILENMRVQAS
EISARQAAEVVENSAKARDKVIEDAKKTRDEKIAEAIRQRDENKTITADEANAIIAEAKRQYDSTVSTARD
KHKEIVSEAKAQAGEHANQVDWETGQVKSKYQAMKDDVIRKMKEMWSDVTNKYEDMKNSASNKVEEIKNTV
SRKFEEQKKAVTDKMSEIKSSIEDKWNTVEKFFSSINLRSIGKSIIEGLGKGIDDASGGLFSKAAEIASDI
KKTISGALEINSPSKVMIPVGSAVPEGVGVGMDKGKRFVVDAAKNVVGTVKKQMGNMPSVFDFGFQTNQYS
IPQNTFSDFSGYMQPQLSYNNPSMAKTIFPNRPGGEQELNLTVNMTNVLDGKELANGSYTYTTKLQNREQK
RRAEF

Orf14 (Tail fiber) (SEQ ID NO:29)
LGKLSFTFNNIRKDYIQMLVGRKRPSWAPVKRRLVRVPHRAGALLLNTETEERRIDVPLVIKAKKDMADLQ
KLKEDLADWLYTEQPAELIFDDELDRTYLALIDGSVDLDEIVNRGRGVITFVCPMPYKLGKTNTHKFTQEW
STETTSYFTNKGSVEAPALIEMTVKKPSTFLDVWFGEYPNNRDYFRIGYPLTVEETTVQERERVMWDEMAT
PIGWTPVTGQFDDMKGTGSFKSRGGYALYCEDYGKDVGFYGAIAKKNIPGGPLQDFEMEAWMTLKSKNIGE
MGRVEVLLLDEASNVVARINMNDLYATAEITRAHMKIGNSGTPNSFRKLVDTSGYYSNTFNQFRGRLRIAR
RGKVWSVYVAKFIDGTEKDGASLVERWIDETGNPMTERKIAQVMLAICKWDNHQPVNEIQIDDLKFWKVNK
VPSNAQPYIFDTGDKIVIDTEKSLVTINGKNAINIKEIFSNFPVIIRGDNRIDIMPPDVNATISYRERYR

FIGURE 1B CONTINUED

Orf15 (SEQ ID NO:31)
MRTPSGILHVVDFKTDQIVAAIQPEDYWDDKRHWELKNNVDMLDFTAFDGTDHAVTLQQQNLVLKEVRDGR
IVPYVITETEKNSDTRSITTYASGAWIQIAKSGIIKPQRIESKTVNEFMDLALLGMKWKRGITEYAGFHTM
TIDEYIDPLTFLKKIASLFKLEIRYRVEIKGSRIIGWYVDMIQKRGHDTGKEIELGKDLVGVTRIEHTRNI
CSALVGFVKGEGDKVITIESINKGLPYIVDADAFQRWNEHGQHKFGFYTPETEELDMTPKRLLTLMEIELK
KRVNSSISYEVEAQSIGRIFGLEHELINEGDTIKIKDTGFTPELYLEARVIAGDESFTDSTQDKYEFGDYR
EIVNQNEELRKIYNRILSSLGNKQEMIDQLDRLVQEANETASNAKKESEAAKTLAEKVQENIKNNTVEIIE
SKNPPTTGLKPFKTLWRDISIGKPGILKIWTGTAWESVVPDVESVKKETLDQVNKDIATTKTELNQKVQEA
QNQATGQFNEVKESLQGVSRTISNVENKQGEIDKKITKFEQDSSGFKTSIESLTKKDTEISNKLNTVESTV
EGTKKTISEVQQTTNDLKKKTTEIEEKAGKITEKLTSLETREVNVRNYVINSDFSNVTNSWIGITNATLFK
FVDVNISEASAIKKGLQITSNKAFVYQKLPADVFKKKKGIASCYINVSSFTPGTDYPRLYMRFTYDQNGTE
KQYYAILKQQEVTNGWIRISIPFDTTGYTGELKEVRVNIATADTTTIDATFTGIMVTFGDLIESWNLAPED
GVTQGVFQSKTTEIEKSVDGVKTTVTNVQNSQAGFEKRMSNVEQTATGLSSTVSNLNNVVSDQGKKLTEAN
TKLEQQATAIGAKVELKQVEDYVAGFKIPELKQTVDKNKQDLLDELANKLATEQFNQKMTLIDNRFTINEQ
GINAAAKKTEVYTKTQADGQFATDSYVRDMESRLQLTEKGVSISVKENDVIAAINMSKENIKLNAARIDLV
GKVNAEWIKAGLLSGCQIRTSNTDNYVSLDDQFIRLYERGVARAFLGHYRRSDGAVQPTFILGSDEKTNAP
EGTLFMSQAGAGWSGAYASIGISNGIVDGAVQKSVYWELQRNGLSVLNANDYHVFYAGNGNWYFRRGKPGL
YQTSLVVEDNSTDSDLRLPNVTIRNSRAAGYTGVIQLKSPVTQNGWGAVQGNFMTPSLREYKSNIRDISFS
ALEKIRSLKIRQFNYKNAVNELYRMREEKSPNDPPLTTEDIKTYYGLIVDECDEMFVDESGKGIHLYSYAS
IGIKGLQEVDATVQEQEVEIANLKSQIASQEDRIARLEELLLQQLINKKPEQP

Orf16 (SEQ ID NO:33)
MDRIDVLLKAFIAAFGGFCGYFLGGWDATLKILVTMVVIDYLTGMIAAGYNGELKSKVGFKGIAKKVVLFL
LVGAAAQLDSALGSNSAIREATIFFFMGNELLSLLENAGRMGIPLPQALTNAVEILGGKQKQEEKKGDVQ

Orf17 (PlyG lysin) (SEQ ID NO:35)
MEIQKKLVDPSKYGTKCPYTMKPKYITVHNTYNDAPAENEVSYMISNNNEVSFHIAVDDKKAIQGIPLERN
AWACGDGNGSGNRQSISVEICYSKSGGDRYYKAEDNAVDVVRQLMSMYNIPIENVRTHQSWSGKYCPHRML
AEGRWGAFIQKVKNGNVATTSPTKQNIIQSGAFSPYETPDVMGALTSLKMTADFILQSDGLTYFISKPTSD
AQLKAMKEYLDRKGWWYEVK Orf18 (SEQ ID NO:37)
MKMYKKLISICIGSTLLLGLTACDSSKQSESSEKTNVKSQPETKKDLTSQDELNKKIKQDAEEVSFVKAN
GDQYEKGKRLKATGTVDLLLKSSALPSFVISTNENDGKGMYTIQIVQSGVQTNENEITLKNGLKISKGSI
VTIYGAYDEKDKTGMPKISATVIEQ Orf19 (SEQ ID NO:39)
VRLKCKLRVIFAEREIRQKEFSKLIGISQTTMSSLVNNTTLPTFLTAYKIAKELKLHMEEIWIEEENENV Orf20 (SEQ ID NO:41)
MRWQYNHLNTTPYLHPSKELCSMYNGSRSRAETESILNHMKNHEVYDRKEYKGYFSLSQVLEEDLYGEEED
VLNWEILMDCYDVVLTRKGIAFREKEEEEQA Orf21 (SEQ ID NO:43)
MTLAGEAIIIWTATGLSVVAMKAAEKMGKSVPHWLPRVTLYTTLTGSFLYLLRYVLVLFL Orf22 (SEQ ID NO:45)
mwklfipyvirslacMHVFLETGIYTLYKRDIRSDFMLELLSVPFAGLIFAIVGERLKGRESDRKKIQVFF
EVSGIAIRREDKLQYPVFLEQKEDDRSTTYIYRLPVGMPSKIIQKVEDVVSEGLSKPVRIDYDNYKLNIRV
FHRDIPKKWSWSKGLVAEGSWCVPMGQSLEKLIYHDFDKTPHMTLGGLTRMGKTVFLKNVVTSLTLAQPEH
INLYIIDLKGGLEFGPYKNLKQVVSIAEKPAEAFMILTNILKKMEEKMEYMKCRHYTNVVETNIKERYFII
VDEGAELCPDKSMKKEQQRLLGACQQMLSHIARIGGALGFRLIFCTQYPTGDTLPRQVKQNSDAKLGFRLP

FIGURE 1B CONTINUED

TQTASSVVIDEAGLETIKSIPGRAIFKTDRLTEIQVPYISNEMMWEHLKGYEVEKHEDANAYANQPSNGDT
CDD

FIGURE 1B CONTINUED

Orf23 (SEQ ID NO:47)
mrwrnmrmqthmqinrqmailatirklqfatrrhlMSIHEMGGIRNANRILKDLSIYTSKVVYNKEHVYYL
NQSGHKLFGEGKVVHHGKVTHALLRNEAWLNLYCPDDWQVETEIKYIKDNKKKKIIPDVKFRDEDRILHAV
EIDRTQKMIVNDEKLKKYEELTQIYKQKHNGKVPVIHFFTITKYREKKLEELANKYNVFVKVYVIATT Orf24 (SEQ ID NO:49)
MKFTLGNSLDELGITKNKLSTESQVRYNTISDLVNGNANAVRFDSLEAIIDALNAIAAEKGINKIYKIDDV
IQYIKKS Orf25 (SEQ ID NO:51)
MAFKASMIASSESKRTALALPFTKSLIVLYLTWDSVDNLFLVIPNSSKEFPSVNFILFSSAALVILYSFY
NINRN Orf26 (SEQ ID NO:53)
MLSSANYTQYKKLQSFRSVEEMNEAICSFLYKHTHELSESAIKVLKFLARHSCKIPGVSFLKVGTIAEALN
ISDRTVRRVLKVLEDFEVVTRHKTIRTEGKLRGGNGHNVYVLLKKYSVTPNVLPKMSQRQDEENLTESKVS
DTKTDKEAKLSESHPLEELKSELNVKETSARESKEIELEDLDETFTPENVPSQFRDVVAPFFKSADKIYKL
YHRVLIAYKRSKIDKPIEQVINQAIQAFKETVFAEKANKIRSTFEGYFYRIVESKFVMERRKECRGLLFDW
LNE Orf27 (SEQ ID NO:55)
LKYAVYVRVSTDRDEQVSSVENQIDICRYWLEKNGYEWDPNAVYFDDGISGTAWLERHAMQLILEKARRNE
LDTVVFKSIHRLARDLRDALEIKEILIGHGIRLVTIEENYDSLYEGGNDIKFEMFAMFAAQLPKTISVSVS
AAMQAKARRGEFIGKPGLGYDVIDKKLVINEKEAEIVREIFDLSYKGYGFKKIANILNDKGTYTKFGQLWS
HTTVGKILKNQTYKGNLVLNSYKTVKVDGKKKRVYTPKERLTIIEDHYPTIVSKELWNAVNSDRASKKKTK
QDTRNEFRGMMFCKHCGEPITAKYSGRYAKGSKKEWVYMKCSNYIRFNRCVNFDPAHYDDIREAIIYGLKQ
QEKELEIHFNPKMHQKRNDKSTEIKKQIKLLKVKKEKLIDLYVEGLIDKEMFSKRDLNFENEIKEQELALL
KLTDQNKRNKEEKKIKEAFSMLDEEKDMHEVFKTLIKKITLSKDKYIDIEYTFSL Orf28 (SEQ ID NO:57)
VIIVEFKDRLRQLRRERNLTQHDLGQAIGVTAGSITVTNNQL Orf29 (SEQ ID NO:59)
MKVIKDETKLKAAFKKSGYKYQELADELEISCSYCYKLINNHNYKKKISYNLASRMAHVLNASVVDLFEEQ
VDFF Orf30 (SEQ ID NO:61)
MREHRGERAMSEIYYKGFIIKETYGERNIEEVFKEAYESFYGVEVKVVKKELGTKRNSAAS Orf31 (SEQ ID NO:63)
MDQLTVASELRLLGRRKVAGYEFTGIEGGFGEGKKAMLVLDIATIHNQPLKEINRRINDNRIRFKDGVDIV
DLKSGGFNPPQLLNLGFSNMQIAKSNNIYLLSERGYAKLLKILEDDKAWELYDILVDEYFNMREKNQVATD
PMSILKLTFEALEGQQQAIEEIKSDVQDLRENTPLFAIECDEISTAVKRQGVILLGGKQSNAYRNRGLRGK
VYRDIYNQLYREFGVKSHKAIKRCHLNVAVKIVEEYTLPIVLSEEISFVNAQMDFTEM Orf32 (SEQ ID NO:65)
MDQLRVIEGEKVDKPDYVEIYLGAFMNAVNELKKQDEETRSLSKDTYKKAIFYGVRYISISKNDSLNYDYL
MNRFLLISYLENLMKVLTPRDFMTIFPIDKNYDGARYEMKDYFFTMNEIKKIGMDTPIGEKIMEFLWDYQN

FIGURE 1B CONTINUED

FKDITLFNLASVSILNKLQKMQGKKTLTEEFAERLGIDTYTKHKEKGGKEYITNDRTGEIQEVKKSRPRYL
KPVQ

Orf33 (SEQ ID NO:67)

MALFRKVHTEFWTDVKVSEDMTPEDKLFMVYLLTNPHTTQLGVYEITPKMIAFEIGLSIESARALLERFEN
HHKLIKYNKLTREIAIKNWGKYNLNRGGKPIEDCLKREIDKVKDLSLIKFILEHTDHAALKRKINLYAGFD
DTSHDTLAIRDQEEEKEQKKEQKEEQEEKEKEKEKQKEEEKEPEEEKTRIKSKASLKSDAKSNPIPYKDIL
DYLNEKANKNFNPKAEGHRKLIRARWNEGYKLEDFKKVIDNKTTQWFGKKSFDGKPLDQFLRPSTLFAQKH
FDNYLNETVNISNQQHGDQIVIPGFRGEMPF

Orf34 (SEQ ID NO:69)

VKKIQDSFEKLTKLKFADEQCDKHTFNKHGKEVIKLVRKMIDDAGTVYCPRCMVEEQNSVLFQQANNHYKK
INRERKKNVLFQHSIIENQSITESRLSTYKTDCQETKENKEKAIKILERIKNGEFLNVYIAGIQGVGKSHL
AYAMLYELVKHYWVISDGEKLNDEHAFKNMKSCLFVEIEKLIRLIQHSFRNIESKYTMDYCISLMVDVDFL
VIDDLGAESGSMNRNGEASDFVHKILYGVTNGRQGANKTTITTSNLSSAQLFQKYDPKLASRLLNGVSKDE
TIVFKTTTDKRIVNLDIGF

Orf35 (SEQ ID NO:71)

MKEVKGKNTKLMEEFDVLLRQLLIKSKTDERVKNFLDDLFEMLSDNKLQSDIDFKTALNKLREKHFPKFDK
GESKND

Orf36 (SEQ ID NO:73)

MTKEKGQAKEVVNVRGMSDDEFIEKYGRLVHHCVWKRYAKKKASIERDTGLDIEDLTQFGMIGLIKARDNF
DLEFGCAFSTYAVPKIIGEIGRAIRDNQKIKVQRTVYGVKGKILNQQLADKEPEEIADILDESVSLVKTAL
EYQPSTDSLNKVVYASGANEELTLERMIEDTKTEDIEETTINRAVIREFKAALPPKEYIVLDMRLQNMTQQ
NIANQMGYSQVQISRILAKINQRAAQFGKEGGLQD

Orf37 (SEQ ID NO:75)

LSVTKGVCIDVDHSDLLHEKVEYFLFPAKPSHYYVSRFNRKGAHFGCYQAERFQITEKEVWTPEPQPNLPE
LNTSLFYRAQLIWRKKGYKDKPLKDYIVQPRGKHCYFWHDRERKKFCGCFPLHWFTDFVPVQSHHIEEKTR
EEVKLLQRPDGQLAFF

Orf38 (SEQ ID NO:77)

MDIKKLFAMQNILDKRVLESKNLSRGEVFEFRILAFLDELGECMKEWRVFKFWSDDRKPRTSIPTGEIIVL
DDGYEVEVYKNPLLEEYVDGLHFAIGLCIDLKTEINFPASMRCETVTEQFFELYHLAIRLKEEPTAFRADV
LLSHYLGLGELLCFSLEEIGHEYIEKNKINHERQSNGY

Orf39 (SEQ ID NO:79)

MRVIEISWWAIAIGLYLLIGVALLIWIIATDSWGSLFLYPVFAVVIVLGWLPLMIRSIVQEISKAIHKWK
RKQKTE

Orf40 (SEQ ID NO:81)

MSGCTIVNVKINKQKRGMKDMKWMYNLDSNNEIWTSDKFEMKEEAIQAALKDWTDKMVADRAAVDNEFQI
GQFKQYSPWINADVLLDELYERATDECGEVAEYWLSGVPMDEGEKLQEQINKVVTEWLKGINEHPSFGSI
ENIETIDASKIEYKEN

Orf41 (Fosfomycin resistance gene) (SEQ ID NO:83)

MYQTWKNLLNSIKKILQAKLLVKGRKLAYFDLNGLWIALNVEEDIPRNEIKQSYTHMAFTVTNEALDHLK
EVLIQNDVNILPGRERDERDQRSLYFTDPDGHKFEFHTGTLQNRLEYYKEDKKHMTFYI

FIGURE 1B CONTINUED

Orf42 (SEQ ID NO:85)
MIVKATIKLELDDSQKNWVSYVREQGGEEAVFHYLEEEVQKKIELADFVEMKYKNK

Orf43 (SEQ ID NO:87)
MDMSLVGNLKELQEKAIDEKVLEFAEEMEIVITKSAASGYSGHRYKIHNENPNRHMMCSKIFIEKLQELLD
GVKVEFKEEEKKNILGGSYYEHYIRFKWND

Orf44 (SEQ ID NO:89)
MTNFLLKILFWRKGVERMKTFNVTFTELKIYEAVIEAESAEKIIDVIKHLKRTEDDLVDKGVIINEVSEIN
VSKEQKFE

Orf45 (SEQ ID NO:91)
VNHHLFNWLRDYQKLEEDIAYLEYNLDKTKAELRRWVSGDLREVRLTAESEGAKVENRIEAIEYELAHKMN
DMYKLKKLISKFRGLENQILKLKYVDGMTLEEIAEAVNYSSSHIKKKHAELVRLIKFVEREGVI

Orf46 (SEQ ID NO:93)
MDVQELSRRLENLEHKVLQVETKADVLNRTAIQKGDKIKVVYPHLGIQGEYLVEKIDNGVLELVAEETMKK
IQE

Orf47 (SEQ ID NO:95)
LKKLSKQELAAVMTHCISTLGEQIVNEHINPQKLAQASALHNDLFDNTTPKERREATISLLGKAIDEFLES
KE

Orf48 (SEQ ID NO:97)
MGKGYFNKAVCLVCGHQDRVNHPSKKEYQEVTVCPECNGAFVDVWKLGKYKRNTQSNEEPLLTITLTDIDA
KPIVHYKGEQIDRKLRVTFDWESQSIDKINRTYIHIEHVPADNKRLNTETIQHNHPIANKEQV

Orf49 (SEQ ID NO:99)
MNGFNKIVNDMQNEQVGNAMLDFALAAKMMFAAFTQFKEAGFNEEQSFELTREILIDSLSKNQ

Orf50 (SEQ ID NO:101)
MQVYCSECDKSYDMQPQVTQLPNRIEKCFFICPHCNHEHIAAYVNDKIRKYQADIAKCHERINKKNLAIED
EMKRLRKRFDRRK

Orf51 (SEQ ID NO:103)
MEGQELTLEKKDSIYLRPRYPHKIDASKIKSLKDVIKILGLMDIRLDDKAVIGLEHLIEKEEE

Orf52 (SEQ ID NO:105)
LKRRKNKMANNKLIIEVTADTTEALEGIKEVTEAANECADALDKLEKIMDKFTNRSDTVELYCEGKLLSKS
TVNHTADSIQCRIIKGEELGGSER

FIGURE 1B CONTINUED

Orf53 (SEQ ID NO:107)
MKKPLRPCCEFHCYNLTRERYCEEHRYKEKETQQDKNRYYDRFKRDKESTAFYRSKAWERLREQALMRDKG
LCLHCKNNRKIKVADMVDHIIPIKVDPSL
KLKLENLQSLCNPCHNRKTAEDKKKYG

FIGURE 2A: Polynucleotide Sequence of Phage W (SEQ ID NO:2)

CTCAACTTCGCaGaAAAATCCGTTTTTGCATATTTTTTTAAGGGGGTGTAATCATGGCTGGAAGAAATAAACAACCACTC
TCTGTTATACAGGGAAAAGGTAGATCAAATCACATTACAAAAAGTGAGAAAAACAGACGAGAAAAACAAGAAGAAGCATT
GCGGGGGCATACTGATAAAATTGAAGCTCCTTCTTATTTGACTGCAGCACAAAAAAAGGAATTCGATACTTTAGCTGCTG
AATTAGTCAGATTGAAAATTTTCAGTAACTTAGATGTTGACAGTTTAGCAAGGTACGTTGATTCTAAAGACCAATATATA
AAAATGGTTCGTCTGCTAAGAAAAACAAAACCTTCAGATGACTTTAAATTGTATTCTCAAATGCAAAGAAGTAAAAATCT
TTTATTCAATGAATGCCGTTCTTCAGCTAGTGATTTAGGTTTGACCATTACATCCCGCTTAAAATTAGTTATTCCAGAAG
TAGATACTTCACAACAAAAGCAAAGTGAAGCGCAAAAGCGTTTTGGTGATCGTATATGAACTGGATAATGGAACGGGTTT
TTGCATATTGCGAGGACATTTTAAACGGCAAGATAAATAGTTGTAAAAAACATCGTTGGGCCATTGAACGATTTATAAGG
GATTATGAGGAGTGTCAAAGTGAAGACAGTCCTTTTTATTTTGATGGAGAGATAGCGGAGGATTTTTACTGGTTTGCAAA
GGAATTTAAGCACGTTGAAGGGATTTTGGCAGGTGAATCCGTAGAATTAACTGATTTTCAATTGTTTCTAGCGGCTAATA
TTTTCGGATTCAAAAAGAAAATAAATGGAGCAAGGCGATTTAGAAAGGTTTTTATTCAGTTAGCGCGTAAAAATGCTAAA
TCTCAGTTTCTTGCTATTGTAGCAGCTTTTTGTACATTTCTTGGAGACGAAAAACAACGGGCTTATATTGCTGGATGGAC
AAGAGACCAATCATCTGAAGTTTATGAAGCTGTAAAAACAGGGATTAGTTCTAGTGAATTGTTAGAAGGTAAATGGAAAG
AGGCTTATAGTACCATTGAAATATTTAAGAATGGTTCAGTTGTCGTTCCACTTTCAAAAGAAGCTAGAAAAACTGGTGAT
GGTAAAAACCCGTCTCTTGGAATTGTCGATGAATATCATGCACATGAAACTGATGAAATTTATGACGTTTTATCGTCTGG
TATGGTGGCAAGGAAAGAGCCGTTAATGTTTATCATAACAACAGCTGGTTTCGACTTATCAAGACCTTGTTATAGAGAGT
ATGAGTATGTCAGTGACATCTTAGACCCGTCAAAAAATGTAGAAAACGATGATTATTTCGTTATGATCTGTGAATTGGAA
AAGAACGATGATATCAAAGATGAGTCGAATTGGATAAAAGCAAACCCAATCGTAGCTACATATGAAGAAGGTTTGGAAGG
TATACGTTCAGATTTGAAGGTTGCTCTTGATAGACCTGAAAAGATGAGGGCTTTTTTAACCAAAAACATGAATATTTGGG
TCGATAAAAAGGACAACGGATACATGGATATGTCAAAATGGCAAAAATGCGAAGTAGATACCTTTGATTTTTCAGGTGCG
ACTCTTTGGATAGGTGGCGACTTATCAATGACAACAGATTTAACTAGTGTCGGTTGGGTTGGaATGGACGATGAAGGTGA
TTTTATTGTTGGACAACATTCATTTATGCCTGAAGCACGTTTGAAAGAAAAGATGGCCATAGATAAGGTGCGTTATGATT
TATGGGCCGAACAAGGGTATTTAACTTTAACGCCTGGTGAAATGGTTGATTATACAATTGTTGAGTCTTGGATAGAAAAC
TTTTCAAAAGACAAAGAAATTCAAGAGTTTGATTACGATAAATGGAATGCGTTACATCTAGCACAAAATTTAGAGAATAA
AGGGTTCGTTTGTGTAGAAATCCCTCAAAGGATTGCTAATTTATCCATTCCGACTAAAAATTTTCGAGAAAAAGTATACG
AAAAGAAAGTTAAACATAATGGAGATCCAGTCCTTTTTTGGGCGCTTAATAATGCTGTTGTTAAAATGGATGATCAGGAA
AACATTATGATTTCGAAAAAAATAAGTAAAAATCGTATTGATCCAGCAGCAGCGGTCTTAAATGCATTTGCTAGGGCTAT
GTATGGAGCAAGTGTCAGGTTTGATGTATCTGAATTTGCAAATAAAGACTTTCTAGGCAAGTTATGGAACTAGGGAGGGG
GTGAACATGTGAAGATAGTGGATTCTGTTAAAAAGTTCTTTAATTTTGAAAAACGCCAAACGTCGCAGGTAATAGAGTTG
AATAAAGACGATGAAAAATTATTAGAATGGCTAGGGATTTCTCCAAGTACTATTAGCGTTAAAGGAAAAAATGCTTTAAA
AGTTGCTACAGTCTTTGCTTGTATCAAAATACTATCTGAATCCGTATCAAAGTTACCGTTGAAAATTTATCAGGAAGATG
AATATGGAATCCAACGCGGTACAAAGCATTATCTCAACAATTTACTGAGACTAAGGCCTAACCCGTATATGTCCAGTATG
AACTTTTTCGGATCATTAGAAGCTCAAAAAAATTTATATGGCAATAGCTACGCTAACATAGAGTTTGATAGAAAAGGTAA
AGTCCAAGCGTTATGGCCGATAGATGCTTCTAAAGTGACAGTATACATTGATGACGTTGGTTTATTAAATTCCAAAACTA
AAATGTGGTATGTAGTAAATACGGGTGGACAACAAAGAGTGTTAAAGCCAGAAGAGATACTGCACTTTaAAAACGGAATA
ACTCTTGATGGTCTTGTCGGTGTTCCTACAATGGAATATTTAAAGTCTACATTAGAAAATTCAGCTTCAGCTGATAAATT
CATAAATAATTTTTACAAACAAGGGTTACAGGTAAAGGGATTAGTTCAATATGTCGGTGATTTAAATGAAGATGCGAAAA
AGGTTTTCCGAGAAAATTTCGAATCAATGTCTAGCGGTCTTCAAAATAGCCATCGTATTGCATTAATGCCAGTAGGATAT
CAATTTCAACCTATTTCATTAAATATGTCAGATGCTCAATTTCTCGAAAATACCGAACTTACTATTAGGCAAATCGCTAC
TGCATTCGGCATTAAAATGCATCAATTAAATGATTTGAGTAAAGCGACTTTAAATAATATTGAGCAGCAGCAACAACAAT
TCTATACCGATACATTACAAGCGACTTTAACAATGTATGAGCAAGAAATGACGTATAAGCTATTTTTAGACAGTGAGTTG
GATAAGGGGTTTTATTCAAAATTCAATGTAGACGCTATTTTAAGAGCGGATATCAAAACGAGATATGAAGCTTACAGAAC
GGGTATTCAAGGCGGTTTCCTTAAACCTAACGAAGCTAGAAGTAAAGAAGATTTACCACCAGAAGCTGGTGGGGATCGTT
TACTTGTTAATGGAAATATGTTGCCGATTGATATGGCTGGACAGGCATATTTGAAGGGAGGTGATACTAATGGAGAAGTC
AGCAAAGAAGGAAATGAAGGAAATTAGAGCTTTGCCAATGACTATTGAAGTCCGTGAAGTTAATGAGGACGAGGGAAAAC
GAACAATTTCGGGATCGATAAAATATAACAATGAAAGTGCCGAAATGCGTGACTGGTGGGGCGATACTTTCGTAGAAGAG
ATTGCTGAGGGAGCTTTTGATGAAAGTTTAAAAGTTCGTGATGTTGTAgGTTTATGGTCTCACGACACATCTCAAGTATT
AgGAAATACTAAAAGTAAAACTTTACGAATCGAAAATGACaAGAAAGAATTACGATTTGAATTAGATATTCCTAATACAA
CTGTTGGGAATGACGCATGGGAATTAATTAAgCGTGGAGATGTTGATGGAGTTTCTTTTGGGATGAAGGTTACAAAAGAC
AAATGGTCATCGGAAGAACGTGAAAATGGAAAGCTTTATAAGCGTTCGATTTTAAATGCTGAACTATATGAAATATCACC
GGTTGCATTCCCTGCATATCCAACGAATGAAGTAAGTGTACGTTCATTGGATGATTTTAAAGCTGGAGAAAAGCGAGTAG
CTGATGAGTTTAGGAAAAGAAAACTACAAATCGAACTAGAGCTTATATAAGGCTCTTTTTTTATTGATAAATTTAAGGAG
TGATTTGAATGTCAAAAGAATTACGTGAATTATTAGCTAAGTTAGAAGGGAAAAAGGAAGAAGTACGCTCTCTTATGGGA
GAAGATAAAGTGGCAGAAGCAGAACAAATGATGGAAGAAGTGCGATCACTTCAGAAAAAAATTGATTTACAACGCTCATT
AGATGAAGCAGAAACGGAAGAACGAAATAATGGAAGAGAAGTTGAAACACGTAATGTAGATGGTGAAATGGAATACCGCG

FIGURE 2A CONTINUED

ATGTGTTTATGAAAGCATTACGCAATAAACCATTAAATGCTGAAGAACGTGAATTTCTTGAGGATGATTTAGAACAACGT
GCCATGTCAGGATTAACTGGGGAAGATGGAGGACTTGTCATCCCTCAAGATATTCAAACGCAAATCAATGAATTAGCTCG
TTCATTTGATGCGCTTGAGCAATATGTAACTGTTGAACCAGTGCGTACACGTTCAGGATCACGAGTATTAGAGAAAAATT
CAGATATGATTCCGTTTGCTGAAATCACTGAAATGGGTGAAATTCCAGAAACTGATAATCCGAAATTTTCAAATGTACAA
TATGCAGTGAAGGACAGAGCAGGTATTTTACCGTTATCTCGTTCATTACTTCAAGATAGTGATCAAAACATCCTAAAGTA
TGTGACTAAATGGCTAGGTAAGAAATCTAAAGTTACACGTAATGTGTTAATCTTGGGCGTAATTGAAAAGTTAACAAAAC
AAGCAATCAAATCTCTGGATGATATTAAAGATGTATTAAATGTTAAATTAGACCCAGCGATTTCTCCGAATGCGATTTTA
CTTACAAACCAAGATGGATTTAATTATTTAGACAAATTAAAAGATAAAGACGGAAAATATATTTTACAGTCAGATCCAAC
GCAAAAAAACAAAAAACTATTTGCTGGTACTAATCCAGTCGTTGTTGTTTCGAATCGTTTCTTAAAATCAAAGGGAACTA
CAGCTAAAAAAGCGCCACTTATTATTGGTGATTTAAAAGAAGCTATTGTTTTATTTAAACGTGAAGATATGGAACTGGCT
TCTACAGATGTAGGTGGTAAAGCATTCACTCGTAATACATTAGATTTACGCGCAATTCAACGTGATGATGTGCAAATGTG
GGATAATGAAGCAGCAGTTTACGGAGAAATCGATTTAAGCGCTCCTGTTGAACAACCTCAAGGGTAAACTAAGGAGGCAT
TTGAATGCTTGTTACCTTAGAAGAAGCTAAAGAATGGATTCGAGTGGACGGAGACGATGACCCAACTATCACTATGTTAA
TTAAAGCGGCTGAATTATATATTTACAAAGCAACTGGCAAAACATTTACTCAAACAAATGAAGATGCTAAGTTGCTTTGT
TTATTTCTGGTGGCTGATTGGTACGGAAATCGACTACTTGTAGGTGAAAAAGCCAGTGAAAAAATCAGaACCATTGTTCA
GAGTATGATATTACAGCTCCAATATGCTTCAGAGCCTCAGGAGGAAAGAAAATGAATCCTGCAAAATTAGATAAACGGCT
TACATTTCAAGTAAAAGATGAAAATGCAAAAGGGCCTGACGGTGATCCGATAGATGGATATAAAGATGCTTTTACCGTAT
GGGGCTCTTTTGTTTATTTAAAGGGAAGGAAATACTTTGAGGCAGCAGCTGCTAATAGTGAGGTTCAAGGAGAAACAGAA
ATCAGAAATCGGGATGATGTAAGTGCAGATATGAAAATTAAGTACAAAAACGTGATTTATGATATTGTTTCCGTTATTCC
AACTCAAGATCATACTTTATTAATCATGTGGAAACGTGGTGAAATGaATGGCTGATGGTaTAGATTTAGATTTATTAGGA
TTTGATCGTTTAGTTACTGAATTAGACCAAATGGGGTTACGGGGAGAGAAAATTGAAGATAAAGCTCTTGCAGCTGGTGG
TGAACCTATTCGTAAAGCCATTGCAGAACGAGCGCCAAGAAGCCCAAGCCCCAAAAAACGATCTAAAAGTGAACCGTGGC
GTACAGGGCAACATGGTGCAGACCAGATAAAAGTAACAAAAGCTAAACTTGAAGGTGGAATAAAAACAGTAAAAATAGGT
CTTAATAAAGCGGATCGTTCCCCGTGGTTCTATTTAAAGTTCCATGAATGGGGTACATCCAAAATGCCAGCACATCCATT
TATAGAGCCGGGTTTTAATGCTTCAAAAGCGGAAGCTGTACGTGCTATGACAGATATTTTAAAGAACGAAATGAGGTTGG
ATTTGTGATAAATTTAAGACCTGATATTTTACAAGCTCTTGAGAATGATCAAGAGCTTGTTTCATTGTTGGGTGGGAAAC
GAATTTATTACCGTAAAGCAAAGAAGGCAGAAGAGTTTCCGCGAATTACGTATTTTGAATTAGACAATAGGCCAGATGGA
TTTGCAGATAATCAAGAGATTGAAAGTGAAATCTTGTTTCAAGTTGATGTTTGGGCAAAGAGTAGTACAACAGCAATCCA
TCAAAAAGTGAATGAAATCATGAAAAGAATTGGTTTCTCACGCTATGCGGTTGCTGATTTATATGAAGAGGATACACAAA
TATTTCATTATGCGATGAGATTCGCAAAAGGAGTGGAATTATAAATGGCTGGAGAAGTTGTAAGAATTAGTTCAACGGTT
GGTGTAGACAACCTTGTATATGCGAAAGTTTTACAAGATGATTCGTCTGCTATTAAATATACAGATGTAAAGAAAATGGA
AGGTGCTGTAAAGGTTAAATTAACTAAAAAAGTAGCTTCTGAGGTTATGTGGAGCGATAACAGAAAATCAGAGATTGCAG
AATCTGATGGCGAAACTGAAGTGGAGATTGAGGTTCGAGGACTTTCACTTTCTACAAAGGCTGACATTGAAGGGTTTCCA
GAAGTAAAAGATGGCGTTTTAGATGAGAAACGTGAAGGTGAGAAACCATATTTAGCTATTGGTTTCCGATTCTTAAAAGC
TAATGATAAGTATCGATATGTTTGGTTATTAAAAGGGAAACTTTCACAAGAGGAAGAAGAAGCTGAAACGAAAAAAGACA
AACCGAACTTCCAAACAACAAAATTGAAAGGTTCCTTTATTGAACGTGATTTTGATGATAGAACGAAATTTACAGCAGAT
GAAGATGAACCAACGTTCACAAAATTAGTTGGAGATAATTGGTTTAATAAAGTATATGAAAAACCAGTGACACAACCACC
AGCAGGAAAGTAAGAGGGAGCAAAAGCTCTCTCTTTTTTATTAAATTTAGGAGGGAAAAACTATGAAATTAACATTAATG
ATTAATAAAGAAAAACAAACTTTTAATATGCCAGAATTTATTCCAGCCCGCCTTATTCGTCAGGCTCCTGAACTTGCTGA
AATTCCAAACAATCCTGGTCCAGAAGATATGGATAAAATGGTTCAATTCGTAGTGAAAGTTTATGATGGTCAATTTACAT
TAGATCAGTATTGGGATGGTGTTGATGCCCGTAAATTCTTATCGACAACTTCAGATGTAATTAACGCAATTATAAATGAA
ACAGTGGAAGCAGCAGGGGGTAGTACTGAATCAGGAGAAGAAGAAAACCCAAACGCATAGAGGGAGGAGGGCTAACGTTC
AGTGAGTTTATGGACGAGCTCTACCTCTCTTTATTGCGACAAGGGTACAAACACCATCACATTGATAATGAGATGGATAT
TTGGCATTATTTGAgACTTAATCGAAAAATGCATGAAAACGGAAATGAAAATTACGAAGGCTCCAATTCAAATGAAATAG
AAGTGCCAGCGGAAAACATTATTTAACGAGGGAGGTGAGACTATGGCGAATGAAATAAATAATCTAGTCGTTAGACTTTC
CCTTGATAACGTAAATTTCAGACAAGGTATCTCGAATTCAGGTCGTGCAGTCAGGACGTTACAGAATGAATTGAAATCTG
TAAGTACAGGAATGGGCGGTTTTGCTAACGCTAGTCAGCAAACACAAGCGAAAATGAATACACTCAGTAGGCTCATTGAT
GCGCAAAAAGAGAAAGTTAAAGCGTTACGACAAGCCTATGATCAAAATAAGGCTAAATTAGGTGAAAATGATGCAGCAAC
CCAGCGATATGCTTCGCAAGTTAATAAGGCAGTTGCTGATTTAAATAGATTTGAAAATGAATTAAAGCAAGTAAACCGTC
AAGCTGAACAAAAAGGGATGGATAAGTTAAACAACTCTTTAAAATCCCTACAAGCTGAATTTCAGTCTATTACAACAGGT
ATGGCGGTTTTTCTAATGCGACAGAACAAACAAGGGCTAAAGTAGATGTTTTATCCCGTATGGTAGATAAACAAAAAGA
GAAGATTAGGGAACTTCAACAAGCCTATAATCGTGCTAAAACAGAAGAAGGCGAAGCGAGTCAATCAGCACAAAGATACG
CTGAACAAATTCATCGGGCAACAGCTGAACTGAATCGATTTGAAACTGGATTACAGCAGTCAAATCGTGAATTAGAACAG
CAAGGGAATCGCCTATTGAACTTCGGAAATCGCATGGAGACATTAGGTAATCATTTGCAAAATGCCGGAATGCAGATCGG
CATGGTATTTGGTGGTATGACTTACGCAATAGGTCGGGGCTTAAAATCAGCAATCACTGAATCAATGAATTTTGAGCAAC
AGATGGCCAATGTAAAAGCTGTTTCTGGATCTACTGGAGCAGAAATGAAAAAGTTAAGTGAATTGGCTGTTAATATGGGA
GAAACAACAAAATACTCCAGTGTTCAAGCAGGTCAAGGTATCGAGGAATTAATAAAGGCTGGTGTTAGCTTACAAGATAT

FIGURE 2A CONTINUED

TATTAACGGCGGATTGGCAGGTGCCCTTAACTTAGCGACGGCAGGGGAATTAGAGTTAGGTGAAGCAGCCGAAATTGCTT
CCACAGCTCTGAATGCATTTAAAGCAGACCATCTTTCAGTTGCGGATGCAGCCAATATTTTATCTGGTGCAGCCAATGCT
TCCGCAACTGATGTAAGAGAGTTAAAATATGGACTTTCAGCTTCATCAGCAGTAGCAGCGGGAGCCGGAATGACGTTTAA
GGATACAGCTACAACTTTAGCGGTATTTGCACAAAATGGTCTTAAGGGATCAGATGCAGGTACATCTTTAAAAACAATGT
TAATGAGGTTAAATCCTTCAACAAAAGAAGCATATAACAAAATGAGAGATTTAGGACTTATTACTTATAATGCACAGGCA
GGTTTTGATTTCTTAGTTAAAAACGGTATTCAACCAGCTTCCAGAAATGTAGGGGATATAGAAGTAGCTTTAGAACAATA
TGTAATGAAAACAGAAGGTGTAACGAAATGGAATGATAAATGTGATACAACGTTTCGCGAATTAGCAACAAGTTCGGCAT
TTTTATCATCAAAATTCTATGATCAACAGGGGCATATTCAAAGTCTAGAAAATATTTCAGGTACACTTCATGAATCGATG
AAAGATTTAACAGACCAACAACGAAGTATGGCTCTGGAAACATTATTTGGTTCCGATGCTGTACGTGGTGCGACTATCTT
GTTTAAAGAAGGCGCCAAAGGTGTCAATGAAATGTGGGATTCCATGTCAAAGGTTACAGCAGCTGATGTAGCAGCGACCA
AAATTGATACTTTAAAGGGACGACTTACATTACTAGATTCAGCGTTTTCCACAATGAAAAAGACAATTGGTGATGCACTA
GCTCCAGTAGTTAGTGTTTTTGTTGCTGGTTTACAAAAACTTGTTGATGGATTCAACTCTTTACCTGGACCAGTACAAAA
GGCAATAGCAATTACAGGTGGTATCGTCCTTGCTTTAACAGCTGTGGCTACAGCAATAGGTGTGGTTTTAGCAGCGTTTG
GAATGATTGCTTCAGGAATTGGTTCTTTATCTCTTGCTTTAGCATCAGTCGGTGGGATTGCTGGAATTGCGGCTGGAGCA
GTTGGATTCTTAGGAAGCGCGCTTGCGGTTTTAACAGGGCCAATTGGTCTAGTAGCAGCGGCTCTTATCGGAACTGGTGT
TGTTGCATATAAAGCATATCAAAAAGCGACTGAAGACAGTATCGCATCAGTAGACCGCTTTGCTACAAATACAGAAGGGA
AAGTAAGCTCCTCAACAAAGAAGGTTCTTGGCGAGTATTTCAAGCTGTCCGATGGTATTAGACAAAAGTTAACTGAAATT
AGATTGAACCATGAAGTAATAACAGAAGAACAGTCGCAAAAGTTGATTGGTCAATATGACAAATTAGCTAATACAATCAT
TGAAAAAACCAACGCAAGGCAGCAAAAAGAAATTGAAGGGCTTAAAAAGTTCTTTGCTGATTCGTATGTATTAACCGCTG
AAGAAGAGAACAAACGAATCGAACAGTTAAATCAGCACTATGAACAAGAAAAGCTAAAAACGCAAGAAAAAGAAAATAAA
ATTAAAGAGATCTTACAAACAGCGGCTAGAGAAAACAGAGAATTAACGACATCCGAACGTATCTCTTTACAAGCATTGCA
GGATGAAATGGACAGAGTTGCTGTTGAGCATATGTCTAAAAATCAAATGGAGCAGAAGGTTATTCTTGAAAATATGCGTG
TGCAGGCTAGTGAAATTTCAGCTAGACAGGCAGCGGAAGTTGTAGAGAATAGCGCCAAAGCAAGAGATAAAGTTATTGAA
GATGCGAAAAAGACCCGTGATGAAAAAATTGCAGAGGCGATTCGCCAACGTGATGAAAATAAAACAATCACTGCTGATGA
AGCGAACGCAATCATTGCAGAGGCAAAACGTCAATATGATAGTACAGTTTCTACAGCTCGAGATAAACATAAAGAAATTG
TGAGTGAAGCAAAAGCGCAAGCTGGTGAACATGCAAATCAGGTAGATTGGGAAACTGGCCAAGTAAAATCGAAATATCAA
GCTATGAAAGACGATGTTATTCGAAAAATGAAAGAAATGTGGTCGGACGTTACCAACAAATATGAAGATATGAAAAACTC
TGCAAGCAACAAAGTAGAGGAGATAAAAAATACAGTTTCAAGAAAATTTGAAGAGCAGAAAAAAGCTGTTACTGATAAGA
TGTCAGAAATAAAAAGTAGTATTGAAGATAAGTGGAATACAGTTGAAAAGTTTTTCAGTTCTATAAATTTACGTTCCATC
GGTAAATCAATCATAGAAGGGCTTGGCAAGGGAATAGATGACGCTTCAGGAGGTCTGTTTAGTAAGGCTGCGGAAATTGC
AAGTGATATTAAGAAGACTATTTCTGGAGCATTAGAAATTAACAGTCCGTCTAAAGTGATGATTCCAGTCGGTAGCGCAG
TTCCAGAAGGTGTTGGGGTTGGTATGGATAAGGGAAAACGATTTGTTGTGGATGCAGCAAAAAATGTAGTCGGAACTGTT
AAGAAACAAATGGGGAATATGCCATCTGTTTTTGATTTTGGATTCCAAACAAATCAATATAGTATCCCGCAAAATACATT
TAGCGATTTCAGTGGATATATGCAACCGCAATTATCTTATAACAATCCATCTATGGCAAAAACAATATTCCCAAATAGAC
CAGGTGGAGAACAAGAACTGAATTTAACCGTAAACATGACTAATGTTTTAGATGGAAAAGAGCTTGCAAACGGAAGTTAC
ACCTATACTACAAAACTTCAAAATCGTGAACAAAAAAGAAGAGCGGAATTTTAAGGGTGGTGAGCACGTTGGGGAAACTT
AGTTTTACTTTTAATAATATTAGAAAAGATTATATTCAAATGCTAGTTGGAAGAAAACGTCCTTCATGGGCTCCAGTAAA
AAGAAGATTAGTAAGAGTCCCTCATCGCGCAGGGGCTCTTTTACTTAATACAGAAACGGAGGAACGTCGTATTGACGTTC
CTCTTGTTATTAAAGCGAAAAAAGATATGGCAGATTTACAAAAGTTAAAAGAAGATTTAGCGGATTGGTTATATACAGAG
CAACCTGCTGAACTTATTTTTGATGATGAGTTAGACAGGACTTATTTATCATTAATTGATGGTTCTGTCGATTTGGACGA
AATAGTCAATAGAGGTAAAGGTGTTATTACTTTTGTTTGTCCAATGCCGTATAAATTAGGGAAAATCAATACTCACAAAT
TTACGCAAGAGTGGTCTACAGAAACAACTTCTTATTTTACTAATAAAGGAAGTGTAGAAGCTCCAGCATTAATTGAAATG
ACAGTGAAAAAACCAAGTACCTTTTTAGATGTATGGTTTGGAGAGTATCCGCATAATCGTGATTATTTCAGAATAGGCTA
CCCTCTGACTGTGGAAGAAACCACGGTACAAGAACGAGAAAGAGTCATGTGGGATGAAATGGCTACTCCTATAGGATGGA
CACCTGTTACTGGACAATTCGAGGAGATGAAAGGACAGGTAGTTTTAAATCAAGAGGTGGTCATGCACTATATTGTGAA
GATTACGGAAAAGAGACAGGATTCTACGGTGCTATAGCCAAGAAAAACATTCCGGGCGGCCCATTACAAGACTTCGAAAT
GGAGGCATGGGTGACTTTAAAGTCCAAAAACATAAGCGAAATGGGACGTGTTGAAGTTCTTCTTTTAGATGAGACGAGTA
ACGTGATATCCCGCATCAATATGAATGATCTATATGCGACCGCTGAAATTACAAGGGCGCATATGACAATTGGAAATAGC
GGAACACCCAATAGTTTTCGAAAATTAGTTGATACAAGTGGATTTTATTCGACAACATTTAACCAATTCCGAGGCGTTT
ACGTATTGCTAGGCGGGGGAAGGTGTGGTCTGTATATGTGGCTAAATTTATAGATGGTACAGAAAAAGATGGAGCTTCAC
TTGTAGAACGTTGGATTGATGAAACAGGAAATCCGATGACAGAACGTAAAATTGCACAAGTTATGATTGCGATTTGCAAG
TGGGATAATCATCAACCTATTAACGAAATGCAAATTGATGATTTAAAAATTTGGAAGGTAAACAAAGTTCCATCTAATGC
ACAACCATATATCTTTGATACTGGAGATAAAATTGTTATCGATACTGAGAAAAGTCTTGTCACGATCAATGGGGAGAAAG
CAATCAATATAAAAGAAATCTTTAGTAATTTTCCTGTCGTAATACGTGGTGAAAATCGTATCGATATTATGCCGCCTGAT
GTAAACGCAACAATCAGTTATAGGGAGAGATATAGATGAGAACACCAAGCGGGATTTTGCATGTTGTGGATTTTAAAACA
GATCAAATCGTCGCAGCTATCCAACCAGAGGACTATTGGGATGACAAACGGCATTGGGAACTTAAAAATAATGTTGACAT
GTTGGATTTCACCGCATTTGATGGAACAGACCATGCAGTTACCTTACAACAACAGAATCTTGTTTTGAAAGAAGTTCGCG

FIGURE 2A CONTINUED

ATGGAAGAATCGTACCATATGTTATTACAGAGACTGAAAAAAATTCCGATACACGATCTATTACCACATATGCTTCAGGA
GCTTGGATTCAAATTGCGAAATCAGGGATTATAAAACCACAACGGATAGAGAGTAAGACGGTTAATGAGTTTATGGATTT
AGCACTCTTAGGTATGAAGTGGAAACGCGGAATTACTGAATATGCTGGATTTCATACAATGACCATCGATGAATATATTG
ACCCACTCACTTTTTTAAAGAAGATTGCATCTTTATTTAAACTGGAAATTCGATATCGTGTTGAGATTAAAGGTTCAAGA
ATCATCGGTTGGTATGTAGATATGATTCAAAAACGTGGTCATGATACAGGCAAAGAAATAGAATTAGGAAAAGATTTAGT
CGGTGTTACGCGAATTGAACATACACGTAATATTTGCTCTGCTTTAGTTGGATTTGTAAAAGGTGAAGGTGACAAAGTAA
TCACTATTGAAAGCATTAATAAAGGTCTACCCTATATCGTAGATGCAGATGCGTTTCAAAGATGGAATGAACACGGACAA
CATAAATTCGGTTTTTATACACCAGAAACAGAAGAATTAGACATGACTCCAAAACGTTTACTGACGCTTATGGAAATAGA
ATTGAAAAAGCGTGTCAACTCTTCAATTTCTTATGAAGTGGAAGCACAATCTATTGGTCGTATTTTCGGTCTAGAACACG
AATTAATTAACGAAGGCGACACGATTAAAATTAAAGATACAGGGTTTACACCAGAATTATATCTTGAAGCGCGAGTAATA
GCTGGGGATGAATCTTTTACAGATTCAACGCAAGATAAATATGAATTCGGAGATTATCGTGAGATAGTTAATCAAAATGA
GGAATTAAGAAAAATTTATAATAGAATCCTTAGTTCGCTTGGTAATAAACAAGAAATGATAGATCAGCTAGACAGATTAG
TTCAAGAAGCTAACGAAACCGCTAGTAATGCAAAGAAGGAGTCAGAAGCAGCAAAAACACTAGCTGAAAAAGTACAAGAA
AATATTAAAAATAATACCGTTGAAATTATAGAATCTAAGAATCCACCGACAACAGGTCTTAAACCATTTAAAACGCTTTG
GCGTGATATTAGTATCGGAAAGCCTGGTATTTTAAAAATATGGACAGGTACAGCGTGGGAATCGGTTGTACCTGATGTTG
AATCTGTAAAAAAAGAAACATTAGATCAGGTTAATAAAGATATCGCAACCACAAAAACAGAGTTAAATCAAAAGGTTCAA
GAAGCCCAGAACCAAGCGACTGGTCAATTCAATGAAGTGAAAGAGAGTTTACAAGGCGTTAGTCGTACGATTTCTAATGT
TGAGAACAAACAAGGTGAAATCGATAAGAAGATTACTAAGTTTGAACAAGATTCAAGTGGATTTAAAACTTCAATTGAAT
CGTTAACGAAAAAAGATACTGAAATTAGTAATAAATTAAATACAGTTGAGTCTACTGTGGAAGGTACGAAAAAGACGATA
TCTGAGGTACAGCAAACAACTAATGATTTAAAGAAAAAAACTACTGAAATAGAAGAGAAGGCTGGAAAAATCACCGAAAA
ACTTACAAGTTTAGAGACAAGAGAAGTTAATGTTCGAAACTATGTAATTAACTCTGATTTTTCGAATGTTACAAATTCTT
GGATTGGAATTACTAATGCAACTCTTTTTAAATTTGTAGATGTGAATATTTCGGAAGCCTCCGCTATTAAGAAAGGTTTA
CAAATAACAAGTAATAAAGCTTTTGTTTATCAGAAGTTACCCGCAGACGTGTTTAAAAAGAAGAAGGGGATAGCTTCTTG
TTATATAAATGTATCAAGTTTTACACCTGGTACAGATTATCCACGTTTATATATGAGATTCACCTATGACCAAAACGGAA
CAGAAAAACAATATTATGCCATTTTAAAACAACAAGAAGTAACTAATGGATGGATTAGGATTTCTATACCATTTGATACA
ACTGGATATACAGGTGAATTAAAAGAAGTACGTGTAAATATAGCTACCGCTGACACAACTACTATCGATGCAACGTTCAC
TGGAATAATGGTTACATTCGGTGACTTAATTGAATCTTGGAATCTCGCTCCAGAAGATGGAGTAACACAAGGTGTTTTTC
AATCTAAAACAACCGAGATTGAAAAAAGTGTGGATGGTGTAAAAACTACTGTAACAAATGTTCAAAATAGCCAAGCTGGA
TTTGAAAAGCGCATGTCTAATGTGGAACAAACAGCAACTGGATTATCTTCTACCGTAAGTAATTTAAACAATGTAGTATC
CGATCAAGGAAAAAAGCTTACTGAAGCAAATACAAAACTCGAACAGCAAGCAACCGCGATTGGAGCAAAAGTTGAGCTTA
AACAAGTAGAGGATTATGTTGCTGGGTTTAAGATTCCTGAGTTGAAACAAACAGTTGATAAAAATAAACAAGATTTATTA
GATGAATTAGCCAATAAGCTTGCAACTGAACAATTTAACCAGAAGATGACTCTGATTGATAACCGTTTCACTATTAATGA
ACAGGGTATCAATGCCGCAGCAAAAAAGACAGAAGTATATACAAAGACGCAAGCAGATGGACAATTTGCTACAGATTCTT
ATGTAAGAGATATGGAGTCGCGCCTGCAGCTAACAGAAAAGGGTGTTAGCATATCTGTAAAAGAAAATGATGTAATCGCA
GCCATTAACATGAGTAAAGAAAACATTAAGTTAAATGCTGCACGAATAGATTTAGTTGGTAAAGTTAATGCGGAGTGGAT
TAAAGCTGGATTGCTGAGCGGTTGCCAAATTAGAACATCAAATACGGATAACTATGTTAGTTTAGATGATCAATTTATAC
GTCTCTATGAAAGAGGAGTTGCTAGAGCATTTCTGGGGCATTACAGAAGATCAGATGGTGCAGTACAACCGACTTTCATC
TTAGGTTCAGATGAAAAGACTAACGCTCCGGAAGGTACTTTGTTTATGTCTCAAGCAGGTGCAGGATGGTCAGGGGCTTA
TGCGAGCATTGGTATTAGCAATGGCATAGTTGATGGTGCAGTCCAAAAGTCTGTGTATTGGGAGTTGCAAAGAAACGGAC
TAAGTGTTCTAAACGCTAATGATTACCATGTTTTTACGCTGGAAATGGAAATTGGTATTTCAGAAGAGGGAAACCAGGG
TTGTATCAAACTTCGTTAGTCGTTGAAGATAATAGTACAGATTCTGATTTAAGATTACCTAATGTAACTATACGTAATAG
CCGTGCAGCAGGATATACAGGAGTTATTCAATTGAAATCCCCTGTTACTCAAAATGGATGGGGTGCTGTTCAAGGGAATT
TTATGACTCCTTCATTACGGGAGTATAAATCTAATATCCGTGATATTTCTTTTTCCGCCTTAGAAAAAATTAGAAGTCTT
AAAATTAGACAATTTAATTATAAGAATGCTGTAAACGAACTATACCGGATGAGAGAAGAGAAAAGTCCCAATGATCCACC
ATTGACAACAGAAGATATTAAAACATACTACGGTTTAATCGTAGATGAATGTGATGAAATGTTTGTGGATGAAAGTGGGA
AAGGAATTCATTTGTACTCATACGCATCCATTGGAATTAAAGGTTTACAAGAAGTTGATGCAACAGTACAGGAACAGGAG
GTAGAAATAGCAAATCTAAAATCACAAATAGCTAGTCAAGAAGATCGGATAGCACGATTAGAAGAATTATTACTACAACA
ATTAATAAATAAGAAACCAGAGCAGCCATAGGCTGGTCTTTTTATTTTGGCCAAAAAGGAGAGGAAAAGATGGATCGTAT
TGATGTATTACTAAAAGCATTTATAGCTGCGTTTGGTGGCTTCTGTGGGtATTTCTTGGGAGGATGGATGCAACATTGA
AAATCTTAGTGACAATGGTAGTTATTGATTATTTAACTGGCATGATTGCAGCAGGGTATAACGGAGAATTAAAAAGCAAA
GTTGGTTTCAAAGGCATCGCCAAAAAGGTGGTGCTTTTTCTTTTGGTCGGAGCGGCCGCTCAACTAGACTCGGCACTTGG
AAGCAACAGTGCAATCCGTGAAGCAACAATTTTCTTCTTCATGGGTAATGAATTACTTTCACTCTTAGAAAATGCCGGGC
GAATGGGTATTCCACTCCCACAAGCATTAACAAATGCAGTTGAGATTTTAGGTGGTAAACAAAAACAAGAAGAGAAAAAA
GGAGATGTTCAGTAATGGAAATCCAAAAAAAATTAGTTGATCCAAGTAAGTATGGTACAAAGTGTCCGTATACAATGAAG
CCTAAATATATCACTGTTCACAACACATATAATGATGCTCCAGCTGAAAATGAAGTGAGTTACATGATTAGTAACAATAA
TGAGGTGTCGTTTCATATTGCAGTAGATGACAAGAAAGCGATTCAAGGTATTCCGTTGGAACGTAATGCATGGGCTTGCG
GAGACGGCAATGGTTCGGGGAATCGTCAATCCATTTCTGTAGAAATCTGTTATTCAAAATCAGGAGGAGATAGATACTAT

FIGURE 2A CONTINUED

AAAGCTGAGGATAATGCTGTTGATGTTGTACGACAACTTATGTCTATGTACAATATTCCGATTGAAAATGTTCGAACTCA
TCAATCCTGGTCAGGTAAATATTGTCCGCATAGAATGTTAGCTGAGGGAAGGTGGGGAGCATTCATTCAGAAGGTTAAGA
ATGGGAATGTGGCGACTACTTCACCAACAAAACAAAACATCATCCAATCAGGGGCTTTCTCACCGTATGAAACCCCTGAT
GTTATGGGAGCATTAACGTCACTTAAAATGACAGCTGATTTTATCTTACAATCGGATGGATTAACTTATTTTATTTCCAA
ACCGACTTCAGATGCACAACTAAAAGCAATGAAAGAATACCTTGACCGTAAAGGTTGGTGGTATGAAGTTAAATAAAACA
AAAGAATAGTTTTATGAACAAAAATAAGAGCCGTCCTGTTGGGCGGCTTTTTTTTATTGCTCAATTACTGTTGCACTAAT
TTTAGGCATTCCTGTTTTATCTTTTTCGTCGTAGGCGCCATAGATTGTTACTATTGATCCTTTAGATATTTTTAATCCGT
TTTTAAGTGTTATTTCATTTTCGTTCGTTTGCACTCCACTTTGGACAATTTGAATAGTGTACATGCCTTTGCCGTCATTT
TCGTTTGTGCTTATGACAAATGAAGGTAATGCTGAAGACTTAAGTAATAAATCTACCGTTCCGGTAGCTTTAAGCCTTTT
TCCTTTTTCGTATTGATCTCCATTTGCCTTAACAAAACTAACTTCTTCAGCATCTTGCTTTATCTTCTTATTTAACTCAT
CCTGAGATGTTAAATCTTTTTTAGTTTCTGGTTGAGATTTGACGTTCGTTTTTTCACTTGATTCACTTTGTTTAGAAGAA
TCACAAGCTGTTAGACCTAACAATAAGGTACTTCCAATGCAAATACTTATAAGTTTTTTATACATTTTCATTCTCCTCCT
CTATCCAAATTTCTTCCATGTGCAATTTTAATTCCTTTGCAATTTTATAGGCTGTAAGAAAGGTAGGTAGCGTCGTGTTA
TTAACGAGTGAACTCATTGTAGTTTGACTAATTCCAATAAGTTTTGAAAACTCCTTTTGACGTATTTCTCTTTCAGCAAA
AATAACACGAAGTTTACATTTTAATCGCACAATATCACCTCTTTAATTATATACAATTCGCATATGGAAATGTGTCCTCC
TTTAATTTAATCAACGAACATTTAGAAAAGTTTAAATGGACAGGCAATATAACTCTTTCTAAGTCATATACCTATATCAA
GACCACGAGGAATACCAAGTGGAACTAAGGACATCAAGAGGGGAGAGGATTACATGCGTTGGCAGTATAATCACTTGAAT
ACAACTCCATATCTTCATCCATCCAAAGAATTATGTTCAATGTACAATGGATCGAGATCAAGAGCAGAGACGGAATCAAT
TTTAAATCACATGAAAAATCATGAAGTTTATGATCGAAAAGAATATAAAGGATATTTCAGTTTGTCACAGGTATTAGAAG
AAGATCTATATGGAGAGGAAGAAGATGTTTTAAACTGGGAAATTCTAATGGATTGTTATGATGTAGTTCTTACAAGAAAA
GGTATTGCATTTCGTGAAAAAGAAGAGGAGGAACAAGCATGACTCTTGCTGGAGAAGCGATTATTATTTGGACGGCAACA
GGGTTGTCAGTAGTTGCAATGAAGGCAGCAGAAAAAATGGGGAAAAGTGTTCCACATTGGCTTCCACGTGTCACTTTGTA
CACAACACTTACAGGCTCGTTTCTATACCTTCTACGTTATGTTCTCGTTTTATTTCTATGAAGGAATACGATGTGGAAAC
TTTTCATTCCTTATGTCATAAGGAGTTTAGCTTGTATGCACGTATTCCTTGAAACAGGGATATATACCCTCTATAAGAGG
GATATAAGGAGTGATTTTATGCTGGAGTTGTTATCAGTACCATTCGCAGGTTTAATTTTCGCCATAGTTGGCGAAAGGCT
CAAAGGAAGAGAGAGTGATCGAAAGAAAATACAAGTTTTTTTTGAAGTAAGCGGAATTGCGATACGTAGAGAGGACAAAT
TACAGTATCCAGTTTTTCTTGAACAAAAAGAGGATGACCGAAGTACAACTTATATATATCGGTTGCCTGTAGGAATGCCG
AGTAAAATTATTCAGAAGGTCGAGGATGTTGTCTCTGAAGGGCTAAGTAAACCTGTCCGAATTGATTATGATAATTACAA
GCTAAATATTCGTGTGTTTCATAGGGATATACCGAAAAAATGGTCATGGTCTAAAGGTTTGGTTGCAGAAGGAAGCTGGT
GTGTTCCAATGGGCCAAAGTTTAGAAAAACTTATCTATCATGATTTTGATAAAACACCACATATGACACTAGGTGGTCTG
ACACGGATGGGAAAAACGGTATTTTTAAAAAATGTAGTTACTTCTCTTACTTTAGCACAACCAGAACATATTAATTTATA
CATTATTGATTTAAAAGGGGGCTTGGAGTTTGGCCGTATAAGAATTTAAAACAGGTAGTTTCTATTGCTGAAAAGCCCG
CAGAAGCTTTTATGATATTAACTAATATCCTCAAGAAGATGGAAGAGAAAATGGAATATATGAAATGTAGACATTATACG
AATGTTGTAGAAACAAATATCAAAGAGCGTTACTTCATAATAGTAGACGAAGGAGCCGAACTTTGCCCAGATAAAAGTAT
GAAAAAAGAACAGCAAAGGTTATTAGGAGCGTGTCAACAAATGCTCTCTCATATAGCGCGCATAGGTGGTGCTTTAGGTT
TTAGATTGATTTTTTGTACACAGTACCCGACAGGGGATACATTACCGCGCCAAGTAAAACAAAATAGTGATGCGAAATTA
GGCTTTAGATTACCGACTCAAACAGCATCAAGTGTTGTTATAGATGAAGCGGGATTAGAAACGATAAAAAGCATTCCCGG
ACGCGCGATTTTCAAAACCGATAGACTTACAGAAATACAAGTGCCTTACATTAGTAATGAGATGATGTGGGAGCATTTAA
AAGGATATGAGGTGGAGAAACATGAGGATGCAAACGCATATGCAAATCAACCGTCAAATGGCGATACTTGCGACGATTAG
AAAGCTACAGTTTGCAACGAGAAGGCATTTAATGAGTATTCATGAAATGGGTGGAATAAGAAATGCAAATCGAATTCTGA
AAGATTTATCTATTTATACAAGTAAGGTAGTTTACAATAAAGAGCATGTATATTATTTAAACCAATCAGGACATAAGTTG
TTTGGCGAAGGGAAAGTTGTACATCATGGTAAAGTTACACACGCTCTTTTACGTAATGAAGCTTGGTTAAATTTATATTG
TCCTGATGATTGGCAAGTAGAAACTGAAATTAAATATATAAAGGATAATAAAAAGAAAAAAATAATTCCAGATGTGAAAT
TTCGTGATGAGGACAGAATACTTCATGCTGTAGAAATAGATCGTACTCAGAAAATGATAGTGAACGATGAAAAATTAAAA
AAATATGAGGAGTTAACGCAGATTTATAAACAGAAGCATAACGGGAAAGTGCCAGTTATTCATTTCTTTACAATCACAAA
ATATAGAGAAAAGAAATTAGAAGAACTGGCAAATAAATATAATGTGTTTGTAAAAGTATATGTAATCGCTACTACTTAAT
GATGAAAAAAAGAGCTGATCATTTTCGAATGATTAGCTCTTTTTTATGTATTGTATTACGTCGTCTATTTTGTAAATTTT
ATTAATTCCTTTTTCTGCAGCAATGGCATTTAAAGCATCAATGATAGCTTCAAGCGAATCAAAACGAACAGCATTAGCAT
TACCATTCACTAAATCACTAATCGTGTTGTATCTTACTTGGGATTCTGTAGATAATTTATTTTTAGTGATCCCCAATTCA
TCTAAAGAATTTCCGAGTGTGAATTTCATTTTATTCTCCTCCGCAGCACTGGTTATCTTGTACTCATTTTACAACATCAA
TCGAAATTAGTAAAACTTTTTTCGTTCAACTATTGACGTTGAATAATTAGAGAGTTATAATTCAACTTAAATAGTTGAAC
TAATTTAGTTGAACTTAAAAGGAGGAACAATTATGAATCGAGTAAATGATTATTTTGGTTTAGAAAGTAAATCAGATTGC
ATTTGGTTTTATGGTTTCTTCAGTATATCTACGATTTTATTTTTAATCGATATGATTATTGCTCTTATATAAGGAGGGGA
GAAAATGCTTAGCTCAGCAAACTATACGCAATATAAAAAATTACAATCATTCCGATCAGTAGAAGAGATGAATGAAGCGA
TTTGTTCTTTTTTATACAAACATACACATGAATTATCCGAATCAGCAATAAAAGTATTGAAATTTCTAGCAAGGCACTCT
TGTAAAATCCCAGGTGTCTCTTTCTTGAAGGTAGGGACAATTGCGGAGGCATTAAATATAAGTGATCGAACTGTTCGCAG
GGTACTAAAAGTATTAGAGGATTTTGAAGTAGTAACTAGACATAAAACAATTCGAACGGAAGGAAAATTACGTGGAGGGA

FIGURE 2A CONTINUED

ACGGACATAACGTCTATGTCCTTCTAAAAAAATATAGTGTCACACCGAATGTCCTACCGAAAATGTCACAGCGACAAGAT
GAAGAAAACCTTACAGAATCAAAGGTTTCAGATACAAAAACGGACAAGGAAGCTAAACTTTCTGAATCACACCCTCTAGA
AGAATTGAAAAGCGAATTAAACGTAAAAGAAACGTCAGCAAGGGAATCTAAAGAAATCGAATTAGAGGATCTAGATGAAA
CTTTTACACCAGAAAATGTACCAAGCCAATTCAGAGATGTGGTAGCTCCATTCTTCAAATCAGCAGATAAAATTTATAAA
TTGTATCATCGAGTATTAATAGCTTATAAACGTTCAAAAATAGACAAGCCTATTGAACAAGTGATAAATCAAGCCATTCA
AGCATTCAAAGAAACTGTCTTCGCAGAAAAAGCAAATAAAATTAGAAGTACTTTTGAAGGTTATTTTTATAGAATTGTTG
AAAGTAAATTTGTAATGGAGAGAAGGAAAGAATGTCGAGGATTATTGTTCGATTGGTTAAATGAATAATATAAAATTGCC
CACAGGGAAAAATATATATATAATTTAATTATCATATTCTTAGTAAATAAGTGGGTGAAAATTTTGAAATACGCTGTTTA
TGTACGAGTTTCAACGGATAGAGATGAGCAAGTTTCATCTGTTGAAAATCAGATTGATATTTGTCGATATTGGTTAGAAA
AAAACGGATATGAGTGGGATCCAAATGCAGTATATTTTGACGATGGTATTTCTGGTACAGCTTGGTTAGAACGTCATGCG
ATGCAACTAATATTAGAAAAAGCAAGACGAAATGAATTGGATACAGTCGTATTTAAATCTATACACCGTTTAGCAAGGGA
TCTAAGGGATGCCTTAGAAATTAAAGAAATTCTAATAGGTCATGGGATACGCTTGGTTACAATTGAAGAAAATTACGATA
GTTTATATGAAGGTGGCAATGATATTAAATTCGAAATGTTTGCCATGTTTGCTGCACAATTACCTAAAACTATATCTGTA
TCTGTTTCTGCTGCAATGCAAGCTAAAGCAAGAAGAGGCGAGTTTATTGGAAAACCGGGATTAGGATACGATGTAATTGA
CAAGAAACTTGTTATCAATGAAAAGGAAGCTGAAATTGTAAGGGAAATTTTTGATTTATCCTATAAAGGCTATGGATTTA
AGAAAATAGCGAATATCCTAAACGATAAAGGCACATATACGAAGTTTGGCCAGTTATGGTCGCATACAACTGTAGGGAAG
ATTTTAAAGAACCAGACGTATAAAGGGAATTTGGTCTTAAATAGTTATAAAACAGTAAAAGTAGATGGAAAGAAGAAAAG
AGTTTACACTCCGAAAGAGAGATTAACAATTATAGAAGACCATTATCCAACAATTGTATCAAAAGAATTATGGAATGCGG
TAAATAGCGATAGGGCAAGTAAAAAGAAAACAAAACAAGATACAAGAAATGAATTTAGAGGAATGATGTTTTGTAAACAT
TGTGGTGAGCCAATTACAGCTAAGTATTCAGGTAGATACGCAAAAGGAAGTAAAAAAGAGTGGGTATATATGAAATGCAG
TAATTATATTAGATTCAATCGCTGCGTTAACTTTGACCCGGCTCATTATGATGATATAAGAGAGGCGATTATCTATGGAT
TGAAGCAGCAAGAAAAaGAACTAGAGATACATTTCAATCCAAAAATGCATCAAAAAAGAAATGATAAATCTACAGAAATT
AAGAAGCAAATTAAGTTGTTAAAAGTGAAAAAAGAGAAGTTGATTGATTTATACGTAGAAGGATTAATCGATAAAGAAAT
GTTTTCGAAGCGGGATCTTAATTTCGAGAATGAAATTAAAGAGCAAGAGTTGGCATTACTTAAATTAACAGATCAGAATA
AGAGAAATAAAGAAGAGAAAAAAATTAAAGAAGCTTTTTCAATGCTCGATGAAGAAAAAGATATGCATGAGGTTTTTAAA
ACTTTAATAAAGAAAATCACACTTAGTAAGGATAAGTATATCGACATCGAATATACATTTTCTTTATAGTTTTAAAGTTG
GTTATTAGTTACTGTGATATTTATCACGGTACCCAATAACCAATGAATATTTGATAAATTGAACATTTTTAGTAAACAAT
ATTTTCTCAATATGAGAATTGCGCTTTACAGAACACATGCTCTCATTAATGTGATAAAATATTCTGTAAATATAATGGAA
AAAGTGTTGCTTATTGAAATGAAGGGGGTAAGTTACTTGAAATTTCATGAAAAAATTATGGGGATGATTGAGGATAGGGA
TGACTTAACAGCTACTAGTGTAGCGTGTAAAATTGGCGTTTCAAAACAATACATGTCAAAATTCAAAAGACAAGGAACTA
TTGGATTCTCTCAATTATTGAAGCTAGCACCTATTTTGAGCGTTGAAGGAAAAAAAGCAAAGCAAACTATGTCCGATTGG
TGTTTAGAATTAGATACCACAGAGTCTATAAAACAAAGTTTTGAATATGCGTGTCTAACTCGTAATACAATTTTATTGAA
ACAATTAATACAAAAGCATAGCAAAGAAACTGGAACAATCCGAGAATATGTTGAAGTGTATACAATCTTGTTTAAATATA
TTAAGAATATAATTAAAGGCTCGGAAATAACAAAGGAATTAAAGAAGATTGGTGCTATTAAAGATAAGGTTTTAGAGATA
TTAACAAAGATTATGGAATGCTATGAATATTATCATCTAAAAAAATTCAATTTAATGTTGGAAACTGCAGAAACGATTGA
TTCACTGGTTAGAGAAATTGAAGGAGAACGAAAATCCTTCATTAAGGAATGTTACAATTATCGTATTGCTGAATTGTTTG
CGCCGATTTTCCTACAAAAGAATAATGTAGATTTGGCTAGGAAGTATGCCCACTTCTTAATTCATGCTAATGTTTGTACA
AAAACAGTCTCTGACGCATATTACATATTAGGTATGTCAAATGTATTAGAAAGTAAAGAACAATGTTTGTTCAATTTAAA
AAAGAGTTACTTGTTAAGTAAGGAAATTAGGGATGCTGATATTGAACAAGAGGCGAGATACAATCTAGATGTTGCTAAAA
TCTATTTTGGGGTAAAACTAGACGAAGACGCTGACAGTAGGTTATTACTGTACCAAAAAAACCCAACATGTGAATTGTCA
ATTATAGCTCTCCAAGATATAATAAGAGACAGAGGAGACAAGGACTTTTTAAATTATTTCATAGCATGTTCTTCCGATGA
AATCGAATGTTTATACGATTTGTTTTATCAATACTTCTACCAAGCTAACTATCTATTTTCAGCGATAGTAGCAAAAGAAT
TGTGTAATAGAGGGGATAAATCTTTGTTGACTCAATCGATGGTTAATTTAGGGAATGAAAAACAAAAAGGGGTTGTTGAT
ATTGAAGAAATTAGTATTAGCAGTTTGTACATTATTAACGGTTCTAACAGTGGGATTGTCGTATAATGAAAATGTACAGA
TAGATAAAAAAATGCAAATGGTTGAAATTAAACCTGGTGGGTAAGGATATTTAAAGAGCGGATTAAAgACCGCTCTTTT
TTTGTTGGTAAACTAAAATGAAAAAAATAAAAGTAATTTACTTTCTGAATTTTCCCTAGAGGAAAGGTTATAATTGGATT
ATAGCAGTTGAGGGGGAATAGAAATGAAAAAAGAAAGTATTTTAAGGTCATTTTTAAAATGTGTAATTTCATGTTCAAAT
AGTGAATTTGAGTTCAATCAACTTATTGAAGTAGCGTTTAATGTTGAACAAAAAATAAAAAAATAGCGATGAAGTAACAC
TACATCACTATTTTGAAGTACTTTTTAATTTTTCTAGACTTTCCATCATTGTTAGCATGTTTTGTAAGACAATTTCTTGA
TGTTCCTCAGGTAGTTGTTCTAAACGGTTTTTTATGTGCAAGTACTTTTGATTCATATCCGCATCTAATTCACGAGAGTC
AGATCGTCGTAAGAGATAATCAACAGGTACACCAAGAAAATCAGCTGCACGTTCAACGGTTTCTCTAGATGCAGGTTTAA
ATCCAGTTTCAAACTTAGAAACGCTACCTGCAGTAACACCGATAGCTTGTCCAAGATCATGTTGTGTTAAATTCCGTTCT
CTTCGTAATTGACGTAACCGATCTTTAAATTCCACAATAATCACCTCATAAGTGGTTTGTTAGGATTATTATAATATTTC
CTAAAGGGAAAATCAATCCGAGTTATTTCTAAGAATAATATAAAATATGTGTAAAAATATATCTTGAATTTTCCCTAAGG
GAATGTTAAGGTGATTTACAAAGATATAGAAAGGAGTTACCACATGAAAGTAATTAAAGACGAGACAAAATTAAAAGCTG
CATTCAAAAAATCTGGGTATAAGTATCAAGAGTTAGCTGACGAATTAGAAATATCCTGCAGCTACTGTTACAAGCTAATT
AACAATCATAATTACAAAAAGAAAATATCGTATAACTTAGCATCCAGAATGGCGCATGTATTAAATGCAAGTGTAGTTGA

FIGURE 2ACONTINUED

TTTGTTTGAAGAGCAAGTCGATTTTTTTaATACCAATATTCCCTGAGGGAACATAGGGGTGAGAGGGCCATGTCAGAAA
TTTATTACAAAGGGTTTATCATCAAGGAAACTTATGGCGAAAGAAATATCGAAGAAGTGTTTAAAGAAGCATATGAGTCA
TTTTATGGGGTTGAAGTTAAGGTtGTTAAAAAGGAATTAGGGACTAAACGCAATAGTGCAGCCAGCTAATCTTTAAACTT
CAGTGAGAACATTCAATGAAGTCGATTATAAAATGGACAAGCCTGAAAGGAGAGAAATGAATGAAAAACGGGAAAAGGTT
GACTAAACGTGAAAAAATGCATCTTAAATCATATAGCTTAAATCCTGATAATTGGTTGGTTTTCAAGAAAGCGGATGGAG
AAATGCATTTAGTACACCGTTATACTAGCACAACTCGTGTAATTCCAAGTTTATAAGTTTAGGAGGGAATAAGATGGATC
AGTTAACAGTAGCAAGTGAATTACGTCTTTTAGGGAGAAGAAAAGTAGCTGGATATGAATTTACTGGAATCGAGGGAGGA
TTTGGTGAAGGTAAAAAAGCAATGTTGGTTTTGGATATAGCTACAATTCATAACCAACCATTAAAAGAAATCAATCGTCG
CATTAATGATAATCGCATTCGATTTAAAGATGGTGTGGATATTGTTGATTTGAAAAGTGGTGGCTTTAACCCACCACAAT
TATTAAACCTTGGTTTCTCAAATATGCAGATAGCGAAATCAAaTAACATCTACCTTCTATCAGAACGAGGTTACGCAAAA
CTATTAAAAATTCTCGAAGATGATAAAGCTTGGGAATTATACGACATATTAGTTGATGAGTACTTCAACATGAGAGAAAA
GAATCAAGTGGCTACAGATCCAATGAGTATTTTAAAACTTACATTCGAAGCATTAGAAGGCCAGCAGCAAGCAATCGAAG
AGATAAAGTCGGATGTACAAGACTTGAGAGAAAATACACCATTATTTGCAATTGAATGTGATGAAATCTCTACAGCTGTA
AAACGTCAAGGAGTCATATTGTTAGGTGGAAAACAGTCTAATGCCTATCGAAATCGTGGATTAAGAGGGAAAGTTTATCG
TGATATCTACAACCAACTATACCGTGAATTCGGAGTGAAAAGTCACAAAGCAATTAAACGTTGTCACTTAAATGTAGCAG
TAAAAATAGTTGAAGAATATACACTTCCAATTGTATTGAGCGAAGAGATTTCTTTTGTAAATGCACAAATGGATTTTACA
GAAATGTAGTTAGTTAAAACATTCTCAACCGGTTTTTTTCTAAGTTAAAAATTTAAAGAAAAGGTGGAAAAGACAATGGa
CCAGTTACGTGTTATTGAGGGAGAAAAAGTGGATAAGCCAGATTATGTTGAGATaTACCTTGGAGCATTTATGAATGCAG
TTAATGAGTTAAAGAAACAGGATGAGGAAACGAGATCATTAAGCAAGGATACGTATAAAAAAGCAATTTTTTATGGAGTT
AGATACATTTCAATATCAAAAAATGACAGTTTGAATTATGACTACCTAATGAATAGATTTCTTTTAATAAGCTATTTAGA
AAATTTGATGAAGGTGTTGACGCCTAGGGATTTTATGACCATATTCCCAATCGATAAAAATTATGATGGCGCTCGTTATG
AAATGAAAGATTACTTTTTTACCATGAATGAAATTAAAAAAATCGGAATGGATACACCTATTGGAGAGAAAATCATGGAG
TTTTTATGGGATTACCAAAACTTTAAAGATATAACACTATTTAACTTAGCCTCTGTAAGCATTTTAAATAAATTGCAGAA
AATGCAAGGTAAAAAAACGTTAACTGAAGAGTTTGCCGAGCGATTAGGTATCGATACTTACACGAAGCATAAAGAAAAGG
GTGGAAAAGAAtATATTACAAATGACCGTACTGGTGAGATCCAAGAAGtTAAAAAATCTAGACCAAGATATTTAAAACCA
GTTCAATGATTGATGTTATTAAGGCTTATAAACAAAGAAAGTAACTTGCGCCAACAAGTTACTAAATAAAAATACTTATA
AAAATATACTTATTAGAAATATAACATACACACTCGATGTATGGAAAGGGTGTTATTATGGCTCTTTTTAGAAAAGTGCA
TACAGAATTTTGGACAGACGTAAAAGTATCAGAAGATATGACGCCAGAAGACAAATTGTTTATGGTGTACCTTTTAACTA
ATCCCCATACAACTCAATTGGGAGTATATGAAATCACACCTAAGATGATAGCTTTTGAAATCGGACTATCAATAGAGTCG
GCTAGAGCACTATTGGAACGTTTTGAAAACCATCATAAATTAATTAAATATAACAAACTGACAAGAGAAATTGCTATAAA
AAATTGGGGCAAATACAACCTGAATAGAGGCGGGAAACCAATTGAAGATTGTCTTAAAAGAGAAATTGATAAAGTGAAAG
ATTTATCTCTAATAAAATTCATTTTAGAACATACAGATCATGCAGCTTTAAAAAGAAAAATCAATCTTTATGCGGGTTTT
GACGATACGTCCCACGATACGTTAGCGATACGTGACCAAGAAGAAGAAAAAGAACAAAAAAAAGAACAAAAAGAAGAACA
AGAAGAAAAAGAAAAAGAAAAAGAAAAACAAAAAGAAGAAGAAAAAGAACCAGAAGAAGAAAAAACAAGAATAAAATCCA
AAGCGTCTTTAAAATCAGACGCAAAGTCCAATCCAATACCGTATAAAGATATATTGGATTACTTGAATGAAAAAGCAAAT
AAAAATTTCAATCCTAAAGCAGAAGGACATAGAAAGTTAATTCGCGCTAGATGGAATGAGGGGTATAAACTAGAGGACTT
TAAAAAAGTTATCGATAACAAAACTACGCAATGGTTTGGTAAGAAAAGTTTTGATGGAAAACCACTAGATCAATTTTTAA
GACCGAGCACGTTATTTGCACAAAAACATTTTGACAACTACTTAAATGAAACGGTCAACATATCCAATCAACAACATGGA
GATCAGATTGTTATACCTGGATTTAGGGGGAAATGCCGTTTTAGAAAGGAGTACTAAATGTGAAAAAGATACAAGATTC
TTTTGAAAAACTTACTAAGTTAAAATTTGCAGATGAACAATGTGATAAGCACACCTTTAATAAACATGGGAAAGAAGTTA
TTAAATTAGTTAGGAAAATGATTGATGATGCAGGAACGGTATATTGTCCCCGCTGCATGGTTGAAGAGCAAAATTCAGTT
TTATTTCAACAAGCAAATAATCATTATAAAAAGATTAATAGAGAACGGAAGAAAAATGTACTCTTTCAACACAGCATCAT
AGAAAATCAATCCATTACAGAATCAAGATTGTCTACATACAAGACGGATTGTCAAGAAACGAAAGAAAACAAAGAAAAAG
CTATAAAAATTCTTGAACGCATAAAAAACGGTGAGTTTTTAAATGTATACATTGCAGGGATTCAAGGAGTAGGAAAAAGC
CATTTAGCGTATGCGATGCTGTATGAATTAGTTAAACACTATTGGGTAATATCAGACGGTGAGAAATTAAATGACGAACA
TGCTTTTAAAAATATGAAAAGCTGCTTATTTGTAGAGATTGAAAAGCTAATTCGATTAATACAGCACTCTTTTAGAAATA
TAGAGTCAAAATATACAATGGATTATTGTATCAGTTTAATGGTAGATGTGGATTTCCTTGTAATCGATGATTTAGGAGCT
GAAAGTGGTTCGATGAATCGAAACGGAGAAGCAAGCGATTTTGTTCATAAAATACTTTATGGTGTTACAAATGGACGGCA
AGGAGCAAATAAAACAACAATTACAACTTCAAATCTGTCAAGCGCTCAATTATTTCAAAAATACGATCCGAAACTAGCAA
GTAGATTGTTAAACGGTGTATCGAAAGATGAAACAATTGTTTTTAAAaCAACCACTGACAAACGAATTGTAAATTTAGAC
ATTGGATTCTAATAAAAGGGGTGCGGAGAAATGAAAGAGGTAAAGGGGAAAAACACCAAATTAATGGAAGAATTTGACGT
GTTATTAAGACAACTGCTGATTAAATCTAAAACAGATGAAAGGGTAAAAAACTTTTTGGATGATCTGTTTGAAATGCTAA
GTGATAATAAGCTGCAGTCTGATATTGATTTCAAAACAGCATTAAATAAGTTAAGAGAAAAGCACTTTCCTAAGTTTGAT
AAAGGAGAGAGCAAAAATGACTAAAGAAAAGGGACAAGCTAAGGAAGTAGTTAATGTTCGTGGAATGTCAGATGATGAGT
TTATAGAGAAATACGGAAGGCTTGTACATCATTGCGTATGGAAAAGATATGCGAAAAAAAAGGCCAGTATAGAGCGTGAT
ACCGGTTTAGATATTGAGGATTTAACACAATTCGGAATGATCGGTTTGATAAAGGCGCGAGATAATTTTGACCTTGAATT
TGGATGTGCGTTTTCAACGTATGCTGTTCCGAAAATTATTGGGGAAATAGGAAGGGCAATTCGGGATAACCAAAAAAATAA

FIGURE 2A CONTINUED

AAGTTCAAAGAACCGTATATGGCGTAAAAGGAAAGATTTTAAATCAACAGTTAGCAGATAAAGAACCAGAAGAAATAGCA
GACATTTTGGATGAGTCAGTATCTTTAGTAAAGACGGCTTTAGAGTATCAACCAAGCACAGATTCACTCAATAAGGTTGT
ATATGCATCTGGAGCTAATGAAGAACTGACATTAGAAAGAATGATAGAGGATACTAAAACGGAAGACATTGAAGAAACAA
CCATTAATCGAGCTGTGATAAGAGAATTTAAAGCTGCATTGCCTCCTAAAGAATATATCGTTTTAGATATGCGTTTACAA
AATATGACGCAACAAAACATTGCAAATCAAATGGGATACAGTCAGGTACAAATTAGCCGTATATTAGCAAAGATTAATCA
AAGAGCTGCTCAATTTGGTAAAGAAGGAGGGCTTCAAGATTGAGTGTTACAAAAGGTGTTTGTATCGATGTAGATCACTC
AGATTTGCTACATGAGAAAGTAGAGTACTTTTTATTCCCTGCTAAACCAAGTCATTACTATGTAAGCAGATTTAATCGTA
AAGGAGCGCATTTTGGTTGTTATCAAGCTGAAAGGTTTCAAATCACGGAAAAGGAAGTATGGACACCAGAACCTCAACCG
AATCTGCCTGAGTTGAATACAAGCTTATTCTATAGAGCTCAGTTGATTTGGCGAAAAAAGGGGTATAAAGATAAACCACT
TAAAGACTACATCGTACAGCCGAGAGGGAAACATTGCTACTTTTGGCATGATCGGGAGCGAAAGAAATTTTGTGGCTGTT
TTCCGCTACATTGGTTTACCGATTTTGTACCAGTTCAAAGTCATCATATAGAAGAAAAAACTAGAGAAGAGGTTAAGTTA
TTACAACGGCCAGATGGACAACTTGCATTTTTTTAACGAAAGAAAGTGAATGGGCGTTTTACCCAGTCATCGATTTAAAA
AAAGGAGTGTTCGTAATGGATATTAAAAAGTTATTTGCAATGCAGAACATTTTGGATAAAAGAGTTTTAGAGTCAAAAAA
TCTTTCTAGAGGAGAAGTATTCGAATTTAGAATACTAGCGTTTTTAGATGAATTAGGCGAATGCATGAAGGAATGGCGAG
TATTTAAGTTTTGGAGCGACGATCGTAAACCGAGAACTAGCATACCTACAGGGGAAATCATAGTACTAGATGATGGTTAT
GAAGTAGAAGTTTATAAAAACCCTTTACTTGAGGAATATGTGGACGGACTACATTTTGCAATTGGACTTTGCATAGATTT
GAAAACAGAAATTAACTTTCCTGCTTCTATGCGTTGCGAGACAGTTACAGAGCAATTTTTCGAATTGTATCATCTAGCAA
TACGATTAAAAGAAGAACCGACAGCATTTAGGGCAGATGTTCTTTTATCCCATTATCTTGGTTTAGGGGAATTGTTGTGC
TTTTCGTTAGAAGAAATTGGACATGAGTACATTGAGAAAAACAAAATCAATCATGAACGTCAAAGTAATGGATACTAATA
CAATTTGAATTTTGTTAAGAAAAAGTGAGTGAGAGATGGAACTATTATGAACTATAGAATTCCAATATTGGGAATCTATA
TTAATTATATAATTTAAAAATGTGGTAATGGTTAAGATTTTAATATAGGGAATTTATGAAGTGTTAGTATGATTTGATTG
GCTGTCTTTAACTTTTTATTAGTAATTTCATATATTGTAGGGTGCAATATTGAAGAAGTATGGGGGGGAGAAAATGGATT
GTTTTAAAAAAGGTAAATTTATACCATTTCCATGTGCTTTACCAATTCCTGAAGCTGGTCCTACTGGCCCAACTGGTCCA
CCTGGATCAGCTGGAGGCTCGACCGGTCCAACTGGTCCAACCGGCCCGCAGGGTTTACAAGGGATTCAAGGGGTTCAAGG
GAATCCAGGAACTACTGGACCTCAAGGAATTCAAGGAATTCAAGGAATTCCAGGGGTTTCAGGTCCTATTGGTCCTATTG
GTCCTACTGGAATCCAAGGAGTTCAAGGCATTCAAGGATTTCCTGGCATTCCAGGTCCTATGGGCCCGATAGGACTAACC
GGTCCGACTGGTATCCAAGGTATTCAAGGGATTCAGGGAGTTCAAGGTATCCAAGGTATTCAAGGGGATGTAGGCCCAAC
TGGCCCTCAGGGAATTCCGGGTATTCCAGGATTAACTGGCCCAACTGGCTCTCAAGGTGTTACTGGAGTTACTGGCCCAT
CCGGAGGCCCACCAGGTCCAACTGGTGCAACAGGTCCAACCGGTCCAGCTGGAGGCCCACCAGGTCCAACAGGTCCAACC
GGTCCAGCTGGAGGTCCAACAGGATTAACTGGCCCGACTGGCCCGACTGGTCCAACAGGAATTCAAGGTATTCAAGGGGT
ACAGGGTACTCAAGGTATTCCGGGTCCAACTGGTCCACAAGGGATCCAAGGAGTTCAAGGACTTCAAGGAATACCAGGCA
TTCCAGGTTCTATGGGCCCAACAGGACTAACTGGTCCGACTGGGCTTCAAGGTATTCAAGGGATTCAGGGGAATCCAGGT
CCGACTGGTCCCTTTGGCCCGACTGGCCCGACCGGGCTTCAAGGTATTCAAGGCTTACAGGGTATTCAAGGTATTCCAGG
ttCCAACAGGACCTCAAGGAATCCAAGGTCCAACAGGACCTGCTAGCACACTTTCCACAAAAGCTATTCTTTTTtGGGGG
TACTAATTCAGGGTTTCAACGTATAGCTGGATCACCGGGTGCAGATTCACAAGACATTCCTTATGTACTTGGCGGAGCTG
GTAGTGTTGTAGGTCTTTCTGCTTCTATAAGTATTAATAATTTACCAATAGGAGTATATACAATACGAGTATGTAAAAAT
GTTCCTATTAATCTTGCTGCTCCGGGGCCTGGCCAAGTAATATCTACAATTATTCTTACAACTACAGCAGTGATTAGTGG
CACTATTATATTGACTATTAATCCTTCTGATATTGGTGCACAACCTGTAAGAGTATTTAACCCTAATTTAGTTATAGCAC
CTGCTACAGTTGCTTGGAGCAGTACAATACCTGGTGACATAGTTGCAAGAGGTGATGCAATGTCACTTTTTATAACTCCA
GGTATTACGCAAAATGCTGTGTATACAGTATTCTTGCATACAGGAAATTAAAGTTTATTTTATGTGAATTTAAGTCCTGT
AAATTGGAATGAAAAATTAAGATATGTATCGGAGTCTTTTTATGTACAAAAGAATAAGAGATTTCTTCTGAACATCTAAA
AGGAATCTCTTATTCTTAATCGATAAATTAGGTTTTAGAAAAATGAAAAGATTTTGTATGAAAATAAATAAAAGAATCCA
TTCGTTACAAACGGATTCTTCCCACAAGGTGTGTAAGAAATTCAAGATAACTCGACCAGAGCATCATGTAGAATTTCTTG
TGATATTAATGTATTCAAAGACATCCAAAAGATGAATGGCAATTAAATAAAATCTTTATTTGAAAATTAAAGATTGCTTT
TGTTAGGGTCTCTATGACTAAGAGTTATCTTAATTTTTTAGGTTTATGAAGTATTTGAGTAATAATTTAGTTTCAGACAA
AGGTGATGTTTAGTAGTAATACCGGTTTGCTTCAGTAGACATTGCAATTGCTTTTGTTTCATGAACTGTACCATATGGAT
GTTCTGGAGGTGCATATATAGCGTAAATTTTAAGTGGTGTATTTCCTGTATTGATTACATTATGCCATTTTCCAGCAGGT
ATCATAATTGCATAGTCATCATAGACCATTTCTTGAAAATCTAATTTATCTTTGTTATCACCCATTTGAACGAGTCCTTG
GCCCTCTTCAATACGTATGAATTGATCAGTTGTAGGGTGTACTTCTAAACCTATGTCATCTCCAACATTAATACTCATTA
AAGTTACTTGTAAGTTTTTTCCTGTCCAGATAGCGGTGCGGTAAGTATTGTTTTGTTTAGTGGCTTGGTTAATATTCAAT
ACAAATGGTCTAGCTCCATAATCTGTTAATCTAACATTTTCACAATAAGGATTCCGGTTGCGGTTCCAAGCATTATTGTT
GTAATTGTAATAATAAGGATTCCAAGCGTAAATCCAATTATTGTTATTCCAGATGCTATCCATTGGGCTTtGAGATTGAT
AATAATAACGTGGAATATGTTGCATATCCAAGCTCCTCTCATAATTGtATCATTTACTTTTTATCCTATGCTGTTGTCTA
TTTATAGGAATGCAGAATAAGGGGAAATGGGCAGTAATAAAAAATATAAAAAAACGTTTTTATTTTTTCAGGAAAAATAA
AAGTAACAAGTTAATAAGGGATGTACTACTGGTATAAAAAACTTAATAAAATAGTTATTTGAATTAAAAAGAGCGCCGTT
GGAGAGTGCGGTGCTCTTAGACCAAGAACTATAACAGGGATTAAGGAAAGAATATTGTATACCAAATTGATAGTAATGCA
AGCCATCCAATTGTCAGCGCTATGTATTTTAAAATTTTCATGATTACTCCTTTTAGGTATAGAGTGCACCAAGCAAGAGG

FIGURE 2A CONTINUED

ATGTTATTAATTTTTAAACAAAATGCTTATTTAAAAACTAAAGAGGGCTTTTTAAAGCGCTCCTTAAGAAAAATAAAAAA
GAATACCTCATGATACTGTATGTATGTTTTTTTAGGAATGTGAGGATTTAAAACAAAATCGTTATTTTATAGATCGGAGT
GAAATTCAAATGATTGTTAAAGCGACAATAAAACTTGAATTAGATGATTCGCAGAAAAATTGGGTTTCTTATGTTAGAGA
ACAAGGTGGAGAAGAAGCGGTATTTCATTATCTGGAAGAAGAAGTGCAGAAGAAAATTGAATTAGCTGATTTTGTGGAGA
TGAAATACAAAAATAAGTAATTTAAACCAAAACGCTATTTTATAAAATAAAACAGCTAGCGTGATTAGCTAGCTGTCCTG
TTAAGAAAAGAAAACGGTGTTTAGCAAATGTTGCTGTTGTAATTGCGAATTACAACCATAGTATGAGCAGAAGTAAAAAT
GTTATGCAAGAAAGTTAAATAAAAACTGCATTTTATTGAAAAGGGGGAATGGATATGTCTCTAGTAGGGAATTTAAAGGA
ACTCCAAGAAAAAGCCATCGATGAAAAGGTATTGGAATTTGCGGAAGAAATGGAAATCGTAATAACTAAAAGTGCCGCAA
GCGGATATTCAGGTCATAGATATAAGATTCATAATGAAAATCCAAATCGGCATATGATGTGTTCAAAAATATTTATAGAA
AAGTTACAAGAATTACTGGACGGTGTGAAGGTTGAATTTAAGGAAGAAGAAAAGAAAAATATTTTAGGCGGATCTTACTA
CGAACATTACATCCGTTTTAAGTGGAATGACTAATTTCTTATTAAAAATTTTATTTTGGAGAAAGGGAGTAGAAAGAATG
AAAACTTTTAATGTGACTTTTACAGAGTTGAAAATATATGAAGCAGTCATTGAAGCGGAGTCAGCGGAAAAGATTATTGA
TGTGATTAAACACTTAAAAAGAACTGAAGATGATTTAGTAGACAAAGGAGTCATCATAAACGAAGTTAGTGAGATAAATG
TTAGTAAAGAACAAAAGTTCGAATAAATCAACTTCTCAGATTGTTTATTTTGAGACGGAAACAACTTTCTGAATATCATA
AGACCTTATTAGCGAAAAAaCTCTTATTCGAGCGTACAAGCCTGTTATACACGTTGCACGGAAATTAGAATGAATTTGTT
AAGGAAGGAAGTATAAAAATGAGGGCTTGGAAGAAAAAACATGTTAAAAGAGCATTTTTGAATCGTCAAAAGGAAATTGA
TAAAGAACGGACTGCTGCAGCTTGGAGAAATATTTTTGTGAAATCAGGAATCATAAAATAAAAAAGGAAAAGCAACTCGT
TGGGGACAAGTCACTTTTCCAGATGGCAATGTAAATCCATTATAGCAAAACaTATGTACaAGCTGTAGCAATAAACAACG
AGATATTTTGACACCTATCGACAATTAGAAATGTGGTTGTTGATCTAGAAATATGAAAGTAGGTGAATCATCATTTGTTT
AACTGGCTGAGAGATTACCAAAAGTTAGAAGAAGACATAGCCTATCTGGAATACAACTTAGATAAGACAAAAGCTGAATT
AAGACGCTGGGTGAGTGGTGATTTGAGAGAAGTACGTTTAACGGCAGAATCTGAAGGTGCAAAAGTTGAAAACCGCATTG
AAGCGATTGAATACGAATTAGCACATAAGATGAACGATATGTATAAATTAAAAAAGTTAATTAGTAAGTTTAGAGGTTTA
GAAAATCAGATACTCAAATTAAAATATGTGGATGGTATGACGTTAGAAGAAATAGCAGAGGCAGTAAATTATAGTTCTAG
TCATATCAAAAAGAAACATGCTGAACTCGTTAGATTAATTAAGTTCGTGGAGCGAGAAGGTGTCATTTAGGTTCACTCCT
AAAATGAATCGAAACGGTTGAAAAAATGATTTATATTGATAGCATACAATTTTAGCAGAAGGGCAACTGGTGCACGGTTG
CTCTTTTTGATTTTGGAGGTTATTAGACGATGGATGTACAAGAGTTGTCGAGACGATTAGAAAATCTAGAACATAAAGTG
CTTCAGGTAGAAACGAAGGCAGATGTGCTAAACCGAACAGCTATACAAAAAGGCGATAAAATAAAAGTGGTGTATCCGCA
TTTAGGGATACAAGGCGAGTATTTAGTGGAGAAAATTGATAATGGTGTGTTGGAATTGGTAGCAGAAGAAACAATGAAAA
AAATACAGGAGTGATTAGGATTGAAGAAGTTATCTAAACAAGAGCTAGCAGCTGTAATGACACATTGTATTTCAACGCTT
GGTGAGCAGATTGTTAATGAGCATATTAATCCCCAGAAGTTGGCGCAAGCAAGTGCACTCCATAACGATCTCTTTGATAA
TACCACTCCTAAAGAACGTAGGGAAGCGACGATCAGTTTACTAGGGAAAGCGATTGATGAGTTTTTAGAGAGTAAGGAGT
GAGGATATGGGAAAGGGATATTTTAATAAGGCTGTATGTTTAGTGTGTGGTCATCAAGATAGAGTGAATCATCCATCTAA
AAAAGAGTATCAAGAAGTAACGGTTTGTCCGGAATGCAACGGTGCTTTTGTAGATGTGTGGAAGCTAGGAAAGTACAAAC
GTAATACACAGTCTAATGAAGAACCTTTATTAACAATTACATTAACAGATATAGATGCTAAACCGATAGTTCATTACAAA
GGTGAACAGATAGATAGAAAGTTACGTGTTACGTTTGATTGGGAATCTCAATCGATTGATAAAATTAATCGGACATACAT
TCATATTGAACATGTACCAGCCGATAACAAACGTTTAAATACCGAGACCATTCAGCATAATCATCCTATTGCAAATAAGG
AACAAGTTTAGATGTTGTCCATATTTGTTAATAGGTAAAAGATAAGTGTTTTATCTGGAAGTTCAAACGTGAATTAAAGA
AATTAAAAAAGGAATATGAAAAGGAGAGTCACTGAATGAACGGGTTTAATAAAATTGTAAACGATATGCAAAATGAACAA
GTAGGAAATGCTATGCTAGATTTTGCTTTGGCCGCTAAAATGATGTTCGCTGCCTTTACACAGTTTAAAGAAGCTGGATT
TAACGAAGAGCAGTCATTCGAATTAACACGTGAGATATTAATTGATTCATTAAGTAAGAATCAATAGATCAATGAGGTGA
AAGGGAATGCAAGTATATTGCTCTGAGTGTGATAAAAGTTATGACATGCAGCCGCAAGTAACACAACTCCCTAATCGTAT
TGAGAAGTGTTTCTTTATTTGTCCTCATTGTAATCATGAACATATAGCTGCGTACGTGAATGATAAGATTCGTAAGTATC
AAGCAGATATAGCAAAGTGTCATGAGCGGATTAATAAAAAGAATCTTGCTATCGAAGATGAAATGAAACGATTAAGGAAG
AGGTTTGACAGGAGAAAGTGAGAGGTGAAGCGAGTTTGAAAATGCTATTAACAAAGCATTGGTGTTTAGATAGAAACTGC
GGATTTGAAGAGACTTCTCATAAGGTACGTGATGGTTGGAAATGTCCTGATTGTAATGGACCAATGGCGTTTCAACAGGT
GAATAAGAAAAAAGaAAGCGCCAAGTGATGGTGCTTTTTATTTTGGAGGAGGATGAAGGATGGAAGGACAGGAGTTAACA
TTGGAAAAGAAAGACAGTATTTATCTTAGACCAAGATACCCTCATAAGATTGACGCAAGTAAAATCAAATCCTTAAAAGA
TGTAATTAAGATTTTAGGATTGATGGATATTCGTTTGGACGACAAGGCGGTCATTGGTCTAGAACACTTGATTGAAAAGG
AGGAAGAATAAAATGGCCAATAACAAATTAATTATTGAAGTAACTGCGGATACAACTGAGGCATTAGAAGGAATTAAAGA
AGTAACTGAAGCAGCTAATGAATGTGCAGATGCGCTGGACAAATTAGAAAAGATTATGGATAAGTTTACAAATCGAAGTG
ATACAGTGGAACTCTATTGTGAAGGTAAATTGTTATCGAAGTCTACAGTTAATCATACAGCTGATTCaATTCAATGTCGC
ATAATCAAGGGAGAAGAGCTTGGAGGAAGTGAACGCTGATGAAGAAACCGCTTAGACCATGCTGCGAATTTCATTGTTAT
AATCTCACACGTGAAAGATATTGTGAGGAACATAGATACAAAGAGAAGGAAACGCAGCAGGATAAGAATAGATACTACGA
CCGATTCAAACGGGACAAAGAGAGTACGGCTTTCTATAGGTCAAAGGCATGGGAAAGGTTAAGAGAGCAGGCACTAATGA
GAGACAAAGGGTTGTGCCTACATTGTAAGAACAATAGAAAGATTAAAGTTGCAGATATGGTTGACCATATCATTCCAATC
AAAGTTGATCCAAGTTTAAAACTCAAATTAGAAAATTTACAATCACTTTGTAATCCATGTCACAACAGAAAAACAGCAGA
AGACAAAAAGAAATACGGGTAGGGGCGGGTCGAAAAACATTCAGGGCGGTCTGTCCGTACcgccgcccc FIGURE 2B: Polypeptide Sequence of Phage W

W phage: Polypeptides Encoded by Polynucleotide Open Reading Frames

Orf1 (SEQ ID NO:4)
MAGRNKQPLSVIQGKGRSNHITKSEKNRREKQEEALRGHTDKIEAPSYLTAAQKKEFDTLAAELVRLKIFS
NLDVDSLARYVDSKDQYIKMVRLLRKTKPSDDFKLYSQMQRSKNLLFNECRSSASDLGLTITSRLKLVIPE
VDTSQQKQSEAQKRFGDRI

Orf2 (SEQ ID NO:6)
MNWIMERVFAYCEDILNGKINSCKKHRWAIERFIRDYEECQSEDSPFYFDGEIAEDFYWFAKEFKHVEGI
LAGESVELTDFQLFLAANIFGFKKKINGARRFRKVFIQLARKNAKSQFLAIVAAFCTFLGDEKQRAYIAG
WTRDQSSEVYEAVKTGISSSELLEGKWKEAYSTIEIFKNGSVVVPLSKEARKTGDGKNPSLGIVDEYHAH
ETDEIYDVLSSGMVARKEPLMFIITTAGFDLSRPCYREYEYVSDILDPSKNVENDDYFVMICELEKNDDI
KDESNWIKANPIVATYEEGLEGIRSDLKVALDRPEKMRAFLTKNMNIWVDKKDNGYMDMSKWQKCEVDTF
DFSGATLWIGGDLSMTTDLTSVGWVGMDDEGDFIVGQHSFMPEARLKEKMAIDKVRYDLWAEQGYLTLTP
GEMVDYTIVESWIENFSKDKEIQEFDYDKWNALHLAQNLENKGFVCVEIPQRIANLSIPTKNFREKVYEK
KVKHNGDPVLFWALNNAVVKMDDQENIMISKKISKNRIDPAAAVLNAFSRAMYGASVRFDVSEFANKDFL
GKLWN

Orf3 (SEQ ID NO:8)
VKIVDSVKKFFNFEKRQTSQVIELNKDDEKLLEWLGISPSTISVKGKNALKVATVFACIKILSESVSKLPL
KIYQEDEYGIQRGTKHYLNNLLRLRPNPYMSSMNFFGSLEAQKNLYGNSYANIEFDRKGKVQALWPIDASK
VTVYIDDVGLLNSKTKMWYVVNTGGQQRVLKPEEILHFKNGITLDGLVGVPTMEYLKSTLENSASADKFIN
NFYKQGLQVKGLVQYVGDLNEDAKKVFRENFESMSSGLQNSHRIALMPVGYQFQPISLNMSDAQFLENTEL
TIRQIATAFGIKMHQLNDLSKATLNNIEQQQQQFYTDTLQATLTMYEQEMTYKLFLDSELDKGFYSKFNVD
AILRADIKTRYEAYRTGIQGGFLKPNEARSKEDLPPEAGGDRLLVNGNMLPIDMAGQAYLKGGDTNGEVSK
EGNEGN

Orf4 (SEQ ID NO:10)
MEKSAKKEMKEIRALPMTIEVREVNEDEGKRTISGSIKYNNESAEMRDWWGDTFVEEIAEGAFDESLKVRD
VVGLWSHDTSQVLGNTKSKTLRIENDKKELRFELDIPNTTVGNDAWELIKRGDVDGVSFGMKVTKDKWSSE
ERENGKLYKRSILNAELYEISPVAFPAYPTNEVSVRSLDDFKAGEKRVADEFRKRKLQIELELI

Orf5 (SEQ ID NO:12)
MSKELRELLAKLEGKKEEVRSLMGEDKVAEAEQMMEEVRSLQKKIDLQRSLDEAETEERNNGREVETRNVD
GEMEYRDVFMKALRNKPLNAEEREFLEDDLEQRAMSGLTGEDGGLVIPQDIQTQINELARSFDALEQYVTV
EPVRTRSGSRVLEKNSDMIPFAEITEMGEIPETDNPKFSNVQYAVKDRAGILPLSRSLLQDSDQNILKYVT
KWLGKKSKVTRNVLILGVIEKLTKQAIKSLDDIKDVLNVKLDPAISPNAILLTNQDGFNYLDKLKDKDGKY
ILQSDPTQKNKKLFAGTNPVVVVSNRFLKSKGTTAKKAPLIIGDLKEAIVLFKREDMELASTDVGGKAFTR
NTLDLRAIQRDDVQMWDNEAAVYGEIDLSAPVEQPQG

Orf6 (SEQ ID NO:14)
MLVTLEEAKEWIRVDGDDDPTITMLIKAAELYIYKATGKTFTQTNEDAKLLCLFLVADWYGNRLLVGEKAS
EKIRTIVQSMILQLQYASEPQEERK

Orf7 (SEQ ID NO:16)
MNPAKLDKRLTFQVKDENAKGPDGDPIDGYKDAFTVWGSFVYLKGRKYFEAAAANSEVQGETEIRNRDDVS
ADMKIKYKNVIYDIVSVIPTQDHTLLIMWKRGEMNG

FIGURE 2B CONTINUED

Orf8 (SEQ ID NO:18)
MKLTLMINKEKQTFNMPEFIPARLIRQAPELAEIPNNPGPEDMDKMVQFVVKVYDGQFTLDQYWDGVDARK
FLSTTSDVINAIINETVEAAGGSTESGEEENPNA

Orf9 (SEQ ID NO:20)
VINLRPDILQALENDQELVSLLGGKRIYYRKAKKAEEFPRITYFELDNRPDGFADNQEIESEILFQVDVWA
KSSTTAIHQKVNEIMKRIGFSRYAVADLYEEDTQIFHYAMRFAKGVEL

Orf10 (SEQ ID NO:22)
MAGEVVRISSTVGVDNLVYAKVLQDDSSAIKYTDVKKMEGAVKVKLTKKVASEVMWSDNRKSEIAESDGET
EVEIEVRGLSLSTKADIEGFPEVKDGVLDEKREGEKPYLAIGFRFLKANDKYRYVWLLKGKLSQEEEEAET
KKDKPNFQTTKLKGSFIERDFDDRTKFTADEDEPTFTKLVGDNWFNKVYEKPVTQPPAGK

Orf11 (SEQ ID NO:24)
MKLTLMINKEKQTFNMPEFIPARLIRQAPELAEIPNNPGPEDMDKMVQFVVKVYDGQFTLDQYWDGVDARK
FLSTTSDVINAIINETVEAAGGSTESGEEENPNA

Orf12 (SEQ ID NO:26)
MDELYLSLLRQGYKHHHIDNEMDIWHYLRLNRKMHENGNENYEGSNSNEIEVPAENII

Orf13 (SEQ ID NO:28)
MANEINNLVVRLSLDNVNFRQGISNSGRAVRTLQNELKSVSTGMGGFANASQQTQAKMNTLSRLIDAQKEK
VKALRQAYDQNKAKLGENDAATQRYASQVNKAVADLNRFENELKQVNRQAEQKGMDKLNNSLKSLQAEFQS
ITTGMGGFSNATEQTRAKVDVLSRMVDKQKEKIRELQQAYNRAKTEEGEASQSAQRYAEQIHRATAELNRF
ETGLQQSNRELEQQGNRLLNFGNRMETLGNHLQNAGMQIGMVFGGMTYAIGRGLKSAITESMNFEQQMANV
KAVSGSTGAEMKKLSELAVNMGETTKYSSVQAGQGIEELIKAGVSLQDIINGGLAGALNLATAGELELGEA
AEIASTALNAFKADHLSVADAANILSGAANASATDVRELKYGLSASSAVAAGAGMTFKDTATTLAVFAQNG
LKGSDAGTSLKTMLMRLNPSTKEAYNKMRDLGLITYNAQAGFDFLVKNGIQPASRNVGDIEVALEQYVMKT
EGVTKWNDKCDTTFRELATSSAFLSSKFYDQQGHIQSLENISGTLHESMKDLTDQQRSMALETLFGSDAVR
GATILFKEGAKGVNEMWDSMSKVTAADVAATKIDTLKGRLTLLDSAFSTMKKTIGDALAPVVSVFVAGLQK
LVDGFNSLPGPVQKAIAITGGIVLALTAVATAIGVVLAAFGMIASGIGSLSLALASVGGIAGIAAGAVGFL
GSALAVLTGPIGLVAAALIGTGVVAYKAYQKATEDSIASVDRFATNTEGKVSSSTKKVLGEYFKLSDGIRQ
KLTEIRLNHEVITEEQSQKLIGQYDKLANTIIEKTNARQQKEIEGLKKFFADSYVLTAEEENKRIEQLNQH
YEQEKLKTQEKENKIKEILQTAARENRELTTSERISLQALQDEMDRVAVEHMSKNQMEQKVILENMRVQAS
EISARQAAEVVENSAKARDKVIEDAKKTRDEKIAEAIRQRDENKTITADEANAIIAEAKRQYDSTVSTARD
KHKEIVSEAKAQAGEHANQVDWETGQVKSKYQAMKDDVIRKMKEMWSDVTNKYEDMKNSASNKVEEIKNTV
SRKFEEQKKAVTDKMSEIKSSIEDKWNTVEKFFSSINLRSIGKSIIEGLGKGIDDASGGLFSKAAEIASDI
KKTISGALEINSPSKVMIPVGSAVPEGVGVGMDKGKRFVVDAAKNVVGTVKKQMGNMPSVFDFGFQTNQYS
IPQNTFSDFSGYMQPQLSYNNPSMAKTIFPNRPGGEQELNLTVNMTNVLDGKELANGSYTYTTKLQNREQK
RRAEF

Orf14 (Tail fiber; this sequence differs from that in γ phage) (SEQ ID NO:30)
MGKLSFTFNNIRKDYIQMLVGRKRPSWAPVKRRLVRVPHRAGALLLNTETEERRIDVPLVIKAKKDMADL
QKLKEDLADWLYTEQPAELIFDDELDRTYLSLIDGSVDLDEIVNRGKGVITFVCPMPYKLGKINTHKFTQ
EWSTETTSYFTNKGSVEAPALIEMTVKKPSTFLDVWFGEYPHNRDYFRIGYPLTVEETTVQERERVMWDE
MATPIGWTPVTGQFEEMKGTGSFKSRGGHALYCEDYGKETGFYGAIAKKNIPGGPLQDFEMEAWVTLKSK
NISEMGRVEVLLLDETSNVISRINMNDLYATAEITRAHMTIGNSGTPNSFRKLVDTSGFYSTTFNQFRGR
LRIARRGKVWSVYVAKFIDGTEKDGASLVERWIDETGNPMTERKIAQVMIAICKWDNHQPINEMQIDDLK
IWKVNKVPSNAQPYIFDTGDKIVIDTEKSLVTINGEKAINIKEIFSNFPVVIRGENRIDIMPPDVNATIS
YRERYR Orf15 (SEQ ID NO:32)

FIGURE 2B CONTINUED

MRTPSGILHVVDFKTDQIVAAIQPEDYWDDKRHWELKNNVDMLDFTAFDGTDHAVTLQQQNLVLKEVRDGR
IVPYVITETEKNSDTRSITTYASGAWIQIAKSGIIKPQRIESKTVNEFMDLALLGMKWKRGITEYAGFHTM
TIDEYIDPLTFLKKIASLFKLEIRYRVEIKGSRIIGWYVDMIQKRGHDTGKEIELGKDLVGVTRIEHTRNI
CSALVGFVKGEGDKVITIESINKGLPYIVDADAFQRWNEHGQHKFGFYTPETEELDMTPKRLLTLMEIELK
KRVNSSISYEVEAQSIGRIFGLEHELINEGDTIKIKDTGFTPELYLEARVIAGDESFTDSTQDKYEFGDYR
EIVNQNEELRKIYNRILSSLGNKQEMIDQLDRLVQEANETASNAKKESEAAKTLAEKVQENIKNNTVEIIE
SKNPPTTGLKPFKTLWRDISIGKPGILKIWTGTAWESVVPDVESVKKETLDQVNKDIATTKTELNQKVQEA
QNQATGQFNEVKESLQGVSRTISNVENKQGEIDKKITKFEQDSSGFKTSIESLTKKDTEISNKLNTVESTV
EGTKKTISEVQQTTNDLKKKTTEIEEKAGKITEKLTSLETREVNVRNYVINSDFSNVTNSWIGITNATLFK
FVDVNISEASAIKKGLQITSNKAFVYQKLPADVFKKKKGIASCYINVSSFTPGTDYPRLYMRFTYDQNGTE
KQYYAILKQQEVTNGWIRISIPFDTTGYTGELKEVRVNIATADTTTIDATFTGIMVTFGDLIESWNLAPED
GVTQGVFQSKTTEIEKSVDGVKTTVTNVQNSQAGFEKRMSNVEQTATGLSSTVSNLNNVVSDQGKKLTEAN
TKLEQQATAIGAKVELKQVEDYVAGFKIPELKQTVDKNKQDLLDELANKLATEQFNQKMTLIDNRFTINEQ
GINAAAKKTEVYTKTQADGQFATDSYVRDMESRLQLTEKGVSISVKENDVIAAINMSKENIKLNAARIDLV
GKVNAEWIKAGLLSGCQIRTSNTDNYVSLDDQFIRLYERGVARAFLGHYRRSDGAVQPTFILGSDEKTNAP
EGTLFMSQAGAGWSGAYASIGISNGIVDGAVQKSVYWELQRNGLSVLNANDYHVFYAGNGNWYFRRGKPGL
YQTSLVVEDNSTDSDLRLPNVTIRNSRAAGYTGVIQLKSPVTQNGWGAVQGNFMTPSLREYKSNIRDISFS
ALEKIRSLKIRQFNYKNAVNELYRMREEKSPNDPPLTTEDIKTYYGLIVDECDEMFVDESGKGIHLYSYAS
IGIKGLQEVDATVQEQEVEIANLKSQIASQEDRIARLEELLLQQLINKKPEQP

Orf16 (SEQ ID NO:34)
MDRIDVLLKAFIAAFGGFCGYFLGGWDATLKILVTMVVIDYLTGMIAAGYNGELKSKVGFKGIAKKVVLFL
LVGAAAQLDSALGSNSAIREATIFFFMGNELLSLLENAGRMGIPLPQALTNAVEILGGKQKQEEKKGDVQ

Orf17 (PlyG lysin) (SEQ ID NO:36)
MEIQKKLVDPSKYGTKCPYTMKPKYITVHNTYNDAPAENEVSYMISNNNEVSFHIAVDDKKAIQGIPLERN
AWACGDGNGSGNRQSISVEICYSKSGGDRYYKAEDNAVDVVRQLMSMYNIPIENVRTHQSWSGKYCPHRML
AEGRWGAFIQKVKNGNVATTSPTKQNIIQSGAFSPYETPDVMGALTSLKMTADFILQSDGLTYFISKPTSD
AQLKAMKEYLDRKGWWYEVK Orf18 (SEQ ID NO:38)
MKMYKKLISICIGSTLLLGLTACDSSKQSESSEKTNVKSQPETKKDLTSQDELNKKIKQDAEEVSFVKAN
GDQYEKGKRLKATGTVDLLLKSSALPSFVISTNENDGKGMYTIQIVQSGVQTNENEITLKNGLKISKGSI
VTIYGAYDEKDKTGMPKISATVIEQ Orf19 (SEQ ID NO:40)
VRLKCKLRVIFAEREIRQKEFSKLIGISQTTMSSLVNNTTLPTFLTAYKIAKELKLHMEEIWIEEENENV Orf20 (SEQ ID NO:42)
MRWQYNHLNTTPYLHPSKELCSMYNGSRSRAETESILNHMKNHEVYDRKEYKGYFSLSQVLEEDLYGEEED
VLNWEILMDCYDVVLTRKGIAFREKEEEEQA Orf21 (SEQ ID NO:44)
MTLAGEAIIIWTATGLSVVAMKAAEKMGKSVPHWLPRVTLYTTLTGSFLYLLRYVLVLFL Orf22 (SEQ ID NO:46)
mwklfipyvirslacMHVFLETGIYTLYKRDIRSDFMLELLSVPFAGLIFAIVGERLKGRESDRKKIQVFF
EVSGIAIRREDKLQYPVFLEQKEDDRSTTYIYRLPVGMPSKIIQKVEDVVSEGLSKPVRIDYDNYKLNIRV
FHRDIPKKWSWSKGLVAEGSWCVPMGQSLEKLIYHDFDKTPHMTLGGLTRMGKTVFLKNVVTSLTLAQPEH
INLYIIDLKGGLEFGPYKNLKQVVSIAEKPAEAFMILTNILKKMEEKMEYMKCRHYTNVVETNIKERYFII
VDEGAELCPDKSMKKEQQRLLGACQQMLSHIARIGGALGFRLIFCTQYPTGDTLPRQVKQNSDAKLGFRLP
TQTASSVVIDEAGLETIKSIPGRAIFKTDRLTEIQVPYISNEMMWEHLKGYEVEKHEDANAYANQPSNGDT
CDD

FIGURE 2B CONTINUED

Orf23 (SEQ ID NO:48)
mrwrnmrmqthmqinrqmailatirklqfatrrhlMSIHEMGGIRNANRILKDLSIYTSKVVYNKEHVYYL
NQSGHKLFGEGKVVHHGKVTHALLRNEAWLNLYCPDDWQVETEIKYIKDNKKKKIIPDVKFRDEDRILHAV
EIDRTQKMIVNDEKLKKYEELTQIYKQKHNGKVPVIHFFTITKYREKKLEELANKYNVFVKVYVIATT Orf24 (SEQ ID NO:50)
MKFTLGNSLDELGITKNKLSTESQVRYNTISDLVNGNANAVRFDSLEAIIDALNAIAAEKGINKIYKIDDV
IQYIKKS Orf25 (SEQ ID NO:52)
MAFKASMIASSESKRTALALPFTKSLIVLYLTWDSVDNLFLVIPNSSKEFPSVNFILFSSAALVILYSFY
NINRN Orf26 (SEQ ID NO:54)
MLSSANYTQYKKLQSFRSVEEMNEAICSFLYKHTHELSESAIKVLKFLARHSCKIPGVSFLKVGTIAEALN
ISDRTVRRVLKVLEDFEVVTRHKTIRTEGKLRGGNGHNVYVLLKKYSVTPNVLPKMSQRQDEENLTESKVS
DTKTDKEAKLSESHPLEELKSELNVKETSARESKEIELEDLDETFTPENVPSQFRDVVAPFFKSADKIYKL
YHRVLIAYKRSKIDKPIEQVINQAIQAFKETVFAEKANKIRSTFEGYFYRIVESKFVMERRKECRGLLFDW
LNE Orf27 (SEQ ID NO:56)
LKYAVYVRVSTDRDEQVSSVENQIDICRYWLEKNGYEWDPNAVYFDDGISGTAWLERHAMQLILEKARRNE
LDTVVFKSIHRLARDLRDALEIKEILIGHGIRLVTIEENYDSLYEGGNDIKFEMFAMFAAQLPKTISVSVS
AAMQAKARRGEFIGKPGLGYDVIDKKLVINEKEAEIVREIFDLSYKGYGFKKIANILNDKGTYTKFGQLWS
HTTVGKILKNQTYKGNLVLNSYKTVKVDGKKKRVYTPKERLTIIEDHYPTIVSKELWNAVNSDRASKKKTK
QDTRNEFRGMMFCKHCGEPITAKYSGRYAKGSKKEWVYMKCSNYIRFNRCVNFDPAHYDDIREAIIYGLKQ
QEKELEIHFNPKMHQKRNDKSTEIKKQIKLLKVKKEKLIDLYVEGLIDKEMFSKRDLNFENEIKEQELALL
KLTDQNKRNKEEKKIKEAFSMLDEEKDMHEVFKTLIKKITLSKDKYIDIEYTFSL Orf28 (SEQ ID NO:58)
MRIALYRTHALINVIKYSVNIMEKVLLIEMKGVSYLKFHEKIMGMIEDRDDLTATSVACKIGVSKQYMSKF
KRQGTIGFSQLLKLAPILSVEGKKAKQTMSDWCLELDTTESIKQSFEYACLTRNTILLKQLIQKHSKETGT
IREYVEVYTILFKYIKNIIKGSEITKELKKIGAIKDKVLEILTKIMECYEYYHLKKFNLMLETAETIDSLV
REIEGERKSFIKECYNYRIAELFAPIFLQKNNVDLARKYAHFLIHANVCTKTVSDAYYILGMSNVLESKEQ
CLFNLKKSYLLSKEIRDADIEQEARYNLDVAKIYFGVKLDEDADSRLLLYQKNPTCELSIIALQDIIRDRG
DRDFLNYFIACSSDEIECLYDLFYQYFYQANYLFSAIVAKELCNRGDKSLLTQSMVNLGNEKQKGVVDIEE
ISISSLYIINGSNSGIVV Orf28.1 (not present in γ phage) (SEQ ID NO:60)
VIIVEFKDRLRQLRRERNLTQHDLGQAIGVTAGSVSKFETGFKPASRETVERAADFLGVPVDYLLGRSDSR
ELDADMNQKYLHIKNRLEQLPEEHQEIVLQNMLTMMESLEKLKSTSK Orf29 (SEQ ID NO:62)
MKVIKDETKLKAAFKKSGYKYQELADELEISCSYCYKLINNHNYKKKISYNLASRMAHVLNASVVDLFEEQ
VDFF Orf30 (SEQ ID NO:64)
MREHRGERAMSEIYYKGFIIKETYGERNIEEVFKEAYESFYGVEVKVVKKELGTKRNSAAS Orf31 (SEQ ID NO:66)

FIGURE 2B CONTINUED

MDQLTVASELRLLGRRKVAGYEFTGIEGGFGEGKKAMLVLDIATIHNQPLKEINRRINDNRIRFKDGVDIV
DLKSGGFNPPQLLNLGFSNMQIAKSNNIYLLSERGYAKLLKILEDDKAWELYDILVDEYFNMREKNQVATD
PMSILKLTFEALEGQQQAIEEIKSDVQDLRENTPLFAIECDEISTAVKRQGVILLGGKQSNAYRNRGLRGK
VYRDIYNQLYREFGVKSHKAIKRCHLNVAVKIVEEYTLPIVLSEEISFVNAQMDFTEM

Orf32 (SEQ ID NO:68)
MDQLRVIEGEKVDKPDYVEIYLGAFMNAVNELKKQDEETRSLSKDTYKKAIFYGVRYISISKNDSLNYDYL
MNRFLLISYLENLMKVLTPRDFMTIFPIDKNYDGARYEMKDYFFTMNEIKKIGMDTPIGEKIMEFLWDYQN
FKDITLFNLASVSILNKLQKMQGKKTLTEEFAERLGIDTYTKHKEKGGKEYITNDRTGEIQEVKKSRPRYL
KPVQ

Orf33 (SEQ ID NO:70)
MALFRKVHTEFWTDVKVSEDMTPEDKLFMVYLLTNPHTTQLGVYEITPKMIAFEIGLSIESARALLERFEN
HHKLIKYNKLTREIAIKNWGKYNLNRGGKPIEDCLKREIDKVKDLSLIKFILEHTDHAALKRKINLYAGFD
DTSHDTLAIRDQEEEKEQKKEQKEEQEEKEKEKEKQKEEEKEPEEEKTRIKSKASLKSDAKSNPIPYKDIL
DYLNEKANKNFNPKAEGHRKLIRARWNEGYKLEDFKKVIDNKTTQWFGKKSFDGKPLDQFLRPSTLFAQKH
FDNYLNETVNISNQQHGDQIVIPGFRGEMPF

Orf34 (SEQ ID NO:72)
VKKIQDSFEKLTKLKFADEQCDKHTFNKHGKEVIKLVRKMIDDAGTVYCPRCMVEEQNSVLFQQANNHYKK
INRERKKNVLFQHSIIENQSITESRLSTYKTDCQETKENKEKAIKILERIKNGEFLNVYIAGIQGVGKSHL
AYAMLYELVKHYWVISDGEKLNDEHAFKNMKSCLFVEIEKLIRLIQHSFRNIESKYTMDYCISLMVDVDFL
VIDDLGAESGSMNRNGEASDFVHKILYGVTNGRQGANKTTITTSNLSSAQLFQKYDPKLASRLLNGVSKDE
TIVFKTTTDKRIVNLDIGF

Orf35 (SEQ ID NO:74)
MKEVKGKNTKLMEEFDVLLRQLLIKSKTDERVKNFLDDLFEMLSDNKLQSDIDFKTALNKLREKHFPKFDK
GESKND

Orf36 (SEQ ID NO:76)
MTKEKGQAKEVVNVRGMSDDEFIEKYGRLVHHCVWKRYAKKKASIERDTGLDIEDLTQFGMIGLIKARDNF
DLEFGCAFSTYAVPKIIGEIGRAIRDNQKIKVQRTVYGVKGKILNQQLADKEPEEIADILDESVSLVKTAL
EYQPSTDSLNKVVYASGANEELTLERMIEDTKTEDIEETTINRAVIREFKAALPPKEYIVLDMRLQNMTQQ
NIANQMGYSQVQISRILAKINQRAAQFGKEGGLQD

Orf37 (SEQ ID NO:78)
LSVTKGVCIDVDHSDLLHEKVEYFLFPAKPSHYYVSRFNRKGAHFGCYQAERFQITEKEVWTPEPQPNLPE
LNTSLFYRAQLIWRKKGYKDKPLKDYIVQPRGKHCYFWHDRERKKFCGCFPLHWFTDFVPVQSHHIEEKTR
EEVKLLQRPDGQLAFF

Orf38 (SEQ ID NO:80)
MDIKKLFAMQNILDKRVLESKNLSRGEVFEFRILAFLDELGECMKEWRVFKFWSDDRKPRTSIPTGEIIVL
DDGYEVEVYKNPLLEEYVDGLHFAIGLCIDLKTEINFPASMRCETVTEQFFELYHLAIRLKEEPTAFRADV
LLSHYLGLGELLCFSLEEIGHEYIEKNKINHERQSNGY

Orf39 (spore surface antigen; replaces 39 in γ phage) (SEQ ID NO:82)
MDCFKKGKFIPFPCALPIPEAGPTGPTGPPGSAGGSTGPTGPTGPQGLQGIQGVQGNPGTTGPQGIQGIQ
GIPGVSGPIGPIGPTGIQGVQGIQGFPGIPGPMGPIGLTGPTGIQGIQGIQGVQGIQGIQGDVGPTGPQG
IPGIPGLTGPTGSQGVTGVTGPSGGPPGPTGATGPTGPAGGPPGPTGPTGPAGGPTGLTGPTGPTGPTGI
QGIQGVQGTQGIPGPTGPQGIQGVQGLQGIPGIPGSMGPTGLTGPTGLQGIQGIQGNPGPTGPFGPTGPT
GLQGIQGLQGIQGIPGSNRTSRNPRSNRTC

FIGURE 2B CONTINUED

Orf40 (replaces 40 in γ phage) (SEQ ID NO:84)
LLAHFPQKLFFFGGTNSGFQRIAGSPGADSQDIPYVLGGAGSVVGLSASTSINNLPIGVYTIRVCKNVPIN
LAAPGPGQVISTIILTTTAVISGTIILTINPSDIGAQPVRVFNPNLVIAPATVAWSSTIPGDIVARGDAMS
LFITPGITQNAVYTVFLHTGN Orf41 (replaces 41 in γ phage) (SEQ ID NO:86)
MQHIPRYYYQSQSPMDSIWNNNNWIYAWNPYYYNYNNNAWNRNRNPYCENVRLTDYGARPFVLNINQATKQ
NNTYRTAIWTGKNLQVTLMSINVGDDIGLEVHPTTDQFIRIEEGQGLVQMGDNKDKLDFQEMVYDDYAIMI
PAGKWHNVINTGNTPLKIYAIYAPPEHPYGTVHETKAIAMSTEANRYYY Orf42 (SEQ ID NO:88)
MIVKATIKLELDDSQKNWVSYVREQGGEEAVFHYLEEEVQKKIELADFVEMKYKNK Orf43 (SEQ ID NO:90)
MDMSLVGNLKELQEKAIDEKVLEFAEEMEIVITKSAASGYSGHRYKIHNENPNRHMMCSKIFIEKLQELLD
GVKVEFKEEEKKNILGGSYYEHYIRFKWND Orf44 (SEQ ID NO:92)
MTNFLLKILFWRKGVERMKTFNVTFTELKIYEAVIEAESAEKIIDVIKHLKRTEDDLVDKGVIINEVSEIN
VSKEQKFE Orf45 (SEQ ID NO:94)
VNHHLFNWLRDYQKLEEDIAYLEYNLDKTKAELRRWVSGDLREVRLTAESEGAKVENRIEAIEYELAHKMN
DMYKLKKLISKFRGLENQILKLKYVDGMTLEEIAEAVNYSSSHIKKKHAELVRLIKFVEREGVI Orf46 (SEQ ID NO:96)
MDVQELSRRLENLEHKVLQVETKADVLNRTAIQKGDKIKVVYPHLGIQGEYLVEKIDNGVLELVAEETMKK
IQE Orf47 (SEQ ID NO:98)
LKKLSKQELAAVMTHCISTLGEQIVNEHINPQKLAQASALHNDLFDNTTPKERREATISLLGKAIDEFLES
KE Orf48 (SEQ ID NO:100)
MGKGYFNKAVCLVCGHQDRVNHPSKKEYQEVTVCPECNGAFVDVWKLGKYKRNTQSNEEPLLTITLTDIDA
KPIVHYKGEQIDRKLRVTFDWESQSIDKINRTYIHIEHVPADNKRLNTETIQHNHPIANKEQV Orf49 (SEQ ID NO:102)
MNGFNKIVNDMQNEQVGNAMLDFALAAKMMFAAFTQFKEAGFNEEQSFELTREILIDSLSKNQ Orf50 (SEQ ID NO:104)
MQVYCSECDKSYDMQPQVTQLPNRIEKCFFICPHCNHEHIAAYVNDKIRKYQADIAKCHERINKKNLAIED
EMKRLRKRFDRRK Orf51 (SEQ ID NO:106)
MEGQELTLEKKDSIYLRPRYPHKIDASKIKSLKDVIKILGLMDIRLDDKAVIGLEHLIEKEEE

FIGURE 2B CONTINUED

Orf52 (SEQ ID NO:108)
LKRRKNKMANNKLIIEVTADTTEALEGIKEVTEAANECADALDKLEKIMDKFTNRSDTVELYCEGKLLSKS
TVNHTADSIQCRIIKGEELGGSER

Orf53 (SEQ ID NO:109)
MKKPLRPCCEFHCYNLTRERYCEEHRYKEKETQQDKNRYYDRFKRDKESTAFYRSKAWERLREQALMRDKG
LCLHCKNNRKIKVADMVDHIIPIKVDPSL
KLKLENLQSLCNPCHNRKTAEDKKKYG a b c

SEQUENCE LISTING

```
<160> NUMBER OF SEQ ID NOS: 109

<210> SEQ ID NO 1
<211> LENGTH: 37373
<212> TYPE: DNA
<213> ORGANISM: Bacillus anthracis

<400> SEQUENCE: 1

ctcaacttcg cagaaaaatc cgtttttgca tattttttta aggggggtgta atcatggctg      60

gaagaaataa acaaccactc tctgttatac agggaaaagg tagatcaaat cacattacaa     120

aaagtgagaa aaacagacga gaaaaacaag aagaagcatt gcgggggcat actgataaaa     180

ttgaagctcc ttcttatttg actgcagcac aaaaaaagga attcgatact ttagctgctg     240

aattagtcag attgaaaatt ttcagtaact tagatgttga cagtttagca aggtacgttg     300

attctaaaga ccaatatata aaaatggttc gtctgctaag aaaaacaaaa ccttcagatg     360

actttaaatt gtattctcaa atgcaaagaa gtaaaaatct tttattcaat gaatgccgtt     420

cttcagctag tgatttaggt ttgaccatta catcccgctt aaaattagtt attccagaag     480

tagatacttc acaacaaaag caaagtgaag cgcaaaagcg ttttggtgat cgtatatgaa     540

ctggataatg gaacgggttt ttgcatattg cgaggacatt ttaaacggca agataaatag     600

ttgtaaaaaa catcgttggg ccattgaacg atttataagg gattatgagg agtgtcaaag     660

tgaagacagt cctttttatt ttgatggaga gatagcggag gatttttact ggtttgcaaa     720

ggaatttaag cacgttgaag ggattttggc aggtgaatcc gtagaattaa ctgattttca     780

attgtttcta gcggctaata ttttcggatt caaaaagaaa ataaatggag caaggcgatt     840

tagaaaggtt tttattcagt tagcgcgtaa aaatgctaaa tctcagtttc ttgctattgt     900

agcagctttt tgtacatttc ttggagacga aaaacaacgg gcttatattg ctggatggac     960

aagagaccaa tcatctgaag tttatgaagc tgtaaaaaca gggattagtt ctagtgaatt    1020

gttagaaggt aaatggaaag aggcttatag taccattgaa atatttaaga atggttcagt    1080

tgtcgttcca ctttcaaaag aagctagaaa aactggtgat ggtaaaaacc cgtctcttgg    1140

aattgtcgat gaatatcatg cacatgaaac tgatgaaatt tatgacgttt tatcgtctgg    1200

tatggtggca aggaaagagc cgttaatgtt tatcataaca acagctggtt tcgacttatc    1260

aagaccttgt tatagagagt atgagtatgt cagtgacatc ttagacccgt caaaaaatgt    1320

agaaaacgat gattatttcg ttatgatctg tgaattggaa aagaacgatg atatcaaaga    1380

tgagtcgaat tggataaaag caaacccaat cgtagctaca tatgaagaag gtttggaagg    1440

tatacgttca gatttgaagg ttgctcttga tagacctgaa aagatgaggg ctttttttaac    1500
```

-continued

```
caaaaacatg aatatttggg tcgataaaaa ggacaacgga tacatggata tgtcaaaatg   1560
gcaaaaatgc gaagtagata cctttgattt ttcaggtgcg actctttgga taggtggcga   1620
cttatcaatg acaacagatt taactagtgt cggttgggtt ggaatggacg atgaaggtga   1680
ttttattgtt ggacaacatt catttatgcc tgaagcacgt ttgaaagaaa agatggccat   1740
agataaggtg cgttatgatt tatgggccga acaagggtat ttaactttaa cgcctggtga   1800
aatggttgat tatacaattg ttgagtcttg gatagaaaac ttttcaaaag acaaagaaat   1860
tcaagagttt gattacgata aatggaatgc gttacatcta gcacaaaatt tagagaataa   1920
agggttcgtt tgtgtagaaa tccctcaaag gattgctaat ttatccattc cgactaaaaa   1980
ttttcgagaa aaagtatacg aaaagaaagt taaacataat ggagatccag tccttttttg   2040
ggcgcttaat aatgctgttg ttaaaatgga tgatcaggaa aacattatga tttcgaaaaa   2100
aataagtaaa aatcgtattg atccagcagc agcggtctta aatgcatttt ctagggctat   2160
gtatggagca agtgtcaggt ttgatgtatc tgaatttgca aataaagact ttctaggcaa   2220
gttatggaac tagggagggg gtgaacatgt gaagatagtg gattctgtta aaaagttctt   2280
taattttgaa aaacgccaaa cgtcgcaggt aatagagttg aataaagacg atgaaaaatt   2340
attagaatgg ctagggattt ctccaagtac tattagcgtt aaaggaaaaa atgctttaaa   2400
agttgctaca gtctttgctt gtatcaaaat actatctgaa tccgtatcaa agttaccgtt   2460
gaaaatttat caggaagatg aatatggaat ccaacgcggt acaaagcatt atctcaacaa   2520
tttactgaga ctaaggccta acccgtatat gtccagtatg aactttttcg gatcattaga   2580
agctcaaaaa aatttatatg gcaatagcta cgctaacata gagtttgata gaaaaggtaa   2640
agtccaagcg ttatggccga tagatgcttc taaagtgaca gtatacattg atgacgttgg   2700
tttattaaat tccaaaacta aaatgtggta tgtagtaaat acgggtggac aacaaagagt   2760
gttaaagcca gaagagatac tgcactttaa aaacggaata actcttgatg gtcttgtcgg   2820
tgttcctaca atggaatatt taaagtctac attagaaaat tcagcttcag ctgataaatt   2880
cataaataat ttttacaaac aagggttaca ggtaaaggga ttagttcaat atgtcggtga   2940
tttaaatgaa gatgcgaaaa aggttttccg agaaaatttc gaatcaatgt ctagcggtct   3000
tcaaaatagc catcgtattg cattaatgcc agtaggatat caatttcaac ctatttcatt   3060
aaatatgtca gatgctcaat ttctcgaaaa taccgaactt actattaggc aaatcgctac   3120
tgcattcggc attaaaatgc atcaattaaa tgatttgagt aaagcgactt taaataatat   3180
tgagcagcag caacaacaat tctataccga tacattacaa gcgactttaa caatgtatga   3240
gcaagaaatg acgtataagc tatttttaga cagtgagttg gataaggggt tttattcaaa   3300
attcaatgta gacgctattt taagagcgga tatcaaaacg agatatgaag cttacagaac   3360
gggtattcaa ggcggtttcc ttaaacctaa cgaagctaga agtaaagaag atttaccacc   3420
agaagctggt ggggatcgtt tacttgttaa tggaaatatg ttgccgattg atatggctgg   3480
acaggcatat ttgaagggag gtgatactaa tggagaagtc agcaaagaag gaaatgaagg   3540
aaattagagc tttgccaatg actattgaag tccgtgaagt taatgaggac gagggaaaac   3600
gaacaatttc gggatcgata aaatataaca atgaaagtgc cgaaatgcgt gactggtggg   3660
gcgatacttt cgtagaagag attgctgagg gagcttttga tgaaagttta aaagttcgtg   3720
atgttgtagg tttatggtct cacgacacat ctcaagtatt aggaaatact aaaagtaaaa   3780
ctttacgaat cgaaaatgac aagaaagaat tacgatttga attagatatt cctaatacaa   3840
ctgttgggaa tgacgcatgg gaattaatta agcgtggaga tgttgatgga gtttcttttg   3900
```

-continued

```
ggatgaaggt tacaaaagac aaatggtcat cggaagaacg tgaaaatgga aagctttata   3960
agcgttcgat tttaaatgct gaactatatg aaatatcacc ggttgcattc cctgcatatc   4020
caacgaatga agtaagtgta cgttcattgg atgattttaa agctggagaa aagcgagtag   4080
ctgatgagtt taggaaaaga aaactacaaa tcgaactaga gcttatataa ggctcttttt   4140
ttattgataa atttaaggag tgatttgaat gtcaaaagaa ttacgtgaat tattagctaa   4200
gttagaaggg aaaaaggaag aagtacgctc tcttatggga gaagataaag tggcagaagc   4260
agaacaaatg atggaagaag tgcgatcact tcagaaaaaa attgatttac aacgctcatt   4320
agatgaagca gaaacggaag aacgaaataa tggaagagaa gttgaaacac gtaatgtaga   4380
tggtgaaatg gaataccgcg atgtgtttat gaaagcatta cgcaataaac cattaaatgc   4440
tgaagaacgt gaatttcttg aggatgattt agaacaacgt gccatgtcag gattaactgg   4500
ggaagatgga ggacttgtca tccctcaaga tattcaaacg caaatcaatg aattagctcg   4560
ttcatttgat gcgcttgagc aatatgtaac tgttgaacca gtgcgtacac gttcaggatc   4620
acgagtatta gagaaaaatt cagatatgat tccgtttgct gaaatcactg aaatgggtga   4680
aattccagaa actgataatc cgaaattttc aaatgtacaa tatgcagtga aggacagagc   4740
aggtatttta ccgttatctc gttcattact tcaagatagt gatcaaaaca tcctaaagta   4800
tgtgactaaa tggctaggta agaaatctaa agttacacgt aatgtgttaa tcttgggcgt   4860
aattgaaaag ttaacaaaac aagcaatcaa atctctggat gatattaaag atgtattaaa   4920
tgttaaatta gacccagcga tttctccgaa tgcgatttta cttacaaacc aagatggatt   4980
taattattta gacaaattaa aagataaaga cggaaaatat attttacagt cagatccaac   5040
gcaaaaaaac aaaaaactat ttgctggtac taatccagtc gttgttgttt cgaatcgttt   5100
cttaaaatca aagggaacta cagctaaaaa agcgccactt attattggtg atttaaaaga   5160
agctattgtt ttatttaaac gtgaagatat ggaactggct tctacagatg taggtggtaa   5220
agcattcact cgtaatacat tagatttacg cgcaattcaa cgtgatgatg tgcaaatgtg   5280
ggataatgaa gcagcagttt acggagaaat cgatttaagc gctcctgttg aacaacctca   5340
agggtaaact aaggaggcat ttgaatgctt gttaccttag aagaagctaa agaatggatt   5400
cgagtggacg gagacgatga cccaactatc actatgttaa ttaaagcggc tgaattatat   5460
atttacaaag caactggcaa aacatttact caaacaaatg aagatgctaa gttgctttgt   5520
ttatttctgg tggctgattg gtacggaaat cgactacttg taggtgaaaa agccagtgaa   5580
aaaatcagaa ccattgttca gagtatgata ttacagctcc aatatgcttc agagcctcag   5640
gaggaaagaa aatgaatcct gcaaaattag ataaacggct tacatttcaa gtaaaagatg   5700
aaaatgcaaa agggcctgac ggtgatccga tagatggata taaagatgct tttaccgtat   5760
ggggctcttt tgtttattta aagggaagga aatactttga ggcagcagct gctaatagtg   5820
aggttcaagg agaaacagaa atcagaaatc gggatgatgt aagtgcagat atgaaaatta   5880
agtacaaaaa cgtgatttat gatattgttt ccgttattcc aactcaagat catactttat   5940
taatcatgtg gaaacgtggt gaaatgaatg gctgatggta tagatttaga tttattagga   6000
tttgatcgtt tagttactga attagaccaa atggggttac ggggagagaa aattgaagat   6060
aaagctcttg cagctggtgg tgaacctatt cgtaaagcca ttgcagaacg agcgccaaga   6120
agcccaagcc ccaaaaaacg atctaaaagt gaaccgtggc gtacagggca acatggtgca   6180
gaccagataa aagtaacaaa agctaaactt gaaggtggaa taaaaacagt aaaaataggt   6240
```

-continued

```
cttaataaag cggatcgttc cccgtggttc tatttaaagt tccatgaatg gggtacatcc   6300
aaaatgccag cacatccatt tatagagccg ggttttaatg cttcaaaagc ggaagctgta   6360
cgtgctatga cagatatttt aaagaacgaa atgaggttgg atttgtgata aatttaagac   6420
ctgatatttt acaagctctt gagaatgatc aagagcttgt ttcattgttg ggtgggaaac   6480
gaatttatta ccgtaaagca aagaaggcag aagagtttcc gcgaattacg tattttgaat   6540
tagacaatag gccagatgga tttgcagata atcaagagat tgaaagtgaa atcttgtttc   6600
aagttgatgt ttgggcaaag agtagtacaa cagcaatcca tcaaaaagtg aatgaaatca   6660
tgaaaagaat tggtttctca cgctatgcgg ttgctgattt atatgaagag gatacacaaa   6720
tatttcatta tgcgatgaga ttcgcaaaag gagtggaatt ataaatggct ggagaagttg   6780
taagaattag ttcaacggtt ggtgtagaca accttgtata tgcgaaagtt ttacaagatg   6840
attcgtctgc tattaaatat acagatgtaa agaaaatgga aggtgctgta aaggttaaat   6900
taactaaaaa agtagcttct gaggttatgt ggagcgataa cagaaaatca gagattgcag   6960
aatctgatgg cgaaactgaa gtggagattg aggttcgagg actttcactt tctacaaagg   7020
ctgacattga agggtttcca gaagtaaaag atggcgtttt agatgagaaa cgtgaaggtg   7080
agaaaccata tttagctatt ggtttccgat tcttaaaagc taatgataag tatcgatatg   7140
tttggttatt aaaagggaaa ctttcacaag aggaagaaga agctgaaacg aaaaaagaca   7200
aaccgaactt ccaaacaaca aaattgaaag gttcctttat tgaacgtgat tttgatgata   7260
gaacgaaatt tacagcagat gaagatgaac caacgttcac aaaattagtt ggagataatt   7320
ggtttaataa agtatatgaa aaaccagtga cacaaccacc agcaggaaag taagagggag   7380
caaaagctct ctcttttta ttaaatttag gagggaaaaa ctatgaaatt aacattaatg   7440
attaataaag aaaaacaaac ttttaatatg ccagaattta ttccagcccg ccttattcgt   7500
caggctcctg aacttgctga aattccaaac aatcctggtc cagaagatat ggataaaatg   7560
gttcaattcg tagtgaaagt ttatgatggt caatttacat tagatcagta ttgggatggt   7620
gttgatgccc gtaaattctt atcgacaact tcagatgtaa ttaacgcaat tataaatgaa   7680
acagtggaag cagcaggggg tagtactgaa tcaggagaag aagaaaaccc aaacgcatag   7740
agggaggagg gctaacgttc agtgagttta tggacgagct ctacctctct ttattgcgac   7800
aagggtacaa acaccatcac attgataatg agatggatat ttggcattat ttgagactta   7860
atcgaaaaat gcatgaaaac ggaaatgaaa attacgaagg ctccaattca aatgaaatag   7920
aagtgccagc ggaaaacatt atttaacgag ggaggtgaga ctatggcgaa tgaaataaat   7980
aatctagtcg ttagactttc ccttgataac gtaaatttca gacaaggtat ctcgaattca   8040
ggtcgtgcag tcaggacgtt acagaatgaa ttgaaatctg taagtacagg aatgggcggt   8100
tttgctaacg ctagtcagca aacacaagcg aaaatgaata cactcagtag gctcattgat   8160
gcgcaaaaag agaaagttaa agcgttacga caagcctatg atcaaaataa ggctaaatta   8220
ggtgaaaatg atgcagcaac ccagcgatat gcttcgcaag ttaataaggc agttgctgat   8280
ttaaatagat ttgaaaatga attaaagcaa gtaaaccgtc aagctgaaca aaaagggatg   8340
gataagttaa acaactcttt aaaatcccta caagctgaat ttcagtctat tacaacaggt   8400
atgggcggtt tttctaatgc gacagaacaa acaagggcta aagtagatgt tttatcccgt   8460
atggtagata aacaaaaaga gaagattagg gaacttcaac aagcctataa tcgtgctaaa   8520
acagaagaag gcgaagcgag tcaatcagca caaagatacg ctgaacaaat tcatcgggca   8580
acagctgaac tgaatcgatt tgaaactgga ttacagcagt caaatcgtga attagaacag   8640
```

-continued

```
caagggaatc gcctattgaa cttcggaaat cgcatggaga cattaggtaa tcatttgcaa   8700
aatgccggaa tgcagatcgg catggtattt ggtggtatga cttacgcaat aggtcggggc   8760
ttaaaatcag caatcactga atcaatgaat tttgagcaac agatggccaa tgtaaaagct   8820
gtttctggat ctactggagc agaaatgaaa aagttaagtg aattggctgt taatatggga   8880
gaaacaacaa aatactccag tgttcaagca ggtcaaggta tcgaggaatt aataaaggct   8940
ggtgttagct tacaagatat tattaacggc ggattggcag gtgcccttaa cttagcgacg   9000
gcaggggaat tagagttagg tgaagcagcc gaaattgctt ccacagctct gaatgcattt   9060
aaagcagacc atctttcagt tgcggatgca gccaatattt tatctggtgc agccaatgct   9120
tccgcaactg atgtaagaga gttaaaatat ggactttcag cttcatcagc agtagcagcg   9180
ggagccggaa tgacgtttaa ggatacagct acaactttag cggtatttgc acaaaatggt   9240
cttaagggat cagatgcagg tacatcttta aaaacaatgt taatgaggtt aaatccttca   9300
acaaaagaag catataacaa aatgagagat ttaggactta ttacttataa tgcacaggca   9360
ggttttgatt tcttagttaa aaacggtatt caaccagctt ccagaaatgt aggggatata   9420
gaagtagctt tagaacaata tgtaatgaaa acagaaggtg taacgaaatg gaatgataaa   9480
tgtgatacaa cgtttcgcga attagcaaca agttcggcat ttttatcatc aaaattctat   9540
gatcaacagg ggcatattca aagtctagaa aatatttcag gtacacttca tgaatcgatg   9600
aaagatttaa cagaccaaca acgaagtatg gctctggaaa cattatttgg ttccgatgct   9660
gtacgtggtg cgactatctt gtttaaagaa ggcgccaaag gtgtcaatga aatgtgggat   9720
tccatgtcaa aggttacagc agctgatgta gcagcgacca aaattgatac tttaaaggga   9780
cgacttacat tactagattc agcgttttcc acaatgaaaa agacaattgg tgatgcacta   9840
gctccagtag ttagtgtttt tgttgctggt ttacaaaaac ttgttgatgg attcaactct   9900
ttacctggac cagtacaaaa ggcaatagca attacaggtg gtatcgtcct tgctttaaca   9960
gctgtggcta cagcaatagg tgtggtttta gcagcgtttg gaatgattgc ttcaggaatt  10020
ggttctttat ctcttgcttt agcatcagtc ggtgggattg ctggaattgc ggctggagca  10080
gttggattct taggaagcgc gcttgcggtt ttaacagggc caattggtct agtagcagcg  10140
gctcttatcg gaactggtgt tgttgcatat aaagcatatc aaaaagcgac tgaagacagt  10200
atcgcatcag tagaccgctt tgctacaaat acagaaggga aagtaagctc ctcaacaaag  10260
aaggttcttg gcgagtattt caagctgtcc gatggtatta gacaaaagtt aactgaaatt  10320
agattgaacc atgaagtaat aacagaagaa cagtcgcaaa agttgattgg tcaatatgac  10380
aaattagcta atacaatcat tgaaaaaacc aacgcaaggc agcaaaaaga aattgaaggg  10440
cttaaaaagt tctttgctga ttcgtatgta ttaaccgctg aagaagagaa caaacgaatc  10500
gaacagttaa atcagcacta tgaacaagaa aagctaaaaa cgcaagaaaa agaaaataaa  10560
attaaagaga tcttacaaac agcggctaga gaaaacagag aattaacgac atccgaacgt  10620
atctctttac aagcattgca ggatgaaatg gacagagttg ctgttgagca tatgtctaaa  10680
aatcaaatgg agcagaaggt tattcttgaa aatatgcgtg tgcaggctag tgaaatttca  10740
gctagacagg cagcggaagt tgtagagaat agcgccaaag caagagataa agttattgaa  10800
gatgcgaaaa agacccgtga tgaaaaaatt gcagaggcga ttcgccaacg tgatgaaaat  10860
aaaacaatca ctgctgatga agcgaacgca atcattgcag aggcaaaacg tcaatatgat  10920
agtacagttt ctacagctcg agataaacat aaagaaattg tgagtgaagc aaaagcgcaa  10980
```

-continued

```
gctggtgaac atgcaaatca ggtagattgg gaaactggcc aagtaaaatc gaaatatcaa  11040
gctatgaaag acgatgttat tcgaaaaatg aaagaaatgt ggtcggacgt taccaacaaa  11100
tatgaagata tgaaaaactc tgcaagcaac aaagtagagg agataaaaaa tacagtttca  11160
agaaaatttg aagagcagaa aaaagctgtt actgataaga tgtcagaaat aaaaagtagt  11220
attgaagata agtggaatac agttgaaaag tttttcagtt ctataaattt acgttccatc  11280
ggtaaatcaa tcatagaagg gcttggcaag ggaatagatg acgcttcagg aggtctgttt  11340
agtaaggctg cggaaattgc aagtgatatt aagaagacta tttctggagc attagaaatt  11400
aacagtccgt ctaaagtgat gattccagtc ggtagcgcag ttccagaagg tgttggggtt  11460
ggtatggata agggaaaacg atttgttgtg gatgcagcaa aaaatgtagt cggaactgtt  11520
aagaaacaaa tggggaatat gccatctgtt tttgattttg gattccaaac aaatcaatat  11580
agtatcccgc aaaatacatt tagcgatttc agtggatata tgcaaccgca attatcttat  11640
aacaatccat ctatggcaaa aacaatattc ccaaatagac caggtggaga acaagaactg  11700
aatttaaccg taaacatgac taatgtttta gatggaaaag agcttgcaaa cggaagttac  11760
acctatacta caaaacttca aaatcgtgaa caaaaaagaa gagcggaatt ttaagggtgg  11820
tgagcacgtt ggggaaactt agttttactt ttaataatat tagaaaagat tatattcaaa  11880
tgctagttgg aagaaaacgt ccttcatggg ctccagtaaa aagaagatta gtaagagtcc  11940
ctcatcgcgc aggggctctt ttacttaata cagaaacgga ggaacgtcgt attgacgttc  12000
ctcttgttat taaagcgaaa aaagatatgg cagatttaca aaagttaaaa gaagatttag  12060
cggattggtt atatacagag caacccgctg aacttatttt tgatgatgag ttagacagga  12120
cttatttagc attaattgat ggttctgtcg atttggatga aatagtcaat agaggtagag  12180
gtgttattac ttttgtttgt ccaatgccgt ataaattagg gaaaacaaat actcacaaat  12240
ttacgcaaga gtggtctaca gaaacaactt cttattttac taataaagga agtgtagaag  12300
ctccagcgtt aattgaaatg acggtgaaaa aaccaagtac ctttttagat gtatggtttg  12360
gagagtatcc gaataatcgt gattatttca gaataggcta ccctctgact gtggaagaaa  12420
ccacggtaca agaacgagaa agagttatgt gggatgaaat ggccactcct ataggatgga  12480
cacccgttac tggacaattc gatgatatga aaggaacagg gagttttaaa tcgcgtggtg  12540
gttatgcgct gtattgtgaa gattacggaa aagatgtagg attctacggt gctatagcca  12600
agaaaaacat tccgggcggc ccattacaag actttgaaat ggaggcatgg atgactttaa  12660
agtctaaaaa tataggtgaa atgggtcgtg ttgaagttct tcttctagat gaggctagta  12720
atgtggtagc ccgcatcaat atgaatgatc tatatgcaac tgccgaaatt acaagggcac  12780
atatgaaaat tggaaatagc ggaacaccca atagttttcg aaaattagtt gatacaagtg  12840
ggtattattc gaatacattt aaccaatttc gagggcgttt gcgtatcgct aggcggggga  12900
aggtgtggtc tgtatatgtg gctaagttta tagatggtac agaaaaagat ggcgcttcgc  12960
ttgtagaacg ttggattgat gaaacaggaa atccaatgac agaacgtaaa attgcacaag  13020
ttatgattgc gatttgcaag tgggataatc accagcctgt taatgaaata caaattgatg  13080
atttgaaatt ttggaaggta aacaaagttc catctaatgc acaaccatat atctttgata  13140
ctggagataa aattgttatc gatactgaga aaagtcttgt cacaatcaac gggaagaatg  13200
caatcaatat aaaagaaatc tttagtaatt ttcctgtcat aatacgtggt gacaatcgta  13260
tcgatattat gccgccagat gtaaacgcaa caatcagtta tagggagaga tatagatgag  13320
aacaccaagc gggattttgc atgttgtgga ttttaaaaca gatcaaatcg tcgcagctat  13380
```

-continued

```
ccaaccagag gactattggg atgacaaacg gcattgggaa cttaaaaata atgttgacat  13440
gttggatttc accgcatttg atggaacaga ccatgcagtt accttacaac aacagaatct  13500
tgttttgaaa gaagttcgcg atggaagaat cgtaccatat gttattacag agactgaaaa  13560
aaattccgat acacgatcta ttaccacata tgcttcagga gcttggattc aaattgcgaa  13620
atcagggatt ataaaaccac aacggataga gagtaagacg gttaatgagt ttatggattt  13680
agcactctta ggtatgaagt ggaaacgcgg aattactgaa tatgctggat ttcatacaat  13740
gaccatcgat gaatatattg acccactcac ttttttaaag aagattgcat ctttatttaa  13800
actggaaatt cgatatcgtg ttgagattaa aggttcaaga atcatcggtt ggtatgtaga  13860
tatgattcaa aaacgtggtc atgatacagg caaagaaata gaattaggaa aagatttagt  13920
cggtgttacg cgaattgaac atacacgtaa tatttgctct gctttagttg gatttgtaaa  13980
aggtgaaggt gacaaagtaa tcactattga aagcattaat aaaggtctac cctatatcgt  14040
agatgcagat gcgtttcaaa gatggaatga acacggacaa cataaattcg gtttttatac  14100
accagaaaca gaagaattag acatgactcc aaaacgttta ctgacgctta tggaaataga  14160
attgaaaaag cgtgtcaact cttcaatttc ttatgaagtg gaagcacaat ctattggtcg  14220
tattttcggt ctagaacacg aattaattaa cgaaggcgac acgattaaaa ttaaagatac  14280
agggtttaca ccagaattat atcttgaagc gcgagtaata gctggggatg aatcttttac  14340
agattcaacg caagataaat atgaattcgg agattatcgt gagatagtta atcaaaatga  14400
ggaattaaga aaaatttata atagaatcct tagttcgctt ggtaataaac aagaaatgat  14460
agatcagcta gacagattag ttcaagaagc taacgaaacc gctagtaatg caaagaagga  14520
gtcagaagca gcaaaaacac tagctgaaaa agtacaagaa aatattaaaa ataataccgt  14580
tgaaattata gaatctaaga atccaccgac aacaggtctt aaaccattta aaacgctttg  14640
gcgtgatatt agtatcggaa agcctggtat tttaaaaata tggacaggta cagcgtggga  14700
atcggttgta cctgatgttg aatctgtaaa aaaagaaaca ttagatcagg ttaataaaga  14760
tatcgcaacc acaaaaacag agttaaatca aaaggttcaa gaagcccaga accaagcgac  14820
tggtcaattc aatgaagtga aagagagttt acaaggcgtt agtcgtacga tttctaatgt  14880
tgagaacaaa caaggtgaaa tcgataagaa gattactaag tttgaacaag attcaagtgg  14940
atttaaaact tcaattgaat cgttaacgaa aaaagatact gaaattagta ataaattaaa  15000
tacagttgag tctactgtgg aaggtacgaa aaagacgata tctgaggtac agcaaacaac  15060
taatgattta aagaaaaaaa ctactgaaat agaagagaag gctggaaaaa tcaccgaaaa  15120
acttacaagt ttagagacaa gagaagttaa tgttcgaaac tatgtaatta actctgattt  15180
ttcgaatgtt acaaattctt ggattggaat tactaatgca actcttttta aatttgtaga  15240
tgtgaatatt tcggaagcct ccgctattaa gaaaggttta caaataacaa gtaataaagc  15300
ttttgtttat cagaagttac ccgcagacgt gtttaaaaag aagaagggga tagcttcttg  15360
ttatataaat gtatcaagtt ttacacctgg tacagattat ccacgtttat atatgagatt  15420
cacctatgac caaaacggaa cagaaaaaca atattatgcc attttaaaac aacaagaagt  15480
aactaatgga tggattagga tttctatacc atttgataca actggatata caggtgaatt  15540
aaaagaagta cgtgtaaata tagctaccgc tgacacaact actatcgatg caacgttcac  15600
tggaataatg gttacattcg gtgacttaat tgaatcttgg aatctcgctc cagaagatgg  15660
agtaacacaa ggtgtttttc aatctaaaac aaccgagatt gaaaaaagtg tggatggtgt  15720
```

-continued

```
aaaaactact gtaacaaatg ttcaaaatag ccaagctgga tttgaaaagc gcatgtctaa  15780
tgtggaacaa acagcaactg gattatcttc taccgtaagt aatttaaaca atgtagtatc  15840
cgatcaagga aaaaagctta ctgaagcaaa tacaaaactc gaacagcaag caaccgcgat  15900
tggagcaaaa gttgagctta aacaagtaga ggattatgtt gctgggttta agattcctga  15960
gttgaaacaa acagttgata aaaataaaca agatttatta gatgaattag ccaataagct  16020
tgcaactgaa caatttaacc agaagatgac tctgattgat aaccgtttca ctattaatga  16080
acagggtatc aatgccgcag caaaaaagac agaagtatat acaaagacgc aagcagatgg  16140
acaatttgct acagattctt atgtaagaga tatggagtcg cgcctgcagc taacagaaaa  16200
gggtgttagc atatctgtaa aagaaaatga tgtaatcgca gccattaaca tgagtaaaga  16260
aaacattaag ttaaatgctg cacgaataga tttagttggt aaagttaatg cggagtggat  16320
taaagctgga ttgctgagcg gttgccaaat tagaacatca aatacggata actatgttag  16380
tttagatgat caatttatac gtctctatga aagaggagtt gctagagcat ttctggggca  16440
ttacagaaga tcagatggtg cagtacaacc gactttcatc ttaggttcag atgaaaagac  16500
taacgctccg gaaggtactt tgtttatgtc tcaagcaggt gcaggatggt caggggctta  16560
tgcgagcatt ggtattagca atggcatagt tgatggtgca gtccaaaagt ctgtgtattg  16620
ggagttgcaa agaaacggac taagtgttct aaacgctaat gattaccatg tttttacgc  16680
tggaaatgga aattggtatt tcagaagagg gaaaccaggg ttgtatcaaa cttcgttagt  16740
cgttgaagat aatagtacag attctgattt aagattacct aatgtaacta tacgtaatag  16800
ccgtgcagca ggatatacag gagttattca attgaaatcc cctgttactc aaaatggatg  16860
gggtgctgtt caagggaatt ttatgactcc ttcattacgg gagtataaat ctaatatccg  16920
tgatatttct ttttccgcct tagaaaaaat tagaagtctt aaaattagac aatttaatta  16980
taagaatgct gtaaacgaac tataccggat gagagaagag aaaagtccca atgatccacc  17040
attgacaaca gaagatatta aaacatacta cggtttaatc gtagatgaat gtgatgaaat  17100
gtttgtggat gaaagtggga aaggaattca tttgtactca tacgcatcca ttggaattaa  17160
aggtttacaa gaagttgatg caacagtaca ggaacaggag gtagaaatag caaatctaaa  17220
atcacaaata gctagtcaag aagatcggat agcacgatta gaagaattat tactacaaca  17280
attaataaat aagaaaccag agcagccata ggctggtctt tttattttgg ccaaaaagga  17340
gaggaaaaga tggatcgtat tgatgtatta ctaaaagcat ttatagctgc gtttggtggc  17400
ttctgtgggt atttcttggg aggatgggat gcaacattga aaatcttagt gacaatggta  17460
gttattgatt atttaactgg catgattgca gcagggtata acggagaatt aaaaagcaaa  17520
gttggtttca aaggcatcgc caaaaaggtg gtgctttttc ttttggtcgg agcggccgct  17580
caactagact cggcacttgg aagcaacagt gcaatccgtg aagcaacaat tttcttcttc  17640
atgggtaatg aattactttc actcttagaa aatgccgggc gaatgggtat tccactccca  17700
caagcattaa caaatgcagt tgagatttta ggtggtaaac aaaaacaaga agagaaaaaa  17760
ggagatgttc agtaatggaa atccaaaaaa aattagttga tccaagtaag tatggtacaa  17820
agtgtccgta tacaatgaag cctaaatata tcactgttca caacacatat aatgatgctc  17880
cagctgaaaa tgaagtgagt tacatgatta gtaacaataa tgaggtgtcg tttcatattg  17940
cagtagatga caagaaagcg attcaaggta ttccgttgga acgtaatgca tgggcttgcg  18000
gagacggcaa tggttcgggg aatcgtcaat ccatttctgt agaaatctgt tattcaaaat  18060
caggaggaga tagatactat aaagctgagg ataatgctgt tgatgttgta cgacaactta  18120
```

-continued

```
tgtctatgta caatattccg attgaaaatg ttcgaactca tcaatcctgg tcaggtaaat  18180
attgtccgca tagaatgtta gctgagggaa ggtggggagc attcattcag aaggttaaga  18240
atgggaatgt ggcgactact tcaccaacaa aacaaaacat catccaatca ggggctttct  18300
caccgtatga aacccctgat gttatgggag cattaacgtc acttaaaatg acagctgatt  18360
ttatcttaca atcggatgga ttaacttatt ttatttccaa accgacttca gatgcacaac  18420
taaaagcaat gaaagaatac cttgaccgta aaggttggtg gtatgaagtt aaataaaaca  18480
aaagaatagt tttatgaaca aaaataagag ccgtcctgtt gggcggcttt tttttattgc  18540
tcaattactg ttgcactaat tttaggcatt cctgttttat ctttttcgtc gtaggcgcca  18600
tagattgtta ctattgatcc tttagatatt tttaatccgt ttttaagtgt tatttcattt  18660
tcgttcgttt gcactccact ttggacaatt tgaatagtgt acatgccttt gccgtcattt  18720
tcgtttgtgc ttatgacaaa tgaaggtaat gctgaagact taagtaataa atctaccgtt  18780
ccggtagctt taagcctttt tcctttttcg tattgatctc catttgcctt aacaaaacta  18840
acttcttcag catcttgctt tatcttctta tttaactcat cctgagatgt taaatctttt  18900
ttagtttctg gttgagattt gacgttcgtt ttttcacttg attcactttg tttagaagaa  18960
tcacaagctg ttagacctaa caataaggta cttccaatgc aaatacttat aagtttttta  19020
tacattttca ttctcctcct ctatccaaat ttcttccatg tgcaatttta attcctttgc  19080
aattttatag gctgtaagaa aggtaggtag cgtcgtgtta ttaacgagtg aactcattgt  19140
agtttgacta attccaataa gttttgaaaa ctccttttga cgtatttctc tttcagcaaa  19200
aataacacga agtttacatt ttaatcgcac aatatcacct ctttaattat atacaattcg  19260
catatggaaa tgtgtcctcc tttaatttaa tcaacgaaca tttagaaaag tttaaatgga  19320
caggcaatat aactctttct aagtcatata cctatatcaa gaccacgagg aataccaagt  19380
ggaactaagg acatcaagag gggagaggat tacatgcgtt ggcagtataa tcacttgaat  19440
acaactccat atcttcatcc atccaaagaa ttatgttcaa tgtacaatgg atcgagatca  19500
agagcagaga cggaatcaat tttaaatcac atgaaaaatc atgaagttta tgatcgaaaa  19560
gaatataaag gatatttcag tttgtcacag gtattagaag aagatctata tggagaggaa  19620
gaagatgttt taaactggga aattctaatg gattgttatg atgtagttct tacaagaaaa  19680
ggtattgcat ttcgtgaaaa agaagaggag gaacaagcat gactcttgct ggagaagcga  19740
ttattatttg gacggcaaca gggttgtcag tagttgcaat gaaggcagca gaaaaaaatgg  19800
ggaaaagtgt tccacattgg cttccacgtg tcactttgta cacaacactt acaggctcgt  19860
ttctatacct tctacgttat gttctcgttt tatttctatg aaggaatacg atgtggaaac  19920
ttttcattcc ttatgtcata aggagtttag cttgtatgca cgtattcctt gaaacaggga  19980
tatataccct ctataagagg gatataagga gtgattttat gctggagttg ttatcagtac  20040
cattcgcagg tttaattttc gccatagttg gcgaaaggct caaaggaaga gagagtgatc  20100
gaaagaaaat acaagttttt tttgaagtaa gcggaattgc gatacgtaga gaggacaaat  20160
tacagtatcc agtttttctt gaacaaaaag aggatgaccg aagtacaact tatatatatc  20220
ggttgcctgt aggaatgccg agtaaaatta ttcagaaggt cgaggatgtt gtctctgaag  20280
ggctaagtaa acctgtccga attgattatg ataattacaa gctaaatatt cgtgtgtttc  20340
atagggatat accgaaaaaa tggtcatggt ctaaaggttt ggttgcagaa ggaagctggt  20400
gtgttccaat gggccaaagt ttagaaaaac ttatctatca tgattttgat aaaacaccac  20460
```

-continued

```
atatgacact aggtggtctg acacggatgg gaaaaacggt atttttaaaa aatgtagtta  20520
cttctcttac tttagcacaa ccagaacata ttaatttata cattattgat ttaaaagggg  20580
gcttggagtt tgggccgtat aagaatttaa aacaggtagt ttctattgct gaaaagcccg  20640
cagaagcttt tatgatatta actaatatcc tcaagaagat ggaagagaaa atggaatata  20700
tgaaatgtag acattatacg aatgttgtag aaacaaatat caaagagcgt tacttcataa  20760
tagtagacga aggagccgaa ctttgcccag ataaaagtat gaaaaaagaa cagcaaaggt  20820
tattaggagc gtgtcaacaa atgctctctc atatagcgcg cataggtggt gctttaggtt  20880
ttagattgat tttttgtaca cagtacccga caggggatac attaccgcgc caagtaaaac  20940
aaaatagtga tgcgaaatta ggctttagat taccgactca aacagcatca agtgttgtta  21000
tagatgaagc gggattagaa acgataaaaa gcattcccgg acgcgcgatt ttcaaaaccg  21060
atagacttac agaaatacaa gtgccttaca ttagtaatga gatgatgtgg gagcatttaa  21120
aaggatatga ggtggagaaa catgaggatg caaacgcata tgcaaatcaa ccgtcaaatg  21180
gcgatacttg cgacgattag aaagctacag tttgcaacga gaaggcattt aatgagtatt  21240
catgaaatgg gtggaataag aaatgcaaat cgaattctga aagatttatc tatttataca  21300
agtaaggtag tttacaataa agagcatgta tattatttaa accaatcagg acataagttg  21360
tttggcgaag ggaaagttgt acatcatggt aaagttacac acgctctttt acgtaatgaa  21420
gcttggttaa atttatattg tcctgatgat tggcaagtag aaactgaaat taaatatata  21480
aaggataata aaaagaaaaa aataattcca gatgtgaaat ttcgtgatga ggacagaata  21540
cttcatgctg tagaaataga tcgtactcag aaaatgatag tgaacgatga aaaattaaaa  21600
aaatatgagg agttaacgca gatttataaa cagaagcata acgggaaagt gccagttatt  21660
catttcttta caatcacaaa atatagagaa aagaaattag aagaactggc aaataaatat  21720
aatgtgtttg taaaagtata tgtaatcgct actacttaat gatgaaaaaa agagctgatc  21780
attttcgaat gattagctct tttttatgta ttgtattacg tcgtctattt tgtaaatttt  21840
attaattcct ttttctgcag caatggcatt taaagcatca atgatagctt caagcgaatc  21900
aaaacgaaca gcattagcat taccattcac taaatcacta atcgtgttgt atcttacttg  21960
ggattctgta gataatttat ttttagtgat ccccaattca tctaaagaat ttccgagtgt  22020
gaatttcatt ttattctcct ccgcagcact ggttatcttg tactcatttt acaacatcaa  22080
tcgaaattag taaaactttt ttcgttcaac tattgacgtt gaataattag agagttataa  22140
ttcaacttaa aaggaggaac aattatgaat cgagtaaatg attattttgg tttagaaagt  22200
aaatcagatt gcatttggtt ttatggtttc ttcagtatat ctacgatttt atttttaatc  22260
gatatgatta ttgctcttat ataaggaggg gagaaaatgc ttagctcagc aaactatacg  22320
caatataaaa aattacaatc attccgatca gtagaagaga tgaatgaagc gatttgttct  22380
tttttataca aacatacaca tgaattatcc gaatcagcaa taaaagtatt gaaatttcta  22440
gcaaggcact cttgtaaaat cccaggtgtc tctttcttga aggtagggac aattgcggag  22500
gcattaaata taagtgatcg aactgttcgc agggtactaa aagtattaga ggattttgaa  22560
gtagtaacta gacataaaac aattcgaacg gaaggaaaat tacgtggagg gaacggacat  22620
aacgtctatg tccttctaaa aaaatatagt gtcacaccga atgtcctacc gaaaatgtca  22680
cagcgacaag atgaagaaaa ccttacagaa tcaaaggttt cagatacaaa aacggacaag  22740
gaagctaaac tttctgaatc acaccctcta gaagaattga aaagcgaatt aaacgtaaaa  22800
gaaacgtcag caagggaatc taaagaaatc gaattagagg atctagatga aacttttaca  22860
```

-continued

```
ccagaaaatg taccaagcca attcagagat gtggtagctc cattcttcaa atcagcagat  22920
aaaatttata aattgtatca tcgagtatta atagcttata aacgttcaaa aatagacaag  22980
cctattgaac aagtgataaa tcaagccatt caagcattca aagaaactgt cttcgcagaa  23040
aaagcaaata aaattagaag tacttttgaa ggttattttt atagaattgt tgaaagtaaa  23100
tttgtaatgg agagaaggaa agaatgtcga ggattattgt tcgattggtt aaatgaataa  23160
tataaaattg cccacaggga aaaatatata tataatttaa ttatcatatt cttagtaaat  23220
aagtgggtga aaattttgaa atacgctgtt tatgtacgag tttcaacgga tagagatgag  23280
caagtttcat ctgttgaaaa tcagattgat atttgtcgat attggttaga aaaaaacgga  23340
tatgagtggg atccaaatgc agtatatttt gacgatggta tttctggtac agcttggtta  23400
gaacgtcatg cgatgcaact aatattagaa aaagcaagac gaaatgaatt ggatacagtc  23460
gtatttaaat ctatacaccg tttagcaagg gatctaaggg atgccttaga aattaaagaa  23520
attctaatag gtcatgggat acgcttggtt acaattgaag aaaattacga tagtttatat  23580
gaaggtggca atgatattaa attcgaaatg tttgccatgt ttgctgcaca attacctaaa  23640
actatatctg tatctgtttc tgctgcaatg caagctaaag caagaagagg cgagtttatt  23700
ggaaaaccgg gattaggata cgatgtaatt gacaagaaac ttgttatcaa tgaaaaggaa  23760
gctgaaattg taagggaaat ttttgattta tcctataaag gctatggatt taagaaaata  23820
gcgaatatcc taaacgataa aggcacatat acgaagtttg gccagttatg gtcgcataca  23880
actgtaggga agattttaaa gaaccagacg tataaaggga atttggtctt aaatagttat  23940
aaaacagtaa aagtagatgg aaagaagaaa agagtttaca ctccgaaaga gagattaaca  24000
attatagaag accattatcc aacaattgta tcaaaagaat tatggaatgc ggtaaatagc  24060
gatagggcaa gtaaaaagaa aacaaaacaa gatacaagaa atgaatttag aggaatgatg  24120
ttttgtaaac attgtggtga gccaattaca gctaagtatt caggtagata cgcaaaagga  24180
agtaaaaaag agtgggtata tatgaaatgc agtaattata ttagattcaa tcgctgcgtt  24240
aactttgacc cggctcatta tgatgatata agagaggcga ttatctatgg attgaagcag  24300
caagaaaaag aactagagat acatttcaat ccaaaaatgc atcaaaaaag aaatgataaa  24360
tctacagaaa ttaagaagca aattaagttg ttaaaagtga aaaaagagaa gttgattgat  24420
ttatacgtag aaggattaat cgataaagaa atgttttcga agcgggatct taatttcgag  24480
aatgaaatta aagagcaaga gttggcatta cttaaattaa cagatcagaa taagagaaat  24540
aaagaagaga aaaaaattaa agaagctttt tcaatgctcg atgaagaaaa agatatgcat  24600
gaggttttta aaactttaat aaagaaaatc acacttagta aggataagta tatcgacatc  24660
gaatatacat tttctttata gttttaaagt tggttattag ttactgtgat actacctgca  24720
gtaacaccga tagcttgtcc aagatcatgt tgtgttaaat tccgttctct tcgtaattga  24780
cgtaaccgat ctttaaattc cacaataatc acctcataag tggtttgtta ggattattat  24840
aatatttcct aaagggaaaa tcaatccgag ttatttctaa gaataatata aaatatgtgt  24900
aaaaatatat cttgaatttt ccctaaggga atgttaaggt gatttacaaa gatatagaaa  24960
ggagttacca catgaaagta attaaagacg agacaaaatt aaaagctgca ttcaaaaaat  25020
ctgggtataa gtatcaagag ttagctgacg aattagaaat atcctgcagc tactgttaca  25080
agctaattaa caatcataat tacaaaaaga aaatatcgta taacttagca tccagaatgg  25140
cgcatgtatt aaatgcaagt gtagttgatt tgtttgaaga gcaagtcgat tttttttaat  25200
```

-continued

```
accaatattc cctgagggaa catagggggtg agagggccat gtcagaaatt tattacaaag  25260
ggtttatcat caaggaaact tatggcgaaa gaaatatcga agaagtgttt aaagaagcat  25320
atgagtcatt ttatggggtt gaagttaagg ttgttaaaaa ggaattaggg actaaacgca  25380
atagtgcagc cagctaatct ttaaacttca gtgagaacat tcaatgaagt cgattataaa  25440
atggacaagc ctgaaaggag agaaatgaat gaaaaacggg aaaaggttga ctaaacgtga  25500
aaaaatgcat cttaaatcat atagcttaaa tcctgataat tggttggttt tcaagaaagc  25560
ggatggagaa atgcatttag tacaccgtta tactagcaca actcgtgtaa ttccaagttt  25620
ataagtttag gagggaataa gatggatcag ttaacagtag caagtgaatt acgtctttta  25680
gggagaagaa aagtagctgg atatgaattt actggaatcg agggaggatt tggtgaaggt  25740
aaaaaagcaa tgttggtttt ggatatagct acaattcata accaaccatt aaaagaaatc  25800
aatcgtcgca ttaatgataa tcgcattcga tttaaagatg gtgtggatat tgttgatttg  25860
aaaagtggtg gctttaaccc accacaatta ttaaaccttg gtttctcaaa tatgcagata  25920
gcgaaatcaa ataacatcta ccttctatca gaacgaggtt acgcaaaact attaaaaatt  25980
ctcgaagatg ataaagcttg ggaattatac gacatattag ttgatgagta cttcaacatg  26040
agagaaaaga atcaagtggc tacagatcca atgagtattt taaaacttac attcgaagca  26100
ttagaaggcc agcagcaagc aatcgaagag ataaagtcgg atgtacaaga cttgagagaa  26160
aatacaccat tatttgcaat tgaatgtgat gaaatctcta cagctgtaaa acgtcaagga  26220
gtcatattgt taggtggaaa acagtctaat gcctatcgaa atcgtggatt aagagggaaa  26280
gtttatcgtg atatctacaa ccaactatac cgtgaattcg gagtgaaaag tcacaaagca  26340
attaaacgtt gtcacttaaa tgtagcagta aaaatagttg aagaatatac acttccaatt  26400
gtattgagcg aagagatttc ttttgtaaat gcacaaatgg attttacaga aatgtagtta  26460
gttaaaacat tctcaaccgg ttttttttcta agttaaaaat ttaaagaaaa ggtggaaaag  26520
acaatggacc agttacgtgt tattgaggga gaaaaagtgg ataagccaga ttatgttgag  26580
atataccttg gagcatttat gaatgcagtt aatgagttaa agaaacagga tgaggaaacg  26640
agatcattaa gcaaggatac gtataaaaaa gcaatttttt atggagttag atacatttca  26700
atatcaaaaa atgacagttt gaattatgac tacctaatga atagatttct tttaataagc  26760
tatttagaaa atttgatgaa ggtgttgacg cctagggatt ttatgaccat attcccaatc  26820
gataaaaatt atgatggcgc tcgttatgaa atgaaagatt actttttttac catgaatgaa  26880
attaaaaaaa tcggaatgga tacacctatt ggagagaaaa tcatggagtt tttatgggat  26940
taccaaaact ttaaagatat aacactattt aacttagcct ctgtaagcat tttaaataaa  27000
ttgcagaaaa tgcaaggtaa aaaaacgtta actgaagagt ttgccgagcg attaggtatc  27060
gatacttaca cgaagcataa agaaaagggt ggaaaagaat atattacaaa tgaccgtact  27120
ggtgagatcc aagaagttaa aaaatctaga ccaagatatt taaaaccagt tcaatgattg  27180
atgttattaa ggcttataaa caaagaaagt aacttgcgcc aacaagttac taaataaaaa  27240
tacttataaa aatatactta ttagaaatat aacatacaca ctcgatgtat ggaaagggtg  27300
ttattatggc tctttttaga aaagtgcata cagaattttg gacagacgta aaagtatcag  27360
aagatatgac gccagaagac aaattgttta tggtgtacct tttaactaat ccccatacaa  27420
ctcaattggg agtatatgaa atcacaccta agatgatagc ttttgaaatc ggactatcaa  27480
tagagtcggc tagagcacta ttggaacgtt ttgaaaacca tcataaatta attaaatata  27540
acaaactgac aagagaaatt gctataaaaa attggggcaa atacaacctg aatagaggcg  27600
```

-continued

```
ggaaaccaat tgaagattgt cttaaaagag aaattgataa agtgaaagat ttatctctaa  27660
taaaattcat tttagaacat acagatcatg cagctttaaa aagaaaaatc aatctttatg  27720
cgggttttga cgatacgtcc cacgatacgt tagcgatacg tgaccaagaa gaagaaaaag  27780
aacaaaaaaa agaacaaaaa gaagaacaag aagaaaaaga aaaagaaaaa gaaaaacaaa  27840
aagaagaaga aaaagaacca gaagaagaaa aaacaagaat aaaatccaaa gcgtctttaa  27900
aatcagacgc aaagtccaat ccaataccgt ataaagatat attggattac ttgaatgaaa  27960
aagcaaataa aaatttcaat cctaaagcag aaggacatag aaagttaatt cgcgctagat  28020
ggaatgaggg gtataaacta gaggacttta aaaaagttat cgataacaaa actacgcaat  28080
ggtttggtaa gaaaagtttt gatggaaaac cactagatca atttttaaga ccgagcacgt  28140
tatttgcaca aaaacatttt gacaactact taaatgaaac ggtcaacata tccaatcaac  28200
aacatggaga tcagattgtt atacctggat ttagggggga aatgccgttt tagaaaggag  28260
tactaaatgt gaaaaagata caagattctt ttgaaaaact tactaagtta aaatttgcag  28320
atgaacaatg tgataagcac acctttaata aacatgggaa agaagttatt aaattagtta  28380
ggaaaatgat tgatgatgca ggaacggtat attgtccccg ctgcatggtt gaagagcaaa  28440
attcagtttt atttcaacaa gcaaataatc attataaaaa gattaataga gaacggaaga  28500
aaaatgtact ctttcaacac agcatcatag aaaatcaatc cattacagaa tcaagattgt  28560
ctacatacaa gacggattgt caagaaacga aagaaaacaa agaaaaagct ataaaaattc  28620
ttgaacgcat aaaaaacggt gagtttttaa atgtatacat tgcagggatt caaggagtag  28680
gaaaaagcca tttagcgtat gcgatgctgt atgaattagt taaacactat tgggtaatat  28740
cagacggtga gaaattaaat gacgaacatg cttttaaaaa tatgaaaagc tgcttatttg  28800
tagagattga aaagctaatt cgattaatac agcactcttt tagaaatata gagtcaaaat  28860
atacaatgga ttattgtatc agtttaatgg tagatgtgga tttccttgta atcgatgatt  28920
taggagctga aagtggttcg atgaatcgaa acggagaagc aagcgatttt gttcataaaa  28980
tactttatgg tgttacaaat ggacggcaag gagcaaataa aacaacaatt acaacttcaa  29040
atctgtcaag cgctcaatta tttcaaaaat acgatccgaa actagcaagt agattgttaa  29100
acggtgtatc gaaagatgaa acaattgttt ttaaaacaac cactgacaaa cgaattgtaa  29160
atttagacat tggattctaa taaaaggggt gcggagaaat gaaagaggta aaggggaaaa  29220
acaccaaatt aatggaagaa tttgacgtgt tattaagaca actgctgatt aaatctaaaa  29280
cagatgaaag ggtaaaaaac tttttggatg atctgtttga aatgctaagt gataataagc  29340
tgcagtctga tattgatttc aaaacagcat taaataagtt aagagaaaag cactttccta  29400
agtttgataa aggagagagc aaaaatgact aaagaaaagg gacaagctaa ggaagtagtt  29460
aatgttcgtg gaatgtcaga tgatgagttt atagagaaat acggaaggct tgtacatcat  29520
tgcgtatgga aaagatatgc gaaaaaaaag gccagtatag agcgtgatac cggtttagat  29580
attgaggatt taacacaatt cggaatgatc ggtttgataa aggcgcgaga taattttgac  29640
cttgaatttg gatgtgcgtt ttcaacgtat gctgttccga aaattattgg ggaaatagga  29700
agggcaattc gggataacca aaaaataaaa gttcaaagaa ccgtatatgg cgtaaaagga  29760
aagattttaa atcaacagtt agcagataaa gaaccagaag aaatagcaga cattttggat  29820
gagtcagtat ctttagtaaa gacggcttta gagtatcaac caagcacaga ttcactcaat  29880
aaggttgtat atgcatctgg agctaatgaa gaactgacat tagaaagaat gatagaggat  29940
```

-continued

```
actaaaacgg aagacattga agaaacaacc attaatcgag ctgtgataag agaatttaaa  30000
gctgcattgc ctcctaaaga atatatcgtt ttagatatgc gtttacaaaa tatgacgcaa  30060
caaaacattg caaatcaaat gggatacagt caggtacaaa ttagccgtat attagcaaag  30120
attaatcaaa gagctgctca atttggtaaa gaaggagggc ttcaagattg agtgttacaa  30180
aaggtgtttg tatcgatgta gatcactcag atttgctaca tgagaaagta gagtactttt  30240
tattccctgc taaaccaagt cattactatg taagcagatt taatcgtaaa ggagcgcatt  30300
ttggttgtta tcaagctgaa aggtttcaaa tcacggaaaa ggaagtatgg acaccagaac  30360
ctcaaccgaa tctgcctgag ttgaatacaa gcttattcta tagagctcag ttgatttggc  30420
gaaaaaaggg gtataaagat aaaccactta aagactacat cgtacagccg agagggaaac  30480
attgctactt ttggcatgat cgggagcgaa agaaattttg tggctgtttt ccgctacatt  30540
ggtttaccga ttttgtacca gttcaaagtc atcatataga agaaaaaact agagaagagg  30600
ttaagttatt acaacggcca gatggacaac ttgcattttt ttaacgaaag aaagtgaatg  30660
ggcgttttac ccagtcatcg atttaaaaaa aggagtgttc gtaatggata ttaaaaagtt  30720
atttgcaatg cagaacattt tggataaaag agttttagag tcaaaaaatc tttctagagg  30780
agaagtattc gaatttagaa tactagcgtt tttagatgaa ttaggcgaat gcatgaagga  30840
atggcgagta tttaagtttt ggagcgacga tcgtaaaccg agaactagca tacctacagg  30900
ggaaatcata gtactagatg atggttatga agtagaagtt tataaaaacc ctttacttga  30960
ggaatatgtg gacggactac attttgcaat tggactttgc atagatttga aaacagaaat  31020
taactttcct gcttctatgc gttgcgagac agttacagag caatttttcg aattgtatca  31080
tctagcaata cgattaaaag aagaaccgac agcatttagg gcagatgttc ttttatccca  31140
ttatcttggt ttaggggaat tgttgtgctt ttcgttagaa gaaattggac atgagtacat  31200
tgagaaaaac aaaatcaatc atgaacgtca aagtaatgga tactaataca atttgaattt  31260
tgttaagaaa tgagggtgat tgaaataagt tggtgggcaa tagcgatcgg tttatatcta  31320
ttgattggag ttgcattact tatatggata atcgcaacgg atagttgggg ttcgttattc  31380
ttatatcctg tttttgcggt agtcattgtt ttgggatggc ttccattaat gataagaagc  31440
attgtacaag agatatctaa agcgattcat aagtggaaaa gaaagcagaa aactgaatag  31500
aagtattatt tcagggaggg agaataaatg atttatgaag ttacagatta ttgcagtcag  31560
tgtgatagaa aaatagagaa ttgcgattgc tgttgtaata agtgtgatga gtggttgcac  31620
gattgtaaat gtaaagataa ataagcaaaa aaggggaatg aaagatatga aatggatgta  31680
caaccttgat agcaataatg agatttggac aagcgataaa tttgaaatga aagaagaagc  31740
tattcaagca gctttaaaag attggacaga taaaatggta gcggatagag cggcagtcga  31800
taatgaattc caaattggac aattcaaaca gtattctcca tggatcaatg cagatgtatt  31860
gttggatgaa ttgtatgaac gagcaaccga tgaatgtgga gaggttgcgg aatattggct  31920
ttcaggtgtg ccgatggacg aaggggaaaa gcttcaagaa caaattaata aggtagttac  31980
agaatggcta aaaggaataa atgagcatcc tagctttggt tcaattgaaa atattgaaac  32040
gatagatgct agcaaaattg aatataaaga aaactaaaca aaagcgttat ttgataaaaa  32100
ataagaaagc cctagctttc ttattatatg taaaaagtca tatgtttttt atcttcttta  32160
tagtactcta accggttttg caaagtgcca gtgtggaact caaacttatg gccatctgga  32220
tctgtaaagt aaagagatct ttggtctctc tcatctcttt ctcggccagg taaaatatta  32280
acatcatttt gaattaatac ttcttttaaa tggtctaatg cttcattagt tacagtgaaa  32340
```

-continued gccatatgtg tataagattg cttaatttca tttcttggta tatcttcttc aacatttaaa 32400
gcaatccata atccatttaa atcaaaatac gctaattttc taccttttac taataatttt 32460
gcttgaagta tttttttgat agaattcaat agatttttcc aagtttgata cagaaaaaca 32520
aatatggtta atgccctgta gcataaaaaa cgccccctat aattaaatga ttttcaatat 32580
ttttatataa agattataaa agtttatgcg cgatttataa aggattacta caaaatagtt 32640
atttgaatta aaaagagcgc cgttggagag tgcggtgctc ttagaccaag aactataaca 32700
gggattaagg aaagaatatt gtataccaaa ttgatagtaa tgcaagccat ccaattgtca 32760
gcgctatgta ttttaaaatt ttcatgatta ctccttttag gtatagagtg caccaagcaa 32820
gaggatgtta ttaattttta aacaaaatgc ttatttaaaa actaaagagg gctttttaaa 32880
gcgctcctta agaaaaataa aaaagaatac ctcatgatac tgtatgtatg tttttttagg 32940
aatgtgagga tttaaaacaa aatcgttatt ttatagatcg gagtgaaatt caaatgattg 33000
ttaaagcgac aataaaactt gaattagatg attcgcagaa aaattgggtt tcttatgtta 33060
gagaacaagg tggagaagaa gcggtatttc attatctgga agaagaagtg cagaagaaaa 33120
ttgaattagc tgattttgtg gagatgaaat acaaaaataa gtaatttaaa ccaaaacgct 33180
attttataaa ataaaacagc tagcgtgatt agctagctgt cctgttaaga aaagaaaacg 33240
gtgtttagca aatgttgctg ttgtaattgc gaattacaac catagtatga gcagaagtaa 33300
aaatgttatg caagaaagtt aaataaaaac tgcattttat tgaaaagggg gaatggatat 33360
gtctctagta gggaatttaa aggaactcca agaaaaagcc atcgatgaaa aggtattgga 33420
atttgcggaa gaaatggaaa tcgtaataac taaaagtgcc gcaagcggat attcaggtca 33480
tagatataag attcataatg aaaatccaaa tcggcatatg atgtgttcaa aaatatttat 33540
agaaaagtta caagaattac tggacggtgt gaaggttgaa tttaaggaag aagaaaagaa 33600
aaatatttta ggcggatctt actacgaaca ttacatccgt tttaagtgga atgactaatt 33660
tcttattaaa aattttattt tggagaaagg gagtagaaag aatgaaaact tttaatgtga 33720
cttttacaga gttgaaaata tatgaagcag tcattgaagc ggagtcagcg gaaaagatta 33780
ttgatgtgat taaacactta aaaagaactg aagatgattt agtagacaaa ggagtcatca 33840
taaacgaagt tagtgagata aatgttagta aagaacaaaa gttcgaataa atcaacttct 33900
cagattgttt attttgagac ggaaacaact ttctgaatat cataagacct tattagcgaa 33960
aaaactctta ttcgagcgta caagcctgtt atacacgttg cacggaaatt agaatgaatt 34020
tgttaaggaa ggaagtataa aaatgagggc ttggaagaaa aaacatgtta aaagagcatt 34080
tttgaatcgt caaaaggaaa ttgataaaga acggactgct gcagcttgga gaaatatttt 34140
tgtgaaatca ggaatcataa aataaaaaag gaaaagcaac tcgttgggga caagtcactt 34200
ttccagatgg caatgtaaat ccattatagc aaaacatatg tacaagctgt agcaataaac 34260
aacgagatat tttgacacct atcgacaatt agaaatgtgg ttgttgatct agaaatatga 34320
aagtaggtga atcatcattt gtttaactgg ctgagagatt accaaaagtt agaagaagac 34380
atagcctatc tggaatacaa cttagataag acaaaagctg aattaagacg ctgggtgagt 34440
ggtgatttga gagaagtacg tttaacggca gaatctgaag gtgcaaaagt tgaaaaccgc 34500
attgaagcga ttgaatacga attagcacat aagatgaacg atatgtataa attaaaaaag 34560
ttaattagta agtttagagg tttagaaaat cagatactca aattaaaata tgtggatggt 34620
atgacgttag aagaaatagc agaggcagta aattatagtt ctagtcatat caaaaagaaa 34680

-continued

```
catgctgaac tcgttagatt aattaagttc gtggagcgag aaggtgtcat ttaggttcac  34740
tcctaaaatg aatcgaaacg gttgaaaaaa tgatttatat tgatagcata caattttagc  34800
agaagggcaa ctggtgcacg gttgctcttt ttgattttgg aggttattag acgatggatg  34860
tacaagagtt gtcgagacga ttagaaaatc tagaacataa agtgcttcag gtagaaacga  34920
aggcagatgt gctaaaccga acagctatac aaaaaggcga taaaataaaa gtggtgtatc  34980
cgcatttagg gatacaaggc gagtatttag tggagaaaat tgataatggt gtgttggaat  35040
tggtagcaga agaaacaatg aaaaaaatac aggagtgatt aggattgaag aagttatcta  35100
aacaagagct agcagctgta atgacacatt gtatttcaac gcttggtgag cagattgtta  35160
atgagcatat taatccccag aagttggcgc aagcaagtgc actccataac gatctctttg  35220
ataataccac tcctaaagaa cgtagggaag cgacgatcag tttactaggg aaagcgattg  35280
atgagttttt agagagtaag gagtgaggat atgggaaagg gatattttaa taaggctgta  35340
tgtttagtgt gtggtcatca agatagagtg aatcatccat ctaaaaaaga gtatcaagaa  35400
gtaacggttt gtccggaatg caacggtgct tttgtagatg tgtggaagct aggaaagtac  35460
aaacgtaata cacagtctaa tgaagaacct ttattaacaa ttacattaac agatatagat  35520
gctaaaccga tagttcatta caaaggtgaa cagatagata gaaagttacg tgttacgttt  35580
gattgggaat ctcaatcgat tgataaaatt aatcggacat acattcatat tgaacatgta  35640
ccagccgata acaaacgttt aaataccgag accattcagc ataatcatcc tattgcaaat  35700
aaggaacaag tttagatgtt gtccatattt gttaataggt aaaagataag tgttttatct  35760
ggaagttcaa acgtgaatta aagaaattaa aaaaggaata tgaaaaggag agtcactgaa  35820
tgaacgggtt taataaaatt gtaaacgata tgcaaaatga acaagtagga aatgctatgc  35880
tagattttgc tttggccgct aaaatgatgt tcgctgcctt tacacagttt aaagaagctg  35940
gatttaacga agagcagtca ttcgaattaa cacgtgagat attaattgat tcattaagta  36000
agaatcaata gatcaatgag gtgaaaggga atgcaagtat attgctctga gtgtgataaa  36060
agttatgaca tgcagccgca agtaacacaa ctccctaatc gtattgagaa gtgtttcttt  36120
atttgtcctc attgtaatca tgaacatata gctgcgtacg tgaatgataa gattcgtaag  36180
tatcaagcag atatagcaaa gtgtcatgag cggattaata aaaagaatct tgctatcgaa  36240
gatgaaatga aacgattaag gaagaggttt gacaggagaa agtgagaggt gaagcgagtt  36300
tgaaaatgct attaacaaag cattggtgtt tagatagaaa ctgcggattt gaagagactt  36360
ctcataaggt acgtgatggt tggaaatgtc ctgattgtaa tggaccaatg gcgtttcaac  36420
aggtgaataa gaaaaaagaa agcgccaagt gatggtgctt tttattttgg aggaggatga  36480
aggatggaag gacaggagtt aacattggaa aagaaagaca gtatttatct tagaccaaga  36540
taccctcata agattgacgc aagtaaaatc aaatccttaa aagatgtaat taagatttta  36600
ggattgatgg atattcgttt ggacgacaag gcggtcattg gtctagaaca cttgattgaa  36660
aaggaggaag aataaaatgg ccaataacaa attaattatt gaagtaactg cggatacaac  36720
tgaggcatta gaaggaatta aagaagtaac tgaagcagct aatgaatgtg cagatgcgct  36780
ggacaaatta gaaaagatta tggataagtt tacaaatcga agtgatacag tggaactcta  36840
ttgtgaaggt aaattgttat cgaagtctac agttaatcat acagctgatt caattcaatg  36900
tcgcataatc aagggagaag agcttggagg aagtgaacgc tgatgaagaa accgcttaga  36960
ccatgctgcg aatttcattg ttataatctc acacgtgaaa gatattgtga ggaacataga  37020
tacaaagaga aggaaacgca gcaggataag aatagatact acgaccgatt caaacgggac  37080
```

-continued

```
aaagagagta cggctttcta taggtcaaag gcatgggaaa ggttaagaga gcaggcacta  37140

atgagagaca aagggttgtg cctacattgt aagaacaata gaaagattaa agttgcagat  37200

atggttgacc atatcattcc aatcaaagtt gatccaagtt taaaactcaa attagaaaat  37260

ttacaatcac tttgtaatcc atgtcacaac agaaaaacag cagaagacaa aaagaaatac  37320

gggtaggggc gggtcgaaaa acattcaggg cggtctgtcc gtaccgccgc ccc         37373
```

<210> SEQ ID NO 2
<211> LENGTH: 40869
<212> TYPE: DNA
<213> ORGANISM: Bacillus anthracis

<400> SEQUENCE: 2

```
ctcaacttcg cagaaaaatc cgtttttgca tattttttta agggggtgta atcatggctg     60

gaagaaataa acaaccactc tctgttatac agggaaaagg tagatcaaat cacattacaa    120

aaagtgagaa aaacagacga gaaaaacaag aagaagcatt gcgggggcat actgataaaa    180

ttgaagctcc ttcttatttg actgcagcac aaaaaaagga attcgatact ttagctgctg    240

aattagtcag attgaaaatt ttcagtaact tagatgttga cagtttagca aggtacgttg    300

attctaaaga ccaatatata aaaatggttc gtctgctaag aaaaacaaaa ccttcagatg    360

actttaaatt gtattctcaa atgcaaagaa gtaaaaatct tttattcaat gaatgccgtt    420

cttcagctag tgatttaggt ttgaccatta catcccgctt aaaattagtt attccagaag    480

tagatacttc acaacaaaag caaagtgaag cgcaaaagcg ttttggtgat cgtatatgaa    540

ctggataatg gaacgggttt ttgcatattg cgaggacatt ttaaacggca agataaatag    600

ttgtaaaaaa catcgttggg ccattgaacg atttataagg gattatgagg agtgtcaaag    660

tgaagacagt cctttttatt ttgatggaga gatagcggag gatttttact ggtttgcaaa    720

ggaatttaag cacgttgaag ggattttggc aggtgaatcc gtagaattaa ctgattttca    780

attgtttcta gcggctaata ttttcggatt caaaaagaaa ataaatggag caaggcgatt    840

tagaaaggtt tttattcagt tagcgcgtaa aaatgctaaa tctcagtttc ttgctattgt    900

agcagctttt tgtacatttc ttggagacga aaaacaacgg gcttatattg ctggatggac    960

aagagaccaa tcatctgaag tttatgaagc tgtaaaaaca gggattagtt ctagtgaatt   1020

gttagaaggt aaatggaaag aggcttatag taccattgaa atatttaaga atggttcagt   1080

tgtcgttcca ctttcaaaag aagctagaaa aactggtgat ggtaaaaacc cgtctcttgg   1140

aattgtcgat gaatatcatg cacatgaaac tgatgaaatt tatgacgttt tatcgtctgg   1200

tatggtggca aggaaagagc cgttaatgtt tatcataaca acagctggtt tcgacttatc   1260

aagaccttgt tatagagagt atgagtatgt cagtgacatc ttagacccgt caaaaaatgt   1320

agaaaacgat gattatttcg ttatgatctg tgaattggaa aagaacgatg atatcaaaga   1380

tgagtcgaat tggataaaag caaacccaat cgtagctaca tatgaagaag gtttggaagg   1440

tatacgttca gatttgaagg ttgctcttga tagacctgaa aagatgaggg ctttttttaac   1500

caaaaacatg aatatttggg tcgataaaaa ggacaacgga tacatggata tgtcaaaatg   1560

gcaaaaatgc gaagtagata cctttgattt ttcaggtgcg actctttgga taggtggcga   1620

cttatcaatg acaacagatt taactagtgt cggttgggtt ggaatggacg atgaaggtga   1680

ttttattgtt ggacaacatt catttatgcc tgaagcacgt ttgaaagaaa agatggccat   1740

agataaggtg cgttatgatt tatgggccga acaagggtat ttaactttaa cgcctggtga   1800
```

-continued

```
aatggttgat tatacaattg ttgagtcttg gatagaaaac ttttcaaaag acaaagaaat   1860
tcaagagttt gattacgata aatggaatgc gttacatcta gcacaaaatt tagagaataa   1920
agggttcgtt tgtgtagaaa tccctcaaag gattgctaat ttatccattc cgactaaaaa   1980
ttttcgagaa aaagtatacg aaaagaaagt taaacataat ggagatccag tcctttttg   2040
ggcgcttaat aatgctgttg ttaaaatgga tgatcaggaa aacattatga tttcgaaaaa   2100
aataagtaaa aatcgtattg atccagcagc agcggtctta aatgcatttg ctagggctat   2160
gtatggagca agtgtcaggt ttgatgtatc tgaatttgca aataaagact ttctaggcaa   2220
gttatggaac tagggagggg gtgaacatgt gaagatagtg gattctgtta aaaagttctt   2280
taattttgaa aaacgccaaa cgtcgcaggt aatagagttg aataaagacg atgaaaaatt   2340
attagaatgg ctagggattt ctccaagtac tattagcgtt aaaggaaaaa atgctttaaa   2400
agttgctaca gtctttgctt gtatcaaaat actatctgaa tccgtatcaa agttaccgtt   2460
gaaaatttat caggaagatg aatatggaat ccaacgcggt acaaagcatt atctcaacaa   2520
tttactgaga ctaaggccta acccgtatat gtccagtatg aactttttcg gatcattaga   2580
agctcaaaaa aatttatatg gcaatagcta cgctaacata gagtttgata gaaaaggtaa   2640
agtccaagcg ttatggccga tagatgcttc taaagtgaca gtatacattg atgacgttgg   2700
tttattaaat tccaaaacta aaatgtggta tgtagtaaat acgggtggac aacaaagagt   2760
gttaaagcca gaagagatac tgcactttaa aaacggaata actcttgatg gtcttgtcgg   2820
tgttcctaca atggaatatt taaagtctac attagaaaat tcagcttcag ctgataaatt   2880
cataaataat ttttacaaac aagggttaca ggtaaaggga ttagttcaat atgtcggtga   2940
tttaaatgaa gatgcgaaaa aggttttccg agaaaatttc gaatcaatgt ctagcggtct   3000
tcaaaatagc catcgtattg cattaatgcc agtaggatat caatttcaac ctatttcatt   3060
aaatatgtca gatgctcaat ttctcgaaaa taccgaactt actattaggc aaatcgctac   3120
tgcattcggc attaaaatgc atcaattaaa tgatttgagt aaagcgactt taaataatat   3180
tgagcagcag caacaacaat tctataccga tacattacaa gcgactttaa caatgtatga   3240
gcaagaaatg acgtataagc tatttttaga cagtgagttg gataaggggt tttattcaaa   3300
attcaatgta gacgctattt taagagcgga tatcaaaacg agatatgaag cttacagaac   3360
gggtattcaa ggcggtttcc ttaaacctaa cgaagctaga agtaaagaag atttaccacc   3420
agaagctggt ggggatcgtt tacttgttaa tggaaatatg ttgccgattg atatggctgg   3480
acaggcatat ttgaagggag gtgatactaa tggagaagtc agcaaagaag gaaatgaagg   3540
aaattagagc tttgccaatg actattgaag tccgtgaagt taatgaggac gagggaaaac   3600
gaacaatttc gggatcgata aaatataaca atgaaagtgc cgaaatgcgt gactggtggg   3660
gcgatacttt cgtagaagag attgctgagg gagcttttga tgaaagttta aaagttcgtg   3720
atgttgtagg tttatggtct cacgacacat ctcaagtatt aggaaatact aaaagtaaaa   3780
ctttacgaat cgaaaatgac aagaaagaat tacgatttga attagatatt cctaatacaa   3840
ctgttgggaa tgacgcatgg gaattaatta agcgtggaga tgttgatgga gtttcttttg   3900
ggatgaaggt tacaaaagac aaatggtcat cggaagaacg tgaaaatgga aagctttata   3960
agcgttcgat tttaaatgct gaactatatg aaatatcacc ggttgcattc cctgcatatc   4020
caacgaatga agtaagtgta cgttcattgg atgattttaa agctggagaa aagcgagtag   4080
ctgatgagtt taggaaaaga aaactacaaa tcgaactaga gcttatataa ggctcttttt   4140
ttattgataa atttaaggag tgatttgaat gtcaaaagaa ttacgtgaat tattagctaa   4200
```

-continued

```
gttagaaggg aaaaaggaag aagtacgctc tcttatggga gaagataaag tggcagaagc   4260
agaacaaatg atggaagaag tgcgatcact tcagaaaaaa attgatttac aacgctcatt   4320
agatgaagca gaaacggaag aacgaaataa tggaagagaa gttgaaacac gtaatgtaga   4380
tggtgaaatg gaataccgcg atgtgtttat gaaagcatta cgcaataaac cattaaatgc   4440
tgaagaacgt gaatttcttg aggatgattt agaacaacgt gccatgtcag gattaactgg   4500
ggaagatgga ggacttgtca tccctcaaga tattcaaacg caaatcaatg aattagctcg   4560
ttcatttgat gcgcttgagc aatatgtaac tgttgaacca gtgcgtacac gttcaggatc   4620
acgagtatta gagaaaaatt cagatatgat tccgtttgct gaaatcactg aaatgggtga   4680
aattccagaa actgataatc cgaaattttc aaatgtacaa tatgcagtga aggacagagc   4740
aggtatttta ccgttatctc gttcattact tcaagatagt gatcaaaaca tcctaaagta   4800
tgtgactaaa tggctaggta agaaatctaa agttacacgt aatgtgttaa tcttgggcgt   4860
aattgaaaag ttaacaaaac aagcaatcaa atctctggat gatattaaag atgtattaaa   4920
tgttaaatta gacccagcga tttctccgaa tgcgatttta cttacaaacc aagatggatt   4980
taattattta gacaaattaa aagataaaga cggaaaatat attttacagt cagatccaac   5040
gcaaaaaaac aaaaaactat ttgctggtac taatccagtc gttgttgttt cgaatcgttt   5100
cttaaaatca aagggaacta cagctaaaaa agcgccactt attattggtg atttaaaaga   5160
agctattgtt ttatttaaac gtgaagatat ggaactggct tctacagatg taggtggtaa   5220
agcattcact cgtaatacat tagatttacg cgcaattcaa cgtgatgatg tgcaaatgtg   5280
ggataatgaa gcagcagttt acggagaaat cgatttaagc gctcctgttg aacaacctca   5340
agggtaaact aaggaggcat ttgaatgctt gttaccttag aagaagctaa agaatggatt   5400
cgagtggacg gagacgatga cccaactatc actatgttaa ttaaagcggc tgaattatat   5460
atttacaaag caactggcaa aacatttact caaacaaatg aagatgctaa gttgctttgt   5520
ttatttctgg tggctgattg gtacggaaat cgactacttg taggtgaaaa agccagtgaa   5580
aaaatcagaa ccattgttca gagtatgata ttacagctcc aatatgcttc agagcctcag   5640
gaggaaagaa aatgaatcct gcaaaattag ataaacggct tacatttcaa gtaaaagatg   5700
aaaatgcaaa agggcctgac ggtgatccga tagatggata taaagatgct tttaccgtat   5760
ggggctcttt tgtttattta aagggaagga aatactttga ggcagcagct gctaatagtg   5820
aggttcaagg agaaacagaa atcagaaatc gggatgatgt aagtgcagat atgaaaatta   5880
agtacaaaaa cgtgatttat gatattgttt ccgttattcc aactcaagat catactttat   5940
taatcatgtg gaaacgtggt gaaatgaatg gctgatggta tagatttaga tttattagga   6000
tttgatcgtt tagttactga attagaccaa atggggttac ggggagagaa aattgaagat   6060
aaagctcttg cagctggtgg tgaacctatt cgtaaagcca ttgcagaacg agcgccaaga   6120
agcccaagcc ccaaaaaacg atctaaaagt gaaccgtggc gtacagggca acatggtgca   6180
gaccagataa aagtaacaaa agctaaactt gaaggtggaa taaaaacagt aaaaataggt   6240
cttaataaag cggatcgttc cccgtggttc tatttaaagt tccatgaatg gggtacatcc   6300
aaaatgccag cacatccatt tatagagccg ggttttaatg cttcaaaagc ggaagctgta   6360
cgtgctatga cagatatttt aaagaacgaa atgaggttgg atttgtgata aatttaagac   6420
ctgatatttt acaagctctt gagaatgatc aagagcttgt ttcattgttg ggtgggaaac   6480
gaatttatta ccgtaaagca aagaaggcag aagagtttcc gcgaattacg tattttgaat   6540
```

-continued

```
tagacaatag gccagatgga tttgcagata atcaagagat tgaaagtgaa atcttgtttc   6600
aagttgatgt ttgggcaaag agtagtacaa cagcaatcca tcaaaaagtg aatgaaatca   6660
tgaaaagaat tggtttctca cgctatgcgg ttgctgattt atatgaagag gatacacaaa   6720
tatttcatta tgcgatgaga ttcgcaaaag gagtggaatt ataaatggct ggagaagttg   6780
taagaattag ttcaacggtt ggtgtagaca accttgtata tgcgaaagtt ttacaagatg   6840
attcgtctgc tattaaatat acagatgtaa agaaaatgga aggtgctgta aaggttaaat   6900
taactaaaaa agtagcttct gaggttatgt ggagcgataa cagaaaatca gagattgcag   6960
aatctgatgg cgaaactgaa gtggagattg aggttcgagg actttcactt tctacaaagg   7020
ctgacattga agggtttcca gaagtaaaag atggcgtttt agatgagaaa cgtgaaggtg   7080
agaaaccata tttagctatt ggtttccgat tcttaaaagc taatgataag tatcgatatg   7140
tttggttatt aaaagggaaa ctttcacaag aggaagaaga agctgaaacg aaaaaagaca   7200
aaccgaactt ccaaacaaca aaattgaaag gttcctttat tgaacgtgat tttgatgata   7260
gaacgaaatt tacagcagat gaagatgaac caacgttcac aaaattagtt ggagataatt   7320
ggtttaataa agtatatgaa aaaccagtga cacaaccacc agcaggaaag taagagggag   7380
caaaagctct ctctttttta ttaaatttag gagggaaaaa ctatgaaatt aacattaatg   7440
attaataaag aaaaacaaac ttttaatatg ccagaattta ttccagcccg ccttattcgt   7500
caggctcctg aacttgctga aattccaaac aatcctggtc cagaagatat ggataaaatg   7560
gttcaattcg tagtgaaagt ttatgatggt caatttacat tagatcagta ttgggatggt   7620
gttgatgccc gtaaattctt atcgacaact tcagatgtaa ttaacgcaat tataaatgaa   7680
acagtggaag cagcaggggg tagtactgaa tcaggagaag aagaaaaccc aaacgcatag   7740
agggaggagg gctaacgttc agtgagttta tggacgagct ctacctctct ttattgcgac   7800
aagggtacaa acaccatcac attgataatg agatggatat ttggcattat ttgagactta   7860
atcgaaaaat gcatgaaaac ggaaatgaaa attacgaagg ctccaattca aatgaaatag   7920
aagtgccagc ggaaaacatt atttaacgag ggaggtgaga ctatggcgaa tgaaataaat   7980
aatctagtcg ttagactttc ccttgataac gtaaatttca gacaaggtat ctcgaattca   8040
ggtcgtgcag tcaggacgtt acagaatgaa ttgaaatctg taagtacagg aatgggcggt   8100
tttgctaacg ctagtcagca aacacaagcg aaaatgaata cactcagtag gctcattgat   8160
gcgcaaaaag agaaagttaa agcgttacga caagcctatg atcaaaataa ggctaaatta   8220
ggtgaaaatg atgcagcaac ccagcgatat gcttcgcaag ttaataaggc agttgctgat   8280
ttaaatagat ttgaaaatga attaaagcaa gtaaaccgtc aagctgaaca aaaagggatg   8340
gataagttaa acaactcttt aaaatcccta caagctgaat ttcagtctat tacaacaggt   8400
atgggcggtt tttctaatgc gacagaacaa acaagggcta aagtagatgt tttatcccgt   8460
atggtagata aacaaaaaga gaagattagg gaacttcaac aagcctataa tcgtgctaaa   8520
acagaagaag gcgaagcgag tcaatcagca caaagatacg ctgaacaaat tcatcgggca   8580
acagctgaac tgaatcgatt tgaaactgga ttacagcagt caaatcgtga attagaacag   8640
caagggaatc gcctattgaa cttcggaaat cgcatggaga cattaggtaa tcatttgcaa   8700
aatgccggaa tgcagatcgg catggtattt ggtggtatga cttacgcaat aggtcggggc   8760
ttaaaatcag caatcactga atcaatgaat tttgagcaac agatggccaa tgtaaaagct   8820
gtttctggat ctactggagc agaaatgaaa aagttaagtg aattggctgt taatatggga   8880
gaaacaacaa aatactccag tgttcaagca ggtcaaggta tcgaggaatt aataaaggct   8940
```

-continued

```
ggtgttagct tacaagatat tattaacggc ggattggcag gtgcccttaa cttagcgacg   9000
gcaggggaat tagagttagg tgaagcagcc gaaattgctt ccacagctct gaatgcattt   9060
aaagcagacc atctttcagt tgcggatgca gccaatattt tatctggtgc agccaatgct   9120
tccgcaactg atgtaagaga gttaaaatat ggactttcag cttcatcagc agtagcagcg   9180
ggagccggaa tgacgtttaa ggatacagct acaactttag cggtatttgc acaaaatggt   9240
cttaagggat cagatgcagg tacatcttta aaaacaatgt taatgaggtt aaatccttca   9300
acaaaagaag catataacaa aatgagagat ttaggactta ttacttataa tgcacaggca   9360
ggttttgatt tcttagttaa aaacggtatt caaccagctt ccagaaatgt aggggatata   9420
gaagtagctt tagaacaata tgtaatgaaa acagaaggtg taacgaaatg gaatgataaa   9480
tgtgatacaa cgtttcgcga attagcaaca agttcggcat tttatcatc aaaattctat    9540
gatcaacagg ggcatattca aagtctagaa aatatttcag gtacacttca tgaatcgatg   9600
aaagatttaa cagaccaaca acgaagtatg gctctggaaa cattatttgg ttccgatgct   9660
gtacgtggtg cgactatctt gtttaaagaa ggcgccaaag gtgtcaatga aatgtgggat   9720
tccatgtcaa aggttacagc agctgatgta gcagcgacca aaattgatac tttaaaggga   9780
cgacttacat tactagattc agcgttttcc acaatgaaaa agacaattgg tgatgcacta   9840
gctccagtag ttagtgtttt tgttgctggt ttacaaaaac ttgttgatgg attcaactct   9900
ttacctggac cagtacaaaa ggcaatagca attacaggtg gtatcgtcct tgctttaaca   9960
gctgtggcta cagcaatagg tgtggtttta gcagcgtttg gaatgattgc ttcaggaatt  10020
ggttctttat ctcttgcttt agcatcagtc ggtgggattg ctggaattgc ggctggagca  10080
gttggattct taggaagcgc gcttgcggtt ttaacagggc caattggtct agtagcagcg  10140
gctcttatcg gaactggtgt tgttgcatat aaagcatatc aaaaagcgac tgaagacagt  10200
atcgcatcag tagaccgctt tgctacaaat acagaaggga aagtaagctc ctcaacaaag  10260
aaggttcttg gcgagtattt caagctgtcc gatggtatta gacaaaagtt aactgaaatt  10320
agattgaacc atgaagtaat aacagaagaa cagtcgcaaa agttgattgg tcaatatgac  10380
aaattagcta atacaatcat tgaaaaaacc aacgcaaggc agcaaaaaga aattgaaggg  10440
cttaaaaagt tctttgctga ttcgtatgta ttaaccgctg aagaagagaa caaacgaatc  10500
gaacagttaa atcagcacta tgaacaagaa aagctaaaaa cgcaagaaaa agaaaataaa  10560
attaaagaga tcttacaaac agcggctaga gaaaacagag aattaacgac atccgaacgt  10620
atctctttac aagcattgca ggatgaaatg gacagagttg ctgttgagca tatgtctaaa  10680
aatcaaatgg agcagaaggt tattcttgaa aatatgcgtg tgcaggctag tgaaatttca  10740
gctagacagg cagcggaagt tgtagagaat agcgccaaag caagagataa agttattgaa  10800
gatgcgaaaa agacccgtga tgaaaaaatt gcagaggcga ttcgccaacg tgatgaaaat  10860
aaaacaatca ctgctgatga agcgaacgca atcattgcag aggcaaaacg tcaatatgat  10920
agtacagttt ctacagctcg agataaacat aaagaaattg tgagtgaagc aaaagcgcaa  10980
gctggtgaac atgcaaatca ggtagattgg gaaactggcc aagtaaaatc gaaatatcaa  11040
gctatgaaag acgatgttat tcgaaaaatg aaagaaatgt ggtcggacgt taccaacaaa  11100
tatgaagata tgaaaaactc tgcaagcaac aaagtagagg agataaaaaa tacagtttca  11160
agaaaatttg aagagcagaa aaaagctgtt actgataaga tgtcagaaat aaaaagtagt  11220
attgaagata agtggaatac agttgaaaag tttttcagtt ctataaattt acgttccatc  11280
```

-continued

```
ggtaaatcaa tcatagaagg gcttggcaag ggaatagatg acgcttcagg aggtctgttt  11340
agtaaggctg cggaaattgc aagtgatatt aagaagacta tttctggagc attagaaatt  11400
aacagtccgt ctaaagtgat gattccagtc ggtagcgcag ttccagaagg tgttggggtt  11460
ggtatggata agggaaaacg atttgttgtg gatgcagcaa aaaatgtagt cggaactgtt  11520
aagaaacaaa tggggaatat gccatctgtt tttgattttg gattccaaac aaatcaatat  11580
agtatcccgc aaaatacatt tagcgatttc agtggatata tgcaaccgca attatcttat  11640
aacaatccat ctatggcaaa aacaatattc ccaaatagac caggtggaga acaagaactg  11700
aatttaaccg taaacatgac taatgtttta gatggaaaag agcttgcaaa cggaagttac  11760
acctatacta caaaacttca aaatcgtgaa caaaaaagaa gagcggaatt ttaagggtgg  11820
tgagcacgtt ggggaaactt agttttactt ttaataatat tagaaaagat tatattcaaa  11880
tgctagttgg aagaaaacgt ccttcatggg ctccagtaaa aagaagatta gtaagagtcc  11940
ctcatcgcgc aggggctctt ttacttaata cagaaacgga ggaacgtcgt attgacgttc  12000
ctcttgttat taaagcgaaa aaagatatgg cagatttaca aaagttaaaa gaagatttag  12060
cggattggtt atatacagag caacctgctg aacttatttt tgatgatgag ttagacagga  12120
cttatttatc attaattgat ggttctgtcg atttggacga aatagtcaat agaggtaaag  12180
gtgttattac ttttgtttgt ccaatgccgt ataaattagg gaaaatcaat actcacaaat  12240
ttacgcaaga gtggtctaca gaaacaactt cttattttac taataaagga agtgtagaag  12300
ctccagcatt aattgaaatg acagtgaaaa aaccaagtac ctttttagat gtatggtttg  12360
gagagtatcc gcataatcgt gattatttca gaataggcta ccctctgact gtggaagaaa  12420
ccacggtaca agaacgagaa agagtcatgt gggatgaaat ggctactcct ataggatgga  12480
cacctgttac tggacaattc gaggagatga aagggacagg tagttttaaa tcaagaggtg  12540
gtcatgcact atattgtgaa gattacggaa aagagacagg attctacggt gctatagcca  12600
agaaaaacat tccgggcggc ccattacaag acttcgaaat ggaggcatgg gtgactttaa  12660
agtccaaaaa cataagcgaa atgggacgtg ttgaagttct tcttttagat gagacgagta  12720
acgtgatatc ccgcatcaat atgaatgatc tatatgcgac cgctgaaatt acaagggcgc  12780
atatgacaat tggaaatagc ggaacaccca atagttttcg aaaattagtt gatacaagtg  12840
gattttattc gacaacattt aaccaattcc gagggcgttt acgtattgct aggcggggga  12900
aggtgtggtc tgtatatgtg gctaaattta tagatggtac agaaaaagat ggagcttcac  12960
ttgtagaacg ttggattgat gaaacaggaa atccgatgac agaacgtaaa attgcacaag  13020
ttatgattgc gatttgcaag tgggataatc atcaacctat taacgaaatg caaattgatg  13080
atttaaaaat ttggaaggta aacaaagttc catctaatgc acaaccatat atctttgata  13140
ctggagataa aattgttatc gatactgaga aaagtcttgt cacgatcaat ggggagaaag  13200
caatcaatat aaaagaaatc tttagtaatt ttcctgtcgt aatacgtggt gaaaatcgta  13260
tcgatattat gccgcctgat gtaaacgcaa caatcagtta tagggagaga tatagatgag  13320
aacaccaagc gggatttttgc atgttgtgga ttttaaaaca gatcaaatcg tcgcagctat  13380
ccaaccagag gactattggg atgacaaacg gcattgggaa cttaaaaata atgttgacat  13440
gttggatttc accgcatttg atggaacaga ccatgcagtt accttacaac aacagaatct  13500
tgttttgaaa gaagttcgcg atggaagaat cgtaccatat gttattacag agactgaaaa  13560
aaattccgat acacgatcta ttaccacata tgcttcagga gcttggattc aaattgcgaa  13620
atcagggatt ataaaaccac aacggataga gagtaagacg gttaatgagt ttatggattt  13680
```

-continued

```
agcactctta ggtatgaagt ggaaacgcgg aattactgaa tatgctggat ttcatacaat  13740
gaccatcgat gaatatattg acccactcac ttttttaaag aagattgcat ctttatttaa  13800
actggaaatt cgatatcgtg ttgagattaa aggttcaaga atcatcggtt ggtatgtaga  13860
tatgattcaa aaacgtggtc atgatacagg caaagaaata gaattaggaa aagatttagt  13920
cggtgttacg cgaattgaac atacacgtaa tatttgctct gctttagttg gatttgtaaa  13980
aggtgaaggt gacaaagtaa tcactattga aagcattaat aaaggtctac cctatatcgt  14040
agatgcagat gcgtttcaaa gatggaatga acacggacaa cataaattcg gtttttatac  14100
accagaaaca gaagaattag acatgactcc aaaacgttta ctgacgctta tggaaataga  14160
attgaaaaag cgtgtcaact cttcaatttc ttatgaagtg gaagcacaat ctattggtcg  14220
tattttcggt ctagaacacg aattaattaa cgaaggcgac acgattaaaa ttaaagatac  14280
agggtttaca ccagaattat atcttgaagc gcgagtaata gctggggatg aatcttttac  14340
agattcaacg caagataaat atgaattcgg agattatcgt gagatagtta atcaaaatga  14400
ggaattaaga aaaatttata atagaatcct tagttcgctt ggtaataaac aagaaatgat  14460
agatcagcta gacagattag ttcaagaagc taacgaaacc gctagtaatg caaagaagga  14520
gtcagaagca gcaaaaacac tagctgaaaa agtacaagaa aatattaaaa ataataccgt  14580
tgaaattata gaatctaaga atccaccgac aacaggtctt aaaccattta aaacgctttg  14640
gcgtgatatt agtatcggaa agcctggtat tttaaaaata tggacaggta cagcgtggga  14700
atcggttgta cctgatgttg aatctgtaaa aaaagaaaca ttagatcagg ttaataaaga  14760
tatcgcaacc acaaaaacag agttaaatca aaaggttcaa gaagcccaga accaagcgac  14820
tggtcaattc aatgaagtga aagagagttt acaaggcgtt agtcgtacga tttctaatgt  14880
tgagaacaaa caaggtgaaa tcgataagaa gattactaag tttgaacaag attcaagtgg  14940
atttaaaact tcaattgaat cgttaacgaa aaaagatact gaaattagta ataaattaaa  15000
tacagttgag tctactgtgg aaggtacgaa aaagacgata tctgaggtac agcaaacaac  15060
taatgattta aagaaaaaaa ctactgaaat agaagagaag gctggaaaaa tcaccgaaaa  15120
acttacaagt ttagagacaa gagaagttaa tgttcgaaac tatgtaatta actctgattt  15180
ttcgaatgtt acaaattctt ggattggaat tactaatgca actcttttta aatttgtaga  15240
tgtgaatatt tcggaagcct ccgctattaa gaaaggttta caaataacaa gtaataaagc  15300
ttttgtttat cagaagttac ccgcagacgt gtttaaaaag aagaagggga tagcttcttg  15360
ttatataaat gtatcaagtt ttacacctgg tacagattat ccacgtttat atatgagatt  15420
cacctatgac caaaacggaa cagaaaaaca atattatgcc attttaaaac aacaagaagt  15480
aactaatgga tggattagga tttctatacc atttgataca actggatata caggtgaatt  15540
aaaagaagta cgtgtaaata tagctaccgc tgacacaact actatcgatg caacgttcac  15600
tggaataatg gttacattcg gtgacttaat tgaatcttgg aatctcgctc cagaagatgg  15660
agtaacacaa ggtgtttttc aatctaaaac aaccgagatt gaaaaaagtg tggatggtgt  15720
aaaaactact gtaacaaatg ttcaaaatag ccaagctgga tttgaaaagc gcatgtctaa  15780
tgtggaacaa acagcaactg gattatcttc taccgtaagt aatttaaaca atgtagtatc  15840
cgatcaagga aaaaagctta ctgaagcaaa tacaaaactc gaacagcaag caaccgcgat  15900
tggagcaaaa gttgagctta aacaagtaga ggattatgtt gctgggttta agattcctga  15960
gttgaaacaa acagttgata aaaataaaca agatttatta gatgaattag ccaataagct  16020
```

-continued

```
tgcaactgaa caatttaacc agaagatgac tctgattgat aaccgtttca ctattaatga  16080
acagggtatc aatgccgcag caaaaaagac agaagtatat acaaagacgc aagcagatgg  16140
acaatttgct acagattctt atgtaagaga tatggagtcg cgcctgcagc taacagaaaa  16200
gggtgttagc atatctgtaa aagaaaatga tgtaatcgca gccattaaca tgagtaaaga  16260
aaacattaag ttaaatgctg cacgaataga tttagttggt aaagttaatg cggagtggat  16320
taaagctgga ttgctgagcg gttgccaaat tagaacatca aatacggata actatgttag  16380
tttagatgat caatttatac gtctctatga aagaggagtt gctagagcat ttctggggca  16440
ttacagaaga tcagatggtg cagtacaacc gactttcatc ttaggttcag atgaaaagac  16500
taacgctccg gaaggtactt tgtttatgtc tcaagcaggt gcaggatggt caggggctta  16560
tgcgagcatt ggtattagca atggcatagt tgatggtgca gtccaaaagt ctgtgtattg  16620
ggagttgcaa agaaacggac taagtgttct aaacgctaat gattaccatg tttttacgc   16680
tggaaatgga aattggtatt tcagaagagg gaaaccaggg ttgtatcaaa cttcgttagt  16740
cgttgaagat aatagtacag attctgattt aagattacct aatgtaacta tacgtaatag  16800
ccgtgcagca ggatatacag gagttattca attgaaatcc cctgttactc aaaatggatg  16860
gggtgctgtt caagggaatt ttatgactcc ttcattacgg gagtataaat ctaatatccg  16920
tgatatttct ttttccgcct tagaaaaaat tagaagtctt aaaattagac aatttaatta  16980
taagaatgct gtaaacgaac tataccggat gagagaagag aaaagtccca atgatccacc  17040
attgacaaca gaagatatta aaacatacta cggtttaatc gtagatgaat gtgatgaaat  17100
gtttgtggat gaaagtggga aaggaattca tttgtactca tacgcatcca ttggaattaa  17160
aggtttacaa gaagttgatg caacagtaca ggaacaggag gtagaaatag caaatctaaa  17220
atcacaaata gctagtcaag aagatcggat agcacgatta gaagaattat tactacaaca  17280
attaataaat aagaaaccag agcagccata ggctggtctt tttattttgg ccaaaaagga  17340
gaggaaaaga tggatcgtat tgatgtatta ctaaaagcat ttatagctgc gtttggtggc  17400
ttctgtgggt atttcttggg aggatgggat gcaacattga aatcttagt  gacaatggta  17460
gttattgatt atttaactgg catgattgca gcagggtata acggagaatt aaaaagcaaa  17520
gttggtttca aggcatcgc  caaaaaggtg gtgctttttc ttttggtcgg agcggccgct  17580
caactagact cggcacttgg aagcaacagt gcaatccgtg aagcaacaat tttcttcttc  17640
atgggtaatg aattactttc actcttagaa aatgccgggc gaatgggtat tccactccca  17700
caagcattaa caaatgcagt tgagatttta ggtggtaaac aaaaacaaga agagaaaaaa  17760
ggagatgttc agtaatggaa atccaaaaaa aattagttga tccaagtaag tatggtacaa  17820
agtgtccgta tacaatgaag cctaaatata tcactgttca caacacatat aatgatgctc  17880
cagctgaaaa tgaagtgagt tacatgatta gtaacaataa tgaggtgtcg tttcatattg  17940
cagtagatga caagaaagcg attcaaggta ttccgttgga acgtaatgca tgggcttgcg  18000
gagacggcaa tggttcgggg aatcgtcaat ccatttctgt agaaatctgt tattcaaaat  18060
caggaggaga tagatactat aaagctgagg ataatgctgt tgatgttgta cgacaactta  18120
tgtctatgta caatattccg attgaaaatg ttcgaactca tcaatcctgg tcaggtaaat  18180
attgtccgca tagaatgtta gctgagggaa ggtggggagc attcattcag aaggttaaga  18240
atgggaatgt ggcgactact tcaccaacaa aacaaaacat catccaatca ggggctttct  18300
caccgtatga aacccctgat gttatgggag cattaacgtc acttaaaatg acagctgatt  18360
ttatcttaca atcggatgga ttaacttatt ttatttccaa accgacttca gatgcacaac  18420
```

-continued

```
taaaagcaat gaaagaatac cttgaccgta aaggttggtg gtatgaagtt aaataaaaca  18480
aaagaatagt tttatgaaca aaaataagag ccgtcctgtt gggcggcttt tttttattgc  18540
tcaattactg ttgcactaat tttaggcatt cctgttttat ctttttcgtc gtaggcgcca  18600
tagattgtta ctattgatcc tttagatatt tttaatccgt ttttaagtgt tatttcattt  18660
tcgttcgttt gcactccact ttggacaatt tgaatagtgt acatgccttt gccgtcattt  18720
tcgtttgtgc ttatgacaaa tgaaggtaat gctgaagact taagtaataa atctaccgtt  18780
ccggtagctt taagcctttt tcctttttcg tattgatctc catttgcctt aacaaaacta  18840
acttcttcag catcttgctt tatcttctta tttaactcat cctgagatgt taaatctttt  18900
ttagtttctg gttgagattt gacgttcgtt ttttcacttg attcactttg tttagaagaa  18960
tcacaagctg ttagacctaa caataaggta cttccaatgc aaatacttat aagtttttta  19020
tacattttca ttctcctcct ctatccaaat ttcttccatg tgcaatttta attcctttgc  19080
aattttatag gctgtaagaa aggtaggtag cgtcgtgtta ttaacgagtg aactcattgt  19140
agtttgacta attccaataa gttttgaaaa ctccttttga cgtatttctc tttcagcaaa  19200
aataacacga agtttacatt ttaatcgcac aatatcacct ctttaattat atacaattcg  19260
catatggaaa tgtgtcctcc tttaatttaa tcaacgaaca tttagaaaag tttaaatgga  19320
caggcaatat aactctttct aagtcatata cctatatcaa gaccacgagg aataccaagt  19380
ggaactaagg acatcaagag gggagaggat tacatgcgtt ggcagtataa tcacttgaat  19440
acaactccat atcttcatcc atccaaagaa ttatgttcaa tgtacaatgg atcgagatca  19500
agagcagaga cggaatcaat tttaaatcac atgaaaaatc atgaagttta tgatcgaaaa  19560
gaatataaag gatatttcag tttgtcacag gtattagaag aagatctata tggagaggaa  19620
gaagatgttt taaactggga aattctaatg gattgttatg atgtagttct tacaagaaaa  19680
ggtattgcat ttcgtgaaaa agaagaggag gaacaagcat gactcttgct ggagaagcga  19740
ttattatttg gacggcaaca gggttgtcag tagttgcaat gaaggcagca gaaaaaaatgg  19800
ggaaaagtgt tccacattgg cttccacgtg tcactttgta cacaacactt acaggctcgt  19860
ttctatacct tctacgttat gttctcgttt tatttctatg aaggaatacg atgtggaaac  19920
ttttcattcc ttatgtcata aggagtttag cttgtatgca cgtattcctt gaaacaggga  19980
tatataccct ctataagagg gatataagga gtgattttat gctggagttg ttatcagtac  20040
cattcgcagg tttaattttc gccatagttg gcgaaaggct caaaggaaga gagagtgatc  20100
gaaagaaaat acaagttttt tttgaagtaa gcggaattgc gatacgtaga gaggacaaat  20160
tacagtatcc agtttttctt gaacaaaaag aggatgaccg aagtacaact tatatatatc  20220
ggttgcctgt aggaatgccg agtaaaatta ttcagaaggt cgaggatgtt gtctctgaag  20280
ggctaagtaa acctgtccga attgattatg ataattacaa gctaaatatt cgtgtgtttc  20340
atagggatat accgaaaaaa tggtcatggt ctaaaggttt ggttgcagaa ggaagctggt  20400
gtgttccaat gggccaaagt ttagaaaaac ttatctatca tgattttgat aaaacaccac  20460
atatgacact aggtggtctg acacggatgg gaaaaacggt atttttaaaa aatgtagtta  20520
cttctcttac tttagcacaa ccagaacata ttaatttata cattattgat ttaaaagggg  20580
gcttggagtt tgggccgtat aagaatttaa aacaggtagt ttctattgct gaaaagcccg  20640
cagaagcttt tatgatatta actaatatcc tcaagaagat ggaagagaaa atggaatata  20700
tgaaatgtag acattatacg aatgttgtag aaacaaatat caaagagcgt tacttcataa  20760
```

-continued

```
tagtagacga aggagccgaa ctttgcccag ataaaagtat gaaaaaagaa cagcaaaggt  20820
tattaggagc gtgtcaacaa atgctctctc atatagcgcg cataggtggt gctttaggtt  20880
ttagattgat tttttgtaca cagtacccga caggggatac attaccgcgc caagtaaaac  20940
aaaatagtga tgcgaaatta ggctttagat taccgactca aacagcatca agtgttgtta  21000
tagatgaagc gggattagaa acgataaaaa gcattcccgg acgcgcgatt ttcaaaaccg  21060
atagacttac agaaatacaa gtgccttaca ttagtaatga gatgatgtgg gagcatttaa  21120
aaggatatga ggtggagaaa catgaggatg caaacgcata tgcaaatcaa ccgtcaaatg  21180
gcgatacttg cgacgattag aaagctacag tttgcaacga gaaggcattt aatgagtatt  21240
catgaaatgg gtggaataag aaatgcaaat cgaattctga aagatttatc tatttataca  21300
agtaaggtag tttacaataa agagcatgta tattatttaa accaatcagg acataagttg  21360
tttggcgaag ggaaagttgt acatcatggt aaagttacac acgctctttt acgtaatgaa  21420
gcttggttaa atttatattg tcctgatgat tggcaagtag aaactgaaat taaatatata  21480
aaggataata aaaagaaaaa aataattcca gatgtgaaat ttcgtgatga ggacagaata  21540
cttcatgctg tagaaataga tcgtactcag aaaatgatag tgaacgatga aaaattaaaa  21600
aaatatgagg agttaacgca gatttataaa cagaagcata acgggaaagt gccagttatt  21660
catttcttta caatcacaaa atatagagaa aagaaattag aagaactggc aaataaatat  21720
aatgtgtttg taaaagtata tgtaatcgct actacttaat gatgaaaaaa agagctgatc  21780
attttcgaat gattagctct tttttatgta ttgtattacg tcgtctattt tgtaaatttt  21840
attaattcct ttttctgcag caatggcatt taaagcatca atgatagctt caagcgaatc  21900
aaaacgaaca gcattagcat taccattcac taaatcacta atcgtgttgt atcttacttg  21960
ggattctgta gataatttat ttttagtgat ccccaattca tctaaagaat ttccgagtgt  22020
gaatttcatt ttattctcct ccgcagcact ggttatcttg tactcatttt acaacatcaa  22080
tcgaaattag taaaactttt ttcgttcaac tattgacgtt gaataattag agagttataa  22140
ttcaacttaa atagttgaac taatttagtt gaacttaaaa ggaggaacaa ttatgaatcg  22200
agtaaatgat tattttggtt tagaaagtaa atcagattgc atttggtttt atggtttctt  22260
cagtatatct acgattttat ttttaatcga tatgattatt gctcttatat aaggagggga  22320
gaaaatgctt agctcagcaa actatacgca atataaaaaa ttacaatcat tccgatcagt  22380
agaagagatg aatgaagcga tttgttcttt tttatacaaa catacacatg aattatccga  22440
atcagcaata aaagtattga aatttctagc aaggcactct tgtaaaatcc caggtgtctc  22500
tttcttgaag gtagggacaa ttgcggaggc attaaatata agtgatcgaa ctgttcgcag  22560
ggtactaaaa gtattagagg attttgaagt agtaactaga cataaaacaa ttcgaacgga  22620
aggaaaatta cgtggaggga acggacataa cgtctatgtc cttctaaaaa aatatagtgt  22680
cacaccgaat gtcctaccga aaatgtcaca gcgacaagat gaagaaaacc ttacagaatc  22740
aaaggtttca gatacaaaaa cggacaagga agctaaactt tctgaatcac accctctaga  22800
agaattgaaa agcgaattaa acgtaaaaga aacgtcagca agggaatcta aagaaatcga  22860
attagaggat ctagatgaaa cttttacacc agaaaatgta ccaagccaat tcagagatgt  22920
ggtagctcca ttcttcaaat cagcagataa aatttataaa ttgtatcatc gagtattaat  22980
agcttataaa cgttcaaaaa tagacaagcc tattgaacaa gtgataaatc aagccattca  23040
agcattcaaa gaaactgtct tcgcagaaaa agcaaataaa attagaagta cttttgaagg  23100
ttatttttat agaattgttg aaagtaaatt tgtaatggag agaaggaaag aatgtcgagg  23160
```

-continued

```
attattgttc gattggttaa atgaataata taaaattgcc cacagggaaa aatatatata  23220
taatttaatt atcatattct tagtaaataa gtgggtgaaa attttgaaat acgctgttta  23280
tgtacgagtt tcaacggata gagatgagca agtttcatct gttgaaaatc agattgatat  23340
ttgtcgatat tggttagaaa aaaacggata tgagtgggat ccaaatgcag tatattttga  23400
cgatggtatt tctggtacag cttggttaga acgtcatgcg atgcaactaa tattagaaaa  23460
agcaagacga aatgaattgg atacagtcgt atttaaatct atacaccgtt tagcaaggga  23520
tctaagggat gccttagaaa ttaaagaaat tctaataggt catgggatac gcttggttac  23580
aattgaagaa aattacgata gtttatatga aggtggcaat gatattaaat tcgaaatgtt  23640
tgccatgttt gctgcacaat tacctaaaac tatatctgta tctgtttctg ctgcaatgca  23700
agctaaagca agaagaggcg agtttattgg aaaaccggga ttaggatacg atgtaattga  23760
caagaaactt gttatcaatg aaaaggaagc tgaaattgta agggaaattt ttgatttatc  23820
ctataaaggc tatggattta agaaaatagc gaatatccta aacgataaag gcacatatac  23880
gaagtttggc cagttatggt cgcatacaac tgtagggaag attttaaaga accagacgta  23940
taaagggaat ttggtcttaa atagttataa aacagtaaaa gtagatggaa agaagaaaag  24000
agtttacact ccgaaagaga gattaacaat tatagaagac cattatccaa caattgtatc  24060
aaaagaatta tggaatgcgg taaatagcga tagggcaagt aaaaagaaaa caaaacaaga  24120
tacaagaaat gaatttagag gaatgatgtt ttgtaaacat tgtggtgagc caattacagc  24180
taagtattca ggtagatacg caaaaggaag taaaaaagag tgggtatata tgaaatgcag  24240
taattatatt agattcaatc gctgcgttaa ctttgacccg gctcattatg atgatataag  24300
agaggcgatt atctatggat tgaagcagca agaaaaagaa ctagagatac atttcaatcc  24360
aaaaatgcat caaaaaagaa atgataaatc tacagaaatt aagaagcaaa ttaagttgtt  24420
aaaagtgaaa aaagagaagt tgattgattt atacgtagaa ggattaatcg ataaagaaat  24480
gttttcgaag cgggatctta atttcgagaa tgaaattaaa gagcaagagt tggcattact  24540
taaattaaca gatcagaata agagaaataa agaagagaaa aaaattaaag aagctttttc  24600
aatgctcgat gaagaaaaag atatgcatga ggtttttaaa actttaataa agaaaatcac  24660
acttagtaag gataagtata tcgacatcga atatacattt tctttatagt tttaaagttg  24720
gttattagtt actgtgatat ttatcacggt acccaataac caatgaatat ttgataaatt  24780
gaacattttt agtaaacaat attttctcaa tatgagaatt gcgctttaca gaacacatgc  24840
tctcattaat gtgataaaat attctgtaaa tataatggaa aaagtgttgc ttattgaaat  24900
gaagggggta agttacttga aatttcatga aaaaattatg gggatgattg aggataggga  24960
tgacttaaca gctactagtg tagcgtgtaa aattggcgtt tcaaaacaat acatgtcaaa  25020
attcaaaaga caaggaacta ttggattctc tcaattattg aagctagcac ctattttgag  25080
cgttgaagga aaaaaagcaa agcaaactat gtccgattgg tgtttagaat tagataccac  25140
agagtctata aaacaaagtt ttgaatatgc gtgtctaact cgtaatacaa ttttattgaa  25200
acaattaata caaaagcata gcaaagaaac tggaacaatc cgagaatatg ttgaagtgta  25260
tacaatcttg tttaaatata ttaagaatat aattaaaggc tcggaaataa caaaggaatt  25320
aaagaagatt ggtgctatta aagataaggt tttagagata ttaacaaaga ttatggaatg  25380
ctatgaatat tatcatctaa aaaaattcaa tttaatgttg gaaactgcag aaacgattga  25440
ttcactggtt agagaaattg aaggagaacg aaaatccttc attaaggaat gttacaatta  25500
```

-continued

```
tcgtattgct gaattgtttg cgccgatttt cctacaaaag aataatgtag atttggctag  25560
gaagtatgcc cacttcttaa ttcatgctaa tgtttgtaca aaaacagtct ctgacgcata  25620
ttacatatta ggtatgtcaa atgtattaga aagtaaagaa caatgtttgt tcaatttaaa  25680
aaagagttac ttgttaagta aggaaattag ggatgctgat attgaacaag aggcgagata  25740
caatctagat gttgctaaaa tctattttgg ggtaaaacta gacgaagacg ctgacagtag  25800
gttattactg taccaaaaaa acccaacatg tgaattgtca attatagctc tccaagatat  25860
aataagagac agaggagaca aggacttttt aaattatttc atagcatgtt cttccgatga  25920
aatcgaatgt ttatacgatt tgttttatca atacttctac caagctaact atctattttc  25980
agcgatagta gcaaaagaat tgtgtaatag aggggataaa tctttgttga ctcaatcgat  26040
ggttaattta gggaatgaaa aacaaaaagg ggttgttgat attgaagaaa ttagtattag  26100
cagtttgtac attattaacg gttctaacag tgggattgtc gtataatgaa aatgtacaga  26160
tagataaaaa aatgcaaatg gttgaaatta aacctggtgg gtaaggatat tttaaagagc  26220
ggattaaaga ccgctctttt tttgttggta aactaaaatg aaaaaaataa aagtaattta  26280
ctttctgaat tttccctaga ggaaaggtta taattggatt atagcagttg agggggaata  26340
gaaatgaaaa aagaaagtat tttaaggtca tttttaaaat gtgtaatttc atgttcaaat  26400
agtgaatttg agttcaatca acttattgaa gtagcgttta atgttgaaca aaaaataaaa  26460
aaatagcgat gaagtaacac tacatcacta ttttgaagta ctttttaatt tttctagact  26520
ttccatcatt gttagcatgt tttgtaagac aatttcttga tgttcctcag gtagttgttc  26580
taaacggttt tttatgtgca agtacttttg attcatatcc gcatctaatt cacgagagtc  26640
agatcgtcct aagagataat caacaggtac accaagaaaa tcagctgcac gttcaacggt  26700
ttctctagat gcaggtttaa atccagtttc aaacttagaa acgctacctg cagtaacacc  26760
gatagcttgt ccaagatcat gttgtgttaa attccgttct cttcgtaatt gacgtaaccg  26820
atctttaaat tccacaataa tcacctcata agtggtttgt taggattatt ataatatttc  26880
ctaaagggaa aatcaatccg agttatttct aagaataata taaaatatgt gtaaaaatat  26940
atcttgaatt ttccctaagg gaatgttaag gtgatttaca aagatataga aaggagttac  27000
cacatgaaag taattaaaga cgagacaaaa ttaaaagctg cattcaaaaa atctgggtat  27060
aagtatcaag agttagctga cgaattagaa atatcctgca gctactgtta caagctaatt  27120
aacaatcata attacaaaaa gaaaatatcg tataacttag catccagaat ggcgcatgta  27180
ttaaatgcaa gtgtagttga tttgtttgaa gagcaagtcg attttttta ataccaatat  27240
tccctgaggg aacatagggg tgagagggcc atgtcagaaa tttattacaa agggtttatc  27300
atcaaggaaa cttatggcga aagaaatatc gaagaagtgt ttaaagaagc atatgagtca  27360
ttttatgggg ttgaagttaa ggttgttaaa aaggaattag ggactaaacg caatagtgca  27420
gccagctaat ctttaaactt cagtgagaac attcaatgaa gtcgattata aaatggacaa  27480
gcctgaaagg agagaaatga atgaaaaacg ggaaaaggtt gactaaacgt gaaaaaatgc  27540
atcttaaatc atatagctta aatcctgata attggttggt tttcaagaaa gcggatggag  27600
aaatgcattt agtacaccgt tatactagca caactcgtgt aattccaagt ttataagttt  27660
aggagggaat aagatggatc agttaacagt agcaagtgaa ttacgtcttt tagggagaag  27720
aaaagtagct ggatatgaat ttactggaat cgagggagga tttggtgaag gtaaaaaagc  27780
aatgttggtt ttggatatag ctacaattca taaccaacca ttaaaagaaa tcaatcgtcg  27840
cattaatgat aatcgcattc gatttaaaga tggtgtggat attgttgatt tgaaaagtgg  27900
```

-continued

```
tggctttaac ccaccacaat tattaaacct tggtttctca aatatgcaga tagcgaaatc  27960
aaataacatc taccttctat cagaacgagg ttacgcaaaa ctattaaaaa ttctcgaaga  28020
tgataaagct tgggaattat acgacatatt agttgatgag tacttcaaca tgagagaaaa  28080
gaatcaagtg gctacagatc caatgagtat tttaaaactt acattcgaag cattagaagg  28140
ccagcagcaa gcaatcgaag agataaagtc ggatgtacaa gacttgagag aaaatacacc  28200
attatttgca attgaatgtg atgaaatctc tacagctgta aaacgtcaag gagtcatatt  28260
gttaggtgga aaacagtcta atgcctatcg aaatcgtgga ttaagaggga aagtttatcg  28320
tgatatctac aaccaactat accgtgaatt cggagtgaaa agtcacaaag caattaaacg  28380
ttgtcactta aatgtagcag taaaaatagt tgaagaatat acacttccaa ttgtattgag  28440
cgaagagatt tcttttgtaa atgcacaaat ggattttaca gaaatgtagt tagttaaaac  28500
attctcaacc ggtttttttc taagttaaaa atttaaagaa aaggtggaaa agacaatgga  28560
ccagttacgt gttattgagg gagaaaaagt ggataagcca gattatgttg agatatacct  28620
tggagcattt atgaatgcag ttaatgagtt aaagaaacag gatgaggaaa cgagatcatt  28680
aagcaaggat acgtataaaa aagcaatttt ttatggagtt agatacattt caatatcaaa  28740
aaatgacagt ttgaattatg actacctaat gaatagattt cttttaataa gctatttaga  28800
aaatttgatg aaggtgttga cgcctaggga ttttatgacc atattcccaa tcgataaaaa  28860
ttatgatggc gctcgttatg aaatgaaaga ttactttttt accatgaatg aaattaaaaa  28920
aatcggaatg gatacaccta ttggagagaa aatcatggag tttttatggg attaccaaaa  28980
ctttaaagat ataacactat ttaacttagc ctctgtaagc attttaaata aattgcagaa  29040
aatgcaaggt aaaaaaacgt taactgaaga gtttgccgag cgattaggta tcgatactta  29100
cacgaagcat aaagaaaagg gtggaaaaga atatattaca aatgaccgta ctggtgagat  29160
ccaagaagtt aaaaaatcta gaccaagata tttaaaacca gttcaatgat tgatgttatt  29220
aaggcttata aacaaagaaa gtaacttgcg ccaacaagtt actaaataaa aatacttata  29280
aaaatatact tattagaaat ataacataca cactcgatgt atggaaaggg tgttattatg  29340
gctcttttta gaaaagtgca tacagaattt tggacagacg taaaagtatc agaagatatg  29400
acgccagaag acaaattgtt tatggtgtac cttttaacta atccccatac aactcaattg  29460
ggagtatatg aaatcacacc taagatgata gcttttgaaa tcggactatc aatagagtcg  29520
gctagagcac tattggaacg ttttgaaaac catcataaat taattaaata taacaaactg  29580
acaagagaaa ttgctataaa aaattggggc aaatacaacc tgaatagagg cgggaaacca  29640
attgaagatt gtcttaaaag agaaattgat aaagtgaaag atttatctct aataaaattc  29700
attttagaac atacagatca tgcagcttta aaaagaaaaa tcaatcttta tgcgggtttt  29760
gacgatacgt cccacgatac gttagcgata cgtgaccaag aagaagaaaa agaacaaaaa  29820
aaagaacaaa aagaagaaca agaagaaaaa gaaaaagaaa aagaaaaaca aaaagaagaa  29880
gaaaaagaac cagaagaaga aaaaacaaga ataaaatcca aagcgtcttt aaaatcagac  29940
gcaaagtcca atccaatacc gtataaagat atattggatt acttgaatga aaaagcaaat  30000
aaaaatttca atcctaaagc agaaggacat agaaagttaa ttcgcgctag atggaatgag  30060
gggtataaac tagaggactt taaaaaagtt atcgataaca aaactacgca atggtttggt  30120
aagaaaagtt ttgatggaaa accactagat caatttttaa gaccgagcac gttatttgca  30180
caaaaacatt ttgacaacta cttaaatgaa acggtcaaca tatccaatca acaacatgga  30240
```

-continued

```
gatcagattg ttatacctgg atttaggggg gaaatgccgt tttagaaagg agtactaaat  30300
gtgaaaaaga tacaagattc ttttgaaaaa cttactaagt taaaatttgc agatgaacaa  30360
tgtgataagc acacctttaa taaacatggg aaagaagtta ttaaattagt taggaaaatg  30420
attgatgatg caggaacggt atattgtccc cgctgcatgg ttgaagagca aaattcagtt  30480
ttatttcaac aagcaaataa tcattataaa aagattaata gagaacggaa gaaaaatgta  30540
ctctttcaac acagcatcat agaaaatcaa tccattacag aatcaagatt gtctacatac  30600
aagacggatt gtcaagaaac gaaagaaaac aaagaaaaag ctataaaaat tcttgaacgc  30660
ataaaaaacg gtgagttttt aaatgtatac attgcaggga ttcaaggagt aggaaaaagc  30720
catttagcgt atgcgatgct gtatgaatta gttaaacact attgggtaat atcagacggt  30780
gagaaattaa atgacgaaca tgcttttaaa aatatgaaaa gctgcttatt tgtagagatt  30840
gaaaagctaa ttcgattaat acagcactct tttagaaata tagagtcaaa atatacaatg  30900
gattattgta tcagtttaat ggtagatgtg gatttccttg taatcgatga tttaggagct  30960
gaaagtggtt cgatgaatcg aaacggagaa gcaagcgatt ttgttcataa aatactttat  31020
ggtgttacaa atggacggca aggagcaaat aaaacaacaa ttacaacttc aaatctgtca  31080
agcgctcaat tatttcaaaa atacgatccg aaactagcaa gtagattgtt aaacggtgta  31140
tcgaaagatg aaacaattgt ttttaaaaca accactgaca aacgaattgt aaatttagac  31200
attggattct aataaaaggg gtgcggagaa atgaaagagg taaaggggaa aaacaccaaa  31260
ttaatggaag aatttgacgt gttattaaga caactgctga ttaaatctaa aacagatgaa  31320
agggtaaaaa actttttgga tgatctgttt gaaatgctaa gtgataataa gctgcagtct  31380
gatattgatt tcaaaacagc attaaataag ttaagagaaa agcactttcc taagtttgat  31440
aaaggagaga gcaaaaatga ctaaagaaaa gggacaagct aaggaagtag ttaatgttcg  31500
tggaatgtca gatgatgagt ttatagagaa atacggaagg cttgtacatc attgcgtatg  31560
gaaaagatat gcgaaaaaaa aggccagtat agagcgtgat accggtttag atattgagga  31620
tttaacacaa ttcggaatga tcggtttgat aaaggcgcga gataattttg accttgaatt  31680
tggatgtgcg ttttcaacgt atgctgttcc gaaaattatt ggggaaatag gaagggcaat  31740
tcgggataac caaaaaataa aagttcaaag aaccgtatat ggcgtaaaag gaaagatttt  31800
aaatcaacag ttagcagata aagaaccaga agaaatagca gacattttgg atgagtcagt  31860
atctttagta aagacggctt tagagtatca accaagcaca gattcactca ataaggttgt  31920
atatgcatct ggagctaatg aagaactgac attagaaaga atgatagagg atactaaaac  31980
ggaagacatt gaagaaacaa ccattaatcg agctgtgata agagaattta aagctgcatt  32040
gcctcctaaa gaatatatcg ttttagatat gcgtttacaa aatatgacgc aacaaaacat  32100
tgcaaatcaa atgggataca gtcaggtaca aattagccgt atattagcaa agattaatca  32160
aagagctgct caatttggta aagaaggagg gcttcaagat tgagtgttac aaaaggtgtt  32220
tgtatcgatg tagatcactc agatttgcta catgagaaag tagagtactt tttattccct  32280
gctaaaccaa gtcattacta tgtaagcaga tttaatcgta aaggagcgca ttttggttgt  32340
tatcaagctg aaaggtttca aatcacggaa aaggaagtat ggacaccaga acctcaaccg  32400
aatctgcctg agttgaatac aagcttattc tatagagctc agttgatttg gcgaaaaaag  32460
gggtataaag ataaaccact taaagactac atcgtacagc cgagagggaa acattgctac  32520
ttttggcatg atcgggagcg aaagaaattt tgtggctgtt ttccgctaca ttggtttacc  32580
gattttgtac cagttcaaag tcatcatata gaagaaaaaa ctagagaaga ggttaagtta  32640
```

-continued ttacaacggc cagatggaca acttgcattt ttttaacgaa agaaagtgaa tgggcgtttt 32700
acccagtcat cgatttaaaa aaaggagtgt tcgtaatgga tattaaaaag ttatttgcaa 32760
tgcagaacat tttggataaa agagttttag agtcaaaaaa tctttctaga ggagaagtat 32820
tcgaatttag aatactagcg tttttagatg aattaggcga atgcatgaag gaatggcgag 32880
tatttaagtt ttggagcgac gatcgtaaac cgagaactag catacctaca ggggaaatca 32940
tagtactaga tgatggttat gaagtagaag tttataaaaa ccctttactt gaggaatatg 33000
tggacggact acattttgca attggacttt gcatagattt gaaaacagaa attaactttc 33060
ctgcttctat gcgttgcgag acagttacag agcaattttt cgaattgtat catctagcaa 33120
tacgattaaa agaagaaccg acagcattta gggcagatgt tcttttatcc cattatcttg 33180
gtttagggga attgttgtgc ttttcgttag aagaaattgg acatgagtac attgagaaaa 33240
acaaaatcaa tcatgaacgt caaagtaatg gatactaata caatttgaat tttgttaaga 33300
aaaagtgagt gagagatgga actattatga actatagaat tccaatattg ggaatctata 33360
ttaattatat aatttaaaaa tgtggtaatg gttaagattt taatataggg aatttatgaa 33420
gtgttagtat gatttgattg gctgtcttta actttttatt agtaatttca tatattgtag 33480
ggtgcaatat tgaagaagta tggggggag aaaatggatt gttttaaaaa aggtaaattt 33540
ataccatttc catgtgcttt accaattcct gaagctggtc ctactggccc aactggtcca 33600
cctggatcag ctggaggctc gaccggtcca actggtccaa ccggcccgca gggtttacaa 33660
gggattcaag gggttcaagg gaatccagga actactggac ctcaaggaat tcaaggaatt 33720
caaggaattc caggggtttc aggtcctatt ggtcctattg gtcctactgg aatccaagga 33780
gttcaaggca ttcaaggatt tcctggcatt ccaggtccta tgggcccgat aggactaacc 33840
ggtccgactg gtatccaagg tattcaaggg attcagggag ttcaaggtat ccaaggtatt 33900
caaggggatg taggcccaac tggccctcag ggaattccgg gtattccagg attaactggc 33960
ccaactggct ctcaaggtgt tactggagtt actggcccat ccggaggccc accaggtcca 34020
actggtgcaa caggtccaac cggtccagct ggaggcccac caggtccaac aggtccaacc 34080
ggtccagctg gaggtccaac aggattaact ggcccgactg gcccgactgg tccaacagga 34140
attcaaggta ttcaaggggt acagggtact caaggtattc cgggtccaac tggtccacaa 34200
gggatccaag gagttcaagg acttcaagga ataccaggca ttccaggttc tatgggccca 34260
acaggactaa ctggtccgac tggggcttcaa ggtattcaag ggattcaggg gaatccaggt 34320
ccgactggtc cctttggccc gactggcccg accgggcttc aaggtattca aggcttacag 34380
ggtattcaag gtattccagg ttccaacagg acctcaagga atccaaggtc caacaggacc 34440
tgctagcaca ctttccacaa aagctattct tttttggggg tactaattca gggtttcaac 34500
gtatagctgg atcaccgggt gcagattcac aagacattcc ttatgtactt ggcggagctg 34560
gtagtgttgt aggtctttct gcttctataa gtattaataa tttaccaata ggagtatata 34620
caatacgagt atgtaaaaat gttcctatta atcttgctgc tccggggcct ggccaagtaa 34680
tatctacaat tattcttaca actacagcag tgattagtgg cactattata ttgactatta 34740
atccttctga tattggtgca caacctgtaa gagtatttaa ccctaattta gttatagcac 34800
ctgctacagt tgcttggagc agtacaatac ctggtgacat agttgcaaga ggtgatgcaa 34860
tgtcactttt tataactcca ggtattacgc aaaatgctgt gtatacagta ttcttgcata 34920
caggaaatta aagtttattt tatgtgaatt taagtcctgt aaattggaat gaaaaattaa 34980

-continued gatatgtatc ggagtctttt tatgtacaaa agaataagag atttcttctg aacatctaaa 35040
aggaatctct tattcttaat cgataaatta ggttttagaa aaatgaaaag attttgtatg 35100
aaaataaata aaagaatcca ttcgttacaa acggattctt cccacaaggt gtgtaagaaa 35160
ttcaagataa ctcgaccaga gcatcatgta gaatttcttg tgatattaat gtattcaaag 35220
acatccaaaa gatgaatggc aattaaataa aatctttatt tgaaaattaa agattgcttt 35280
tgttagggtc tctatgacta agagttatct taatttttta ggtttatgaa gtatttgagt 35340
aataatttag tttcagacaa aggtgatgtt tagtagtaat accggtttgc ttcagtagac 35400
attgcaattg cttttgtttc atgaactgta ccatatggat gttctggagg tgcatatata 35460
gcgtaaattt taagtggtgt atttcctgta ttgattacat tatgccattt tccagcaggt 35520
atcataattg catagtcatc atagaccatt tcttgaaaat ctaatttatc tttgttatca 35580
cccatttgaa cgagtccttg gccctcttca atacgtatga attgatcagt tgtagggtgt 35640
acttctaaac ctatgtcatc tccaacatta atactcatta aagttacttg taagtttttt 35700
cctgtccaga tagcggtgcg gtaagtattg ttttgtttag tggcttggtt aatattcaat 35760
acaaatggtc tagctccata atctgttaat ctaacatttt cacaataagg attccggttg 35820
cggttccaag cattattgtt gtaattgtaa taataaggat tccaagcgta aatccaatta 35880
ttgttattcc agatgctatc cattgggctt tgagattgat aataataacg tggaatatgt 35940
tgcatatcca agctcctctc ataattgtat catttacttt ttatcctatg ctgttgtcta 36000
tttataggaa tgcagaataa ggggaaatgg gcagtaataa aaaatataaa aaaacgtttt 36060
tattttttca ggaaaaaataa aagtaacaag ttaataaggg atgtactact ggtataaaaa 36120
acttaataaa atagttattt gaattaaaaa gagcgccgtt ggagagtgcg gtgctcttag 36180
accaagaact ataacaggga ttaaggaaag aatattgtat accaaattga tagtaatgca 36240
agccatccaa ttgtcagcgc tatgtatttt aaaattttca tgattactcc ttttaggtat 36300
agagtgcacc aagcaagagg atgttattaa tttttaaaca aaatgcttat ttaaaaacta 36360
aagagggctt tttaaagcgc tccttaagaa aaataaaaaa gaatacctca tgatactgta 36420
tgtatgtttt tttaggaatg tgaggattta aaacaaaatc gttattttat agatcggagt 36480
gaaattcaaa tgattgttaa agcgacaata aaacttgaat tagatgattc gcagaaaaat 36540
tgggtttctt atgttagaga acaaggtgga gaagaagcgg tatttcatta tctggaagaa 36600
gaagtgcaga agaaaattga attagctgat tttgtggaga tgaaatacaa aaataagtaa 36660
tttaaaccaa aacgctattt tataaaataa aacagctagc gtgattagct agctgtcctg 36720
ttaagaaaag aaaacggtgt ttagcaaatg ttgctgttgt aattgcgaat tacaaccata 36780
gtatgagcag aagtaaaaat gttatgcaag aaagttaaat aaaaactgca ttttattgaa 36840
aagggggaat ggatatgtct ctagtaggga atttaaagga actccaagaa aaagccatcg 36900
atgaaaaggt attggaattt gcggaagaaa tggaaatcgt aataactaaa agtgccgcaa 36960
gcggatattc aggtcataga tataagattc ataatgaaaa tccaaatcgg catatgatgt 37020
gttcaaaaat atttatagaa aagttacaag aattactgga cggtgtgaag gttgaattta 37080
aggaagaaga aaagaaaaat attttaggcg gatcttacta cgaacattac atccgtttta 37140
agtggaatga ctaatttctt attaaaaatt ttattttgga gaaagggagt agaaagaatg 37200
aaaactttta atgtgacttt tacagagttg aaaatatatg aagcagtcat tgaagcggag 37260
tcagcggaaa agattattga tgtgattaaa cacttaaaaa gaactgaaga tgatttagta 37320
gacaaaggag tcatcataaa cgaagttagt gagataaatg ttagtaaaga acaaaagttc 37380

-continued

```
gaataaatca acttctcaga ttgtttattt tgagacggaa acaactttct gaatatcata  37440
agaccttatt agcgaaaaaa ctcttattcg agcgtacaag cctgttatac acgttgcacg  37500
gaaattagaa tgaatttgtt aaggaaggaa gtataaaaat gagggcttgg aagaaaaaac  37560
atgttaaaag agcatttttg aatcgtcaaa aggaaattga taaagaacgg actgctgcag  37620
cttggagaaa tatttttgtg aaatcaggaa tcataaaata aaaaaggaaa agcaactcgt  37680
tggggacaag tcacttttcc agatggcaat gtaaatccat tatagcaaaa catatgtaca  37740
agctgtagca ataaacaacg agatattttg acacctatcg acaattagaa atgtggttgt  37800
tgatctagaa atatgaaagt aggtgaatca tcatttgttt aactggctga gagattacca  37860
aaagttagaa gaagacatag cctatctgga atacaactta gataagacaa aagctgaatt  37920
aagacgctgg gtgagtggtg atttgagaga agtacgttta acggcagaat ctgaaggtgc  37980
aaaagttgaa aaccgcattg aagcgattga atacgaatta gcacataaga tgaacgatat  38040
gtataaatta aaaaagttaa ttagtaagtt tagaggttta gaaaatcaga tactcaaatt  38100
aaaatatgtg gatggtatga cgttagaaga aatagcagag gcagtaaatt atagttctag  38160
tcatatcaaa aagaaacatg ctgaactcgt tagattaatt aagttcgtgg agcgagaagg  38220
tgtcatttag gttcactcct aaaatgaatc gaaacggttg aaaaaatgat ttatattgat  38280
agcatacaat tttagcagaa gggcaactgg tgcacggttg ctctttttga ttttggaggt  38340
tattagacga tggatgtaca agagttgtcg agacgattag aaaatctaga acataaagtg  38400
cttcaggtag aaacgaaggc agatgtgcta aaccgaacag ctatacaaaa aggcgataaa  38460
ataaaagtgg tgtatccgca tttagggata caaggcgagt atttagtgga gaaaattgat  38520
aatggtgtgt tggaattggt agcagaagaa acaatgaaaa aaatacagga gtgattagga  38580
ttgaagaagt tatctaaaca agagctagca gctgtaatga cacattgtat ttcaacgctt  38640
ggtgagcaga ttgttaatga gcatattaat ccccagaagt tggcgcaagc aagtgcactc  38700
cataacgatc tctttgataa taccactcct aaagaacgta gggaagcgac gatcagttta  38760
ctagggaaag cgattgatga gtttttagag agtaaggagt gaggatatgg gaaagggata  38820
ttttaataag gctgtatgtt tagtgtgtgg tcatcaagat agagtgaatc atccatctaa  38880
aaaagagtat caagaagtaa cggtttgtcc ggaatgcaac ggtgcttttg tagatgtgtg  38940
gaagctagga aagtacaaac gtaatacaca gtctaatgaa gaacctttat taacaattac  39000
attaacagat atagatgcta aaccgatagt tcattacaaa ggtgaacaga tagatagaaa  39060
gttacgtgtt acgtttgatt gggaatctca atcgattgat aaaattaatc ggacatacat  39120
tcatattgaa catgtaccag ccgataacaa acgtttaaat accgagacca ttcagcataa  39180
tcatcctatt gcaaataagg aacaagttta gatgttgtcc atatttgtta ataggtaaaa  39240
gataagtgtt ttatctggaa gttcaaacgt gaattaaaga aattaaaaaa ggaatatgaa  39300
aaggagagtc actgaatgaa cgggtttaat aaaattgtaa acgatatgca aaatgaacaa  39360
gtaggaaatg ctatgctaga ttttgctttg gccgctaaaa tgatgttcgc tgcctttaca  39420
cagtttaaag aagctggatt taacgaagag cagtcattcg aattaacacg tgagatatta  39480
attgattcat taagtaagaa tcaatagatc aatgaggtga aagggaatgc aagtatattg  39540
ctctgagtgt gataaaagtt atgacatgca gccgcaagta acacaactcc ctaatcgtat  39600
tgagaagtgt ttctttattt gtcctcattg taatcatgaa catatagctg cgtacgtgaa  39660
tgataagatt cgtaagtatc aagcagatat agcaaagtgt catgagcgga ttaataaaaa  39720
```

-continued

```
gaatcttgct atcgaagatg aaatgaaacg attaaggaag aggtttgaca ggagaaagtg  39780

agaggtgaag cgagtttgaa aatgctatta acaaagcatt ggtgtttaga tagaaactgc  39840

ggatttgaag agacttctca taaggtacgt gatggttgga aatgtcctga ttgtaatgga  39900

ccaatggcgt ttcaacaggt gaataagaaa aaagaaagcg ccaagtgatg gtgcttttta  39960

ttttggagga ggatgaagga tggaaggaca ggagttaaca ttggaaaaga aagacagtat  40020

ttatcttaga ccaagatacc ctcataagat tgacgcaagt aaaatcaaat ccttaaaaga  40080

tgtaattaag attttaggat tgatggatat tcgtttggac gacaaggcgg tcattggtct  40140

agaacacttg attgaaaagg aggaagaata aaatggccaa taacaaatta attattgaag  40200

taactgcgga tacaactgag gcattagaag gaattaaaga agtaactgaa gcagctaatg  40260

aatgtgcaga tgcgctggac aaattagaaa agattatgga taagtttaca aatcgaagtg  40320

atacagtgga actctattgt gaaggtaaat tgttatcgaa gtctacagtt aatcatacag  40380

ctgattcaat tcaatgtcgc ataatcaagg gagaagagct tggaggaagt gaacgctgat  40440

gaagaaaccg cttagaccat gctgcgaatt tcattgttat aatctcacac gtgaaagata  40500

ttgtgaggaa catagataca aagagaagga aacgcagcag gataagaata gatactacga  40560

ccgattcaaa cgggacaaag agagtacggc tttctatagg tcaaaggcat gggaaaggtt  40620

aagagagcag gcactaatga gagacaaagg gttgtgccta cattgtaaga acaatagaaa  40680

gattaaagtt gcagatatgg ttgaccatat cattccaatc aaagttgatc caagtttaaa  40740

actcaaatta gaaaatttac aatcactttg taatccatgt cacaacagaa aaacagcaga  40800

agacaaaaag aaatacgggt aggggcgggt cgaaaaacat tcagggcggt ctgtccgtac  40860

cgccgcccc                                                          40869
```

<210> SEQ ID NO 3
<211> LENGTH: 161
<212> TYPE: PRT
<213> ORGANISM: Bacillus anthracis

<400> SEQUENCE: 3

```
Met Ala Gly Arg Asn Lys Gln Pro Leu Ser Val Ile Gln Gly Lys Gly
1               5                   10                  15

Arg Ser Asn His Ile Thr Lys Ser Glu Lys Asn Arg Arg Glu Lys Gln
            20                  25                  30

Glu Glu Ala Leu Arg Gly His Thr Asp Lys Ile Glu Ala Pro Ser Tyr
        35                  40                  45

Leu Thr Ala Ala Gln Lys Lys Glu Phe Asp Thr Leu Ala Ala Glu Leu
    50                  55                  60

Val Arg Leu Lys Ile Phe Ser Asn Leu Asp Val Asp Ser Leu Ala Arg
65                  70                  75                  80

Tyr Val Asp Ser Lys Asp Gln Tyr Ile Lys Met Val Arg Leu Leu Arg
                85                  90                  95

Lys Thr Lys Pro Ser Asp Asp Phe Lys Leu Tyr Ser Gln Met Gln Arg
            100                 105                 110

Ser Lys Asn Leu Leu Phe Asn Glu Cys Arg Ser Ser Ala Ser Asp Leu
        115                 120                 125

Gly Leu Thr Ile Thr Ser Arg Leu Lys Leu Val Ile Pro Glu Val Asp
    130                 135                 140

Thr Ser Gln Gln Lys Gln Ser Glu Ala Gln Lys Arg Phe Gly Asp Arg
145                 150                 155                 160

Ile
```

<210> SEQ ID NO 4
<211> LENGTH: 161
<212> TYPE: PRT
<213> ORGANISM: Bacillus anthracis

<400> SEQUENCE: 4

```
Met Ala Gly Arg Asn Lys Gln Pro Leu Ser Val Ile Gln Gly Lys Gly
1               5                   10                  15

Arg Ser Asn His Ile Thr Lys Ser Glu Lys Asn Arg Arg Glu Lys Gln
            20                  25                  30

Glu Glu Ala Leu Arg Gly His Thr Asp Lys Ile Glu Ala Pro Ser Tyr
        35                  40                  45

Leu Thr Ala Ala Gln Lys Lys Glu Phe Asp Thr Leu Ala Ala Glu Leu
    50                  55                  60

Val Arg Leu Lys Ile Phe Ser Asn Leu Asp Val Asp Ser Leu Ala Arg
65                  70                  75                  80

Tyr Val Asp Ser Lys Asp Gln Tyr Ile Lys Met Val Arg Leu Leu Arg
                85                  90                  95

Lys Thr Lys Pro Ser Asp Asp Phe Lys Leu Tyr Ser Gln Met Gln Arg
            100                 105                 110

Ser Lys Asn Leu Leu Phe Asn Glu Cys Arg Ser Ser Ala Ser Asp Leu
        115                 120                 125

Gly Leu Thr Ile Thr Ser Arg Leu Lys Leu Val Ile Pro Glu Val Asp
    130                 135                 140

Thr Ser Gln Gln Lys Gln Ser Glu Ala Gln Lys Arg Phe Gly Asp Arg
145                 150                 155                 160

Ile
```

<210> SEQ ID NO 5
<211> LENGTH: 565
<212> TYPE: PRT
<213> ORGANISM: Bacillus anthracis

<400> SEQUENCE: 5

```
Met Asn Trp Ile Met Glu Arg Val Phe Ala Tyr Cys Glu Asp Ile Leu
1               5                   10                  15

Asn Gly Lys Ile Asn Ser Cys Lys Lys His Arg Trp Ala Ile Glu Arg
            20                  25                  30

Phe Ile Arg Asp Tyr Glu Glu Cys Gln Ser Glu Asp Ser Pro Phe Tyr
        35                  40                  45

Phe Asp Gly Glu Ile Ala Glu Asp Phe Tyr Trp Phe Ala Lys Glu Phe
    50                  55                  60

Lys His Val Glu Gly Ile Leu Ala Gly Glu Ser Val Glu Leu Thr Asp
65                  70                  75                  80

Phe Gln Leu Phe Leu Ala Ala Asn Ile Phe Gly Phe Lys Lys Lys Ile
                85                  90                  95

Asn Gly Ala Arg Arg Phe Arg Lys Val Phe Ile Gln Leu Ala Arg Lys
            100                 105                 110

Asn Ala Lys Ser Gln Phe Leu Ala Ile Val Ala Ala Phe Cys Thr Phe
        115                 120                 125

Leu Gly Asp Glu Lys Gln Arg Ala Tyr Ile Ala Gly Trp Thr Arg Asp
    130                 135                 140

Gln Ser Ser Glu Val Tyr Glu Ala Val Lys Thr Gly Ile Ser Ser Ser
145                 150                 155                 160
```

-continued

```
Glu Leu Leu Glu Gly Lys Trp Lys Glu Ala Tyr Ser Thr Ile Glu Ile
                165                 170                 175

Phe Lys Asn Gly Ser Val Val Val Pro Leu Ser Lys Glu Ala Arg Lys
            180                 185                 190

Thr Gly Asp Gly Lys Asn Pro Ser Leu Gly Ile Val Asp Glu Tyr His
        195                 200                 205

Ala His Glu Thr Asp Glu Ile Tyr Asp Val Leu Ser Ser Gly Met Val
    210                 215                 220

Ala Arg Lys Glu Pro Leu Met Phe Ile Ile Thr Thr Ala Gly Phe Asp
225                 230                 235                 240

Leu Ser Arg Pro Cys Tyr Arg Glu Tyr Glu Tyr Val Ser Asp Ile Leu
                245                 250                 255

Asp Pro Ser Lys Asn Val Glu Asn Asp Asp Tyr Phe Val Met Ile Cys
            260                 265                 270

Glu Leu Glu Lys Asn Asp Asp Ile Lys Asp Glu Ser Asn Trp Ile Lys
        275                 280                 285

Ala Asn Pro Ile Val Ala Thr Tyr Glu Glu Gly Leu Glu Gly Ile Arg
    290                 295                 300

Ser Asp Leu Lys Val Ala Leu Asp Arg Pro Glu Lys Met Arg Ala Phe
305                 310                 315                 320

Leu Thr Lys Asn Met Asn Ile Trp Val Asp Lys Lys Asp Asn Gly Tyr
                325                 330                 335

Met Asp Met Ser Lys Trp Gln Lys Cys Glu Val Asp Thr Phe Asp Phe
            340                 345                 350

Ser Gly Ala Thr Leu Trp Ile Gly Gly Asp Leu Ser Met Thr Thr Asp
        355                 360                 365

Leu Thr Ser Val Gly Trp Val Gly Met Asp Asp Glu Gly Asp Phe Ile
    370                 375                 380

Val Gly Gln His Ser Phe Met Pro Glu Ala Arg Leu Lys Glu Lys Met
385                 390                 395                 400

Ala Ile Asp Lys Val Arg Tyr Asp Leu Trp Ala Glu Gln Gly Tyr Leu
                405                 410                 415

Thr Leu Thr Pro Gly Glu Met Val Asp Tyr Thr Ile Val Glu Ser Trp
            420                 425                 430

Ile Glu Asn Phe Ser Lys Asp Lys Glu Ile Gln Glu Phe Asp Tyr Asp
        435                 440                 445

Lys Trp Asn Ala Leu His Leu Ala Gln Asn Leu Glu Asn Lys Gly Phe
    450                 455                 460

Val Cys Val Glu Ile Pro Gln Arg Ile Ala Asn Leu Ser Ile Pro Thr
465                 470                 475                 480

Lys Asn Phe Arg Glu Lys Val Tyr Glu Lys Lys Val Lys His Asn Gly
                485                 490                 495

Asp Pro Val Leu Phe Trp Ala Leu Asn Asn Ala Val Val Lys Met Asp
            500                 505                 510

Asp Gln Glu Asn Ile Met Ile Ser Lys Lys Ile Ser Lys Asn Arg Ile
        515                 520                 525

Asp Pro Ala Ala Ala Val Leu Asn Ala Phe Ser Arg Ala Met Tyr Gly
    530                 535                 540

Ala Ser Val Arg Phe Asp Val Ser Glu Phe Ala Asn Lys Asp Phe Leu
545                 550                 555                 560

Gly Lys Leu Trp Asn
                565
```

-continued

<210> SEQ ID NO 6
<211> LENGTH: 565
<212> TYPE: PRT
<213> ORGANISM: Bacillus anthracis

<400> SEQUENCE: 6

```
Met Asn Trp Ile Met Glu Arg Val Phe Ala Tyr Cys Glu Asp Ile Leu
1               5                   10                  15

Asn Gly Lys Ile Asn Ser Cys Lys Lys His Arg Trp Ala Ile Glu Arg
            20                  25                  30

Phe Ile Arg Asp Tyr Glu Glu Cys Gln Ser Glu Asp Ser Pro Phe Tyr
        35                  40                  45

Phe Asp Gly Glu Ile Ala Glu Asp Phe Tyr Trp Phe Ala Lys Glu Phe
    50                  55                  60

Lys His Val Glu Gly Ile Leu Ala Gly Glu Ser Val Glu Leu Thr Asp
65                  70                  75                  80

Phe Gln Leu Phe Leu Ala Ala Asn Ile Phe Gly Phe Lys Lys Lys Ile
                85                  90                  95

Asn Gly Ala Arg Arg Phe Arg Lys Val Phe Ile Gln Leu Ala Arg Lys
            100                 105                 110

Asn Ala Lys Ser Gln Phe Leu Ala Ile Val Ala Ala Phe Cys Thr Phe
        115                 120                 125

Leu Gly Asp Glu Lys Gln Arg Ala Tyr Ile Ala Gly Trp Thr Arg Asp
    130                 135                 140

Gln Ser Ser Glu Val Tyr Glu Ala Val Lys Thr Gly Ile Ser Ser Ser
145                 150                 155                 160

Glu Leu Leu Glu Gly Lys Trp Lys Glu Ala Tyr Ser Thr Ile Glu Ile
                165                 170                 175

Phe Lys Asn Gly Ser Val Val Val Pro Leu Ser Lys Glu Ala Arg Lys
            180                 185                 190

Thr Gly Asp Gly Lys Asn Pro Ser Leu Gly Ile Val Asp Glu Tyr His
        195                 200                 205

Ala His Glu Thr Asp Glu Ile Tyr Asp Val Leu Ser Ser Gly Met Val
    210                 215                 220

Ala Arg Lys Glu Pro Leu Met Phe Ile Ile Thr Thr Ala Gly Phe Asp
225                 230                 235                 240

Leu Ser Arg Pro Cys Tyr Arg Glu Tyr Glu Tyr Val Ser Asp Ile Leu
                245                 250                 255

Asp Pro Ser Lys Asn Val Glu Asn Asp Asp Tyr Phe Val Met Ile Cys
            260                 265                 270

Glu Leu Glu Lys Asn Asp Asp Ile Lys Asp Glu Ser Asn Trp Ile Lys
        275                 280                 285

Ala Asn Pro Ile Val Ala Thr Tyr Glu Glu Gly Leu Glu Gly Ile Arg
    290                 295                 300

Ser Asp Leu Lys Val Ala Leu Asp Arg Pro Glu Lys Met Arg Ala Phe
305                 310                 315                 320

Leu Thr Lys Asn Met Asn Ile Trp Val Asp Lys Lys Asp Asn Gly Tyr
                325                 330                 335

Met Asp Met Ser Lys Trp Gln Lys Cys Glu Val Asp Thr Phe Asp Phe
            340                 345                 350

Ser Gly Ala Thr Leu Trp Ile Gly Gly Asp Leu Ser Met Thr Thr Asp
        355                 360                 365

Leu Thr Ser Val Gly Trp Val Gly Met Asp Asp Glu Gly Asp Phe Ile
    370                 375                 380
```

-continued

Val Gly Gln His Ser Phe Met Pro Glu Ala Arg Leu Lys Glu Lys Met
385 390 395 400

Ala Ile Asp Lys Val Arg Tyr Asp Leu Trp Ala Glu Gln Gly Tyr Leu
405 410 415

Thr Leu Thr Pro Gly Glu Met Val Asp Tyr Thr Ile Val Glu Ser Trp
420 425 430

Ile Glu Asn Phe Ser Lys Asp Lys Glu Ile Gln Glu Phe Asp Tyr Asp
435 440 445

Lys Trp Asn Ala Leu His Leu Ala Gln Asn Leu Glu Asn Lys Gly Phe
450 455 460

Val Cys Val Glu Ile Pro Gln Arg Ile Ala Asn Leu Ser Ile Pro Thr
465 470 475 480

Lys Asn Phe Arg Glu Lys Val Tyr Glu Lys Lys Val Lys His Asn Gly
485 490 495

Asp Pro Val Leu Phe Trp Ala Leu Asn Asn Ala Val Val Lys Met Asp
500 505 510

Asp Gln Glu Asn Ile Met Ile Ser Lys Lys Ile Ser Lys Asn Arg Ile
515 520 525

Asp Pro Ala Ala Ala Val Leu Asn Ala Phe Ser Arg Ala Met Tyr Gly
530 535 540

Ala Ser Val Arg Phe Asp Val Ser Glu Phe Ala Asn Lys Asp Phe Leu
545 550 555 560

Gly Lys Leu Trp Asn
565

<210> SEQ ID NO 7
<211> LENGTH: 432
<212> TYPE: PRT
<213> ORGANISM: Bacillus anthracis

<400> SEQUENCE: 7

Val Lys Ile Val Asp Ser Val Lys Lys Phe Phe Asn Phe Glu Lys Arg
1 5 10 15

Gln Thr Ser Gln Val Ile Glu Leu Asn Lys Asp Asp Glu Lys Leu Leu
20 25 30

Glu Trp Leu Gly Ile Ser Pro Ser Thr Ile Ser Val Lys Gly Lys Asn
35 40 45

Ala Leu Lys Val Ala Thr Val Phe Ala Cys Ile Lys Ile Leu Ser Glu
50 55 60

Ser Val Ser Lys Leu Pro Leu Lys Ile Tyr Gln Glu Asp Glu Tyr Gly
65 70 75 80

Ile Gln Arg Gly Thr Lys His Tyr Leu Asn Asn Leu Leu Arg Leu Arg
85 90 95

Pro Asn Pro Tyr Met Ser Ser Met Asn Phe Phe Gly Ser Leu Glu Ala
100 105 110

Gln Lys Asn Leu Tyr Gly Asn Ser Tyr Ala Asn Ile Glu Phe Asp Arg
115 120 125

Lys Gly Lys Val Gln Ala Leu Trp Pro Ile Asp Ala Ser Lys Val Thr
130 135 140

Val Tyr Ile Asp Asp Val Gly Leu Leu Asn Ser Lys Thr Lys Met Trp
145 150 155 160

Tyr Val Val Asn Thr Gly Gly Gln Gln Arg Val Leu Lys Pro Glu Glu
165 170 175

Ile Leu His Phe Lys Asn Gly Ile Thr Leu Asp Gly Leu Val Gly Val
180 185 190

-continued

```
Pro Thr Met Glu Tyr Leu Lys Ser Thr Leu Glu Asn Ser Ala Ser Ala
        195                 200                 205

Asp Lys Phe Ile Asn Asn Phe Tyr Lys Gln Gly Leu Gln Val Lys Gly
    210                 215                 220

Leu Val Gln Tyr Val Gly Asp Leu Asn Glu Asp Ala Lys Lys Val Phe
225                 230                 235                 240

Arg Glu Asn Phe Glu Ser Met Ser Ser Gly Leu Gln Asn Ser His Arg
                245                 250                 255

Ile Ala Leu Met Pro Val Gly Tyr Gln Phe Gln Pro Ile Ser Leu Asn
            260                 265                 270

Met Ser Asp Ala Gln Phe Leu Glu Asn Thr Glu Leu Thr Ile Arg Gln
        275                 280                 285

Ile Ala Thr Ala Phe Gly Ile Lys Met His Gln Leu Asn Asp Leu Ser
    290                 295                 300

Lys Ala Thr Leu Asn Asn Ile Glu Gln Gln Gln Gln Gln Phe Tyr Thr
305                 310                 315                 320

Asp Thr Leu Gln Ala Thr Leu Thr Met Tyr Glu Gln Glu Met Thr Tyr
                325                 330                 335

Lys Leu Phe Leu Asp Ser Glu Leu Asp Lys Gly Phe Tyr Ser Lys Phe
            340                 345                 350

Asn Val Asp Ala Ile Leu Arg Ala Asp Ile Lys Thr Arg Tyr Glu Ala
        355                 360                 365

Tyr Arg Thr Gly Ile Gln Gly Gly Phe Leu Lys Pro Asn Glu Ala Arg
    370                 375                 380

Ser Lys Glu Asp Leu Pro Pro Glu Ala Gly Gly Asp Arg Leu Leu Val
385                 390                 395                 400

Asn Gly Asn Met Leu Pro Ile Asp Met Ala Gly Gln Ala Tyr Leu Lys
                405                 410                 415

Gly Gly Asp Thr Asn Gly Glu Val Ser Lys Glu Gly Asn Glu Gly Asn
            420                 425                 430


<210> SEQ ID NO 8
<211> LENGTH: 432
<212> TYPE: PRT
<213> ORGANISM: Bacillus anthracis

<400> SEQUENCE: 8

Val Lys Ile Val Asp Ser Val Lys Lys Phe Phe Asn Phe Glu Lys Arg
1               5                   10                  15

Gln Thr Ser Gln Val Ile Glu Leu Asn Lys Asp Asp Glu Lys Leu Leu
            20                  25                  30

Glu Trp Leu Gly Ile Ser Pro Ser Thr Ile Ser Val Lys Gly Lys Asn
        35                  40                  45

Ala Leu Lys Val Ala Thr Val Phe Ala Cys Ile Lys Ile Leu Ser Glu
    50                  55                  60

Ser Val Ser Lys Leu Pro Leu Lys Ile Tyr Gln Glu Asp Glu Tyr Gly
65                  70                  75                  80

Ile Gln Arg Gly Thr Lys His Tyr Leu Asn Asn Leu Leu Arg Leu Arg
                85                  90                  95

Pro Asn Pro Tyr Met Ser Ser Met Asn Phe Phe Gly Ser Leu Glu Ala
            100                 105                 110

Gln Lys Asn Leu Tyr Gly Asn Ser Tyr Ala Asn Ile Glu Phe Asp Arg
        115                 120                 125

Lys Gly Lys Val Gln Ala Leu Trp Pro Ile Asp Ala Ser Lys Val Thr
```

-continued

```
    130                 135                 140

Val Tyr Ile Asp Asp Val Gly Leu Leu Asn Ser Lys Thr Lys Met Trp
145                 150                 155                 160

Tyr Val Val Asn Thr Gly Gly Gln Gln Arg Val Leu Lys Pro Glu Glu
                165                 170                 175

Ile Leu His Phe Lys Asn Gly Ile Thr Leu Asp Gly Leu Val Gly Val
            180                 185                 190

Pro Thr Met Glu Tyr Leu Lys Ser Thr Leu Glu Asn Ser Ala Ser Ala
        195                 200                 205

Asp Lys Phe Ile Asn Asn Phe Tyr Lys Gln Gly Leu Gln Val Lys Gly
    210                 215                 220

Leu Val Gln Tyr Val Gly Asp Leu Asn Glu Asp Ala Lys Lys Val Phe
225                 230                 235                 240

Arg Glu Asn Phe Glu Ser Met Ser Ser Gly Leu Gln Asn Ser His Arg
                245                 250                 255

Ile Ala Leu Met Pro Val Gly Tyr Gln Phe Gln Pro Ile Ser Leu Asn
            260                 265                 270

Met Ser Asp Ala Gln Phe Leu Glu Asn Thr Glu Leu Thr Ile Arg Gln
        275                 280                 285

Ile Ala Thr Ala Phe Gly Ile Lys Met His Gln Leu Asn Asp Leu Ser
    290                 295                 300

Lys Ala Thr Leu Asn Asn Ile Glu Gln Gln Gln Gln Gln Phe Tyr Thr
305                 310                 315                 320

Asp Thr Leu Gln Ala Thr Leu Thr Met Tyr Glu Gln Glu Met Thr Tyr
                325                 330                 335

Lys Leu Phe Leu Asp Ser Glu Leu Asp Lys Gly Phe Tyr Ser Lys Phe
            340                 345                 350

Asn Val Asp Ala Ile Leu Arg Ala Asp Ile Lys Thr Arg Tyr Glu Ala
        355                 360                 365

Tyr Arg Thr Gly Ile Gln Gly Gly Phe Leu Lys Pro Asn Glu Ala Arg
    370                 375                 380

Ser Lys Glu Asp Leu Pro Pro Glu Ala Gly Gly Asp Arg Leu Leu Val
385                 390                 395                 400

Asn Gly Asn Met Leu Pro Ile Asp Met Ala Gly Gln Ala Tyr Leu Lys
                405                 410                 415

Gly Gly Asp Thr Asn Gly Glu Val Ser Lys Glu Gly Asn Glu Gly Asn
            420                 425                 430


<210> SEQ ID NO 9
<211> LENGTH: 206
<212> TYPE: PRT
<213> ORGANISM: Bacillus anthracis

<400> SEQUENCE: 9

Met Glu Lys Ser Ala Lys Lys Glu Met Lys Glu Ile Arg Ala Leu Pro
1               5                   10                  15

Met Thr Ile Glu Val Arg Glu Val Asn Glu Asp Glu Gly Lys Arg Thr
            20                  25                  30

Ile Ser Gly Ser Ile Lys Tyr Asn Asn Glu Ser Ala Glu Met Arg Asp
        35                  40                  45

Trp Trp Gly Asp Thr Phe Val Glu Glu Ile Ala Glu Gly Ala Phe Asp
    50                  55                  60

Glu Ser Leu Lys Val Arg Asp Val Val Gly Leu Trp Ser His Asp Thr
65                  70                  75                  80
```

-continued

```
Ser Gln Val Leu Gly Asn Thr Lys Ser Lys Thr Leu Arg Ile Glu Asn
                85                  90                  95

Asp Lys Lys Glu Leu Arg Phe Glu Leu Asp Ile Pro Asn Thr Thr Val
            100                 105                 110

Gly Asn Asp Ala Trp Glu Leu Ile Lys Arg Gly Asp Val Asp Gly Val
        115                 120                 125

Ser Phe Gly Met Lys Val Thr Lys Asp Lys Trp Ser Ser Glu Glu Arg
    130                 135                 140

Glu Asn Gly Lys Leu Tyr Lys Arg Ser Ile Leu Asn Ala Glu Leu Tyr
145                 150                 155                 160

Glu Ile Ser Pro Val Ala Phe Pro Ala Tyr Pro Thr Asn Glu Val Ser
                165                 170                 175

Val Arg Ser Leu Asp Asp Phe Lys Ala Gly Glu Lys Arg Val Ala Asp
            180                 185                 190

Glu Phe Arg Lys Arg Lys Leu Gln Ile Glu Leu Glu Leu Ile
        195                 200                 205


<210> SEQ ID NO 10
<211> LENGTH: 206
<212> TYPE: PRT
<213> ORGANISM: Bacillus anthracis

<400> SEQUENCE: 10

Met Glu Lys Ser Ala Lys Lys Glu Met Lys Glu Ile Arg Ala Leu Pro
1               5                   10                  15

Met Thr Ile Glu Val Arg Glu Val Asn Glu Asp Glu Gly Lys Arg Thr
            20                  25                  30

Ile Ser Gly Ser Ile Lys Tyr Asn Asn Glu Ser Ala Glu Met Arg Asp
        35                  40                  45

Trp Trp Gly Asp Thr Phe Val Glu Glu Ile Ala Glu Gly Ala Phe Asp
    50                  55                  60

Glu Ser Leu Lys Val Arg Asp Val Val Gly Leu Trp Ser His Asp Thr
65                  70                  75                  80

Ser Gln Val Leu Gly Asn Thr Lys Ser Lys Thr Leu Arg Ile Glu Asn
                85                  90                  95

Asp Lys Lys Glu Leu Arg Phe Glu Leu Asp Ile Pro Asn Thr Thr Val
            100                 105                 110

Gly Asn Asp Ala Trp Glu Leu Ile Lys Arg Gly Asp Val Asp Gly Val
        115                 120                 125

Ser Phe Gly Met Lys Val Thr Lys Asp Lys Trp Ser Ser Glu Glu Arg
    130                 135                 140

Glu Asn Gly Lys Leu Tyr Lys Arg Ser Ile Leu Asn Ala Glu Leu Tyr
145                 150                 155                 160

Glu Ile Ser Pro Val Ala Phe Pro Ala Tyr Pro Thr Asn Glu Val Ser
                165                 170                 175

Val Arg Ser Leu Asp Asp Phe Lys Ala Gly Glu Lys Arg Val Ala Asp
            180                 185                 190

Glu Phe Arg Lys Arg Lys Leu Gln Ile Glu Leu Glu Leu Ile
        195                 200                 205


<210> SEQ ID NO 11
<211> LENGTH: 392
<212> TYPE: PRT
<213> ORGANISM: Bacillus anthracis

<400> SEQUENCE: 11
```

-continued

```
Met Ser Lys Glu Leu Arg Glu Leu Leu Ala Lys Leu Glu Gly Lys Lys
1               5                   10                  15

Glu Glu Val Arg Ser Leu Met Gly Glu Asp Lys Val Ala Glu Ala Glu
            20                  25                  30

Gln Met Met Glu Glu Val Arg Ser Leu Gln Lys Lys Ile Asp Leu Gln
        35                  40                  45

Arg Ser Leu Asp Glu Ala Glu Thr Glu Glu Arg Asn Asn Gly Arg Glu
    50                  55                  60

Val Glu Thr Arg Asn Val Asp Gly Glu Met Glu Tyr Arg Asp Val Phe
65                  70                  75                  80

Met Lys Ala Leu Arg Asn Lys Pro Leu Asn Ala Glu Glu Arg Glu Phe
                85                  90                  95

Leu Glu Asp Asp Leu Glu Gln Arg Ala Met Ser Gly Leu Thr Gly Glu
            100                 105                 110

Asp Gly Gly Leu Val Ile Pro Gln Asp Ile Gln Thr Gln Ile Asn Glu
        115                 120                 125

Leu Ala Arg Ser Phe Asp Ala Leu Glu Gln Tyr Val Thr Val Glu Pro
    130                 135                 140

Val Arg Thr Arg Ser Gly Ser Arg Val Leu Glu Lys Asn Ser Asp Met
145                 150                 155                 160

Ile Pro Phe Ala Glu Ile Thr Glu Met Gly Glu Ile Pro Glu Thr Asp
                165                 170                 175

Asn Pro Lys Phe Ser Asn Val Gln Tyr Ala Val Lys Asp Arg Ala Gly
            180                 185                 190

Ile Leu Pro Leu Ser Arg Ser Leu Leu Gln Asp Ser Asp Gln Asn Ile
        195                 200                 205

Leu Lys Tyr Val Thr Lys Trp Leu Gly Lys Lys Ser Lys Val Thr Arg
    210                 215                 220

Asn Val Leu Ile Leu Gly Val Ile Glu Lys Leu Thr Lys Gln Ala Ile
225                 230                 235                 240

Lys Ser Leu Asp Asp Ile Lys Asp Val Leu Asn Val Lys Leu Asp Pro
                245                 250                 255

Ala Ile Ser Pro Asn Ala Ile Leu Leu Thr Asn Gln Asp Gly Phe Asn
            260                 265                 270

Tyr Leu Asp Lys Leu Lys Asp Lys Asp Gly Lys Tyr Ile Leu Gln Ser
        275                 280                 285

Asp Pro Thr Gln Lys Asn Lys Lys Leu Phe Ala Gly Thr Asn Pro Val
    290                 295                 300

Val Val Val Ser Asn Arg Phe Leu Lys Ser Lys Gly Thr Thr Ala Lys
305                 310                 315                 320

Lys Ala Pro Leu Ile Ile Gly Asp Leu Lys Glu Ala Ile Val Leu Phe
                325                 330                 335

Lys Arg Glu Asp Met Glu Leu Ala Ser Thr Asp Val Gly Gly Lys Ala
            340                 345                 350

Phe Thr Arg Asn Thr Leu Asp Leu Arg Ala Ile Gln Arg Asp Asp Val
        355                 360                 365

Gln Met Trp Asp Asn Glu Ala Ala Val Tyr Gly Glu Ile Asp Leu Ser
    370                 375                 380

Ala Pro Val Glu Gln Pro Gln Gly
385                 390
```

<210> SEQ ID NO 12
<211> LENGTH: 392
<212> TYPE: PRT

-continued

<213> ORGANISM: Bacillus anthracis

<400> SEQUENCE: 12

```
Met Ser Lys Glu Leu Arg Glu Leu Leu Ala Lys Leu Glu Gly Lys Lys
1               5                   10                  15

Glu Glu Val Arg Ser Leu Met Gly Glu Asp Lys Val Ala Glu Ala Glu
            20                  25                  30

Gln Met Met Glu Glu Val Arg Ser Leu Gln Lys Lys Ile Asp Leu Gln
        35                  40                  45

Arg Ser Leu Asp Glu Ala Glu Thr Glu Glu Arg Asn Asn Gly Arg Glu
    50                  55                  60

Val Glu Thr Arg Asn Val Asp Gly Glu Met Glu Tyr Arg Asp Val Phe
65                  70                  75                  80

Met Lys Ala Leu Arg Asn Lys Pro Leu Asn Ala Glu Glu Arg Glu Phe
                85                  90                  95

Leu Glu Asp Asp Leu Glu Gln Arg Ala Met Ser Gly Leu Thr Gly Glu
            100                 105                 110

Asp Gly Gly Leu Val Ile Pro Gln Asp Ile Gln Thr Gln Ile Asn Glu
        115                 120                 125

Leu Ala Arg Ser Phe Asp Ala Leu Glu Gln Tyr Val Thr Val Glu Pro
    130                 135                 140

Val Arg Thr Arg Ser Gly Ser Arg Val Leu Glu Lys Asn Ser Asp Met
145                 150                 155                 160

Ile Pro Phe Ala Glu Ile Thr Glu Met Gly Glu Ile Pro Glu Thr Asp
                165                 170                 175

Asn Pro Lys Phe Ser Asn Val Gln Tyr Ala Val Lys Asp Arg Ala Gly
            180                 185                 190

Ile Leu Pro Leu Ser Arg Ser Leu Leu Gln Asp Ser Asp Gln Asn Ile
        195                 200                 205

Leu Lys Tyr Val Thr Lys Trp Leu Gly Lys Lys Ser Lys Val Thr Arg
    210                 215                 220

Asn Val Leu Ile Leu Gly Val Ile Glu Lys Leu Thr Lys Gln Ala Ile
225                 230                 235                 240

Lys Ser Leu Asp Asp Ile Lys Asp Val Leu Asn Val Lys Leu Asp Pro
                245                 250                 255

Ala Ile Ser Pro Asn Ala Ile Leu Leu Thr Asn Gln Asp Gly Phe Asn
            260                 265                 270

Tyr Leu Asp Lys Leu Lys Asp Lys Asp Gly Lys Tyr Ile Leu Gln Ser
        275                 280                 285

Asp Pro Thr Gln Lys Asn Lys Lys Leu Phe Ala Gly Thr Asn Pro Val
    290                 295                 300

Val Val Val Ser Asn Arg Phe Leu Lys Ser Lys Gly Thr Thr Ala Lys
305                 310                 315                 320

Lys Ala Pro Leu Ile Ile Gly Asp Leu Lys Glu Ala Ile Val Leu Phe
                325                 330                 335

Lys Arg Glu Asp Met Glu Leu Ala Ser Thr Asp Val Gly Gly Lys Ala
            340                 345                 350

Phe Thr Arg Asn Thr Leu Asp Leu Arg Ala Ile Gln Arg Asp Asp Val
        355                 360                 365

Gln Met Trp Asp Asn Glu Ala Ala Val Tyr Gly Glu Ile Asp Leu Ser
    370                 375                 380

Ala Pro Val Glu Gln Pro Gln Gly
385                 390
```

-continued

<210> SEQ ID NO 13
<211> LENGTH: 96
<212> TYPE: PRT
<213> ORGANISM: Bacillus anthracis

<400> SEQUENCE: 13

```
Met Leu Val Thr Leu Glu Glu Ala Lys Glu Trp Ile Arg Val Asp Gly
1               5                   10                  15

Asp Asp Asp Pro Thr Ile Thr Met Leu Ile Lys Ala Ala Glu Leu Tyr
            20                  25                  30

Ile Tyr Lys Ala Thr Gly Lys Thr Phe Thr Gln Thr Asn Glu Asp Ala
        35                  40                  45

Lys Leu Leu Cys Leu Phe Leu Val Ala Asp Trp Tyr Gly Asn Arg Leu
    50                  55                  60

Leu Val Gly Glu Lys Ala Ser Glu Lys Ile Arg Thr Ile Val Gln Ser
65                  70                  75                  80

Met Ile Leu Gln Leu Gln Tyr Ala Ser Glu Pro Gln Glu Glu Arg Lys
                85                  90                  95
```

<210> SEQ ID NO 14
<211> LENGTH: 96
<212> TYPE: PRT
<213> ORGANISM: Bacillus anthracis

<400> SEQUENCE: 14

```
Met Leu Val Thr Leu Glu Glu Ala Lys Glu Trp Ile Arg Val Asp Gly
1               5                   10                  15

Asp Asp Asp Pro Thr Ile Thr Met Leu Ile Lys Ala Ala Glu Leu Tyr
            20                  25                  30

Ile Tyr Lys Ala Thr Gly Lys Thr Phe Thr Gln Thr Asn Glu Asp Ala
        35                  40                  45

Lys Leu Leu Cys Leu Phe Leu Val Ala Asp Trp Tyr Gly Asn Arg Leu
    50                  55                  60

Leu Val Gly Glu Lys Ala Ser Glu Lys Ile Arg Thr Ile Val Gln Ser
65                  70                  75                  80

Met Ile Leu Gln Leu Gln Tyr Ala Ser Glu Pro Gln Glu Glu Arg Lys
                85                  90                  95
```

<210> SEQ ID NO 15
<211> LENGTH: 107
<212> TYPE: PRT
<213> ORGANISM: Bacillus anthracis

<400> SEQUENCE: 15

```
Met Asn Pro Ala Lys Leu Asp Lys Arg Leu Thr Phe Gln Val Lys Asp
1               5                   10                  15

Glu Asn Ala Lys Gly Pro Asp Gly Asp Pro Ile Asp Gly Tyr Lys Asp
            20                  25                  30

Ala Phe Thr Val Trp Gly Ser Phe Val Tyr Leu Lys Gly Arg Lys Tyr
        35                  40                  45

Phe Glu Ala Ala Ala Ala Asn Ser Glu Val Gln Gly Glu Thr Glu Ile
    50                  55                  60

Arg Asn Arg Asp Asp Val Ser Ala Asp Met Lys Ile Lys Tyr Lys Asn
65                  70                  75                  80

Val Ile Tyr Asp Ile Val Ser Val Ile Pro Thr Gln Asp His Thr Leu
                85                  90                  95

Leu Ile Met Trp Lys Arg Gly Glu Met Asn Gly
```

-continued

```
            100                 105


<210> SEQ ID NO 16
<211> LENGTH: 107
<212> TYPE: PRT
<213> ORGANISM: Bacillus anthracis

<400> SEQUENCE: 16

Met Asn Pro Ala Lys Leu Asp Lys Arg Leu Thr Phe Gln Val Lys Asp
1               5                   10                  15

Glu Asn Ala Lys Gly Pro Asp Gly Asp Pro Ile Asp Gly Tyr Lys Asp
            20                  25                  30

Ala Phe Thr Val Trp Gly Ser Phe Val Tyr Leu Lys Gly Arg Lys Tyr
        35                  40                  45

Phe Glu Ala Ala Ala Ala Asn Ser Glu Val Gln Gly Glu Thr Glu Ile
    50                  55                  60

Arg Asn Arg Asp Asp Val Ser Ala Asp Met Lys Ile Lys Tyr Lys Asn
65                  70                  75                  80

Val Ile Tyr Asp Ile Val Ser Val Ile Pro Thr Gln Asp His Thr Leu
                85                  90                  95

Leu Ile Met Trp Lys Arg Gly Glu Met Asn Gly
            100                 105


<210> SEQ ID NO 17
<211> LENGTH: 105
<212> TYPE: PRT
<213> ORGANISM: Bacillus anthracis

<400> SEQUENCE: 17

Met Lys Leu Thr Leu Met Ile Asn Lys Glu Lys Gln Thr Phe Asn Met
1               5                   10                  15

Pro Glu Phe Ile Pro Ala Arg Leu Ile Arg Gln Ala Pro Glu Leu Ala
            20                  25                  30

Glu Ile Pro Asn Asn Pro Gly Pro Glu Asp Met Asp Lys Met Val Gln
        35                  40                  45

Phe Val Val Lys Val Tyr Asp Gly Gln Phe Thr Leu Asp Gln Tyr Trp
    50                  55                  60

Asp Gly Val Asp Ala Arg Lys Phe Leu Ser Thr Thr Ser Asp Val Ile
65                  70                  75                  80

Asn Ala Ile Ile Asn Glu Thr Val Glu Ala Ala Gly Gly Ser Thr Glu
                85                  90                  95

Ser Gly Glu Glu Glu Asn Pro Asn Ala
            100                 105


<210> SEQ ID NO 18
<211> LENGTH: 105
<212> TYPE: PRT
<213> ORGANISM: Bacillus anthracis

<400> SEQUENCE: 18

Met Lys Leu Thr Leu Met Ile Asn Lys Glu Lys Gln Thr Phe Asn Met
1               5                   10                  15

Pro Glu Phe Ile Pro Ala Arg Leu Ile Arg Gln Ala Pro Glu Leu Ala
            20                  25                  30

Glu Ile Pro Asn Asn Pro Gly Pro Glu Asp Met Asp Lys Met Val Gln
        35                  40                  45

Phe Val Val Lys Val Tyr Asp Gly Gln Phe Thr Leu Asp Gln Tyr Trp
    50                  55                  60
```

-continued

```
Asp Gly Val Asp Ala Arg Lys Phe Leu Ser Thr Thr Ser Asp Val Ile
65                  70                  75                  80

Asn Ala Ile Ile Asn Glu Thr Val Glu Ala Ala Gly Gly Ser Thr Glu
                85                  90                  95

Ser Gly Glu Glu Glu Asn Pro Asn Ala
            100                 105


<210> SEQ ID NO 19
<211> LENGTH: 119
<212> TYPE: PRT
<213> ORGANISM: Bacillus anthracis

<400> SEQUENCE: 19

Val Ile Asn Leu Arg Pro Asp Ile Leu Gln Ala Leu Glu Asn Asp Gln
1               5                   10                  15

Glu Leu Val Ser Leu Leu Gly Gly Lys Arg Ile Tyr Tyr Arg Lys Ala
            20                  25                  30

Lys Lys Ala Glu Glu Phe Pro Arg Ile Thr Tyr Phe Glu Leu Asp Asn
        35                  40                  45

Arg Pro Asp Gly Phe Ala Asp Asn Gln Glu Ile Glu Ser Glu Ile Leu
    50                  55                  60

Phe Gln Val Asp Val Trp Ala Lys Ser Ser Thr Thr Ala Ile His Gln
65                  70                  75                  80

Lys Val Asn Glu Ile Met Lys Arg Ile Gly Phe Ser Arg Tyr Ala Val
                85                  90                  95

Ala Asp Leu Tyr Glu Glu Asp Thr Gln Ile Phe His Tyr Ala Met Arg
            100                 105                 110

Phe Ala Lys Gly Val Glu Leu
        115


<210> SEQ ID NO 20
<211> LENGTH: 119
<212> TYPE: PRT
<213> ORGANISM: Bacillus anthracis

<400> SEQUENCE: 20

Val Ile Asn Leu Arg Pro Asp Ile Leu Gln Ala Leu Glu Asn Asp Gln
1               5                   10                  15

Glu Leu Val Ser Leu Leu Gly Gly Lys Arg Ile Tyr Tyr Arg Lys Ala
            20                  25                  30

Lys Lys Ala Glu Glu Phe Pro Arg Ile Thr Tyr Phe Glu Leu Asp Asn
        35                  40                  45

Arg Pro Asp Gly Phe Ala Asp Asn Gln Glu Ile Glu Ser Glu Ile Leu
    50                  55                  60

Phe Gln Val Asp Val Trp Ala Lys Ser Ser Thr Thr Ala Ile His Gln
65                  70                  75                  80

Lys Val Asn Glu Ile Met Lys Arg Ile Gly Phe Ser Arg Tyr Ala Val
                85                  90                  95

Ala Asp Leu Tyr Glu Glu Asp Thr Gln Ile Phe His Tyr Ala Met Arg
            100                 105                 110

Phe Ala Lys Gly Val Glu Leu
        115


<210> SEQ ID NO 21
<211> LENGTH: 202
<212> TYPE: PRT
<213> ORGANISM: Bacillus anthracis
```

-continued

<400> SEQUENCE: 21

```
Met Ala Gly Glu Val Val Arg Ile Ser Ser Thr Val Gly Val Asp Asn
1               5                   10                  15

Leu Val Tyr Ala Lys Val Leu Gln Asp Asp Ser Ser Ala Ile Lys Tyr
            20                  25                  30

Thr Asp Val Lys Lys Met Glu Gly Ala Val Lys Val Lys Leu Thr Lys
        35                  40                  45

Lys Val Ala Ser Glu Val Met Trp Ser Asp Asn Arg Lys Ser Glu Ile
    50                  55                  60

Ala Glu Ser Asp Gly Glu Thr Glu Val Glu Ile Glu Val Arg Gly Leu
65                  70                  75                  80

Ser Leu Ser Thr Lys Ala Asp Ile Glu Gly Phe Pro Glu Val Lys Asp
                85                  90                  95

Gly Val Leu Asp Glu Lys Arg Glu Gly Glu Lys Pro Tyr Leu Ala Ile
            100                 105                 110

Gly Phe Arg Phe Leu Lys Ala Asn Asp Lys Tyr Arg Tyr Val Trp Leu
        115                 120                 125

Leu Lys Gly Lys Leu Ser Gln Glu Glu Glu Glu Ala Glu Thr Lys Lys
    130                 135                 140

Asp Lys Pro Asn Phe Gln Thr Thr Lys Leu Lys Gly Ser Phe Ile Glu
145                 150                 155                 160

Arg Asp Phe Asp Asp Arg Thr Lys Phe Thr Ala Asp Glu Asp Glu Pro
                165                 170                 175

Thr Phe Thr Lys Leu Val Gly Asp Asn Trp Phe Asn Lys Val Tyr Glu
            180                 185                 190

Lys Pro Val Thr Gln Pro Pro Ala Gly Lys
        195                 200
```

<210> SEQ ID NO 22
<211> LENGTH: 202
<212> TYPE: PRT
<213> ORGANISM: Bacillus anthracis

<400> SEQUENCE: 22

```
Met Ala Gly Glu Val Val Arg Ile Ser Ser Thr Val Gly Val Asp Asn
1               5                   10                  15

Leu Val Tyr Ala Lys Val Leu Gln Asp Asp Ser Ser Ala Ile Lys Tyr
            20                  25                  30

Thr Asp Val Lys Lys Met Glu Gly Ala Val Lys Val Lys Leu Thr Lys
        35                  40                  45

Lys Val Ala Ser Glu Val Met Trp Ser Asp Asn Arg Lys Ser Glu Ile
    50                  55                  60

Ala Glu Ser Asp Gly Glu Thr Glu Val Glu Ile Glu Val Arg Gly Leu
65                  70                  75                  80

Ser Leu Ser Thr Lys Ala Asp Ile Glu Gly Phe Pro Glu Val Lys Asp
                85                  90                  95

Gly Val Leu Asp Glu Lys Arg Glu Gly Glu Lys Pro Tyr Leu Ala Ile
            100                 105                 110

Gly Phe Arg Phe Leu Lys Ala Asn Asp Lys Tyr Arg Tyr Val Trp Leu
        115                 120                 125

Leu Lys Gly Lys Leu Ser Gln Glu Glu Glu Glu Ala Glu Thr Lys Lys
    130                 135                 140

Asp Lys Pro Asn Phe Gln Thr Thr Lys Leu Lys Gly Ser Phe Ile Glu
145                 150                 155                 160
```

-continued

```
Arg Asp Phe Asp Asp Arg Thr Lys Phe Thr Ala Asp Glu Asp Glu Pro
                165                 170                 175

Thr Phe Thr Lys Leu Val Gly Asp Asn Trp Phe Asn Lys Val Tyr Glu
            180                 185                 190

Lys Pro Val Thr Gln Pro Pro Ala Gly Lys
        195                 200


<210> SEQ ID NO 23
<211> LENGTH: 105
<212> TYPE: PRT
<213> ORGANISM: Bacillus anthracis

<400> SEQUENCE: 23

Met Lys Leu Thr Leu Met Ile Asn Lys Glu Lys Gln Thr Phe Asn Met
1               5                   10                  15

Pro Glu Phe Ile Pro Ala Arg Leu Ile Arg Gln Ala Pro Glu Leu Ala
            20                  25                  30

Glu Ile Pro Asn Asn Pro Gly Pro Glu Asp Met Asp Lys Met Val Gln
        35                  40                  45

Phe Val Val Lys Val Tyr Asp Gly Gln Phe Thr Leu Asp Gln Tyr Trp
    50                  55                  60

Asp Gly Val Asp Ala Arg Lys Phe Leu Ser Thr Thr Ser Asp Val Ile
65                  70                  75                  80

Asn Ala Ile Ile Asn Glu Thr Val Glu Ala Ala Gly Gly Ser Thr Glu
                85                  90                  95

Ser Gly Glu Glu Glu Asn Pro Asn Ala
            100                 105


<210> SEQ ID NO 24
<211> LENGTH: 105
<212> TYPE: PRT
<213> ORGANISM: Bacillus anthracis

<400> SEQUENCE: 24

Met Lys Leu Thr Leu Met Ile Asn Lys Glu Lys Gln Thr Phe Asn Met
1               5                   10                  15

Pro Glu Phe Ile Pro Ala Arg Leu Ile Arg Gln Ala Pro Glu Leu Ala
            20                  25                  30

Glu Ile Pro Asn Asn Pro Gly Pro Glu Asp Met Asp Lys Met Val Gln
        35                  40                  45

Phe Val Val Lys Val Tyr Asp Gly Gln Phe Thr Leu Asp Gln Tyr Trp
    50                  55                  60

Asp Gly Val Asp Ala Arg Lys Phe Leu Ser Thr Thr Ser Asp Val Ile
65                  70                  75                  80

Asn Ala Ile Ile Asn Glu Thr Val Glu Ala Ala Gly Gly Ser Thr Glu
                85                  90                  95

Ser Gly Glu Glu Glu Asn Pro Asn Ala
            100                 105


<210> SEQ ID NO 25
<211> LENGTH: 58
<212> TYPE: PRT
<213> ORGANISM: Bacillus anthracis

<400> SEQUENCE: 25

Met Asp Glu Leu Tyr Leu Ser Leu Leu Arg Gln Gly Tyr Lys His His
1               5                   10                  15
```

-continued

His Ile Asp Asn Glu Met Asp Ile Trp His Tyr Leu Arg Leu Asn Arg
20 25 30

Lys Met His Glu Asn Gly Asn Glu Asn Tyr Glu Gly Ser Asn Ser Asn
35 40 45

Glu Ile Glu Val Pro Ala Glu Asn Ile Ile
50 55

<210> SEQ ID NO 26
<211> LENGTH: 58
<212> TYPE: PRT
<213> ORGANISM: Bacillus anthracis

<400> SEQUENCE: 26

Met Asp Glu Leu Tyr Leu Ser Leu Leu Arg Gln Gly Tyr Lys His His
1 5 10 15

His Ile Asp Asn Glu Met Asp Ile Trp His Tyr Leu Arg Leu Asn Arg
20 25 30

Lys Met His Glu Asn Gly Asn Glu Asn Tyr Glu Gly Ser Asn Ser Asn
35 40 45

Glu Ile Glu Val Pro Ala Glu Asn Ile Ile
50 55

<210> SEQ ID NO 27
<211> LENGTH: 1283
<212> TYPE: PRT
<213> ORGANISM: Bacillus anthracis

<400> SEQUENCE: 27

Met Ala Asn Glu Ile Asn Asn Leu Val Val Arg Leu Ser Leu Asp Asn
1 5 10 15

Val Asn Phe Arg Gln Gly Ile Ser Asn Ser Gly Arg Ala Val Arg Thr
20 25 30

Leu Gln Asn Glu Leu Lys Ser Val Ser Thr Gly Met Gly Gly Phe Ala
35 40 45

Asn Ala Ser Gln Gln Thr Gln Ala Lys Met Asn Thr Leu Ser Arg Leu
50 55 60

Ile Asp Ala Gln Lys Glu Lys Val Lys Ala Leu Arg Gln Ala Tyr Asp
65 70 75 80

Gln Asn Lys Ala Lys Leu Gly Glu Asn Asp Ala Ala Thr Gln Arg Tyr
85 90 95

Ala Ser Gln Val Asn Lys Ala Val Ala Asp Leu Asn Arg Phe Glu Asn
100 105 110

Glu Leu Lys Gln Val Asn Arg Gln Ala Glu Gln Lys Gly Met Asp Lys
115 120 125

Leu Asn Asn Ser Leu Lys Ser Leu Gln Ala Glu Phe Gln Ser Ile Thr
130 135 140

Thr Gly Met Gly Gly Phe Ser Asn Ala Thr Glu Gln Thr Arg Ala Lys
145 150 155 160

Val Asp Val Leu Ser Arg Met Val Asp Lys Gln Lys Glu Lys Ile Arg
165 170 175

Glu Leu Gln Gln Ala Tyr Asn Arg Ala Lys Thr Glu Glu Gly Glu Ala
180 185 190

Ser Gln Ser Ala Gln Arg Tyr Ala Glu Gln Ile His Arg Ala Thr Ala
195 200 205

Glu Leu Asn Arg Phe Glu Thr Gly Leu Gln Gln Ser Asn Arg Glu Leu
210 215 220

-continued

```
Glu Gln Gln Gly Asn Arg Leu Leu Asn Phe Gly Asn Arg Met Glu Thr
225                 230                 235                 240

Leu Gly Asn His Leu Gln Asn Ala Gly Met Gln Ile Gly Met Val Phe
                245                 250                 255

Gly Gly Met Thr Tyr Ala Ile Gly Arg Gly Leu Lys Ser Ala Ile Thr
            260                 265                 270

Glu Ser Met Asn Phe Glu Gln Gln Met Ala Asn Val Lys Ala Val Ser
        275                 280                 285

Gly Ser Thr Gly Ala Glu Met Lys Lys Leu Ser Glu Leu Ala Val Asn
    290                 295                 300

Met Gly Glu Thr Thr Lys Tyr Ser Ser Val Gln Ala Gly Gln Gly Ile
305                 310                 315                 320

Glu Glu Leu Ile Lys Ala Gly Val Ser Leu Gln Asp Ile Ile Asn Gly
                325                 330                 335

Gly Leu Ala Gly Ala Leu Asn Leu Ala Thr Ala Gly Glu Leu Glu Leu
            340                 345                 350

Gly Glu Ala Ala Glu Ile Ala Ser Thr Ala Leu Asn Ala Phe Lys Ala
        355                 360                 365

Asp His Leu Ser Val Ala Asp Ala Ala Asn Ile Leu Ser Gly Ala Ala
    370                 375                 380

Asn Ala Ser Ala Thr Asp Val Arg Glu Leu Lys Tyr Gly Leu Ser Ala
385                 390                 395                 400

Ser Ser Ala Val Ala Ala Gly Ala Gly Met Thr Phe Lys Asp Thr Ala
                405                 410                 415

Thr Thr Leu Ala Val Phe Ala Gln Asn Gly Leu Lys Gly Ser Asp Ala
            420                 425                 430

Gly Thr Ser Leu Lys Thr Met Leu Met Arg Leu Asn Pro Ser Thr Lys
        435                 440                 445

Glu Ala Tyr Asn Lys Met Arg Asp Leu Gly Leu Ile Thr Tyr Asn Ala
    450                 455                 460

Gln Ala Gly Phe Asp Phe Leu Val Lys Asn Gly Ile Gln Pro Ala Ser
465                 470                 475                 480

Arg Asn Val Gly Asp Ile Glu Val Ala Leu Glu Gln Tyr Val Met Lys
                485                 490                 495

Thr Glu Gly Val Thr Lys Trp Asn Asp Lys Cys Asp Thr Thr Phe Arg
            500                 505                 510

Glu Leu Ala Thr Ser Ser Ala Phe Leu Ser Ser Lys Phe Tyr Asp Gln
        515                 520                 525

Gln Gly His Ile Gln Ser Leu Glu Asn Ile Ser Gly Thr Leu His Glu
    530                 535                 540

Ser Met Lys Asp Leu Thr Asp Gln Gln Arg Ser Met Ala Leu Glu Thr
545                 550                 555                 560

Leu Phe Gly Ser Asp Ala Val Arg Gly Ala Thr Ile Leu Phe Lys Glu
                565                 570                 575

Gly Ala Lys Gly Val Asn Glu Met Trp Asp Ser Met Ser Lys Val Thr
            580                 585                 590

Ala Ala Asp Val Ala Ala Thr Lys Ile Asp Thr Leu Lys Gly Arg Leu
        595                 600                 605

Thr Leu Leu Asp Ser Ala Phe Ser Thr Met Lys Lys Thr Ile Gly Asp
    610                 615                 620

Ala Leu Ala Pro Val Val Ser Val Phe Val Ala Gly Leu Gln Lys Leu
625                 630                 635                 640

Val Asp Gly Phe Asn Ser Leu Pro Gly Pro Val Gln Lys Ala Ile Ala
```

-continued

```
                645                 650                 655
Ile Thr Gly Gly Ile Val Leu Ala Leu Thr Ala Val Ala Thr Ala Ile
            660                 665                 670
Gly Val Val Leu Ala Ala Phe Gly Met Ile Ala Ser Gly Ile Gly Ser
        675                 680                 685
Leu Ser Leu Ala Leu Ala Ser Val Gly Gly Ile Ala Gly Ile Ala Ala
    690                 695                 700
Gly Ala Val Gly Phe Leu Gly Ser Ala Leu Ala Val Leu Thr Gly Pro
705                 710                 715                 720
Ile Gly Leu Val Ala Ala Ala Leu Ile Gly Thr Gly Val Val Ala Tyr
                725                 730                 735
Lys Ala Tyr Gln Lys Ala Thr Glu Asp Ser Ile Ala Ser Val Asp Arg
            740                 745                 750
Phe Ala Thr Asn Thr Glu Gly Lys Val Ser Ser Ser Thr Lys Lys Val
        755                 760                 765
Leu Gly Glu Tyr Phe Lys Leu Ser Asp Gly Ile Arg Gln Lys Leu Thr
    770                 775                 780
Glu Ile Arg Leu Asn His Glu Val Ile Thr Glu Glu Gln Ser Gln Lys
785                 790                 795                 800
Leu Ile Gly Gln Tyr Asp Lys Leu Ala Asn Thr Ile Ile Glu Lys Thr
                805                 810                 815
Asn Ala Arg Gln Gln Lys Glu Ile Glu Gly Leu Lys Lys Phe Phe Ala
            820                 825                 830
Asp Ser Tyr Val Leu Thr Ala Glu Glu Glu Asn Lys Arg Ile Glu Gln
        835                 840                 845
Leu Asn Gln His Tyr Glu Gln Glu Lys Leu Lys Thr Gln Glu Lys Glu
    850                 855                 860
Asn Lys Ile Lys Glu Ile Leu Gln Thr Ala Ala Arg Glu Asn Arg Glu
865                 870                 875                 880
Leu Thr Thr Ser Glu Arg Ile Ser Leu Gln Ala Leu Gln Asp Glu Met
                885                 890                 895
Asp Arg Val Ala Val Glu His Met Ser Lys Asn Gln Met Glu Gln Lys
            900                 905                 910
Val Ile Leu Glu Asn Met Arg Val Gln Ala Ser Glu Ile Ser Ala Arg
        915                 920                 925
Gln Ala Ala Glu Val Val Glu Asn Ser Ala Lys Ala Arg Asp Lys Val
    930                 935                 940
Ile Glu Asp Ala Lys Lys Thr Arg Asp Glu Lys Ile Ala Glu Ala Ile
945                 950                 955                 960
Arg Gln Arg Asp Glu Asn Lys Thr Ile Thr Ala Asp Glu Ala Asn Ala
                965                 970                 975
Ile Ile Ala Glu Ala Lys Arg Gln Tyr Asp Ser Thr Val Ser Thr Ala
            980                 985                 990
Arg Asp Lys His Lys Glu Ile Val  Ser Glu Ala Lys Ala  Gln Ala Gly
        995                 1000                1005
Glu His  Ala Asn Gln Val Asp  Trp Glu Thr Gly Gln  Val Lys Ser
    1010                1015                1020
Lys Tyr  Gln Ala Met Lys Asp  Asp Val Ile Arg Lys  Met Lys Glu
    1025                1030                1035
Met Trp  Ser Asp Val Thr Asn  Lys Tyr Glu Asp Met  Lys Asn Ser
    1040                1045                1050
Ala Ser  Asn Lys Val Glu Glu  Ile Lys Asn Thr Val  Ser Arg Lys
    1055                1060                1065
```

```
Phe Glu  Glu Gln Lys Lys Ala  Val Thr Asp Lys Met  Ser Glu Ile
    1070                 1075                 1080

Lys Ser  Ser Ile Glu Asp Lys  Trp Asn Thr Val Glu  Lys Phe Phe
    1085                 1090                 1095

Ser Ser  Ile Asn Leu Arg Ser  Ile Gly Lys Ser Ile  Ile Glu Gly
    1100                 1105                 1110

Leu Gly  Lys Gly Ile Asp Asp  Ala Ser Gly Gly Leu  Phe Ser Lys
    1115                 1120                 1125

Ala Ala  Glu Ile Ala Ser Asp  Ile Lys Lys Thr Ile  Ser Gly Ala
    1130                 1135                 1140

Leu Glu  Ile Asn Ser Pro Ser  Lys Val Met Ile Pro  Val Gly Ser
    1145                 1150                 1155

Ala Val  Pro Glu Gly Val Gly  Val Gly Met Asp Lys  Gly Lys Arg
    1160                 1165                 1170

Phe Val  Val Asp Ala Ala Lys  Asn Val Val Gly Thr  Val Lys Lys
    1175                 1180                 1185

Gln Met  Gly Asn Met Pro Ser  Val Phe Asp Phe Gly  Phe Gln Thr
    1190                 1195                 1200

Asn Gln  Tyr Ser Ile Pro Gln  Asn Thr Phe Ser Asp  Phe Ser Gly
    1205                 1210                 1215

Tyr Met  Gln Pro Gln Leu Ser  Tyr Asn Asn Pro Ser  Met Ala Lys
    1220                 1225                 1230

Thr Ile  Phe Pro Asn Arg Pro  Gly Gly Glu Gln Glu  Leu Asn Leu
    1235                 1240                 1245

Thr Val  Asn Met Thr Asn Val  Leu Asp Gly Lys Glu  Leu Ala Asn
    1250                 1255                 1260

Gly Ser  Tyr Thr Tyr Thr Thr  Lys Leu Gln Asn Arg  Glu Gln Lys
    1265                 1270                 1275

Arg Arg  Ala Glu Phe
    1280


<210> SEQ ID NO 28
<211> LENGTH: 1283
<212> TYPE: PRT
<213> ORGANISM: Bacillus anthracis

<400> SEQUENCE: 28

Met Ala Asn Glu Ile Asn Asn Leu Val Val Arg Leu Ser Leu Asp Asn
1               5                   10                  15

Val Asn Phe Arg Gln Gly Ile Ser Asn Ser Gly Arg Ala Val Arg Thr
            20                  25                  30

Leu Gln Asn Glu Leu Lys Ser Val Ser Thr Gly Met Gly Gly Phe Ala
        35                  40                  45

Asn Ala Ser Gln Gln Thr Gln Ala Lys Met Asn Thr Leu Ser Arg Leu
    50                  55                  60

Ile Asp Ala Gln Lys Glu Lys Val Lys Ala Leu Arg Gln Ala Tyr Asp
65                  70                  75                  80

Gln Asn Lys Ala Lys Leu Gly Glu Asn Asp Ala Ala Thr Gln Arg Tyr
                85                  90                  95

Ala Ser Gln Val Asn Lys Ala Val Ala Asp Leu Asn Arg Phe Glu Asn
            100                 105                 110

Glu Leu Lys Gln Val Asn Arg Gln Ala Glu Gln Lys Gly Met Asp Lys
        115                 120                 125

Leu Asn Asn Ser Leu Lys Ser Leu Gln Ala Glu Phe Gln Ser Ile Thr
```

-continued

```
    130                 135                 140

Thr Gly Met Gly Gly Phe Ser Asn Ala Thr Glu Gln Thr Arg Ala Lys
145                 150                 155                 160

Val Asp Val Leu Ser Arg Met Val Asp Lys Gln Lys Glu Lys Ile Arg
                165                 170                 175

Glu Leu Gln Gln Ala Tyr Asn Arg Ala Lys Thr Glu Glu Gly Glu Ala
            180                 185                 190

Ser Gln Ser Ala Gln Arg Tyr Ala Glu Gln Ile His Arg Ala Thr Ala
        195                 200                 205

Glu Leu Asn Arg Phe Glu Thr Gly Leu Gln Gln Ser Asn Arg Glu Leu
    210                 215                 220

Glu Gln Gln Gly Asn Arg Leu Leu Asn Phe Gly Asn Arg Met Glu Thr
225                 230                 235                 240

Leu Gly Asn His Leu Gln Asn Ala Gly Met Gln Ile Gly Met Val Phe
                245                 250                 255

Gly Gly Met Thr Tyr Ala Ile Gly Arg Gly Leu Lys Ser Ala Ile Thr
            260                 265                 270

Glu Ser Met Asn Phe Glu Gln Gln Met Ala Asn Val Lys Ala Val Ser
        275                 280                 285

Gly Ser Thr Gly Ala Glu Met Lys Lys Leu Ser Glu Leu Ala Val Asn
    290                 295                 300

Met Gly Glu Thr Thr Lys Tyr Ser Ser Val Gln Ala Gly Gln Gly Ile
305                 310                 315                 320

Glu Glu Leu Ile Lys Ala Gly Val Ser Leu Gln Asp Ile Ile Asn Gly
                325                 330                 335

Gly Leu Ala Gly Ala Leu Asn Leu Ala Thr Ala Gly Glu Leu Glu Leu
            340                 345                 350

Gly Glu Ala Ala Glu Ile Ala Ser Thr Ala Leu Asn Ala Phe Lys Ala
        355                 360                 365

Asp His Leu Ser Val Ala Asp Ala Ala Asn Ile Leu Ser Gly Ala Ala
    370                 375                 380

Asn Ala Ser Ala Thr Asp Val Arg Glu Leu Lys Tyr Gly Leu Ser Ala
385                 390                 395                 400

Ser Ser Ala Val Ala Ala Gly Ala Gly Met Thr Phe Lys Asp Thr Ala
                405                 410                 415

Thr Thr Leu Ala Val Phe Ala Gln Asn Gly Leu Lys Gly Ser Asp Ala
            420                 425                 430

Gly Thr Ser Leu Lys Thr Met Leu Met Arg Leu Asn Pro Ser Thr Lys
        435                 440                 445

Glu Ala Tyr Asn Lys Met Arg Asp Leu Gly Leu Ile Thr Tyr Asn Ala
    450                 455                 460

Gln Ala Gly Phe Asp Phe Leu Val Lys Asn Gly Ile Gln Pro Ala Ser
465                 470                 475                 480

Arg Asn Val Gly Asp Ile Glu Val Ala Leu Glu Gln Tyr Val Met Lys
                485                 490                 495

Thr Glu Gly Val Thr Lys Trp Asn Asp Lys Cys Asp Thr Thr Phe Arg
            500                 505                 510

Glu Leu Ala Thr Ser Ser Ala Phe Leu Ser Ser Lys Phe Tyr Asp Gln
        515                 520                 525

Gln Gly His Ile Gln Ser Leu Glu Asn Ile Ser Gly Thr Leu His Glu
    530                 535                 540

Ser Met Lys Asp Leu Thr Asp Gln Gln Arg Ser Met Ala Leu Glu Thr
545                 550                 555                 560
```

-continued

```
Leu Phe Gly Ser Asp Ala Val Arg Gly Ala Thr Ile Leu Phe Lys Glu
                565                 570                 575

Gly Ala Lys Gly Val Asn Glu Met Trp Asp Ser Met Ser Lys Val Thr
            580                 585                 590

Ala Ala Asp Val Ala Ala Thr Lys Ile Asp Thr Leu Lys Gly Arg Leu
        595                 600                 605

Thr Leu Leu Asp Ser Ala Phe Ser Thr Met Lys Lys Thr Ile Gly Asp
    610                 615                 620

Ala Leu Ala Pro Val Val Ser Val Phe Val Ala Gly Leu Gln Lys Leu
625                 630                 635                 640

Val Asp Gly Phe Asn Ser Leu Pro Gly Pro Val Gln Lys Ala Ile Ala
                645                 650                 655

Ile Thr Gly Gly Ile Val Leu Ala Leu Thr Ala Val Ala Thr Ala Ile
            660                 665                 670

Gly Val Val Leu Ala Ala Phe Gly Met Ile Ala Ser Gly Ile Gly Ser
        675                 680                 685

Leu Ser Leu Ala Leu Ala Ser Val Gly Gly Ile Ala Gly Ile Ala Ala
    690                 695                 700

Gly Ala Val Gly Phe Leu Gly Ser Ala Leu Ala Val Leu Thr Gly Pro
705                 710                 715                 720

Ile Gly Leu Val Ala Ala Ala Leu Ile Gly Thr Gly Val Val Ala Tyr
                725                 730                 735

Lys Ala Tyr Gln Lys Ala Thr Glu Asp Ser Ile Ala Ser Val Asp Arg
            740                 745                 750

Phe Ala Thr Asn Thr Glu Gly Lys Val Ser Ser Ser Thr Lys Lys Val
        755                 760                 765

Leu Gly Glu Tyr Phe Lys Leu Ser Asp Gly Ile Arg Gln Lys Leu Thr
    770                 775                 780

Glu Ile Arg Leu Asn His Glu Val Ile Thr Glu Glu Gln Ser Gln Lys
785                 790                 795                 800

Leu Ile Gly Gln Tyr Asp Lys Leu Ala Asn Thr Ile Ile Glu Lys Thr
                805                 810                 815

Asn Ala Arg Gln Gln Lys Glu Ile Glu Gly Leu Lys Lys Phe Phe Ala
            820                 825                 830

Asp Ser Tyr Val Leu Thr Ala Glu Glu Glu Asn Lys Arg Ile Glu Gln
        835                 840                 845

Leu Asn Gln His Tyr Glu Gln Glu Lys Leu Lys Thr Gln Glu Lys Glu
    850                 855                 860

Asn Lys Ile Lys Glu Ile Leu Gln Thr Ala Ala Arg Glu Asn Arg Glu
865                 870                 875                 880

Leu Thr Thr Ser Glu Arg Ile Ser Leu Gln Ala Leu Gln Asp Glu Met
                885                 890                 895

Asp Arg Val Ala Val Glu His Met Ser Lys Asn Gln Met Glu Gln Lys
            900                 905                 910

Val Ile Leu Glu Asn Met Arg Val Gln Ala Ser Glu Ile Ser Ala Arg
        915                 920                 925

Gln Ala Ala Glu Val Val Glu Asn Ser Ala Lys Ala Arg Asp Lys Val
    930                 935                 940

Ile Glu Asp Ala Lys Lys Thr Arg Asp Glu Lys Ile Ala Glu Ala Ile
945                 950                 955                 960

Arg Gln Arg Asp Glu Asn Lys Thr Ile Thr Ala Asp Glu Ala Asn Ala
                965                 970                 975
```

-continued

```
Ile Ile Ala Glu Ala Lys Arg Gln Tyr Asp Ser Thr Val Ser Thr Ala
            980                 985                 990

Arg Asp Lys His Lys Glu Ile Val  Ser Glu Ala Lys Ala  Gln Ala Gly
        995                 1000                1005

Glu His  Ala Asn Gln Val Asp  Trp Glu Thr Gly Gln  Val Lys Ser
    1010                 1015                 1020

Lys Tyr  Gln Ala Met Lys Asp  Asp Val Ile Arg Lys  Met Lys Glu
    1025                 1030                 1035

Met Trp  Ser Asp Val Thr Asn  Lys Tyr Glu Asp Met  Lys Asn Ser
    1040                 1045                 1050

Ala Ser  Asn Lys Val Glu Glu  Ile Lys Asn Thr Val  Ser Arg Lys
    1055                 1060                 1065

Phe Glu  Glu Gln Lys Lys Ala  Val Thr Asp Lys Met  Ser Glu Ile
    1070                 1075                 1080

Lys Ser  Ser Ile Glu Asp Lys  Trp Asn Thr Val Glu  Lys Phe Phe
    1085                 1090                 1095

Ser Ser  Ile Asn Leu Arg Ser  Ile Gly Lys Ser Ile  Ile Glu Gly
    1100                 1105                 1110

Leu Gly  Lys Gly Ile Asp Asp  Ala Ser Gly Gly Leu  Phe Ser Lys
    1115                 1120                 1125

Ala Ala  Glu Ile Ala Ser Asp  Ile Lys Lys Thr Ile  Ser Gly Ala
    1130                 1135                 1140

Leu Glu  Ile Asn Ser Pro Ser  Lys Val Met Ile Pro  Val Gly Ser
    1145                 1150                 1155

Ala Val  Pro Glu Gly Val Gly  Val Gly Met Asp Lys  Gly Lys Arg
    1160                 1165                 1170

Phe Val  Val Asp Ala Ala Lys  Asn Val Val Gly Thr  Val Lys Lys
    1175                 1180                 1185

Gln Met  Gly Asn Met Pro Ser  Val Phe Asp Phe Gly  Phe Gln Thr
    1190                 1195                 1200

Asn Gln  Tyr Ser Ile Pro Gln  Asn Thr Phe Ser Asp  Phe Ser Gly
    1205                 1210                 1215

Tyr Met  Gln Pro Gln Leu Ser  Tyr Asn Asn Pro Ser  Met Ala Lys
    1220                 1225                 1230

Thr Ile  Phe Pro Asn Arg Pro  Gly Gly Glu Gln Glu  Leu Asn Leu
    1235                 1240                 1245

Thr Val  Asn Met Thr Asn Val  Leu Asp Gly Lys Glu  Leu Ala Asn
    1250                 1255                 1260

Gly Ser  Tyr Thr Tyr Thr Thr  Lys Leu Gln Asn Arg  Glu Gln Lys
    1265                 1270                 1275

Arg Arg  Ala Glu Phe
    1280


<210> SEQ ID NO 29
<211> LENGTH: 496
<212> TYPE: PRT
<213> ORGANISM: Bacillus anthracis

<400> SEQUENCE: 29

Leu Gly Lys Leu Ser Phe Thr Phe Asn Asn Ile Arg Lys Asp Tyr Ile
1               5                   10                  15

Gln Met Leu Val Gly Arg Lys Arg Pro Ser Trp Ala Pro Val Lys Arg
            20                  25                  30

Arg Leu Val Arg Val Pro His Arg Ala Gly Ala Leu Leu Leu Asn Thr
        35                  40                  45
```

-continued

```
Glu Thr Glu Glu Arg Arg Ile Asp Val Pro Leu Val Ile Lys Ala Lys
    50                  55                  60

Lys Asp Met Ala Asp Leu Gln Lys Leu Lys Glu Asp Leu Ala Asp Trp
65                  70                  75                  80

Leu Tyr Thr Glu Gln Pro Ala Glu Leu Ile Phe Asp Asp Glu Leu Asp
                85                  90                  95

Arg Thr Tyr Leu Ala Leu Ile Asp Gly Ser Val Asp Leu Asp Glu Ile
            100                 105                 110

Val Asn Arg Gly Arg Gly Val Ile Thr Phe Val Cys Pro Met Pro Tyr
        115                 120                 125

Lys Leu Gly Lys Thr Asn Thr His Lys Phe Thr Gln Glu Trp Ser Thr
    130                 135                 140

Glu Thr Thr Ser Tyr Phe Thr Asn Lys Gly Ser Val Glu Ala Pro Ala
145                 150                 155                 160

Leu Ile Glu Met Thr Val Lys Lys Pro Ser Thr Phe Leu Asp Val Trp
                165                 170                 175

Phe Gly Glu Tyr Pro Asn Asn Arg Asp Tyr Phe Arg Ile Gly Tyr Pro
            180                 185                 190

Leu Thr Val Glu Glu Thr Thr Val Gln Glu Arg Glu Arg Val Met Trp
        195                 200                 205

Asp Glu Met Ala Thr Pro Ile Gly Trp Thr Pro Val Thr Gly Gln Phe
    210                 215                 220

Asp Asp Met Lys Gly Thr Gly Ser Phe Lys Ser Arg Gly Gly Tyr Ala
225                 230                 235                 240

Leu Tyr Cys Glu Asp Tyr Gly Lys Asp Val Gly Phe Tyr Gly Ala Ile
                245                 250                 255

Ala Lys Lys Asn Ile Pro Gly Gly Pro Leu Gln Asp Phe Glu Met Glu
            260                 265                 270

Ala Trp Met Thr Leu Lys Ser Lys Asn Ile Gly Glu Met Gly Arg Val
        275                 280                 285

Glu Val Leu Leu Leu Asp Glu Ala Ser Asn Val Val Ala Arg Ile Asn
    290                 295                 300

Met Asn Asp Leu Tyr Ala Thr Ala Glu Ile Thr Arg Ala His Met Lys
305                 310                 315                 320

Ile Gly Asn Ser Gly Thr Pro Asn Ser Phe Arg Lys Leu Val Asp Thr
                325                 330                 335

Ser Gly Tyr Tyr Ser Asn Thr Phe Asn Gln Phe Arg Gly Arg Leu Arg
            340                 345                 350

Ile Ala Arg Arg Gly Lys Val Trp Ser Val Tyr Val Ala Lys Phe Ile
        355                 360                 365

Asp Gly Thr Glu Lys Asp Gly Ala Ser Leu Val Glu Arg Trp Ile Asp
    370                 375                 380

Glu Thr Gly Asn Pro Met Thr Glu Arg Lys Ile Ala Gln Val Met Ile
385                 390                 395                 400

Ala Ile Cys Lys Trp Asp Asn His Gln Pro Val Asn Glu Ile Gln Ile
                405                 410                 415

Asp Asp Leu Lys Phe Trp Lys Val Asn Lys Val Pro Ser Asn Ala Gln
            420                 425                 430

Pro Tyr Ile Phe Asp Thr Gly Asp Lys Ile Val Ile Asp Thr Glu Lys
        435                 440                 445

Ser Leu Val Thr Ile Asn Gly Lys Asn Ala Ile Asn Ile Lys Glu Ile
    450                 455                 460
```

-continued

```
Phe Ser Asn Phe Pro Val Ile Ile Arg Gly Asp Asn Arg Ile Asp Ile
465                 470                 475                 480

Met Pro Pro Asp Val Asn Ala Thr Ile Ser Tyr Arg Glu Arg Tyr Arg
                485                 490                 495


<210> SEQ ID NO 30
<211> LENGTH: 496
<212> TYPE: PRT
<213> ORGANISM: Bacillus anthracis

<400> SEQUENCE: 30

Met Gly Lys Leu Ser Phe Thr Phe Asn Asn Ile Arg Lys Asp Tyr Ile
1               5                   10                  15

Gln Met Leu Val Gly Arg Lys Arg Pro Ser Trp Ala Pro Val Lys Arg
            20                  25                  30

Arg Leu Val Arg Val Pro His Arg Ala Gly Ala Leu Leu Leu Asn Thr
        35                  40                  45

Glu Thr Glu Glu Arg Arg Ile Asp Val Pro Leu Val Ile Lys Ala Lys
    50                  55                  60

Lys Asp Met Ala Asp Leu Gln Lys Leu Lys Glu Asp Leu Ala Asp Trp
65                  70                  75                  80

Leu Tyr Thr Glu Gln Pro Ala Glu Leu Ile Phe Asp Asp Glu Leu Asp
                85                  90                  95

Arg Thr Tyr Leu Ser Leu Ile Asp Gly Ser Val Asp Leu Asp Glu Ile
            100                 105                 110

Val Asn Arg Gly Lys Gly Val Ile Thr Phe Val Cys Pro Met Pro Tyr
        115                 120                 125

Lys Leu Gly Lys Ile Asn Thr His Lys Phe Thr Gln Glu Trp Ser Thr
    130                 135                 140

Glu Thr Thr Ser Tyr Phe Thr Asn Lys Gly Ser Val Glu Ala Pro Ala
145                 150                 155                 160

Leu Ile Glu Met Thr Val Lys Lys Pro Ser Thr Phe Leu Asp Val Trp
                165                 170                 175

Phe Gly Glu Tyr Pro His Asn Arg Asp Tyr Phe Arg Ile Gly Tyr Pro
            180                 185                 190

Leu Thr Val Glu Glu Thr Thr Val Gln Glu Arg Glu Arg Val Met Trp
        195                 200                 205

Asp Glu Met Ala Thr Pro Ile Gly Trp Thr Pro Val Thr Gly Gln Phe
    210                 215                 220

Glu Glu Met Lys Gly Thr Gly Ser Phe Lys Ser Arg Gly Gly His Ala
225                 230                 235                 240

Leu Tyr Cys Glu Asp Tyr Gly Lys Glu Thr Gly Phe Tyr Gly Ala Ile
                245                 250                 255

Ala Lys Lys Asn Ile Pro Gly Gly Pro Leu Gln Asp Phe Glu Met Glu
            260                 265                 270

Ala Trp Val Thr Leu Lys Ser Lys Asn Ile Ser Glu Met Gly Arg Val
        275                 280                 285

Glu Val Leu Leu Leu Asp Glu Thr Ser Asn Val Ile Ser Arg Ile Asn
    290                 295                 300

Met Asn Asp Leu Tyr Ala Thr Ala Glu Ile Thr Arg Ala His Met Thr
305                 310                 315                 320

Ile Gly Asn Ser Gly Thr Pro Asn Ser Phe Arg Lys Leu Val Asp Thr
                325                 330                 335

Ser Gly Phe Tyr Ser Thr Thr Phe Asn Gln Phe Arg Gly Arg Leu Arg
            340                 345                 350
```

-continued

Ile Ala Arg Arg Gly Lys Val Trp Ser Val Tyr Val Ala Lys Phe Ile
355 360 365

Asp Gly Thr Glu Lys Asp Gly Ala Ser Leu Val Glu Arg Trp Ile Asp
370 375 380

Glu Thr Gly Asn Pro Met Thr Glu Arg Lys Ile Ala Gln Val Met Ile
385 390 395 400

Ala Ile Cys Lys Trp Asp Asn His Gln Pro Ile Asn Glu Met Gln Ile
405 410 415

Asp Asp Leu Lys Ile Trp Lys Val Asn Lys Val Pro Ser Asn Ala Gln
420 425 430

Pro Tyr Ile Phe Asp Thr Gly Asp Lys Ile Val Ile Asp Thr Glu Lys
435 440 445

Ser Leu Val Thr Ile Asn Gly Glu Lys Ala Ile Asn Ile Lys Glu Ile
450 455 460

Phe Ser Asn Phe Pro Val Val Ile Arg Gly Glu Asn Arg Ile Asp Ile
465 470 475 480

Met Pro Pro Asp Val Asn Ala Thr Ile Ser Tyr Arg Glu Arg Tyr Arg
485 490 495

<210> SEQ ID NO 31
<211> LENGTH: 1331
<212> TYPE: PRT
<213> ORGANISM: Bacillus anthracis

<400> SEQUENCE: 31

Met Arg Thr Pro Ser Gly Ile Leu His Val Val Asp Phe Lys Thr Asp
1 5 10 15

Gln Ile Val Ala Ala Ile Gln Pro Glu Asp Tyr Trp Asp Asp Lys Arg
20 25 30

His Trp Glu Leu Lys Asn Asn Val Asp Met Leu Asp Phe Thr Ala Phe
35 40 45

Asp Gly Thr Asp His Ala Val Thr Leu Gln Gln Gln Asn Leu Val Leu
50 55 60

Lys Glu Val Arg Asp Gly Arg Ile Val Pro Tyr Val Ile Thr Glu Thr
65 70 75 80

Glu Lys Asn Ser Asp Thr Arg Ser Ile Thr Thr Tyr Ala Ser Gly Ala
85 90 95

Trp Ile Gln Ile Ala Lys Ser Gly Ile Ile Lys Pro Gln Arg Ile Glu
100 105 110

Ser Lys Thr Val Asn Glu Phe Met Asp Leu Ala Leu Leu Gly Met Lys
115 120 125

Trp Lys Arg Gly Ile Thr Glu Tyr Ala Gly Phe His Thr Met Thr Ile
130 135 140

Asp Glu Tyr Ile Asp Pro Leu Thr Phe Leu Lys Lys Ile Ala Ser Leu
145 150 155 160

Phe Lys Leu Glu Ile Arg Tyr Arg Val Glu Ile Lys Gly Ser Arg Ile
165 170 175

Ile Gly Trp Tyr Val Asp Met Ile Gln Lys Arg Gly His Asp Thr Gly
180 185 190

Lys Glu Ile Glu Leu Gly Lys Asp Leu Val Gly Val Thr Arg Ile Glu
195 200 205

His Thr Arg Asn Ile Cys Ser Ala Leu Val Gly Phe Val Lys Gly Glu
210 215 220

Gly Asp Lys Val Ile Thr Ile Glu Ser Ile Asn Lys Gly Leu Pro Tyr

-continued

```
225                 230                 235                 240

Ile Val Asp Ala Asp Ala Phe Gln Arg Trp Asn Glu His Gly Gln His
                245                 250                 255

Lys Phe Gly Phe Tyr Thr Pro Glu Thr Glu Glu Leu Asp Met Thr Pro
            260                 265                 270

Lys Arg Leu Leu Thr Leu Met Glu Ile Glu Leu Lys Lys Arg Val Asn
        275                 280                 285

Ser Ser Ile Ser Tyr Glu Val Glu Ala Gln Ser Ile Gly Arg Ile Phe
    290                 295                 300

Gly Leu Glu His Glu Leu Ile Asn Glu Gly Asp Thr Ile Lys Ile Lys
305                 310                 315                 320

Asp Thr Gly Phe Thr Pro Glu Leu Tyr Leu Glu Ala Arg Val Ile Ala
                325                 330                 335

Gly Asp Glu Ser Phe Thr Asp Ser Thr Gln Asp Lys Tyr Glu Phe Gly
            340                 345                 350

Asp Tyr Arg Glu Ile Val Asn Gln Asn Glu Glu Leu Arg Lys Ile Tyr
        355                 360                 365

Asn Arg Ile Leu Ser Ser Leu Gly Asn Lys Gln Glu Met Ile Asp Gln
    370                 375                 380

Leu Asp Arg Leu Val Gln Glu Ala Asn Glu Thr Ala Ser Asn Ala Lys
385                 390                 395                 400

Lys Glu Ser Glu Ala Ala Lys Thr Leu Ala Glu Lys Val Gln Glu Asn
                405                 410                 415

Ile Lys Asn Asn Thr Val Glu Ile Ile Glu Ser Lys Asn Pro Pro Thr
            420                 425                 430

Thr Gly Leu Lys Pro Phe Lys Thr Leu Trp Arg Asp Ile Ser Ile Gly
        435                 440                 445

Lys Pro Gly Ile Leu Lys Ile Trp Thr Gly Thr Ala Trp Glu Ser Val
    450                 455                 460

Val Pro Asp Val Glu Ser Val Lys Lys Glu Thr Leu Asp Gln Val Asn
465                 470                 475                 480

Lys Asp Ile Ala Thr Thr Lys Thr Glu Leu Asn Gln Lys Val Gln Glu
                485                 490                 495

Ala Gln Asn Gln Ala Thr Gly Gln Phe Asn Glu Val Lys Glu Ser Leu
            500                 505                 510

Gln Gly Val Ser Arg Thr Ile Ser Asn Val Glu Asn Lys Gln Gly Glu
        515                 520                 525

Ile Asp Lys Lys Ile Thr Lys Phe Glu Gln Asp Ser Ser Gly Phe Lys
    530                 535                 540

Thr Ser Ile Glu Ser Leu Thr Lys Lys Asp Thr Glu Ile Ser Asn Lys
545                 550                 555                 560

Leu Asn Thr Val Glu Ser Thr Val Glu Gly Thr Lys Lys Thr Ile Ser
                565                 570                 575

Glu Val Gln Gln Thr Thr Asn Asp Leu Lys Lys Lys Thr Thr Glu Ile
            580                 585                 590

Glu Glu Lys Ala Gly Lys Ile Thr Glu Lys Leu Thr Ser Leu Glu Thr
        595                 600                 605

Arg Glu Val Asn Val Arg Asn Tyr Val Ile Asn Ser Asp Phe Ser Asn
    610                 615                 620

Val Thr Asn Ser Trp Ile Gly Ile Thr Asn Ala Thr Leu Phe Lys Phe
625                 630                 635                 640

Val Asp Val Asn Ile Ser Glu Ala Ser Ala Ile Lys Lys Gly Leu Gln
                645                 650                 655
```

-continued

```
Ile Thr Ser Asn Lys Ala Phe Val Tyr Gln Lys Leu Pro Ala Asp Val
            660                 665                 670

Phe Lys Lys Lys Lys Gly Ile Ala Ser Cys Tyr Ile Asn Val Ser Ser
        675                 680                 685

Phe Thr Pro Gly Thr Asp Tyr Pro Arg Leu Tyr Met Arg Phe Thr Tyr
    690                 695                 700

Asp Gln Asn Gly Thr Glu Lys Gln Tyr Tyr Ala Ile Leu Lys Gln Gln
705                 710                 715                 720

Glu Val Thr Asn Gly Trp Ile Arg Ile Ser Ile Pro Phe Asp Thr Thr
                725                 730                 735

Gly Tyr Thr Gly Glu Leu Lys Glu Val Arg Val Asn Ile Ala Thr Ala
            740                 745                 750

Asp Thr Thr Thr Ile Asp Ala Thr Phe Thr Gly Ile Met Val Thr Phe
        755                 760                 765

Gly Asp Leu Ile Glu Ser Trp Asn Leu Ala Pro Glu Asp Gly Val Thr
    770                 775                 780

Gln Gly Val Phe Gln Ser Lys Thr Thr Glu Ile Glu Lys Ser Val Asp
785                 790                 795                 800

Gly Val Lys Thr Thr Val Thr Asn Val Gln Asn Ser Gln Ala Gly Phe
                805                 810                 815

Glu Lys Arg Met Ser Asn Val Glu Gln Thr Ala Thr Gly Leu Ser Ser
            820                 825                 830

Thr Val Ser Asn Leu Asn Asn Val Val Ser Asp Gln Gly Lys Lys Leu
        835                 840                 845

Thr Glu Ala Asn Thr Lys Leu Glu Gln Gln Ala Thr Ala Ile Gly Ala
    850                 855                 860

Lys Val Glu Leu Lys Gln Val Glu Asp Tyr Val Ala Gly Phe Lys Ile
865                 870                 875                 880

Pro Glu Leu Lys Gln Thr Val Asp Lys Asn Lys Gln Asp Leu Leu Asp
                885                 890                 895

Glu Leu Ala Asn Lys Leu Ala Thr Glu Gln Phe Asn Gln Lys Met Thr
            900                 905                 910

Leu Ile Asp Asn Arg Phe Thr Ile Asn Glu Gln Gly Ile Asn Ala Ala
        915                 920                 925

Ala Lys Lys Thr Glu Val Tyr Thr Lys Thr Gln Ala Asp Gly Gln Phe
    930                 935                 940

Ala Thr Asp Ser Tyr Val Arg Asp Met Glu Ser Arg Leu Gln Leu Thr
945                 950                 955                 960

Glu Lys Gly Val Ser Ile Ser Val Lys Glu Asn Asp Val Ile Ala Ala
                965                 970                 975

Ile Asn Met Ser Lys Glu Asn Ile Lys Leu Asn Ala Ala Arg Ile Asp
            980                 985                 990

Leu Val Gly Lys Val Asn Ala Glu  Trp Ile Lys Ala Gly  Leu Leu Ser
        995                 1000                1005

Gly Cys  Gln Ile Arg Thr Ser  Asn Thr Asp Asn Tyr  Val Ser Leu
    1010                1015                1020

Asp Asp  Gln Phe Ile Arg Leu  Tyr Glu Arg Gly Val  Ala Arg Ala
    1025                1030                1035

Phe Leu  Gly His Tyr Arg Arg  Ser Asp Gly Ala Val  Gln Pro Thr
    1040                1045                1050

Phe Ile  Leu Gly Ser Asp Glu  Lys Thr Asn Ala Pro  Glu Gly Thr
    1055                1060                1065
```

-continued

```
Leu Phe  Met Ser Gln Ala Gly  Ala Gly Trp Ser Gly  Ala Tyr Ala
    1070                 1075                 1080

Ser Ile  Gly Ile Ser Asn Gly  Ile Val Asp Gly Ala  Val Gln Lys
    1085                 1090                 1095

Ser Val  Tyr Trp Glu Leu Gln  Arg Asn Gly Leu Ser  Val Leu Asn
    1100                 1105                 1110

Ala Asn  Asp Tyr His Val Phe  Tyr Ala Gly Asn Gly  Asn Trp Tyr
    1115                 1120                 1125

Phe Arg  Arg Gly Lys Pro Gly  Leu Tyr Gln Thr Ser  Leu Val Val
    1130                 1135                 1140

Glu Asp  Asn Ser Thr Asp Ser  Asp Leu Arg Leu Pro  Asn Val Thr
    1145                 1150                 1155

Ile Arg  Asn Ser Arg Ala Ala  Gly Tyr Thr Gly Val  Ile Gln Leu
    1160                 1165                 1170

Lys Ser  Pro Val Thr Gln Asn  Gly Trp Gly Ala Val  Gln Gly Asn
    1175                 1180                 1185

Phe Met  Thr Pro Ser Leu Arg  Glu Tyr Lys Ser Asn  Ile Arg Asp
    1190                 1195                 1200

Ile Ser  Phe Ser Ala Leu Glu  Lys Ile Arg Ser Leu  Lys Ile Arg
    1205                 1210                 1215

Gln Phe  Asn Tyr Lys Asn Ala  Val Asn Glu Leu Tyr  Arg Met Arg
    1220                 1225                 1230

Glu Glu  Lys Ser Pro Asn Asp  Pro Pro Leu Thr Thr  Glu Asp Ile
    1235                 1240                 1245

Lys Thr  Tyr Tyr Gly Leu Ile  Val Asp Glu Cys Asp  Glu Met Phe
    1250                 1255                 1260

Val Asp  Glu Ser Gly Lys Gly  Ile His Leu Tyr Ser  Tyr Ala Ser
    1265                 1270                 1275

Ile Gly  Ile Lys Gly Leu Gln  Glu Val Asp Ala Thr  Val Gln Glu
    1280                 1285                 1290

Gln Glu  Val Glu Ile Ala Asn  Leu Lys Ser Gln Ile  Ala Ser Gln
    1295                 1300                 1305

Glu Asp  Arg Ile Ala Arg Leu  Glu Glu Leu Leu Leu  Gln Gln Leu
    1310                 1315                 1320

Ile Asn  Lys Lys Pro Glu Gln  Pro
    1325                 1330


<210> SEQ ID NO 32
<211> LENGTH: 1331
<212> TYPE: PRT
<213> ORGANISM: Bacillus anthracis

<400> SEQUENCE: 32

Met Arg Thr Pro Ser Gly Ile Leu His Val Val Asp Phe Lys Thr Asp
1               5                   10                  15

Gln Ile Val Ala Ala Ile Gln Pro Glu Asp Tyr Trp Asp Asp Lys Arg
            20                  25                  30

His Trp Glu Leu Lys Asn Asn Val Asp Met Leu Asp Phe Thr Ala Phe
        35                  40                  45

Asp Gly Thr Asp His Ala Val Thr Leu Gln Gln Gln Asn Leu Val Leu
    50                  55                  60

Lys Glu Val Arg Asp Gly Arg Ile Val Pro Tyr Val Ile Thr Glu Thr
65                  70                  75                  80

Glu Lys Asn Ser Asp Thr Arg Ser Ile Thr Thr Tyr Ala Ser Gly Ala
                85                  90                  95
```

-continued

```
Trp Ile Gln Ile Ala Lys Ser Gly Ile Ile Lys Pro Gln Arg Ile Glu
            100                 105                 110

Ser Lys Thr Val Asn Glu Phe Met Asp Leu Ala Leu Leu Gly Met Lys
        115                 120                 125

Trp Lys Arg Gly Ile Thr Glu Tyr Ala Gly Phe His Thr Met Thr Ile
    130                 135                 140

Asp Glu Tyr Ile Asp Pro Leu Thr Phe Leu Lys Lys Ile Ala Ser Leu
145                 150                 155                 160

Phe Lys Leu Glu Ile Arg Tyr Arg Val Glu Ile Lys Gly Ser Arg Ile
                165                 170                 175

Ile Gly Trp Tyr Val Asp Met Ile Gln Lys Arg Gly His Asp Thr Gly
            180                 185                 190

Lys Glu Ile Glu Leu Gly Lys Asp Leu Val Gly Val Thr Arg Ile Glu
        195                 200                 205

His Thr Arg Asn Ile Cys Ser Ala Leu Val Gly Phe Val Lys Gly Glu
    210                 215                 220

Gly Asp Lys Val Ile Thr Ile Glu Ser Ile Asn Lys Gly Leu Pro Tyr
225                 230                 235                 240

Ile Val Asp Ala Asp Ala Phe Gln Arg Trp Asn Glu His Gly Gln His
                245                 250                 255

Lys Phe Gly Phe Tyr Thr Pro Glu Thr Glu Glu Leu Asp Met Thr Pro
            260                 265                 270

Lys Arg Leu Leu Thr Leu Met Glu Ile Glu Leu Lys Lys Arg Val Asn
        275                 280                 285

Ser Ser Ile Ser Tyr Glu Val Glu Ala Gln Ser Ile Gly Arg Ile Phe
    290                 295                 300

Gly Leu Glu His Glu Leu Ile Asn Glu Gly Asp Thr Ile Lys Ile Lys
305                 310                 315                 320

Asp Thr Gly Phe Thr Pro Glu Leu Tyr Leu Glu Ala Arg Val Ile Ala
                325                 330                 335

Gly Asp Glu Ser Phe Thr Asp Ser Thr Gln Asp Lys Tyr Glu Phe Gly
            340                 345                 350

Asp Tyr Arg Glu Ile Val Asn Gln Asn Glu Glu Leu Arg Lys Ile Tyr
        355                 360                 365

Asn Arg Ile Leu Ser Ser Leu Gly Asn Lys Gln Glu Met Ile Asp Gln
    370                 375                 380

Leu Asp Arg Leu Val Gln Glu Ala Asn Glu Thr Ala Ser Asn Ala Lys
385                 390                 395                 400

Lys Glu Ser Glu Ala Ala Lys Thr Leu Ala Glu Lys Val Gln Glu Asn
                405                 410                 415

Ile Lys Asn Asn Thr Val Glu Ile Ile Glu Ser Lys Asn Pro Pro Thr
            420                 425                 430

Thr Gly Leu Lys Pro Phe Lys Thr Leu Trp Arg Asp Ile Ser Ile Gly
        435                 440                 445

Lys Pro Gly Ile Leu Lys Ile Trp Thr Gly Thr Ala Trp Glu Ser Val
    450                 455                 460

Val Pro Asp Val Glu Ser Val Lys Lys Glu Thr Leu Asp Gln Val Asn
465                 470                 475                 480

Lys Asp Ile Ala Thr Thr Lys Thr Glu Leu Asn Gln Lys Val Gln Glu
                485                 490                 495

Ala Gln Asn Gln Ala Thr Gly Gln Phe Asn Glu Val Lys Glu Ser Leu
            500                 505                 510
```

-continued

```
Gln Gly Val Ser Arg Thr Ile Ser Asn Val Glu Asn Lys Gln Gly Glu
        515                 520                 525

Ile Asp Lys Lys Ile Thr Lys Phe Glu Gln Asp Ser Ser Gly Phe Lys
    530                 535                 540

Thr Ser Ile Glu Ser Leu Thr Lys Lys Asp Thr Glu Ile Ser Asn Lys
545                 550                 555                 560

Leu Asn Thr Val Glu Ser Thr Val Glu Gly Thr Lys Lys Thr Ile Ser
                565                 570                 575

Glu Val Gln Gln Thr Thr Asn Asp Leu Lys Lys Lys Thr Thr Glu Ile
            580                 585                 590

Glu Glu Lys Ala Gly Lys Ile Thr Glu Lys Leu Thr Ser Leu Glu Thr
        595                 600                 605

Arg Glu Val Asn Val Arg Asn Tyr Val Ile Asn Ser Asp Phe Ser Asn
    610                 615                 620

Val Thr Asn Ser Trp Ile Gly Ile Thr Asn Ala Thr Leu Phe Lys Phe
625                 630                 635                 640

Val Asp Val Asn Ile Ser Glu Ala Ser Ala Ile Lys Lys Gly Leu Gln
                645                 650                 655

Ile Thr Ser Asn Lys Ala Phe Val Tyr Gln Lys Leu Pro Ala Asp Val
            660                 665                 670

Phe Lys Lys Lys Lys Gly Ile Ala Ser Cys Tyr Ile Asn Val Ser Ser
        675                 680                 685

Phe Thr Pro Gly Thr Asp Tyr Pro Arg Leu Tyr Met Arg Phe Thr Tyr
    690                 695                 700

Asp Gln Asn Gly Thr Glu Lys Gln Tyr Tyr Ala Ile Leu Lys Gln Gln
705                 710                 715                 720

Glu Val Thr Asn Gly Trp Ile Arg Ile Ser Ile Pro Phe Asp Thr Thr
                725                 730                 735

Gly Tyr Thr Gly Glu Leu Lys Glu Val Arg Val Asn Ile Ala Thr Ala
            740                 745                 750

Asp Thr Thr Thr Ile Asp Ala Thr Phe Thr Gly Ile Met Val Thr Phe
        755                 760                 765

Gly Asp Leu Ile Glu Ser Trp Asn Leu Ala Pro Glu Asp Gly Val Thr
    770                 775                 780

Gln Gly Val Phe Gln Ser Lys Thr Thr Glu Ile Glu Lys Ser Val Asp
785                 790                 795                 800

Gly Val Lys Thr Thr Val Thr Asn Val Gln Asn Ser Gln Ala Gly Phe
                805                 810                 815

Glu Lys Arg Met Ser Asn Val Glu Gln Thr Ala Thr Gly Leu Ser Ser
            820                 825                 830

Thr Val Ser Asn Leu Asn Asn Val Val Ser Asp Gln Gly Lys Lys Leu
        835                 840                 845

Thr Glu Ala Asn Thr Lys Leu Glu Gln Gln Ala Thr Ala Ile Gly Ala
    850                 855                 860

Lys Val Glu Leu Lys Gln Val Glu Asp Tyr Val Ala Gly Phe Lys Ile
865                 870                 875                 880

Pro Glu Leu Lys Gln Thr Val Asp Lys Asn Lys Gln Asp Leu Leu Asp
                885                 890                 895

Glu Leu Ala Asn Lys Leu Ala Thr Glu Gln Phe Asn Gln Lys Met Thr
            900                 905                 910

Leu Ile Asp Asn Arg Phe Thr Ile Asn Glu Gln Gly Ile Asn Ala Ala
        915                 920                 925

Ala Lys Lys Thr Glu Val Tyr Thr Lys Thr Gln Ala Asp Gly Gln Phe
```

-continued

```
    930                 935                 940

Ala Thr Asp Ser Tyr Val Arg Asp Met Glu Ser Arg Leu Gln Leu Thr
945                 950                 955                 960

Glu Lys Gly Val Ser Ile Ser Val Lys Glu Asn Asp Val Ile Ala Ala
                965                 970                 975

Ile Asn Met Ser Lys Glu Asn Ile Lys Leu Asn Ala Ala Arg Ile Asp
            980                 985                 990

Leu Val Gly Lys Val Asn Ala Glu  Trp Ile Lys Ala Gly  Leu Leu Ser
        995                 1000                1005

Gly Cys  Gln Ile Arg Thr Ser  Asn Thr Asp Asn Tyr  Val Ser Leu
    1010                 1015                1020

Asp Asp  Gln Phe Ile Arg Leu  Tyr Glu Arg Gly Val  Ala Arg Ala
    1025                 1030                1035

Phe Leu  Gly His Tyr Arg Arg  Ser Asp Gly Ala Val  Gln Pro Thr
    1040                 1045                1050

Phe Ile  Leu Gly Ser Asp Glu  Lys Thr Asn Ala Pro  Glu Gly Thr
    1055                 1060                1065

Leu Phe  Met Ser Gln Ala Gly  Ala Gly Trp Ser Gly  Ala Tyr Ala
    1070                 1075                1080

Ser Ile  Gly Ile Ser Asn Gly  Ile Val Asp Gly Ala  Val Gln Lys
    1085                 1090                1095

Ser Val  Tyr Trp Glu Leu Gln  Arg Asn Gly Leu Ser  Val Leu Asn
    1100                 1105                1110

Ala Asn  Asp Tyr His Val Phe  Tyr Ala Gly Asn Gly  Asn Trp Tyr
    1115                 1120                1125

Phe Arg  Arg Gly Lys Pro Gly  Leu Tyr Gln Thr Ser  Leu Val Val
    1130                 1135                1140

Glu Asp  Asn Ser Thr Asp Ser  Asp Leu Arg Leu Pro  Asn Val Thr
    1145                 1150                1155

Ile Arg  Asn Ser Arg Ala Ala  Gly Tyr Thr Gly Val  Ile Gln Leu
    1160                 1165                1170

Lys Ser  Pro Val Thr Gln Asn  Gly Trp Gly Ala Val  Gln Gly Asn
    1175                 1180                1185

Phe Met  Thr Pro Ser Leu Arg  Glu Tyr Lys Ser Asn  Ile Arg Asp
    1190                 1195                1200

Ile Ser  Phe Ser Ala Leu Glu  Lys Ile Arg Ser Leu  Lys Ile Arg
    1205                 1210                1215

Gln Phe  Asn Tyr Lys Asn Ala  Val Asn Glu Leu Tyr  Arg Met Arg
    1220                 1225                1230

Glu Glu  Lys Ser Pro Asn Asp  Pro Pro Leu Thr Thr  Glu Asp Ile
    1235                 1240                1245

Lys Thr  Tyr Tyr Gly Leu Ile  Val Asp Glu Cys Asp  Glu Met Phe
    1250                 1255                1260

Val Asp  Glu Ser Gly Lys Gly  Ile His Leu Tyr Ser  Tyr Ala Ser
    1265                 1270                1275

Ile Gly  Ile Lys Gly Leu Gln  Glu Val Asp Ala Thr  Val Gln Glu
    1280                 1285                1290

Gln Glu  Val Glu Ile Ala Asn  Leu Lys Ser Gln Ile  Ala Ser Gln
    1295                 1300                1305

Glu Asp  Arg Ile Ala Arg Leu  Glu Glu Leu Leu Leu  Gln Gln Leu
    1310                 1315                1320

Ile Asn  Lys Lys Pro Glu Gln  Pro
    1325                 1330
```

-continued

<210> SEQ ID NO 33
<211> LENGTH: 141
<212> TYPE: PRT
<213> ORGANISM: Bacillus anthracis

<400> SEQUENCE: 33

```
Met Asp Arg Ile Asp Val Leu Leu Lys Ala Phe Ile Ala Ala Phe Gly
1               5                   10                  15

Gly Phe Cys Gly Tyr Phe Leu Gly Gly Trp Asp Ala Thr Leu Lys Ile
            20                  25                  30

Leu Val Thr Met Val Val Ile Asp Tyr Leu Thr Gly Met Ile Ala Ala
        35                  40                  45

Gly Tyr Asn Gly Glu Leu Lys Ser Lys Val Gly Phe Lys Gly Ile Ala
    50                  55                  60

Lys Lys Val Val Leu Phe Leu Leu Val Gly Ala Ala Ala Gln Leu Asp
65                  70                  75                  80

Ser Ala Leu Gly Ser Asn Ser Ala Ile Arg Glu Ala Thr Ile Phe Phe
                85                  90                  95

Phe Met Gly Asn Glu Leu Leu Ser Leu Leu Glu Asn Ala Gly Arg Met
            100                 105                 110

Gly Ile Pro Leu Pro Gln Ala Leu Thr Asn Ala Val Glu Ile Leu Gly
        115                 120                 125

Gly Lys Gln Lys Gln Glu Glu Lys Lys Gly Asp Val Gln
    130                 135                 140
```

<210> SEQ ID NO 34
<211> LENGTH: 141
<212> TYPE: PRT
<213> ORGANISM: Bacillus anthracis

<400> SEQUENCE: 34

```
Met Asp Arg Ile Asp Val Leu Leu Lys Ala Phe Ile Ala Ala Phe Gly
1               5                   10                  15

Gly Phe Cys Gly Tyr Phe Leu Gly Gly Trp Asp Ala Thr Leu Lys Ile
            20                  25                  30

Leu Val Thr Met Val Val Ile Asp Tyr Leu Thr Gly Met Ile Ala Ala
        35                  40                  45

Gly Tyr Asn Gly Glu Leu Lys Ser Lys Val Gly Phe Lys Gly Ile Ala
    50                  55                  60

Lys Lys Val Val Leu Phe Leu Leu Val Gly Ala Ala Ala Gln Leu Asp
65                  70                  75                  80

Ser Ala Leu Gly Ser Asn Ser Ala Ile Arg Glu Ala Thr Ile Phe Phe
                85                  90                  95

Phe Met Gly Asn Glu Leu Leu Ser Leu Leu Glu Asn Ala Gly Arg Met
            100                 105                 110

Gly Ile Pro Leu Pro Gln Ala Leu Thr Asn Ala Val Glu Ile Leu Gly
        115                 120                 125

Gly Lys Gln Lys Gln Glu Glu Lys Lys Gly Asp Val Gln
    130                 135                 140
```

<210> SEQ ID NO 35
<211> LENGTH: 233
<212> TYPE: PRT
<213> ORGANISM: Bacillus anthracis

<400> SEQUENCE: 35

-continued

```
Met Glu Ile Gln Lys Lys Leu Val Asp Pro Ser Lys Tyr Gly Thr Lys
1               5                   10                  15

Cys Pro Tyr Thr Met Lys Pro Lys Tyr Ile Thr Val His Asn Thr Tyr
            20                  25                  30

Asn Asp Ala Pro Ala Glu Asn Glu Val Ser Tyr Met Ile Ser Asn Asn
        35                  40                  45

Asn Glu Val Ser Phe His Ile Ala Val Asp Asp Lys Lys Ala Ile Gln
    50                  55                  60

Gly Ile Pro Leu Glu Arg Asn Ala Trp Ala Cys Gly Asp Gly Asn Gly
65                  70                  75                  80

Ser Gly Asn Arg Gln Ser Ile Ser Val Glu Ile Cys Tyr Ser Lys Ser
                85                  90                  95

Gly Gly Asp Arg Tyr Tyr Lys Ala Glu Asp Asn Ala Val Asp Val Val
            100                 105                 110

Arg Gln Leu Met Ser Met Tyr Asn Ile Pro Ile Glu Asn Val Arg Thr
        115                 120                 125

His Gln Ser Trp Ser Gly Lys Tyr Cys Pro His Arg Met Leu Ala Glu
    130                 135                 140

Gly Arg Trp Gly Ala Phe Ile Gln Lys Val Lys Asn Gly Asn Val Ala
145                 150                 155                 160

Thr Thr Ser Pro Thr Lys Gln Asn Ile Ile Gln Ser Gly Ala Phe Ser
                165                 170                 175

Pro Tyr Glu Thr Pro Asp Val Met Gly Ala Leu Thr Ser Leu Lys Met
            180                 185                 190

Thr Ala Asp Phe Ile Leu Gln Ser Asp Gly Leu Thr Tyr Phe Ile Ser
        195                 200                 205

Lys Pro Thr Ser Asp Ala Gln Leu Lys Ala Met Lys Glu Tyr Leu Asp
    210                 215                 220

Arg Lys Gly Trp Trp Tyr Glu Val Lys
225                 230
```

```
<210> SEQ ID NO 36
<211> LENGTH: 233
<212> TYPE: PRT
<213> ORGANISM: Bacillus anthracis

<400> SEQUENCE: 36

Met Glu Ile Gln Lys Lys Leu Val Asp Pro Ser Lys Tyr Gly Thr Lys
1               5                   10                  15

Cys Pro Tyr Thr Met Lys Pro Lys Tyr Ile Thr Val His Asn Thr Tyr
            20                  25                  30

Asn Asp Ala Pro Ala Glu Asn Glu Val Ser Tyr Met Ile Ser Asn Asn
        35                  40                  45

Asn Glu Val Ser Phe His Ile Ala Val Asp Asp Lys Lys Ala Ile Gln
    50                  55                  60

Gly Ile Pro Leu Glu Arg Asn Ala Trp Ala Cys Gly Asp Gly Asn Gly
65                  70                  75                  80

Ser Gly Asn Arg Gln Ser Ile Ser Val Glu Ile Cys Tyr Ser Lys Ser
                85                  90                  95

Gly Gly Asp Arg Tyr Tyr Lys Ala Glu Asp Asn Ala Val Asp Val Val
            100                 105                 110

Arg Gln Leu Met Ser Met Tyr Asn Ile Pro Ile Glu Asn Val Arg Thr
        115                 120                 125

His Gln Ser Trp Ser Gly Lys Tyr Cys Pro His Arg Met Leu Ala Glu
    130                 135                 140
```

-continued

```
Gly Arg Trp Gly Ala Phe Ile Gln Lys Val Lys Asn Gly Asn Val Ala
145                 150                 155                 160

Thr Thr Ser Pro Thr Lys Gln Asn Ile Ile Gln Ser Gly Ala Phe Ser
                165                 170                 175

Pro Tyr Glu Thr Pro Asp Val Met Gly Ala Leu Thr Ser Leu Lys Met
            180                 185                 190

Thr Ala Asp Phe Ile Leu Gln Ser Asp Gly Leu Thr Tyr Phe Ile Ser
        195                 200                 205

Lys Pro Thr Ser Asp Ala Gln Leu Lys Ala Met Lys Glu Tyr Leu Asp
    210                 215                 220

Arg Lys Gly Trp Trp Tyr Glu Val Lys
225                 230


<210> SEQ ID NO 37
<211> LENGTH: 165
<212> TYPE: PRT
<213> ORGANISM: Bacillus anthracis

<400> SEQUENCE: 37

Met Lys Met Tyr Lys Lys Leu Ile Ser Ile Cys Ile Gly Ser Thr Leu
1               5                   10                  15

Leu Leu Gly Leu Thr Ala Cys Asp Ser Ser Lys Gln Ser Glu Ser Ser
            20                  25                  30

Glu Lys Thr Asn Val Lys Ser Gln Pro Glu Thr Lys Lys Asp Leu Thr
        35                  40                  45

Ser Gln Asp Glu Leu Asn Lys Lys Ile Lys Gln Asp Ala Glu Glu Val
    50                  55                  60

Ser Phe Val Lys Ala Asn Gly Asp Gln Tyr Glu Lys Gly Lys Arg Leu
65                  70                  75                  80

Lys Ala Thr Gly Thr Val Asp Leu Leu Leu Lys Ser Ser Ala Leu Pro
                85                  90                  95

Ser Phe Val Ile Ser Thr Asn Glu Asn Asp Gly Lys Gly Met Tyr Thr
            100                 105                 110

Ile Gln Ile Val Gln Ser Gly Val Gln Thr Asn Glu Asn Glu Ile Thr
        115                 120                 125

Leu Lys Asn Gly Leu Lys Ile Ser Lys Gly Ser Ile Val Thr Ile Tyr
    130                 135                 140

Gly Ala Tyr Asp Glu Lys Asp Lys Thr Gly Met Pro Lys Ile Ser Ala
145                 150                 155                 160

Thr Val Ile Glu Gln
                165


<210> SEQ ID NO 38
<211> LENGTH: 165
<212> TYPE: PRT
<213> ORGANISM: Bacillus anthracis

<400> SEQUENCE: 38

Met Lys Met Tyr Lys Lys Leu Ile Ser Ile Cys Ile Gly Ser Thr Leu
1               5                   10                  15

Leu Leu Gly Leu Thr Ala Cys Asp Ser Ser Lys Gln Ser Glu Ser Ser
            20                  25                  30

Glu Lys Thr Asn Val Lys Ser Gln Pro Glu Thr Lys Lys Asp Leu Thr
        35                  40                  45

Ser Gln Asp Glu Leu Asn Lys Lys Ile Lys Gln Asp Ala Glu Glu Val
    50                  55                  60
```

-continued

Ser Phe Val Lys Ala Asn Gly Asp Gln Tyr Glu Lys Gly Lys Arg Leu
65 70 75 80

Lys Ala Thr Gly Thr Val Asp Leu Leu Leu Lys Ser Ser Ala Leu Pro
85 90 95

Ser Phe Val Ile Ser Thr Asn Glu Asn Asp Gly Lys Gly Met Tyr Thr
100 105 110

Ile Gln Ile Val Gln Ser Gly Val Gln Thr Asn Glu Asn Glu Ile Thr
115 120 125

Leu Lys Asn Gly Leu Lys Ile Ser Lys Gly Ser Ile Val Thr Ile Tyr
130 135 140

Gly Ala Tyr Asp Glu Lys Asp Lys Thr Gly Met Pro Lys Ile Ser Ala
145 150 155 160

Thr Val Ile Glu Gln
165

<210> SEQ ID NO 39
<211> LENGTH: 70
<212> TYPE: PRT
<213> ORGANISM: Bacillus anthracis

<400> SEQUENCE: 39

Val Arg Leu Lys Cys Lys Leu Arg Val Ile Phe Ala Glu Arg Glu Ile
1 5 10 15

Arg Gln Lys Glu Phe Ser Lys Leu Ile Gly Ile Ser Gln Thr Thr Met
20 25 30

Ser Ser Leu Val Asn Asn Thr Thr Leu Pro Thr Phe Leu Thr Ala Tyr
35 40 45

Lys Ile Ala Lys Glu Leu Lys Leu His Met Glu Glu Ile Trp Ile Glu
50 55 60

Glu Glu Asn Glu Asn Val
65 70

<210> SEQ ID NO 40
<211> LENGTH: 70
<212> TYPE: PRT
<213> ORGANISM: Bacillus anthracis

<400> SEQUENCE: 40

Val Arg Leu Lys Cys Lys Leu Arg Val Ile Phe Ala Glu Arg Glu Ile
1 5 10 15

Arg Gln Lys Glu Phe Ser Lys Leu Ile Gly Ile Ser Gln Thr Thr Met
20 25 30

Ser Ser Leu Val Asn Asn Thr Thr Leu Pro Thr Phe Leu Thr Ala Tyr
35 40 45

Lys Ile Ala Lys Glu Leu Lys Leu His Met Glu Glu Ile Trp Ile Glu
50 55 60

Glu Glu Asn Glu Asn Val
65 70

<210> SEQ ID NO 41
<211> LENGTH: 102
<212> TYPE: PRT
<213> ORGANISM: Bacillus anthracis

<400> SEQUENCE: 41

Met Arg Trp Gln Tyr Asn His Leu Asn Thr Thr Pro Tyr Leu His Pro
1 5 10 15

-continued

```
Ser Lys Glu Leu Cys Ser Met Tyr Asn Gly Ser Arg Ser Arg Ala Glu
            20                  25                  30

Thr Glu Ser Ile Leu Asn His Met Lys Asn His Glu Val Tyr Asp Arg
        35                  40                  45

Lys Glu Tyr Lys Gly Tyr Phe Ser Leu Ser Gln Val Leu Glu Glu Asp
    50                  55                  60

Leu Tyr Gly Glu Glu Glu Asp Val Leu Asn Trp Glu Ile Leu Met Asp
65                  70                  75                  80

Cys Tyr Asp Val Val Leu Thr Arg Lys Gly Ile Ala Phe Arg Glu Lys
                85                  90                  95

Glu Glu Glu Glu Gln Ala
            100


<210> SEQ ID NO 42
<211> LENGTH: 102
<212> TYPE: PRT
<213> ORGANISM: Bacillus anthracis

<400> SEQUENCE: 42

Met Arg Trp Gln Tyr Asn His Leu Asn Thr Thr Pro Tyr Leu His Pro
1               5                   10                  15

Ser Lys Glu Leu Cys Ser Met Tyr Asn Gly Ser Arg Ser Arg Ala Glu
            20                  25                  30

Thr Glu Ser Ile Leu Asn His Met Lys Asn His Glu Val Tyr Asp Arg
        35                  40                  45

Lys Glu Tyr Lys Gly Tyr Phe Ser Leu Ser Gln Val Leu Glu Glu Asp
    50                  55                  60

Leu Tyr Gly Glu Glu Glu Asp Val Leu Asn Trp Glu Ile Leu Met Asp
65                  70                  75                  80

Cys Tyr Asp Val Val Leu Thr Arg Lys Gly Ile Ala Phe Arg Glu Lys
                85                  90                  95

Glu Glu Glu Glu Gln Ala
            100


<210> SEQ ID NO 43
<211> LENGTH: 60
<212> TYPE: PRT
<213> ORGANISM: Bacillus anthracis

<400> SEQUENCE: 43

Met Thr Leu Ala Gly Glu Ala Ile Ile Ile Trp Thr Ala Thr Gly Leu
1               5                   10                  15

Ser Val Val Ala Met Lys Ala Ala Glu Lys Met Gly Lys Ser Val Pro
            20                  25                  30

His Trp Leu Pro Arg Val Thr Leu Tyr Thr Thr Leu Thr Gly Ser Phe
        35                  40                  45

Leu Tyr Leu Leu Arg Tyr Val Leu Val Leu Phe Leu
    50                  55                  60


<210> SEQ ID NO 44
<211> LENGTH: 60
<212> TYPE: PRT
<213> ORGANISM: Bacillus anthracis

<400> SEQUENCE: 44

Met Thr Leu Ala Gly Glu Ala Ile Ile Ile Trp Thr Ala Thr Gly Leu
1               5                   10                  15

Ser Val Val Ala Met Lys Ala Ala Glu Lys Met Gly Lys Ser Val Pro
```

```
            20                  25                  30

His Trp Leu Pro Arg Val Thr Leu Tyr Thr Thr Leu Thr Gly Ser Phe
        35                  40                  45

Leu Tyr Leu Leu Arg Tyr Val Leu Val Leu Phe Leu
    50                  55                  60


<210> SEQ ID NO 45
<211> LENGTH: 429
<212> TYPE: PRT
<213> ORGANISM: Bacillus anthracis

<400> SEQUENCE: 45

Met Trp Lys Leu Phe Ile Pro Tyr Val Ile Arg Ser Leu Ala Cys Met
1               5                   10                  15

His Val Phe Leu Glu Thr Gly Ile Tyr Thr Leu Tyr Lys Arg Asp Ile
            20                  25                  30

Arg Ser Asp Phe Met Leu Glu Leu Leu Ser Val Pro Phe Ala Gly Leu
        35                  40                  45

Ile Phe Ala Ile Val Gly Glu Arg Leu Lys Gly Arg Glu Ser Asp Arg
    50                  55                  60

Lys Lys Ile Gln Val Phe Phe Glu Val Ser Gly Ile Ala Ile Arg Arg
65                  70                  75                  80

Glu Asp Lys Leu Gln Tyr Pro Val Phe Leu Glu Gln Lys Glu Asp Asp
                85                  90                  95

Arg Ser Thr Thr Tyr Ile Tyr Arg Leu Pro Val Gly Met Pro Ser Lys
            100                 105                 110

Ile Ile Gln Lys Val Glu Asp Val Val Ser Glu Gly Leu Ser Lys Pro
        115                 120                 125

Val Arg Ile Asp Tyr Asp Asn Tyr Lys Leu Asn Ile Arg Val Phe His
    130                 135                 140

Arg Asp Ile Pro Lys Lys Trp Ser Trp Ser Lys Gly Leu Val Ala Glu
145                 150                 155                 160

Gly Ser Trp Cys Val Pro Met Gly Gln Ser Leu Glu Lys Leu Ile Tyr
                165                 170                 175

His Asp Phe Asp Lys Thr Pro His Met Thr Leu Gly Gly Leu Thr Arg
            180                 185                 190

Met Gly Lys Thr Val Phe Leu Lys Asn Val Val Thr Ser Leu Thr Leu
        195                 200                 205

Ala Gln Pro Glu His Ile Asn Leu Tyr Ile Ile Asp Leu Lys Gly Gly
    210                 215                 220

Leu Glu Phe Gly Pro Tyr Lys Asn Leu Lys Gln Val Val Ser Ile Ala
225                 230                 235                 240

Glu Lys Pro Ala Glu Ala Phe Met Ile Leu Thr Asn Ile Leu Lys Lys
                245                 250                 255

Met Glu Glu Lys Met Glu Tyr Met Lys Cys Arg His Tyr Thr Asn Val
            260                 265                 270

Val Glu Thr Asn Ile Lys Glu Arg Tyr Phe Ile Ile Val Asp Glu Gly
        275                 280                 285

Ala Glu Leu Cys Pro Asp Lys Ser Met Lys Lys Glu Gln Gln Arg Leu
    290                 295                 300

Leu Gly Ala Cys Gln Gln Met Leu Ser His Ile Ala Arg Ile Gly Gly
305                 310                 315                 320

Ala Leu Gly Phe Arg Leu Ile Phe Cys Thr Gln Tyr Pro Thr Gly Asp
                325                 330                 335
```

-continued

```
Thr Leu Pro Arg Gln Val Lys Gln Asn Ser Asp Ala Lys Leu Gly Phe
            340                 345                 350

Arg Leu Pro Thr Gln Thr Ala Ser Ser Val Val Ile Asp Glu Ala Gly
        355                 360                 365

Leu Glu Thr Ile Lys Ser Ile Pro Gly Arg Ala Ile Phe Lys Thr Asp
    370                 375                 380

Arg Leu Thr Glu Ile Gln Val Pro Tyr Ile Ser Asn Glu Met Met Trp
385                 390                 395                 400

Glu His Leu Lys Gly Tyr Glu Val Glu Lys His Glu Asp Ala Asn Ala
                405                 410                 415

Tyr Ala Asn Gln Pro Ser Asn Gly Asp Thr Cys Asp Asp
            420                 425


<210> SEQ ID NO 46
<211> LENGTH: 429
<212> TYPE: PRT
<213> ORGANISM: Bacillus anthracis

<400> SEQUENCE: 46

Met Trp Lys Leu Phe Ile Pro Tyr Val Ile Arg Ser Leu Ala Cys Met
1               5                   10                  15

His Val Phe Leu Glu Thr Gly Ile Tyr Thr Leu Tyr Lys Arg Asp Ile
            20                  25                  30

Arg Ser Asp Phe Met Leu Glu Leu Leu Ser Val Pro Phe Ala Gly Leu
        35                  40                  45

Ile Phe Ala Ile Val Gly Glu Arg Leu Lys Gly Arg Glu Ser Asp Arg
    50                  55                  60

Lys Lys Ile Gln Val Phe Phe Glu Val Ser Gly Ile Ala Ile Arg Arg
65                  70                  75                  80

Glu Asp Lys Leu Gln Tyr Pro Val Phe Leu Glu Gln Lys Glu Asp Asp
                85                  90                  95

Arg Ser Thr Thr Tyr Ile Tyr Arg Leu Pro Val Gly Met Pro Ser Lys
            100                 105                 110

Ile Ile Gln Lys Val Glu Asp Val Val Ser Glu Gly Leu Ser Lys Pro
        115                 120                 125

Val Arg Ile Asp Tyr Asp Asn Tyr Lys Leu Asn Ile Arg Val Phe His
    130                 135                 140

Arg Asp Ile Pro Lys Lys Trp Ser Trp Ser Lys Gly Leu Val Ala Glu
145                 150                 155                 160

Gly Ser Trp Cys Val Pro Met Gly Gln Ser Leu Glu Lys Leu Ile Tyr
                165                 170                 175

His Asp Phe Asp Lys Thr Pro His Met Thr Leu Gly Gly Leu Thr Arg
            180                 185                 190

Met Gly Lys Thr Val Phe Leu Lys Asn Val Val Thr Ser Leu Thr Leu
        195                 200                 205

Ala Gln Pro Glu His Ile Asn Leu Tyr Ile Ile Asp Leu Lys Gly Gly
    210                 215                 220

Leu Glu Phe Gly Pro Tyr Lys Asn Leu Lys Gln Val Val Ser Ile Ala
225                 230                 235                 240

Glu Lys Pro Ala Glu Ala Phe Met Ile Leu Thr Asn Ile Leu Lys Lys
                245                 250                 255

Met Glu Glu Lys Met Glu Tyr Met Lys Cys Arg His Tyr Thr Asn Val
            260                 265                 270

Val Glu Thr Asn Ile Lys Glu Arg Tyr Phe Ile Ile Val Asp Glu Gly
        275                 280                 285
```

-continued

```
Ala Glu Leu Cys Pro Asp Lys Ser Met Lys Lys Glu Gln Gln Arg Leu
    290                 295                 300

Leu Gly Ala Cys Gln Gln Met Leu Ser His Ile Ala Arg Ile Gly Gly
305                 310                 315                 320

Ala Leu Gly Phe Arg Leu Ile Phe Cys Thr Gln Tyr Pro Thr Gly Asp
                325                 330                 335

Thr Leu Pro Arg Gln Val Lys Gln Asn Ser Asp Ala Lys Leu Gly Phe
            340                 345                 350

Arg Leu Pro Thr Gln Thr Ala Ser Ser Val Val Ile Asp Glu Ala Gly
        355                 360                 365

Leu Glu Thr Ile Lys Ser Ile Pro Gly Arg Ala Ile Phe Lys Thr Asp
    370                 375                 380

Arg Leu Thr Glu Ile Gln Val Pro Tyr Ile Ser Asn Glu Met Met Trp
385                 390                 395                 400

Glu His Leu Lys Gly Tyr Glu Val Glu Lys His Glu Asp Ala Asn Ala
                405                 410                 415

Tyr Ala Asn Gln Pro Ser Asn Gly Asp Thr Cys Asp Asp
            420                 425


<210> SEQ ID NO 47
<211> LENGTH: 210
<212> TYPE: PRT
<213> ORGANISM: Bacillus anthracis

<400> SEQUENCE: 47

Met Arg Trp Arg Asn Met Arg Met Gln Thr His Met Gln Ile Asn Arg
1               5                   10                  15

Gln Met Ala Ile Leu Ala Thr Ile Arg Lys Leu Gln Phe Ala Thr Arg
            20                  25                  30

Arg His Leu Met Ser Ile His Glu Met Gly Gly Ile Arg Asn Ala Asn
        35                  40                  45

Arg Ile Leu Lys Asp Leu Ser Ile Tyr Thr Ser Lys Val Val Tyr Asn
    50                  55                  60

Lys Glu His Val Tyr Tyr Leu Asn Gln Ser Gly His Lys Leu Phe Gly
65                  70                  75                  80

Glu Gly Lys Val Val His His Gly Lys Val Thr His Ala Leu Leu Arg
                85                  90                  95

Asn Glu Ala Trp Leu Asn Leu Tyr Cys Pro Asp Asp Trp Gln Val Glu
            100                 105                 110

Thr Glu Ile Lys Tyr Ile Lys Asp Asn Lys Lys Lys Lys Ile Ile Pro
        115                 120                 125

Asp Val Lys Phe Arg Asp Glu Asp Arg Ile Leu His Ala Val Glu Ile
    130                 135                 140

Asp Arg Thr Gln Lys Met Ile Val Asn Asp Glu Lys Leu Lys Lys Tyr
145                 150                 155                 160

Glu Glu Leu Thr Gln Ile Tyr Lys Gln Lys His Asn Gly Lys Val Pro
                165                 170                 175

Val Ile His Phe Phe Thr Ile Thr Lys Tyr Arg Glu Lys Lys Leu Glu
            180                 185                 190

Glu Leu Ala Asn Lys Tyr Asn Val Phe Val Lys Val Tyr Val Ile Ala
        195                 200                 205

Thr Thr
    210
```

-continued

<210> SEQ ID NO 48
<211> LENGTH: 210
<212> TYPE: PRT
<213> ORGANISM: Bacillus anthracis

<400> SEQUENCE: 48

```
Met Arg Trp Arg Asn Met Arg Met Gln Thr His Met Gln Ile Asn Arg
1               5                   10                  15

Gln Met Ala Ile Leu Ala Thr Ile Arg Lys Leu Gln Phe Ala Thr Arg
            20                  25                  30

Arg His Leu Met Ser Ile His Glu Met Gly Gly Ile Arg Asn Ala Asn
        35                  40                  45

Arg Ile Leu Lys Asp Leu Ser Ile Tyr Thr Ser Lys Val Val Tyr Asn
    50                  55                  60

Lys Glu His Val Tyr Tyr Leu Asn Gln Ser Gly His Lys Leu Phe Gly
65                  70                  75                  80

Glu Gly Lys Val Val His His Gly Lys Val Thr His Ala Leu Leu Arg
                85                  90                  95

Asn Glu Ala Trp Leu Asn Leu Tyr Cys Pro Asp Asp Trp Gln Val Glu
            100                 105                 110

Thr Glu Ile Lys Tyr Ile Lys Asp Asn Lys Lys Lys Lys Ile Ile Pro
        115                 120                 125

Asp Val Lys Phe Arg Asp Glu Asp Arg Ile Leu His Ala Val Glu Ile
    130                 135                 140

Asp Arg Thr Gln Lys Met Ile Val Asn Asp Glu Lys Leu Lys Lys Tyr
145                 150                 155                 160

Glu Glu Leu Thr Gln Ile Tyr Lys Gln Lys His Asn Gly Lys Val Pro
                165                 170                 175

Val Ile His Phe Phe Thr Ile Thr Lys Tyr Arg Glu Lys Lys Leu Glu
            180                 185                 190

Glu Leu Ala Asn Lys Tyr Asn Val Phe Val Lys Val Tyr Val Ile Ala
        195                 200                 205

Thr Thr
    210
```

<210> SEQ ID NO 49
<211> LENGTH: 78
<212> TYPE: PRT
<213> ORGANISM: Bacillus anthracis

<400> SEQUENCE: 49

```
Met Lys Phe Thr Leu Gly Asn Ser Leu Asp Glu Leu Gly Ile Thr Lys
1               5                   10                  15

Asn Lys Leu Ser Thr Glu Ser Gln Val Arg Tyr Asn Thr Ile Ser Asp
            20                  25                  30

Leu Val Asn Gly Asn Ala Asn Ala Val Arg Phe Asp Ser Leu Glu Ala
        35                  40                  45

Ile Ile Asp Ala Leu Asn Ala Ile Ala Ala Glu Lys Gly Ile Asn Lys
    50                  55                  60

Ile Tyr Lys Ile Asp Asp Val Ile Gln Tyr Ile Lys Lys Ser
65                  70                  75
```

<210> SEQ ID NO 50
<211> LENGTH: 78
<212> TYPE: PRT
<213> ORGANISM: Bacillus anthracis

<400> SEQUENCE: 50

-continued

```
Met Lys Phe Thr Leu Gly Asn Ser Leu Asp Glu Leu Gly Ile Thr Lys
1               5                   10                  15

Asn Lys Leu Ser Thr Glu Ser Gln Val Arg Tyr Asn Thr Ile Ser Asp
            20                  25                  30

Leu Val Asn Gly Asn Ala Asn Ala Val Arg Phe Asp Ser Leu Glu Ala
        35                  40                  45

Ile Ile Asp Ala Leu Asn Ala Ile Ala Ala Glu Lys Gly Ile Asn Lys
    50                  55                  60

Ile Tyr Lys Ile Asp Asp Val Ile Gln Tyr Ile Lys Lys Ser
65                  70                  75


<210> SEQ ID NO 51
<211> LENGTH: 75
<212> TYPE: PRT
<213> ORGANISM: Bacillus anthracis

<400> SEQUENCE: 51

Met Ala Phe Lys Ala Ser Met Ile Ala Ser Ser Glu Ser Lys Arg Thr
1               5                   10                  15

Ala Leu Ala Leu Pro Phe Thr Lys Ser Leu Ile Val Leu Tyr Leu Thr
            20                  25                  30

Trp Asp Ser Val Asp Asn Leu Phe Leu Val Ile Pro Asn Ser Ser Lys
        35                  40                  45

Glu Phe Pro Ser Val Asn Phe Ile Leu Phe Ser Ser Ala Ala Leu Val
    50                  55                  60

Ile Leu Tyr Ser Phe Tyr Asn Ile Asn Arg Asn
65                  70                  75


<210> SEQ ID NO 52
<211> LENGTH: 78
<212> TYPE: PRT
<213> ORGANISM: Bacillus anthracis

<400> SEQUENCE: 52

Met Lys Phe Thr Leu Gly Asn Ser Leu Asp Glu Leu Gly Ile Thr Lys
1               5                   10                  15

Asn Lys Leu Ser Thr Glu Ser Gln Val Arg Tyr Asn Thr Ile Ser Asp
            20                  25                  30

Leu Val Asn Gly Asn Ala Asn Ala Val Arg Phe Asp Ser Leu Glu Ala
        35                  40                  45

Ile Ile Asp Ala Leu Asn Ala Ile Ala Ala Glu Lys Gly Ile Asn Lys
    50                  55                  60

Ile Tyr Lys Ile Asp Asp Val Ile Gln Tyr Ile Lys Lys Ser
65                  70                  75


<210> SEQ ID NO 53
<211> LENGTH: 287
<212> TYPE: PRT
<213> ORGANISM: Bacillus anthracis

<400> SEQUENCE: 53

Met Leu Ser Ser Ala Asn Tyr Thr Gln Tyr Lys Lys Leu Gln Ser Phe
1               5                   10                  15

Arg Ser Val Glu Glu Met Asn Glu Ala Ile Cys Ser Phe Leu Tyr Lys
            20                  25                  30

His Thr His Glu Leu Ser Glu Ser Ala Ile Lys Val Leu Lys Phe Leu
        35                  40                  45
```

-continued

```
Ala Arg His Ser Cys Lys Ile Pro Gly Val Ser Phe Leu Lys Val Gly
    50                  55                  60

Thr Ile Ala Glu Ala Leu Asn Ile Ser Asp Arg Thr Val Arg Arg Val
65                  70                  75                  80

Leu Lys Val Leu Glu Asp Phe Glu Val Val Thr Arg His Lys Thr Ile
                85                  90                  95

Arg Thr Glu Gly Lys Leu Arg Gly Gly Asn Gly His Asn Val Tyr Val
            100                 105                 110

Leu Leu Lys Lys Tyr Ser Val Thr Pro Asn Val Leu Pro Lys Met Ser
        115                 120                 125

Gln Arg Gln Asp Glu Glu Asn Leu Thr Glu Ser Lys Val Ser Asp Thr
    130                 135                 140

Lys Thr Asp Lys Glu Ala Lys Leu Ser Glu Ser His Pro Leu Glu Glu
145                 150                 155                 160

Leu Lys Ser Glu Leu Asn Val Lys Glu Thr Ser Ala Arg Glu Ser Lys
                165                 170                 175

Glu Ile Glu Leu Glu Asp Leu Asp Glu Thr Phe Thr Pro Glu Asn Val
            180                 185                 190

Pro Ser Gln Phe Arg Asp Val Val Ala Pro Phe Phe Lys Ser Ala Asp
        195                 200                 205

Lys Ile Tyr Lys Leu Tyr His Arg Val Leu Ile Ala Tyr Lys Arg Ser
    210                 215                 220

Lys Ile Asp Lys Pro Ile Glu Gln Val Ile Asn Gln Ala Ile Gln Ala
225                 230                 235                 240

Phe Lys Glu Thr Val Phe Ala Glu Lys Ala Asn Lys Ile Arg Ser Thr
                245                 250                 255

Phe Glu Gly Tyr Phe Tyr Arg Ile Val Glu Ser Lys Phe Val Met Glu
            260                 265                 270

Arg Arg Lys Glu Cys Arg Gly Leu Leu Phe Asp Trp Leu Asn Glu
        275                 280                 285


<210> SEQ ID NO 54
<211> LENGTH: 287
<212> TYPE: PRT
<213> ORGANISM: Bacillus anthracis

<400> SEQUENCE: 54

Met Leu Ser Ser Ala Asn Tyr Thr Gln Tyr Lys Lys Leu Gln Ser Phe
1               5                   10                  15

Arg Ser Val Glu Glu Met Asn Glu Ala Ile Cys Ser Phe Leu Tyr Lys
            20                  25                  30

His Thr His Glu Leu Ser Glu Ser Ala Ile Lys Val Leu Lys Phe Leu
        35                  40                  45

Ala Arg His Ser Cys Lys Ile Pro Gly Val Ser Phe Leu Lys Val Gly
    50                  55                  60

Thr Ile Ala Glu Ala Leu Asn Ile Ser Asp Arg Thr Val Arg Arg Val
65                  70                  75                  80

Leu Lys Val Leu Glu Asp Phe Glu Val Val Thr Arg His Lys Thr Ile
                85                  90                  95

Arg Thr Glu Gly Lys Leu Arg Gly Gly Asn Gly His Asn Val Tyr Val
            100                 105                 110

Leu Leu Lys Lys Tyr Ser Val Thr Pro Asn Val Leu Pro Lys Met Ser
        115                 120                 125

Gln Arg Gln Asp Glu Glu Asn Leu Thr Glu Ser Lys Val Ser Asp Thr
    130                 135                 140
```

-continued

```
Lys Thr Asp Lys Glu Ala Lys Leu Ser Glu Ser His Pro Leu Glu Glu
145                 150                 155                 160

Leu Lys Ser Glu Leu Asn Val Lys Glu Thr Ser Ala Arg Glu Ser Lys
                165                 170                 175

Glu Ile Glu Leu Glu Asp Leu Asp Glu Thr Phe Thr Pro Glu Asn Val
            180                 185                 190

Pro Ser Gln Phe Arg Asp Val Val Ala Pro Phe Phe Lys Ser Ala Asp
        195                 200                 205

Lys Ile Tyr Lys Leu Tyr His Arg Val Leu Ile Ala Tyr Lys Arg Ser
    210                 215                 220

Lys Ile Asp Lys Pro Ile Glu Gln Val Ile Asn Gln Ala Ile Gln Ala
225                 230                 235                 240

Phe Lys Glu Thr Val Phe Ala Glu Lys Ala Asn Lys Ile Arg Ser Thr
                245                 250                 255

Phe Glu Gly Tyr Phe Tyr Arg Ile Val Glu Ser Lys Phe Val Met Glu
            260                 265                 270

Arg Arg Lys Glu Cys Arg Gly Leu Leu Phe Asp Trp Leu Asn Glu
        275                 280                 285


<210> SEQ ID NO 55
<211> LENGTH: 481
<212> TYPE: PRT
<213> ORGANISM: Bacillus anthracis

<400> SEQUENCE: 55

Leu Lys Tyr Ala Val Tyr Val Arg Val Ser Thr Asp Arg Asp Glu Gln
1               5                   10                  15

Val Ser Ser Val Glu Asn Gln Ile Asp Ile Cys Arg Tyr Trp Leu Glu
            20                  25                  30

Lys Asn Gly Tyr Glu Trp Asp Pro Asn Ala Val Tyr Phe Asp Asp Gly
        35                  40                  45

Ile Ser Gly Thr Ala Trp Leu Glu Arg His Ala Met Gln Leu Ile Leu
    50                  55                  60

Glu Lys Ala Arg Arg Asn Glu Leu Asp Thr Val Val Phe Lys Ser Ile
65                  70                  75                  80

His Arg Leu Ala Arg Asp Leu Arg Asp Ala Leu Glu Ile Lys Glu Ile
                85                  90                  95

Leu Ile Gly His Gly Ile Arg Leu Val Thr Ile Glu Glu Asn Tyr Asp
            100                 105                 110

Ser Leu Tyr Glu Gly Gly Asn Asp Ile Lys Phe Glu Met Phe Ala Met
        115                 120                 125

Phe Ala Ala Gln Leu Pro Lys Thr Ile Ser Val Ser Val Ser Ala Ala
    130                 135                 140

Met Gln Ala Lys Ala Arg Arg Gly Glu Phe Ile Gly Lys Pro Gly Leu
145                 150                 155                 160

Gly Tyr Asp Val Ile Asp Lys Lys Leu Val Ile Asn Glu Lys Glu Ala
                165                 170                 175

Glu Ile Val Arg Glu Ile Phe Asp Leu Ser Tyr Lys Gly Tyr Gly Phe
            180                 185                 190

Lys Lys Ile Ala Asn Ile Leu Asn Asp Lys Gly Thr Tyr Thr Lys Phe
        195                 200                 205

Gly Gln Leu Trp Ser His Thr Thr Val Gly Lys Ile Leu Lys Asn Gln
    210                 215                 220

Thr Tyr Lys Gly Asn Leu Val Leu Asn Ser Tyr Lys Thr Val Lys Val
```

-continued

```
225                 230                 235                 240

Asp Gly Lys Lys Lys Arg Val Tyr Thr Pro Lys Glu Arg Leu Thr Ile
                245                 250                 255

Ile Glu Asp His Tyr Pro Thr Ile Val Ser Lys Glu Leu Trp Asn Ala
            260                 265                 270

Val Asn Ser Asp Arg Ala Ser Lys Lys Lys Thr Lys Gln Asp Thr Arg
        275                 280                 285

Asn Glu Phe Arg Gly Met Met Phe Cys Lys His Cys Gly Glu Pro Ile
    290                 295                 300

Thr Ala Lys Tyr Ser Gly Arg Tyr Ala Lys Gly Ser Lys Lys Glu Trp
305                 310                 315                 320

Val Tyr Met Lys Cys Ser Asn Tyr Ile Arg Phe Asn Arg Cys Val Asn
                325                 330                 335

Phe Asp Pro Ala His Tyr Asp Asp Ile Arg Glu Ala Ile Ile Tyr Gly
            340                 345                 350

Leu Lys Gln Gln Glu Lys Glu Leu Glu Ile His Phe Asn Pro Lys Met
        355                 360                 365

His Gln Lys Arg Asn Asp Lys Ser Thr Glu Ile Lys Lys Gln Ile Lys
    370                 375                 380

Leu Leu Lys Val Lys Lys Glu Lys Leu Ile Asp Leu Tyr Val Glu Gly
385                 390                 395                 400

Leu Ile Asp Lys Glu Met Phe Ser Lys Arg Asp Leu Asn Phe Glu Asn
                405                 410                 415

Glu Ile Lys Glu Gln Glu Leu Ala Leu Leu Lys Leu Thr Asp Gln Asn
            420                 425                 430

Lys Arg Asn Lys Glu Glu Lys Lys Ile Lys Glu Ala Phe Ser Met Leu
        435                 440                 445

Asp Glu Glu Lys Asp Met His Glu Val Phe Lys Thr Leu Ile Lys Lys
    450                 455                 460

Ile Thr Leu Ser Lys Asp Lys Tyr Ile Asp Ile Glu Tyr Thr Phe Ser
465                 470                 475                 480

Leu


<210> SEQ ID NO 56
<211> LENGTH: 481
<212> TYPE: PRT
<213> ORGANISM: Bacillus anthracis

<400> SEQUENCE: 56

Leu Lys Tyr Ala Val Tyr Val Arg Val Ser Thr Asp Arg Asp Glu Gln
1               5                   10                  15

Val Ser Ser Val Glu Asn Gln Ile Asp Ile Cys Arg Tyr Trp Leu Glu
            20                  25                  30

Lys Asn Gly Tyr Glu Trp Asp Pro Asn Ala Val Tyr Phe Asp Asp Gly
        35                  40                  45

Ile Ser Gly Thr Ala Trp Leu Glu Arg His Ala Met Gln Leu Ile Leu
    50                  55                  60

Glu Lys Ala Arg Arg Asn Glu Leu Asp Thr Val Val Phe Lys Ser Ile
65                  70                  75                  80

His Arg Leu Ala Arg Asp Leu Arg Asp Ala Leu Glu Ile Lys Glu Ile
                85                  90                  95

Leu Ile Gly His Gly Ile Arg Leu Val Thr Ile Glu Glu Asn Tyr Asp
            100                 105                 110

Ser Leu Tyr Glu Gly Gly Asn Asp Ile Lys Phe Glu Met Phe Ala Met
```

-continued

```
        115                 120                 125

Phe Ala Ala Gln Leu Pro Lys Thr Ile Ser Val Ser Val Ser Ala Ala
    130                 135                 140

Met Gln Ala Lys Ala Arg Arg Gly Glu Phe Ile Gly Lys Pro Gly Leu
145                 150                 155                 160

Gly Tyr Asp Val Ile Asp Lys Lys Leu Val Ile Asn Glu Lys Glu Ala
                165                 170                 175

Glu Ile Val Arg Glu Ile Phe Asp Leu Ser Tyr Lys Gly Tyr Gly Phe
            180                 185                 190

Lys Lys Ile Ala Asn Ile Leu Asn Asp Lys Gly Thr Tyr Thr Lys Phe
        195                 200                 205

Gly Gln Leu Trp Ser His Thr Thr Val Gly Lys Ile Leu Lys Asn Gln
    210                 215                 220

Thr Tyr Lys Gly Asn Leu Val Leu Asn Ser Tyr Lys Thr Val Lys Val
225                 230                 235                 240

Asp Gly Lys Lys Lys Arg Val Tyr Thr Pro Lys Glu Arg Leu Thr Ile
                245                 250                 255

Ile Glu Asp His Tyr Pro Thr Ile Val Ser Lys Glu Leu Trp Asn Ala
            260                 265                 270

Val Asn Ser Asp Arg Ala Ser Lys Lys Lys Thr Lys Gln Asp Thr Arg
        275                 280                 285

Asn Glu Phe Arg Gly Met Met Phe Cys Lys His Cys Gly Glu Pro Ile
    290                 295                 300

Thr Ala Lys Tyr Ser Gly Arg Tyr Ala Lys Gly Ser Lys Lys Glu Trp
305                 310                 315                 320

Val Tyr Met Lys Cys Ser Asn Tyr Ile Arg Phe Asn Arg Cys Val Asn
                325                 330                 335

Phe Asp Pro Ala His Tyr Asp Asp Ile Arg Glu Ala Ile Ile Tyr Gly
            340                 345                 350

Leu Lys Gln Gln Glu Lys Glu Leu Glu Ile His Phe Asn Pro Lys Met
        355                 360                 365

His Gln Lys Arg Asn Asp Lys Ser Thr Glu Ile Lys Lys Gln Ile Lys
    370                 375                 380

Leu Leu Lys Val Lys Lys Glu Lys Leu Ile Asp Leu Tyr Val Glu Gly
385                 390                 395                 400

Leu Ile Asp Lys Glu Met Phe Ser Lys Arg Asp Leu Asn Phe Glu Asn
                405                 410                 415

Glu Ile Lys Glu Gln Glu Leu Ala Leu Leu Lys Leu Thr Asp Gln Asn
            420                 425                 430

Lys Arg Asn Lys Glu Glu Lys Lys Ile Lys Glu Ala Phe Ser Met Leu
        435                 440                 445

Asp Glu Glu Lys Asp Met His Glu Val Phe Lys Thr Leu Ile Lys Lys
    450                 455                 460

Ile Thr Leu Ser Lys Asp Lys Tyr Ile Asp Ile Glu Tyr Thr Phe Ser
465                 470                 475                 480

Leu


<210> SEQ ID NO 57
<211> LENGTH: 42
<212> TYPE: PRT
<213> ORGANISM: Bacillus anthracis

<400> SEQUENCE: 57

Val Ile Ile Val Glu Phe Lys Asp Arg Leu Arg Gln Leu Arg Arg Glu
```

-continued

```
1               5                   10                  15

Arg Asn Leu Thr Gln His Asp Leu Gly Gln Ala Ile Gly Val Thr Ala
            20                  25                  30

Gly Ser Ile Thr Val Thr Asn Asn Gln Leu
        35                  40


<210> SEQ ID NO 58
<211> LENGTH: 444
<212> TYPE: PRT
<213> ORGANISM: Bacillus anthracis

<400> SEQUENCE: 58

Met Arg Ile Ala Leu Tyr Arg Thr His Ala Leu Ile Asn Val Ile Lys
1               5                   10                  15

Tyr Ser Val Asn Ile Met Glu Lys Val Leu Leu Ile Glu Met Lys Gly
            20                  25                  30

Val Ser Tyr Leu Lys Phe His Glu Lys Ile Met Gly Met Ile Glu Asp
        35                  40                  45

Arg Asp Asp Leu Thr Ala Thr Ser Val Ala Cys Lys Ile Gly Val Ser
    50                  55                  60

Lys Gln Tyr Met Ser Lys Phe Lys Arg Gln Gly Thr Ile Gly Phe Ser
65                  70                  75                  80

Gln Leu Leu Lys Leu Ala Pro Ile Leu Ser Val Glu Gly Lys Lys Ala
                85                  90                  95

Lys Gln Thr Met Ser Asp Trp Cys Leu Glu Leu Asp Thr Thr Glu Ser
            100                 105                 110

Ile Lys Gln Ser Phe Glu Tyr Ala Cys Leu Thr Arg Asn Thr Ile Leu
        115                 120                 125

Leu Lys Gln Leu Ile Gln Lys His Ser Lys Glu Thr Gly Thr Ile Arg
    130                 135                 140

Glu Tyr Val Glu Val Tyr Thr Ile Leu Phe Lys Tyr Ile Lys Asn Ile
145                 150                 155                 160

Ile Lys Gly Ser Glu Ile Thr Lys Glu Leu Lys Lys Ile Gly Ala Ile
                165                 170                 175

Lys Asp Lys Val Leu Glu Ile Leu Thr Lys Ile Met Glu Cys Tyr Glu
            180                 185                 190

Tyr Tyr His Leu Lys Lys Phe Asn Leu Met Leu Glu Thr Ala Glu Thr
        195                 200                 205

Ile Asp Ser Leu Val Arg Glu Ile Glu Gly Glu Arg Lys Ser Phe Ile
    210                 215                 220

Lys Glu Cys Tyr Asn Tyr Arg Ile Ala Glu Leu Phe Ala Pro Ile Phe
225                 230                 235                 240

Leu Gln Lys Asn Asn Val Asp Leu Ala Arg Lys Tyr Ala His Phe Leu
                245                 250                 255

Ile His Ala Asn Val Cys Thr Lys Thr Val Ser Asp Ala Tyr Tyr Ile
            260                 265                 270

Leu Gly Met Ser Asn Val Leu Glu Ser Lys Glu Gln Cys Leu Phe Asn
        275                 280                 285

Leu Lys Lys Ser Tyr Leu Leu Ser Lys Glu Ile Arg Asp Ala Asp Ile
    290                 295                 300

Glu Gln Glu Ala Arg Tyr Asn Leu Asp Val Ala Lys Ile Tyr Phe Gly
305                 310                 315                 320

Val Lys Leu Asp Glu Asp Ala Asp Ser Arg Leu Leu Leu Tyr Gln Lys
                325                 330                 335
```

-continued

```
Asn Pro Thr Cys Glu Leu Ser Ile Ile Ala Leu Gln Asp Ile Ile Arg
            340                 345                 350

Asp Arg Gly Asp Lys Asp Phe Leu Asn Tyr Phe Ile Ala Cys Ser Ser
        355                 360                 365

Asp Glu Ile Glu Cys Leu Tyr Asp Leu Phe Tyr Gln Tyr Phe Tyr Gln
    370                 375                 380

Ala Asn Tyr Leu Phe Ser Ala Ile Val Ala Lys Glu Leu Cys Asn Arg
385                 390                 395                 400

Gly Asp Lys Ser Leu Leu Thr Gln Ser Met Val Asn Leu Gly Asn Glu
                405                 410                 415

Lys Gln Lys Gly Val Val Asp Ile Glu Glu Ile Ser Ile Ser Ser Leu
            420                 425                 430

Tyr Ile Ile Asn Gly Ser Asn Ser Gly Ile Val Val
        435                 440


<210> SEQ ID NO 59
<211> LENGTH: 75
<212> TYPE: PRT
<213> ORGANISM: Bacillus anthracis

<400> SEQUENCE: 59

Met Lys Val Ile Lys Asp Glu Thr Lys Leu Lys Ala Ala Phe Lys Lys
1               5                   10                  15

Ser Gly Tyr Lys Tyr Gln Glu Leu Ala Asp Glu Leu Glu Ile Ser Cys
            20                  25                  30

Ser Tyr Cys Tyr Lys Leu Ile Asn Asn His Asn Tyr Lys Lys Lys Ile
        35                  40                  45

Ser Tyr Asn Leu Ala Ser Arg Met Ala His Val Leu Asn Ala Ser Val
    50                  55                  60

Val Asp Leu Phe Glu Glu Gln Val Asp Phe Phe
65                  70                  75


<210> SEQ ID NO 60
<211> LENGTH: 118
<212> TYPE: PRT
<213> ORGANISM: Bacillus anthracis

<400> SEQUENCE: 60

Val Ile Ile Val Glu Phe Lys Asp Arg Leu Arg Gln Leu Arg Arg Glu
1               5                   10                  15

Arg Asn Leu Thr Gln His Asp Leu Gly Gln Ala Ile Gly Val Thr Ala
            20                  25                  30

Gly Ser Val Ser Lys Phe Glu Thr Gly Phe Lys Pro Ala Ser Arg Glu
        35                  40                  45

Thr Val Glu Arg Ala Ala Asp Phe Leu Gly Val Pro Val Asp Tyr Leu
    50                  55                  60

Leu Gly Arg Ser Asp Ser Arg Glu Leu Asp Ala Asp Met Asn Gln Lys
65                  70                  75                  80

Tyr Leu His Ile Lys Asn Arg Leu Glu Gln Leu Pro Glu Glu His Gln
                85                  90                  95

Glu Ile Val Leu Gln Asn Met Leu Thr Met Met Glu Ser Leu Glu Lys
            100                 105                 110

Leu Lys Ser Thr Ser Lys
        115


<210> SEQ ID NO 61
<211> LENGTH: 61
```

-continued

<212> TYPE: PRT
<213> ORGANISM: Bacillus anthracis

<400> SEQUENCE: 61

```
Met Arg Glu His Arg Gly Glu Arg Ala Met Ser Glu Ile Tyr Tyr Lys
1               5                   10                  15

Gly Phe Ile Ile Lys Glu Thr Tyr Gly Glu Arg Asn Ile Glu Glu Val
            20                  25                  30

Phe Lys Glu Ala Tyr Glu Ser Phe Tyr Gly Val Glu Val Lys Val Val
        35                  40                  45

Lys Lys Glu Leu Gly Thr Lys Arg Asn Ser Ala Ala Ser
    50                  55                  60
```

<210> SEQ ID NO 62
<211> LENGTH: 75
<212> TYPE: PRT
<213> ORGANISM: Bacillus anthracis

<400> SEQUENCE: 62

```
Met Lys Val Ile Lys Asp Glu Thr Lys Leu Lys Ala Ala Phe Lys Lys
1               5                   10                  15

Ser Gly Tyr Lys Tyr Gln Glu Leu Ala Asp Glu Leu Glu Ile Ser Cys
            20                  25                  30

Ser Tyr Cys Tyr Lys Leu Ile Asn Asn His Asn Tyr Lys Lys Lys Ile
        35                  40                  45

Ser Tyr Asn Leu Ala Ser Arg Met Ala His Val Leu Asn Ala Ser Val
    50                  55                  60

Val Asp Leu Phe Glu Glu Gln Val Asp Phe Phe
65                  70                  75
```

<210> SEQ ID NO 63
<211> LENGTH: 271
<212> TYPE: PRT
<213> ORGANISM: Bacillus anthracis

<400> SEQUENCE: 63

```
Met Asp Gln Leu Thr Val Ala Ser Glu Leu Arg Leu Leu Gly Arg Arg
1               5                   10                  15

Lys Val Ala Gly Tyr Glu Phe Thr Gly Ile Glu Gly Gly Phe Gly Glu
            20                  25                  30

Gly Lys Lys Ala Met Leu Val Leu Asp Ile Ala Thr Ile His Asn Gln
        35                  40                  45

Pro Leu Lys Glu Ile Asn Arg Arg Ile Asn Asp Asn Arg Ile Arg Phe
    50                  55                  60

Lys Asp Gly Val Asp Ile Val Asp Leu Lys Ser Gly Gly Phe Asn Pro
65                  70                  75                  80

Pro Gln Leu Leu Asn Leu Gly Phe Ser Asn Met Gln Ile Ala Lys Ser
                85                  90                  95

Asn Asn Ile Tyr Leu Leu Ser Glu Arg Gly Tyr Ala Lys Leu Leu Lys
            100                 105                 110

Ile Leu Glu Asp Asp Lys Ala Trp Glu Leu Tyr Asp Ile Leu Val Asp
        115                 120                 125

Glu Tyr Phe Asn Met Arg Glu Lys Asn Gln Val Ala Thr Asp Pro Met
    130                 135                 140

Ser Ile Leu Lys Leu Thr Phe Glu Ala Leu Glu Gly Gln Gln Gln Ala
145                 150                 155                 160

Ile Glu Glu Ile Lys Ser Asp Val Gln Asp Leu Arg Glu Asn Thr Pro
```

-continued

```
                165                 170                 175

Leu Phe Ala Ile Glu Cys Asp Glu Ile Ser Thr Ala Val Lys Arg Gln
            180                 185                 190

Gly Val Ile Leu Leu Gly Gly Lys Gln Ser Asn Ala Tyr Arg Asn Arg
        195                 200                 205

Gly Leu Arg Gly Lys Val Tyr Arg Asp Ile Tyr Asn Gln Leu Tyr Arg
    210                 215                 220

Glu Phe Gly Val Lys Ser His Lys Ala Ile Lys Arg Cys His Leu Asn
225                 230                 235                 240

Val Ala Val Lys Ile Val Glu Glu Tyr Thr Leu Pro Ile Val Leu Ser
                245                 250                 255

Glu Glu Ile Ser Phe Val Asn Ala Gln Met Asp Phe Thr Glu Met
            260                 265                 270


<210> SEQ ID NO 64
<211> LENGTH: 61
<212> TYPE: PRT
<213> ORGANISM: Bacillus anthracis

<400> SEQUENCE: 64

Met Arg Glu His Arg Gly Glu Arg Ala Met Ser Glu Ile Tyr Tyr Lys
1               5                   10                  15

Gly Phe Ile Ile Lys Glu Thr Tyr Gly Glu Arg Asn Ile Glu Glu Val
            20                  25                  30

Phe Lys Glu Ala Tyr Glu Ser Phe Tyr Gly Val Glu Val Lys Val Val
        35                  40                  45

Lys Lys Glu Leu Gly Thr Lys Arg Asn Ser Ala Ala Ser
    50                  55                  60


<210> SEQ ID NO 65
<211> LENGTH: 217
<212> TYPE: PRT
<213> ORGANISM: Bacillus anthracis

<400> SEQUENCE: 65

Met Asp Gln Leu Arg Val Ile Glu Gly Glu Lys Val Asp Lys Pro Asp
1               5                   10                  15

Tyr Val Glu Ile Tyr Leu Gly Ala Phe Met Asn Ala Val Asn Glu Leu
            20                  25                  30

Lys Lys Gln Asp Glu Glu Thr Arg Ser Leu Ser Lys Asp Thr Tyr Lys
        35                  40                  45

Lys Ala Ile Phe Tyr Gly Val Arg Tyr Ile Ser Ile Ser Lys Asn Asp
    50                  55                  60

Ser Leu Asn Tyr Asp Tyr Leu Met Asn Arg Phe Leu Leu Ile Ser Tyr
65                  70                  75                  80

Leu Glu Asn Leu Met Lys Val Leu Thr Pro Arg Asp Phe Met Thr Ile
                85                  90                  95

Phe Pro Ile Asp Lys Asn Tyr Asp Gly Ala Arg Tyr Glu Met Lys Asp
            100                 105                 110

Tyr Phe Phe Thr Met Asn Glu Ile Lys Lys Ile Gly Met Asp Thr Pro
        115                 120                 125

Ile Gly Glu Lys Ile Met Glu Phe Leu Trp Asp Tyr Gln Asn Phe Lys
    130                 135                 140

Asp Ile Thr Leu Phe Asn Leu Ala Ser Val Ser Ile Leu Asn Lys Leu
145                 150                 155                 160

Gln Lys Met Gln Gly Lys Lys Thr Leu Thr Glu Glu Phe Ala Glu Arg
```

-continued

```
                165                 170                 175

Leu Gly Ile Asp Thr Tyr Thr Lys His Lys Glu Lys Gly Gly Lys Glu
            180                 185                 190

Tyr Ile Thr Asn Asp Arg Thr Gly Glu Ile Gln Glu Val Lys Lys Ser
        195                 200                 205

Arg Pro Arg Tyr Leu Lys Pro Val Gln
    210                 215


<210> SEQ ID NO 66
<211> LENGTH: 271
<212> TYPE: PRT
<213> ORGANISM: Bacillus anthracis

<400> SEQUENCE: 66

Met Asp Gln Leu Thr Val Ala Ser Glu Leu Arg Leu Leu Gly Arg Arg
1               5                   10                  15

Lys Val Ala Gly Tyr Glu Phe Thr Gly Ile Glu Gly Gly Phe Gly Glu
            20                  25                  30

Gly Lys Lys Ala Met Leu Val Leu Asp Ile Ala Thr Ile His Asn Gln
        35                  40                  45

Pro Leu Lys Glu Ile Asn Arg Arg Ile Asn Asp Asn Arg Ile Arg Phe
    50                  55                  60

Lys Asp Gly Val Asp Ile Val Asp Leu Lys Ser Gly Gly Phe Asn Pro
65                  70                  75                  80

Pro Gln Leu Leu Asn Leu Gly Phe Ser Asn Met Gln Ile Ala Lys Ser
                85                  90                  95

Asn Asn Ile Tyr Leu Leu Ser Glu Arg Gly Tyr Ala Lys Leu Leu Lys
            100                 105                 110

Ile Leu Glu Asp Asp Lys Ala Trp Glu Leu Tyr Asp Ile Leu Val Asp
        115                 120                 125

Glu Tyr Phe Asn Met Arg Glu Lys Asn Gln Val Ala Thr Asp Pro Met
    130                 135                 140

Ser Ile Leu Lys Leu Thr Phe Glu Ala Leu Glu Gly Gln Gln Gln Ala
145                 150                 155                 160

Ile Glu Glu Ile Lys Ser Asp Val Gln Asp Leu Arg Glu Asn Thr Pro
                165                 170                 175

Leu Phe Ala Ile Glu Cys Asp Glu Ile Ser Thr Ala Val Lys Arg Gln
            180                 185                 190

Gly Val Ile Leu Leu Gly Gly Lys Gln Ser Asn Ala Tyr Arg Asn Arg
        195                 200                 205

Gly Leu Arg Gly Lys Val Tyr Arg Asp Ile Tyr Asn Gln Leu Tyr Arg
    210                 215                 220

Glu Phe Gly Val Lys Ser His Lys Ala Ile Lys Arg Cys His Leu Asn
225                 230                 235                 240

Val Ala Val Lys Ile Val Glu Glu Tyr Thr Leu Pro Ile Val Leu Ser
                245                 250                 255

Glu Glu Ile Ser Phe Val Asn Ala Gln Met Asp Phe Thr Glu Met
            260                 265                 270


<210> SEQ ID NO 67
<211> LENGTH: 315
<212> TYPE: PRT
<213> ORGANISM: Bacillus anthracis

<400> SEQUENCE: 67

Met Ala Leu Phe Arg Lys Val His Thr Glu Phe Trp Thr Asp Val Lys
```

-continued

```
1               5                   10                  15

Val Ser Glu Asp Met Thr Pro Glu Asp Lys Leu Phe Met Val Tyr Leu
            20                  25                  30

Leu Thr Asn Pro His Thr Thr Gln Leu Gly Val Tyr Glu Ile Thr Pro
        35                  40                  45

Lys Met Ile Ala Phe Glu Ile Gly Leu Ser Ile Glu Ser Ala Arg Ala
    50                  55                  60

Leu Leu Glu Arg Phe Glu Asn His His Lys Leu Ile Lys Tyr Asn Lys
65                  70                  75                  80

Leu Thr Arg Glu Ile Ala Ile Lys Asn Trp Gly Lys Tyr Asn Leu Asn
                85                  90                  95

Arg Gly Gly Lys Pro Ile Glu Asp Cys Leu Lys Arg Glu Ile Asp Lys
            100                 105                 110

Val Lys Asp Leu Ser Leu Ile Lys Phe Ile Leu Glu His Thr Asp His
        115                 120                 125

Ala Ala Leu Lys Arg Lys Ile Asn Leu Tyr Ala Gly Phe Asp Asp Thr
    130                 135                 140

Ser His Asp Thr Leu Ala Ile Arg Asp Gln Glu Glu Glu Lys Glu Gln
145                 150                 155                 160

Lys Lys Glu Gln Lys Glu Glu Gln Glu Glu Lys Glu Lys Glu Lys Glu
                165                 170                 175

Lys Gln Lys Glu Glu Glu Lys Glu Pro Glu Glu Glu Lys Thr Arg Ile
            180                 185                 190

Lys Ser Lys Ala Ser Leu Lys Ser Asp Ala Lys Ser Asn Pro Ile Pro
        195                 200                 205

Tyr Lys Asp Ile Leu Asp Tyr Leu Asn Glu Lys Ala Asn Lys Asn Phe
    210                 215                 220

Asn Pro Lys Ala Glu Gly His Arg Lys Leu Ile Arg Ala Arg Trp Asn
225                 230                 235                 240

Glu Gly Tyr Lys Leu Glu Asp Phe Lys Lys Val Ile Asp Asn Lys Thr
                245                 250                 255

Thr Gln Trp Phe Gly Lys Lys Ser Phe Asp Gly Lys Pro Leu Asp Gln
            260                 265                 270

Phe Leu Arg Pro Ser Thr Leu Phe Ala Gln Lys His Phe Asp Asn Tyr
        275                 280                 285

Leu Asn Glu Thr Val Asn Ile Ser Asn Gln Gln His Gly Asp Gln Ile
    290                 295                 300

Val Ile Pro Gly Phe Arg Gly Glu Met Pro Phe
305                 310                 315


<210> SEQ ID NO 68
<211> LENGTH: 217
<212> TYPE: PRT
<213> ORGANISM: Bacillus anthracis

<400> SEQUENCE: 68

Met Asp Gln Leu Arg Val Ile Glu Gly Glu Lys Val Asp Lys Pro Asp
1               5                   10                  15

Tyr Val Glu Ile Tyr Leu Gly Ala Phe Met Asn Ala Val Asn Glu Leu
            20                  25                  30

Lys Lys Gln Asp Glu Glu Thr Arg Ser Leu Ser Lys Asp Thr Tyr Lys
        35                  40                  45

Lys Ala Ile Phe Tyr Gly Val Arg Tyr Ile Ser Ile Ser Lys Asn Asp
    50                  55                  60
```

-continued

```
Ser Leu Asn Tyr Asp Tyr Leu Met Asn Arg Phe Leu Leu Ile Ser Tyr
65                  70                  75                  80

Leu Glu Asn Leu Met Lys Val Leu Thr Pro Arg Asp Phe Met Thr Ile
                85                  90                  95

Phe Pro Ile Asp Lys Asn Tyr Asp Gly Ala Arg Tyr Glu Met Lys Asp
            100                 105                 110

Tyr Phe Phe Thr Met Asn Glu Ile Lys Lys Ile Gly Met Asp Thr Pro
        115                 120                 125

Ile Gly Glu Lys Ile Met Glu Phe Leu Trp Asp Tyr Gln Asn Phe Lys
    130                 135                 140

Asp Ile Thr Leu Phe Asn Leu Ala Ser Val Ser Ile Leu Asn Lys Leu
145                 150                 155                 160

Gln Lys Met Gln Gly Lys Lys Thr Leu Thr Glu Glu Phe Ala Glu Arg
                165                 170                 175

Leu Gly Ile Asp Thr Tyr Thr Lys His Lys Glu Lys Gly Gly Lys Glu
            180                 185                 190

Tyr Ile Thr Asn Asp Arg Thr Gly Glu Ile Gln Glu Val Lys Lys Ser
        195                 200                 205

Arg Pro Arg Tyr Leu Lys Pro Val Gln
    210                 215
```

<210> SEQ ID NO 69
<211> LENGTH: 303
<212> TYPE: PRT
<213> ORGANISM: Bacillus anthracis

<400> SEQUENCE: 69

```
Val Lys Lys Ile Gln Asp Ser Phe Glu Lys Leu Thr Lys Leu Lys Phe
1               5                   10                  15

Ala Asp Glu Gln Cys Asp Lys His Thr Phe Asn Lys His Gly Lys Glu
            20                  25                  30

Val Ile Lys Leu Val Arg Lys Met Ile Asp Asp Ala Gly Thr Val Tyr
        35                  40                  45

Cys Pro Arg Cys Met Val Glu Glu Gln Asn Ser Val Leu Phe Gln Gln
    50                  55                  60

Ala Asn Asn His Tyr Lys Lys Ile Asn Arg Glu Arg Lys Lys Asn Val
65                  70                  75                  80

Leu Phe Gln His Ser Ile Ile Glu Asn Gln Ser Ile Thr Glu Ser Arg
                85                  90                  95

Leu Ser Thr Tyr Lys Thr Asp Cys Gln Glu Thr Lys Glu Asn Lys Glu
            100                 105                 110

Lys Ala Ile Lys Ile Leu Glu Arg Ile Lys Asn Gly Glu Phe Leu Asn
        115                 120                 125

Val Tyr Ile Ala Gly Ile Gln Gly Val Gly Lys Ser His Leu Ala Tyr
    130                 135                 140

Ala Met Leu Tyr Glu Leu Val Lys His Tyr Trp Val Ile Ser Asp Gly
145                 150                 155                 160

Glu Lys Leu Asn Asp Glu His Ala Phe Lys Asn Met Lys Ser Cys Leu
                165                 170                 175

Phe Val Glu Ile Glu Lys Leu Ile Arg Leu Ile Gln His Ser Phe Arg
            180                 185                 190

Asn Ile Glu Ser Lys Tyr Thr Met Asp Tyr Cys Ile Ser Leu Met Val
        195                 200                 205

Asp Val Asp Phe Leu Val Ile Asp Asp Leu Gly Ala Glu Ser Gly Ser
    210                 215                 220
```

-continued

```
Met Asn Arg Asn Gly Glu Ala Ser Asp Phe Val His Lys Ile Leu Tyr
225                 230                 235                 240

Gly Val Thr Asn Gly Arg Gln Gly Ala Asn Lys Thr Thr Ile Thr Thr
                245                 250                 255

Ser Asn Leu Ser Ser Ala Gln Leu Phe Gln Lys Tyr Asp Pro Lys Leu
            260                 265                 270

Ala Ser Arg Leu Leu Asn Gly Val Ser Lys Asp Glu Thr Ile Val Phe
        275                 280                 285

Lys Thr Thr Thr Asp Lys Arg Ile Val Asn Leu Asp Ile Gly Phe
    290                 295                 300


<210> SEQ ID NO 70
<211> LENGTH: 315
<212> TYPE: PRT
<213> ORGANISM: Bacillus anthracis

<400> SEQUENCE: 70

Met Ala Leu Phe Arg Lys Val His Thr Glu Phe Trp Thr Asp Val Lys
1               5                   10                  15

Val Ser Glu Asp Met Thr Pro Glu Asp Lys Leu Phe Met Val Tyr Leu
            20                  25                  30

Leu Thr Asn Pro His Thr Thr Gln Leu Gly Val Tyr Glu Ile Thr Pro
        35                  40                  45

Lys Met Ile Ala Phe Glu Ile Gly Leu Ser Ile Glu Ser Ala Arg Ala
    50                  55                  60

Leu Leu Glu Arg Phe Glu Asn His His Lys Leu Ile Lys Tyr Asn Lys
65                  70                  75                  80

Leu Thr Arg Glu Ile Ala Ile Lys Asn Trp Gly Lys Tyr Asn Leu Asn
                85                  90                  95

Arg Gly Gly Lys Pro Ile Glu Asp Cys Leu Lys Arg Glu Ile Asp Lys
            100                 105                 110

Val Lys Asp Leu Ser Leu Ile Lys Phe Ile Leu Glu His Thr Asp His
        115                 120                 125

Ala Ala Leu Lys Arg Lys Ile Asn Leu Tyr Ala Gly Phe Asp Asp Thr
    130                 135                 140

Ser His Asp Thr Leu Ala Ile Arg Asp Gln Glu Glu Glu Lys Glu Gln
145                 150                 155                 160

Lys Lys Glu Gln Lys Glu Glu Gln Glu Glu Lys Glu Lys Glu Lys Glu
                165                 170                 175

Lys Gln Lys Glu Glu Glu Lys Glu Pro Glu Glu Glu Lys Thr Arg Ile
            180                 185                 190

Lys Ser Lys Ala Ser Leu Lys Ser Asp Ala Lys Ser Asn Pro Ile Pro
        195                 200                 205

Tyr Lys Asp Ile Leu Asp Tyr Leu Asn Glu Lys Ala Asn Lys Asn Phe
    210                 215                 220

Asn Pro Lys Ala Glu Gly His Arg Lys Leu Ile Arg Ala Arg Trp Asn
225                 230                 235                 240

Glu Gly Tyr Lys Leu Glu Asp Phe Lys Lys Val Ile Asp Asn Lys Thr
                245                 250                 255

Thr Gln Trp Phe Gly Lys Lys Ser Phe Asp Gly Lys Pro Leu Asp Gln
            260                 265                 270

Phe Leu Arg Pro Ser Thr Leu Phe Ala Gln Lys His Phe Asp Asn Tyr
        275                 280                 285

Leu Asn Glu Thr Val Asn Ile Ser Asn Gln Gln His Gly Asp Gln Ile
```

-continued

```
    290                 295                 300

Val Ile Pro Gly Phe Arg Gly Glu Met Pro Phe
305                 310                 315


<210> SEQ ID NO 71
<211> LENGTH: 77
<212> TYPE: PRT
<213> ORGANISM: Bacillus anthracis

<400> SEQUENCE: 71

Met Lys Glu Val Lys Gly Lys Asn Thr Lys Leu Met Glu Glu Phe Asp
1               5                   10                  15

Val Leu Leu Arg Gln Leu Leu Ile Lys Ser Lys Thr Asp Glu Arg Val
            20                  25                  30

Lys Asn Phe Leu Asp Asp Leu Phe Glu Met Leu Ser Asp Asn Lys Leu
        35                  40                  45

Gln Ser Asp Ile Asp Phe Lys Thr Ala Leu Asn Lys Leu Arg Glu Lys
    50                  55                  60

His Phe Pro Lys Phe Asp Lys Gly Glu Ser Lys Asn Asp
65                  70                  75


<210> SEQ ID NO 72
<211> LENGTH: 303
<212> TYPE: PRT
<213> ORGANISM: Bacillus anthracis

<400> SEQUENCE: 72

Val Lys Lys Ile Gln Asp Ser Phe Glu Lys Leu Thr Lys Leu Lys Phe
1               5                   10                  15

Ala Asp Glu Gln Cys Asp Lys His Thr Phe Asn Lys His Gly Lys Glu
            20                  25                  30

Val Ile Lys Leu Val Arg Lys Met Ile Asp Asp Ala Gly Thr Val Tyr
        35                  40                  45

Cys Pro Arg Cys Met Val Glu Glu Gln Asn Ser Val Leu Phe Gln Gln
    50                  55                  60

Ala Asn Asn His Tyr Lys Lys Ile Asn Arg Glu Arg Lys Lys Asn Val
65                  70                  75                  80

Leu Phe Gln His Ser Ile Ile Glu Asn Gln Ser Ile Thr Glu Ser Arg
                85                  90                  95

Leu Ser Thr Tyr Lys Thr Asp Cys Gln Glu Thr Lys Glu Asn Lys Glu
            100                 105                 110

Lys Ala Ile Lys Ile Leu Glu Arg Ile Lys Asn Gly Glu Phe Leu Asn
        115                 120                 125

Val Tyr Ile Ala Gly Ile Gln Gly Val Gly Lys Ser His Leu Ala Tyr
    130                 135                 140

Ala Met Leu Tyr Glu Leu Val Lys His Tyr Trp Val Ile Ser Asp Gly
145                 150                 155                 160

Glu Lys Leu Asn Asp Glu His Ala Phe Lys Asn Met Lys Ser Cys Leu
                165                 170                 175

Phe Val Glu Ile Glu Lys Leu Ile Arg Leu Ile Gln His Ser Phe Arg
            180                 185                 190

Asn Ile Glu Ser Lys Tyr Thr Met Asp Tyr Cys Ile Ser Leu Met Val
        195                 200                 205

Asp Val Asp Phe Leu Val Ile Asp Asp Leu Gly Ala Glu Ser Gly Ser
    210                 215                 220

Met Asn Arg Asn Gly Glu Ala Ser Asp Phe Val His Lys Ile Leu Tyr
```

-continued

```
225                 230                 235                 240

Gly Val Thr Asn Gly Arg Gln Gly Ala Asn Lys Thr Thr Ile Thr Thr
                245                 250                 255

Ser Asn Leu Ser Ser Ala Gln Leu Phe Gln Lys Tyr Asp Pro Lys Leu
            260                 265                 270

Ala Ser Arg Leu Leu Asn Gly Val Ser Lys Asp Glu Thr Ile Val Phe
        275                 280                 285

Lys Thr Thr Thr Asp Lys Arg Ile Val Asn Leu Asp Ile Gly Phe
    290                 295                 300


<210> SEQ ID NO 73
<211> LENGTH: 248
<212> TYPE: PRT
<213> ORGANISM: Bacillus anthracis

<400> SEQUENCE: 73

Met Thr Lys Glu Lys Gly Gln Ala Lys Glu Val Val Asn Val Arg Gly
1               5                   10                  15

Met Ser Asp Asp Glu Phe Ile Glu Lys Tyr Gly Arg Leu Val His His
            20                  25                  30

Cys Val Trp Lys Arg Tyr Ala Lys Lys Lys Ala Ser Ile Glu Arg Asp
        35                  40                  45

Thr Gly Leu Asp Ile Glu Asp Leu Thr Gln Phe Gly Met Ile Gly Leu
    50                  55                  60

Ile Lys Ala Arg Asp Asn Phe Asp Leu Glu Phe Gly Cys Ala Phe Ser
65                  70                  75                  80

Thr Tyr Ala Val Pro Lys Ile Ile Gly Glu Ile Gly Arg Ala Ile Arg
                85                  90                  95

Asp Asn Gln Lys Ile Lys Val Gln Arg Thr Val Tyr Gly Val Lys Gly
            100                 105                 110

Lys Ile Leu Asn Gln Gln Leu Ala Asp Lys Glu Pro Glu Glu Ile Ala
        115                 120                 125

Asp Ile Leu Asp Glu Ser Val Ser Leu Val Lys Thr Ala Leu Glu Tyr
    130                 135                 140

Gln Pro Ser Thr Asp Ser Leu Asn Lys Val Val Tyr Ala Ser Gly Ala
145                 150                 155                 160

Asn Glu Glu Leu Thr Leu Glu Arg Met Ile Glu Asp Thr Lys Thr Glu
                165                 170                 175

Asp Ile Glu Glu Thr Thr Ile Asn Arg Ala Val Ile Arg Glu Phe Lys
            180                 185                 190

Ala Ala Leu Pro Pro Lys Glu Tyr Ile Val Leu Asp Met Arg Leu Gln
        195                 200                 205

Asn Met Thr Gln Gln Asn Ile Ala Asn Gln Met Gly Tyr Ser Gln Val
    210                 215                 220

Gln Ile Ser Arg Ile Leu Ala Lys Ile Asn Gln Arg Ala Ala Gln Phe
225                 230                 235                 240

Gly Lys Glu Gly Gly Leu Gln Asp
                245


<210> SEQ ID NO 74
<211> LENGTH: 77
<212> TYPE: PRT
<213> ORGANISM: Bacillus anthracis

<400> SEQUENCE: 74

Met Lys Glu Val Lys Gly Lys Asn Thr Lys Leu Met Glu Glu Phe Asp
```

-continued

```
1               5                   10                  15

Val Leu Leu Arg Gln Leu Leu Ile Lys Ser Lys Thr Asp Glu Arg Val
            20                  25                  30

Lys Asn Phe Leu Asp Asp Leu Phe Glu Met Leu Ser Asp Asn Lys Leu
        35                  40                  45

Gln Ser Asp Ile Asp Phe Lys Thr Ala Leu Asn Lys Leu Arg Glu Lys
    50                  55                  60

His Phe Pro Lys Phe Asp Lys Gly Glu Ser Lys Asn Asp
65                  70                  75


<210> SEQ ID NO 75
<211> LENGTH: 158
<212> TYPE: PRT
<213> ORGANISM: Bacillus anthracis

<400> SEQUENCE: 75

Leu Ser Val Thr Lys Gly Val Cys Ile Asp Val Asp His Ser Asp Leu
1               5                   10                  15

Leu His Glu Lys Val Glu Tyr Phe Leu Phe Pro Ala Lys Pro Ser His
            20                  25                  30

Tyr Tyr Val Ser Arg Phe Asn Arg Lys Gly Ala His Phe Gly Cys Tyr
        35                  40                  45

Gln Ala Glu Arg Phe Gln Ile Thr Glu Lys Glu Val Trp Thr Pro Glu
    50                  55                  60

Pro Gln Pro Asn Leu Pro Glu Leu Asn Thr Ser Leu Phe Tyr Arg Ala
65                  70                  75                  80

Gln Leu Ile Trp Arg Lys Lys Gly Tyr Lys Asp Lys Pro Leu Lys Asp
                85                  90                  95

Tyr Ile Val Gln Pro Arg Gly Lys His Cys Tyr Phe Trp His Asp Arg
            100                 105                 110

Glu Arg Lys Lys Phe Cys Gly Cys Phe Pro Leu His Trp Phe Thr Asp
        115                 120                 125

Phe Val Pro Val Gln Ser His His Ile Glu Glu Lys Thr Arg Glu Glu
    130                 135                 140

Val Lys Leu Leu Gln Arg Pro Asp Gly Gln Leu Ala Phe Phe
145                 150                 155


<210> SEQ ID NO 76
<211> LENGTH: 248
<212> TYPE: PRT
<213> ORGANISM: Bacillus anthracis

<400> SEQUENCE: 76

Met Thr Lys Glu Lys Gly Gln Ala Lys Glu Val Val Asn Val Arg Gly
1               5                   10                  15

Met Ser Asp Asp Glu Phe Ile Glu Lys Tyr Gly Arg Leu Val His His
            20                  25                  30

Cys Val Trp Lys Arg Tyr Ala Lys Lys Lys Ala Ser Ile Glu Arg Asp
        35                  40                  45

Thr Gly Leu Asp Ile Glu Asp Leu Thr Gln Phe Gly Met Ile Gly Leu
    50                  55                  60

Ile Lys Ala Arg Asp Asn Phe Asp Leu Glu Phe Gly Cys Ala Phe Ser
65                  70                  75                  80

Thr Tyr Ala Val Pro Lys Ile Ile Gly Glu Ile Gly Arg Ala Ile Arg
                85                  90                  95

Asp Asn Gln Lys Ile Lys Val Gln Arg Thr Val Tyr Gly Val Lys Gly
```

-continued

```
            100                 105                 110

Lys Ile Leu Asn Gln Gln Leu Ala Asp Lys Glu Pro Glu Glu Ile Ala
        115                 120                 125

Asp Ile Leu Asp Glu Ser Val Ser Leu Val Lys Thr Ala Leu Glu Tyr
    130                 135                 140

Gln Pro Ser Thr Asp Ser Leu Asn Lys Val Val Tyr Ala Ser Gly Ala
145                 150                 155                 160

Asn Glu Glu Leu Thr Leu Glu Arg Met Ile Glu Asp Thr Lys Thr Glu
                165                 170                 175

Asp Ile Glu Glu Thr Thr Ile Asn Arg Ala Val Ile Arg Glu Phe Lys
            180                 185                 190

Ala Ala Leu Pro Pro Lys Glu Tyr Ile Val Leu Asp Met Arg Leu Gln
        195                 200                 205

Asn Met Thr Gln Gln Asn Ile Ala Asn Gln Met Gly Tyr Ser Gln Val
    210                 215                 220

Gln Ile Ser Arg Ile Leu Ala Lys Ile Asn Gln Arg Ala Ala Gln Phe
225                 230                 235                 240

Gly Lys Glu Gly Gly Leu Gln Asp
                245


<210> SEQ ID NO 77
<211> LENGTH: 180
<212> TYPE: PRT
<213> ORGANISM: Bacillus anthracis

<400> SEQUENCE: 77

Met Asp Ile Lys Lys Leu Phe Ala Met Gln Asn Ile Leu Asp Lys Arg
1               5                   10                  15

Val Leu Glu Ser Lys Asn Leu Ser Arg Gly Glu Val Phe Glu Phe Arg
            20                  25                  30

Ile Leu Ala Phe Leu Asp Glu Leu Gly Glu Cys Met Lys Glu Trp Arg
        35                  40                  45

Val Phe Lys Phe Trp Ser Asp Asp Arg Lys Pro Arg Thr Ser Ile Pro
    50                  55                  60

Thr Gly Glu Ile Ile Val Leu Asp Asp Gly Tyr Glu Val Glu Val Tyr
65                  70                  75                  80

Lys Asn Pro Leu Leu Glu Glu Tyr Val Asp Gly Leu His Phe Ala Ile
                85                  90                  95

Gly Leu Cys Ile Asp Leu Lys Thr Glu Ile Asn Phe Pro Ala Ser Met
            100                 105                 110

Arg Cys Glu Thr Val Thr Glu Gln Phe Phe Glu Leu Tyr His Leu Ala
        115                 120                 125

Ile Arg Leu Lys Glu Glu Pro Thr Ala Phe Arg Ala Asp Val Leu Leu
    130                 135                 140

Ser His Tyr Leu Gly Leu Gly Glu Leu Leu Cys Phe Ser Leu Glu Glu
145                 150                 155                 160

Ile Gly His Glu Tyr Ile Glu Lys Asn Lys Ile Asn His Glu Arg Gln
                165                 170                 175

Ser Asn Gly Tyr
            180


<210> SEQ ID NO 78
<211> LENGTH: 158
<212> TYPE: PRT
<213> ORGANISM: Bacillus anthracis
```

-continued

<400> SEQUENCE: 78

Leu Ser Val Thr Lys Gly Val Cys Ile Asp Val Asp His Ser Asp Leu
1               5                   10                  15

Leu His Glu Lys Val Glu Tyr Phe Leu Phe Pro Ala Lys Pro Ser His
            20                  25                  30

Tyr Tyr Val Ser Arg Phe Asn Arg Lys Gly Ala His Phe Gly Cys Tyr
        35                  40                  45

Gln Ala Glu Arg Phe Gln Ile Thr Glu Lys Glu Val Trp Thr Pro Glu
    50                  55                  60

Pro Gln Pro Asn Leu Pro Glu Leu Asn Thr Ser Leu Phe Tyr Arg Ala
65                  70                  75                  80

Gln Leu Ile Trp Arg Lys Lys Gly Tyr Lys Asp Lys Pro Leu Lys Asp
                85                  90                  95

Tyr Ile Val Gln Pro Arg Gly Lys His Cys Tyr Phe Trp His Asp Arg
            100                 105                 110

Glu Arg Lys Lys Phe Cys Gly Cys Phe Pro Leu His Trp Phe Thr Asp
        115                 120                 125

Phe Val Pro Val Gln Ser His His Ile Glu Glu Lys Thr Arg Glu Glu
    130                 135                 140

Val Lys Leu Leu Gln Arg Pro Asp Gly Gln Leu Ala Phe Phe
145                 150                 155

<210> SEQ ID NO 79
<211> LENGTH: 76
<212> TYPE: PRT
<213> ORGANISM: Bacillus anthracis

<400> SEQUENCE: 79

Met Arg Val Ile Glu Ile Ser Trp Trp Ala Ile Ala Ile Gly Leu Tyr
1               5                   10                  15

Leu Leu Ile Gly Val Ala Leu Leu Ile Trp Ile Ile Ala Thr Asp Ser
            20                  25                  30

Trp Gly Ser Leu Phe Leu Tyr Pro Val Phe Ala Val Val Ile Val Leu
        35                  40                  45

Gly Trp Leu Pro Leu Met Ile Arg Ser Ile Val Gln Glu Ile Ser Lys
    50                  55                  60

Ala Ile His Lys Trp Lys Arg Lys Gln Lys Thr Glu
65                  70                  75

<210> SEQ ID NO 80
<211> LENGTH: 180
<212> TYPE: PRT
<213> ORGANISM: Bacillus anthracis

<400> SEQUENCE: 80

Met Asp Ile Lys Lys Leu Phe Ala Met Gln Asn Ile Leu Asp Lys Arg
1               5                   10                  15

Val Leu Glu Ser Lys Asn Leu Ser Arg Gly Glu Val Phe Glu Phe Arg
            20                  25                  30

Ile Leu Ala Phe Leu Asp Glu Leu Gly Glu Cys Met Lys Glu Trp Arg
        35                  40                  45

Val Phe Lys Phe Trp Ser Asp Asp Arg Lys Pro Arg Thr Ser Ile Pro
    50                  55                  60

Thr Gly Glu Ile Ile Val Leu Asp Asp Gly Tyr Glu Val Glu Val Tyr
65                  70                  75                  80

Lys Asn Pro Leu Leu Glu Glu Tyr Val Asp Gly Leu His Phe Ala Ile

-continued

```
                85                  90                  95

Gly Leu Cys Ile Asp Leu Lys Thr Glu Ile Asn Phe Pro Ala Ser Met
            100                 105                 110

Arg Cys Glu Thr Val Thr Glu Gln Phe Phe Glu Leu Tyr His Leu Ala
        115                 120                 125

Ile Arg Leu Lys Glu Glu Pro Thr Ala Phe Arg Ala Asp Val Leu Leu
    130                 135                 140

Ser His Tyr Leu Gly Leu Gly Glu Leu Leu Cys Phe Ser Leu Glu Glu
145                 150                 155                 160

Ile Gly His Glu Tyr Ile Glu Lys Asn Lys Ile Asn His Glu Arg Gln
                165                 170                 175

Ser Asn Gly Tyr
            180


<210> SEQ ID NO 81
<211> LENGTH: 156
<212> TYPE: PRT
<213> ORGANISM: Bacillus anthracis

<400> SEQUENCE: 81

Met Ser Gly Cys Thr Ile Val Asn Val Lys Ile Asn Lys Gln Lys Arg
1               5                   10                  15

Gly Met Lys Asp Met Lys Trp Met Tyr Asn Leu Asp Ser Asn Asn Glu
            20                  25                  30

Ile Trp Thr Ser Asp Lys Phe Glu Met Lys Glu Glu Ala Ile Gln Ala
        35                  40                  45

Ala Leu Lys Asp Trp Thr Asp Lys Met Val Ala Asp Arg Ala Ala Val
    50                  55                  60

Asp Asn Glu Phe Gln Ile Gly Gln Phe Lys Gln Tyr Ser Pro Trp Ile
65                  70                  75                  80

Asn Ala Asp Val Leu Leu Asp Glu Leu Tyr Glu Arg Ala Thr Asp Glu
                85                  90                  95

Cys Gly Glu Val Ala Glu Tyr Trp Leu Ser Gly Val Pro Met Asp Glu
            100                 105                 110

Gly Glu Lys Leu Gln Glu Gln Ile Asn Lys Val Val Thr Glu Trp Leu
        115                 120                 125

Lys Gly Ile Asn Glu His Pro Ser Phe Gly Ser Ile Glu Asn Ile Glu
    130                 135                 140

Thr Ile Asp Ala Ser Lys Ile Glu Tyr Lys Glu Asn
145                 150                 155


<210> SEQ ID NO 82
<211> LENGTH: 310
<212> TYPE: PRT
<213> ORGANISM: Bacillus anthracis

<400> SEQUENCE: 82

Met Asp Cys Phe Lys Lys Gly Lys Phe Ile Pro Phe Pro Cys Ala Leu
1               5                   10                  15

Pro Ile Pro Glu Ala Gly Pro Thr Gly Pro Thr Gly Pro Pro Gly Ser
            20                  25                  30

Ala Gly Gly Ser Thr Gly Pro Thr Gly Pro Thr Gly Pro Gln Gly Leu
        35                  40                  45

Gln Gly Ile Gln Gly Val Gln Gly Asn Pro Gly Thr Thr Gly Pro Gln
    50                  55                  60

Gly Ile Gln Gly Ile Gln Gly Ile Pro Gly Val Ser Gly Pro Ile Gly
```

-continued

```
65                  70                  75                  80

Pro Ile Gly Pro Thr Gly Ile Gln Gly Val Gln Gly Ile Gln Gly Phe
                85                  90                  95

Pro Gly Ile Pro Gly Pro Met Gly Pro Ile Gly Leu Thr Gly Pro Thr
            100                 105                 110

Gly Ile Gln Gly Ile Gln Gly Ile Gln Gly Val Gln Gly Ile Gln Gly
        115                 120                 125

Ile Gln Gly Asp Val Gly Pro Thr Gly Pro Gln Gly Ile Pro Gly Ile
    130                 135                 140

Pro Gly Leu Thr Gly Pro Thr Gly Ser Gln Gly Val Thr Gly Val Thr
145                 150                 155                 160

Gly Pro Ser Gly Gly Pro Pro Gly Pro Thr Gly Ala Thr Gly Pro Thr
                165                 170                 175

Gly Pro Ala Gly Gly Pro Pro Gly Pro Thr Gly Pro Thr Gly Pro Ala
            180                 185                 190

Gly Gly Pro Thr Gly Leu Thr Gly Pro Thr Gly Pro Thr Gly Pro Thr
        195                 200                 205

Gly Ile Gln Gly Ile Gln Gly Val Gln Gly Thr Gln Gly Ile Pro Gly
    210                 215                 220

Pro Thr Gly Pro Gln Gly Ile Gln Gly Val Gln Gly Leu Gln Gly Ile
225                 230                 235                 240

Pro Gly Ile Pro Gly Ser Met Gly Pro Thr Gly Leu Thr Gly Pro Thr
                245                 250                 255

Gly Leu Gln Gly Ile Gln Gly Ile Gln Gly Asn Pro Gly Pro Thr Gly
            260                 265                 270

Pro Phe Gly Pro Thr Gly Pro Thr Gly Leu Gln Gly Ile Gln Gly Leu
        275                 280                 285

Gln Gly Ile Gln Gly Ile Pro Gly Ser Asn Arg Thr Ser Arg Asn Pro
    290                 295                 300

Arg Ser Asn Arg Thr Cys
305                 310


<210> SEQ ID NO 83
<211> LENGTH: 129
<212> TYPE: PRT
<213> ORGANISM: Bacillus anthracis

<400> SEQUENCE: 83

Met Tyr Gln Thr Trp Lys Asn Leu Leu Asn Ser Ile Lys Lys Ile Leu
1               5                   10                  15

Gln Ala Lys Leu Leu Val Lys Gly Arg Lys Leu Ala Tyr Phe Asp Leu
            20                  25                  30

Asn Gly Leu Trp Ile Ala Leu Asn Val Glu Glu Asp Ile Pro Arg Asn
        35                  40                  45

Glu Ile Lys Gln Ser Tyr Thr His Met Ala Phe Thr Val Thr Asn Glu
    50                  55                  60

Ala Leu Asp His Leu Lys Glu Val Leu Ile Gln Asn Asp Val Asn Ile
65                  70                  75                  80

Leu Pro Gly Arg Glu Arg Asp Glu Arg Asp Gln Arg Ser Leu Tyr Phe
                85                  90                  95

Thr Asp Pro Asp Gly His Lys Phe Glu Phe His Thr Gly Thr Leu Gln
            100                 105                 110

Asn Arg Leu Glu Tyr Tyr Lys Glu Asp Lys Lys His Met Thr Phe Tyr
        115                 120                 125
```

-continued

Ile

<210> SEQ ID NO 84
<211> LENGTH: 163
<212> TYPE: PRT
<213> ORGANISM: Bacillus anthracis

<400> SEQUENCE: 84

Leu Leu Ala His Phe Pro Gln Lys Leu Phe Phe Phe Gly Gly Thr Asn
1 5 10 15

Ser Gly Phe Gln Arg Ile Ala Gly Ser Pro Gly Ala Asp Ser Gln Asp
20 25 30

Ile Pro Tyr Val Leu Gly Gly Ala Gly Ser Val Val Gly Leu Ser Ala
35 40 45

Ser Ile Ser Ile Asn Asn Leu Pro Ile Gly Val Tyr Thr Ile Arg Val
50 55 60

Cys Lys Asn Val Pro Ile Asn Leu Ala Ala Pro Gly Pro Gly Gln Val
65 70 75 80

Ile Ser Thr Ile Ile Leu Thr Thr Thr Ala Val Ile Ser Gly Thr Ile
85 90 95

Ile Leu Thr Ile Asn Pro Ser Asp Ile Gly Ala Gln Pro Val Arg Val
100 105 110

Phe Asn Pro Asn Leu Val Ile Ala Pro Ala Thr Val Ala Trp Ser Ser
115 120 125

Thr Ile Pro Gly Asp Ile Val Ala Arg Gly Asp Ala Met Ser Leu Phe
130 135 140

Ile Thr Pro Gly Ile Thr Gln Asn Ala Val Tyr Thr Val Phe Leu His
145 150 155 160

Thr Gly Asn

<210> SEQ ID NO 85
<211> LENGTH: 56
<212> TYPE: PRT
<213> ORGANISM: Bacillus anthracis

<400> SEQUENCE: 85

Met Ile Val Lys Ala Thr Ile Lys Leu Glu Leu Asp Asp Ser Gln Lys
1 5 10 15

Asn Trp Val Ser Tyr Val Arg Glu Gln Gly Gly Glu Glu Ala Val Phe
20 25 30

His Tyr Leu Glu Glu Glu Val Gln Lys Lys Ile Glu Leu Ala Asp Phe
35 40 45

Val Glu Met Lys Tyr Lys Asn Lys
50 55

<210> SEQ ID NO 86
<211> LENGTH: 191
<212> TYPE: PRT
<213> ORGANISM: Bacillus anthracis

<400> SEQUENCE: 86

Met Gln His Ile Pro Arg Tyr Tyr Tyr Gln Ser Gln Ser Pro Met Asp
1 5 10 15

Ser Ile Trp Asn Asn Asn Asn Trp Ile Tyr Ala Trp Asn Pro Tyr Tyr
20 25 30

Tyr Asn Tyr Asn Asn Asn Ala Trp Asn Arg Asn Arg Asn Pro Tyr Cys
35 40 45

-continued

```
Glu Asn Val Arg Leu Thr Asp Tyr Gly Ala Arg Pro Phe Val Leu Asn
    50                  55                  60

Ile Asn Gln Ala Thr Lys Gln Asn Asn Thr Tyr Arg Thr Ala Ile Trp
65                  70                  75                  80

Thr Gly Lys Asn Leu Gln Val Thr Leu Met Ser Ile Asn Val Gly Asp
                85                  90                  95

Asp Ile Gly Leu Glu Val His Pro Thr Thr Asp Gln Phe Ile Arg Ile
            100                 105                 110

Glu Glu Gly Gln Gly Leu Val Gln Met Gly Asp Asn Lys Asp Lys Leu
        115                 120                 125

Asp Phe Gln Glu Met Val Tyr Asp Asp Tyr Ala Ile Met Ile Pro Ala
    130                 135                 140

Gly Lys Trp His Asn Val Ile Asn Thr Gly Asn Thr Pro Leu Lys Ile
145                 150                 155                 160

Tyr Ala Ile Tyr Ala Pro Pro Glu His Pro Tyr Gly Thr Val His Glu
                165                 170                 175

Thr Lys Ala Ile Ala Met Ser Thr Glu Ala Asn Arg Tyr Tyr Tyr
            180                 185                 190


<210> SEQ ID NO 87
<211> LENGTH: 101
<212> TYPE: PRT
<213> ORGANISM: Bacillus anthracis

<400> SEQUENCE: 87

Met Asp Met Ser Leu Val Gly Asn Leu Lys Glu Leu Gln Glu Lys Ala
1               5                   10                  15

Ile Asp Glu Lys Val Leu Glu Phe Ala Glu Glu Met Glu Ile Val Ile
            20                  25                  30

Thr Lys Ser Ala Ala Ser Gly Tyr Ser Gly His Arg Tyr Lys Ile His
        35                  40                  45

Asn Glu Asn Pro Asn Arg His Met Met Cys Ser Lys Ile Phe Ile Glu
    50                  55                  60

Lys Leu Gln Glu Leu Leu Asp Gly Val Lys Val Glu Phe Lys Glu Glu
65                  70                  75                  80

Glu Lys Lys Asn Ile Leu Gly Gly Ser Tyr Tyr Glu His Tyr Ile Arg
                85                  90                  95

Phe Lys Trp Asn Asp
            100


<210> SEQ ID NO 88
<211> LENGTH: 56
<212> TYPE: PRT
<213> ORGANISM: Bacillus anthracis

<400> SEQUENCE: 88

Met Ile Val Lys Ala Thr Ile Lys Leu Glu Leu Asp Asp Ser Gln Lys
1               5                   10                  15

Asn Trp Val Ser Tyr Val Arg Glu Gln Gly Gly Glu Glu Ala Val Phe
            20                  25                  30

His Tyr Leu Glu Glu Glu Val Gln Lys Lys Ile Glu Leu Ala Asp Phe
        35                  40                  45

Val Glu Met Lys Tyr Lys Asn Lys
    50                  55


<210> SEQ ID NO 89
<211> LENGTH: 79
```

-continued

<212> TYPE: PRT
<213> ORGANISM: Bacillus anthracis

<400> SEQUENCE: 89

Met Thr Asn Phe Leu Leu Lys Ile Leu Phe Trp Arg Lys Gly Val Glu
1 5 10 15

Arg Met Lys Thr Phe Asn Val Thr Phe Thr Glu Leu Lys Ile Tyr Glu
20 25 30

Ala Val Ile Glu Ala Glu Ser Ala Glu Lys Ile Ile Asp Val Ile Lys
35 40 45

His Leu Lys Arg Thr Glu Asp Asp Leu Val Asp Lys Gly Val Ile Ile
50 55 60

Asn Glu Val Ser Glu Ile Asn Val Ser Lys Glu Gln Lys Phe Glu
65 70 75

<210> SEQ ID NO 90
<211> LENGTH: 101
<212> TYPE: PRT
<213> ORGANISM: Bacillus anthracis

<400> SEQUENCE: 90

Met Asp Met Ser Leu Val Gly Asn Leu Lys Glu Leu Gln Glu Lys Ala
1 5 10 15

Ile Asp Glu Lys Val Leu Glu Phe Ala Glu Glu Met Glu Ile Val Ile
20 25 30

Thr Lys Ser Ala Ala Ser Gly Tyr Ser Gly His Arg Tyr Lys Ile His
35 40 45

Asn Glu Asn Pro Asn Arg His Met Met Cys Ser Lys Ile Phe Ile Glu
50 55 60

Lys Leu Gln Glu Leu Leu Asp Gly Val Lys Val Glu Phe Lys Glu Glu
65 70 75 80

Glu Lys Lys Asn Ile Leu Gly Gly Ser Tyr Tyr Glu His Tyr Ile Arg
85 90 95

Phe Lys Trp Asn Asp
100

<210> SEQ ID NO 91
<211> LENGTH: 135
<212> TYPE: PRT
<213> ORGANISM: Bacillus anthracis

<400> SEQUENCE: 91

Val Asn His His Leu Phe Asn Trp Leu Arg Asp Tyr Gln Lys Leu Glu
1 5 10 15

Glu Asp Ile Ala Tyr Leu Glu Tyr Asn Leu Asp Lys Thr Lys Ala Glu
20 25 30

Leu Arg Arg Trp Val Ser Gly Asp Leu Arg Glu Val Arg Leu Thr Ala
35 40 45

Glu Ser Glu Gly Ala Lys Val Glu Asn Arg Ile Glu Ala Ile Glu Tyr
50 55 60

Glu Leu Ala His Lys Met Asn Asp Met Tyr Lys Leu Lys Lys Leu Ile
65 70 75 80

Ser Lys Phe Arg Gly Leu Glu Asn Gln Ile Leu Lys Leu Lys Tyr Val
85 90 95

Asp Gly Met Thr Leu Glu Glu Ile Ala Glu Ala Val Asn Tyr Ser Ser
100 105 110

Ser His Ile Lys Lys Lys His Ala Glu Leu Val Arg Leu Ile Lys Phe

-continued

```
        115                 120                 125

Val Glu Arg Glu Gly Val Ile
    130                 135


<210> SEQ ID NO 92
<211> LENGTH: 79
<212> TYPE: PRT
<213> ORGANISM: Bacillus anthracis

<400> SEQUENCE: 92

Met Thr Asn Phe Leu Leu Lys Ile Leu Phe Trp Arg Lys Gly Val Glu
1               5                   10                  15

Arg Met Lys Thr Phe Asn Val Thr Phe Thr Glu Leu Lys Ile Tyr Glu
            20                  25                  30

Ala Val Ile Glu Ala Glu Ser Ala Glu Lys Ile Ile Asp Val Ile Lys
        35                  40                  45

His Leu Lys Arg Thr Glu Asp Asp Leu Val Asp Lys Gly Val Ile Ile
    50                  55                  60

Asn Glu Val Ser Glu Ile Asn Val Ser Lys Glu Gln Lys Phe Glu
65                  70                  75


<210> SEQ ID NO 93
<211> LENGTH: 74
<212> TYPE: PRT
<213> ORGANISM: Bacillus anthracis

<400> SEQUENCE: 93

Met Asp Val Gln Glu Leu Ser Arg Arg Leu Glu Asn Leu Glu His Lys
1               5                   10                  15

Val Leu Gln Val Glu Thr Lys Ala Asp Val Leu Asn Arg Thr Ala Ile
            20                  25                  30

Gln Lys Gly Asp Lys Ile Lys Val Val Tyr Pro His Leu Gly Ile Gln
        35                  40                  45

Gly Glu Tyr Leu Val Glu Lys Ile Asp Asn Gly Val Leu Glu Leu Val
    50                  55                  60

Ala Glu Glu Thr Met Lys Lys Ile Gln Glu
65                  70


<210> SEQ ID NO 94
<211> LENGTH: 135
<212> TYPE: PRT
<213> ORGANISM: Bacillus anthracis

<400> SEQUENCE: 94

Val Asn His His Leu Phe Asn Trp Leu Arg Asp Tyr Gln Lys Leu Glu
1               5                   10                  15

Glu Asp Ile Ala Tyr Leu Glu Tyr Asn Leu Asp Lys Thr Lys Ala Glu
            20                  25                  30

Leu Arg Arg Trp Val Ser Gly Asp Leu Arg Glu Val Arg Leu Thr Ala
        35                  40                  45

Glu Ser Glu Gly Ala Lys Val Glu Asn Arg Ile Glu Ala Ile Glu Tyr
    50                  55                  60

Glu Leu Ala His Lys Met Asn Asp Met Tyr Lys Leu Lys Lys Leu Ile
65                  70                  75                  80

Ser Lys Phe Arg Gly Leu Glu Asn Gln Ile Leu Lys Leu Lys Tyr Val
                85                  90                  95

Asp Gly Met Thr Leu Glu Glu Ile Ala Glu Ala Val Asn Tyr Ser Ser
            100                 105                 110
```

-continued

```
Ser His Ile Lys Lys Lys His Ala Glu Leu Val Arg Leu Ile Lys Phe
        115                 120                 125

Val Glu Arg Glu Gly Val Ile
    130                 135


<210> SEQ ID NO 95
<211> LENGTH: 73
<212> TYPE: PRT
<213> ORGANISM: Bacillus anthracis

<400> SEQUENCE: 95

Leu Lys Lys Leu Ser Lys Gln Glu Leu Ala Ala Val Met Thr His Cys
1               5                   10                  15

Ile Ser Thr Leu Gly Glu Gln Ile Val Asn Glu His Ile Asn Pro Gln
            20                  25                  30

Lys Leu Ala Gln Ala Ser Ala Leu His Asn Asp Leu Phe Asp Asn Thr
        35                  40                  45

Thr Pro Lys Glu Arg Arg Glu Ala Thr Ile Ser Leu Leu Gly Lys Ala
    50                  55                  60

Ile Asp Glu Phe Leu Glu Ser Lys Glu
65                  70


<210> SEQ ID NO 96
<211> LENGTH: 74
<212> TYPE: PRT
<213> ORGANISM: Bacillus anthracis

<400> SEQUENCE: 96

Met Asp Val Gln Glu Leu Ser Arg Arg Leu Glu Asn Leu Glu His Lys
1               5                   10                  15

Val Leu Gln Val Glu Thr Lys Ala Asp Val Leu Asn Arg Thr Ala Ile
            20                  25                  30

Gln Lys Gly Asp Lys Ile Lys Val Val Tyr Pro His Leu Gly Ile Gln
        35                  40                  45

Gly Glu Tyr Leu Val Glu Lys Ile Asp Asn Gly Val Leu Glu Leu Val
    50                  55                  60

Ala Glu Glu Thr Met Lys Lys Ile Gln Glu
65                  70


<210> SEQ ID NO 97
<211> LENGTH: 134
<212> TYPE: PRT
<213> ORGANISM: Bacillus anthracis

<400> SEQUENCE: 97

Met Gly Lys Gly Tyr Phe Asn Lys Ala Val Cys Leu Val Cys Gly His
1               5                   10                  15

Gln Asp Arg Val Asn His Pro Ser Lys Lys Glu Tyr Gln Glu Val Thr
            20                  25                  30

Val Cys Pro Glu Cys Asn Gly Ala Phe Val Asp Val Trp Lys Leu Gly
        35                  40                  45

Lys Tyr Lys Arg Asn Thr Gln Ser Asn Glu Glu Pro Leu Leu Thr Ile
    50                  55                  60

Thr Leu Thr Asp Ile Asp Ala Lys Pro Ile Val His Tyr Lys Gly Glu
65                  70                  75                  80

Gln Ile Asp Arg Lys Leu Arg Val Thr Phe Asp Trp Glu Ser Gln Ser
                85                  90                  95
```

-continued

```
Ile Asp Lys Ile Asn Arg Thr Tyr Ile His Ile Glu His Val Pro Ala
            100                 105                 110

Asp Asn Lys Arg Leu Asn Thr Glu Thr Ile Gln His Asn His Pro Ile
        115                 120                 125

Ala Asn Lys Glu Gln Val
    130


<210> SEQ ID NO 98
<211> LENGTH: 73
<212> TYPE: PRT
<213> ORGANISM: Bacillus anthracis

<400> SEQUENCE: 98

Leu Lys Lys Leu Ser Lys Gln Glu Leu Ala Ala Val Met Thr His Cys
1               5                   10                  15

Ile Ser Thr Leu Gly Glu Gln Ile Val Asn Glu His Ile Asn Pro Gln
            20                  25                  30

Lys Leu Ala Gln Ala Ser Ala Leu His Asn Asp Leu Phe Asp Asn Thr
        35                  40                  45

Thr Pro Lys Glu Arg Arg Glu Ala Thr Ile Ser Leu Leu Gly Lys Ala
    50                  55                  60

Ile Asp Glu Phe Leu Glu Ser Lys Glu
65                  70


<210> SEQ ID NO 99
<211> LENGTH: 63
<212> TYPE: PRT
<213> ORGANISM: Bacillus anthracis

<400> SEQUENCE: 99

Met Asn Gly Phe Asn Lys Ile Val Asn Asp Met Gln Asn Glu Gln Val
1               5                   10                  15

Gly Asn Ala Met Leu Asp Phe Ala Leu Ala Ala Lys Met Met Phe Ala
            20                  25                  30

Ala Phe Thr Gln Phe Lys Glu Ala Gly Phe Asn Glu Glu Gln Ser Phe
        35                  40                  45

Glu Leu Thr Arg Glu Ile Leu Ile Asp Ser Leu Ser Lys Asn Gln
    50                  55                  60


<210> SEQ ID NO 100
<211> LENGTH: 134
<212> TYPE: PRT
<213> ORGANISM: Bacillus anthracis

<400> SEQUENCE: 100

Met Gly Lys Gly Tyr Phe Asn Lys Ala Val Cys Leu Val Cys Gly His
1               5                   10                  15

Gln Asp Arg Val Asn His Pro Ser Lys Lys Glu Tyr Gln Glu Val Thr
            20                  25                  30

Val Cys Pro Glu Cys Asn Gly Ala Phe Val Asp Val Trp Lys Leu Gly
        35                  40                  45

Lys Tyr Lys Arg Asn Thr Gln Ser Asn Glu Glu Pro Leu Leu Thr Ile
    50                  55                  60

Thr Leu Thr Asp Ile Asp Ala Lys Pro Ile Val His Tyr Lys Gly Glu
65                  70                  75                  80

Gln Ile Asp Arg Lys Leu Arg Val Thr Phe Asp Trp Glu Ser Gln Ser
                85                  90                  95

Ile Asp Lys Ile Asn Arg Thr Tyr Ile His Ile Glu His Val Pro Ala
```

-continued

```
            100                 105                 110

Asp Asn Lys Arg Leu Asn Thr Glu Thr Ile Gln His Asn His Pro Ile
        115                 120                 125

Ala Asn Lys Glu Gln Val
    130


<210> SEQ ID NO 101
<211> LENGTH: 84
<212> TYPE: PRT
<213> ORGANISM: Bacillus anthracis

<400> SEQUENCE: 101

Met Gln Val Tyr Cys Ser Glu Cys Asp Lys Ser Tyr Asp Met Gln Pro
1               5                   10                  15

Gln Val Thr Gln Leu Pro Asn Arg Ile Glu Lys Cys Phe Phe Ile Cys
            20                  25                  30

Pro His Cys Asn His Glu His Ile Ala Ala Tyr Val Asn Asp Lys Ile
        35                  40                  45

Arg Lys Tyr Gln Ala Asp Ile Ala Lys Cys His Glu Arg Ile Asn Lys
    50                  55                  60

Lys Asn Leu Ala Ile Glu Asp Glu Met Lys Arg Leu Arg Lys Arg Phe
65                  70                  75                  80

Asp Arg Arg Lys


<210> SEQ ID NO 102
<211> LENGTH: 63
<212> TYPE: PRT
<213> ORGANISM: Bacillus anthracis

<400> SEQUENCE: 102

Met Asn Gly Phe Asn Lys Ile Val Asn Asp Met Gln Asn Glu Gln Val
1               5                   10                  15

Gly Asn Ala Met Leu Asp Phe Ala Leu Ala Ala Lys Met Met Phe Ala
            20                  25                  30

Ala Phe Thr Gln Phe Lys Glu Ala Gly Phe Asn Glu Glu Gln Ser Phe
        35                  40                  45

Glu Leu Thr Arg Glu Ile Leu Ile Asp Ser Leu Ser Lys Asn Gln
    50                  55                  60


<210> SEQ ID NO 103
<211> LENGTH: 63
<212> TYPE: PRT
<213> ORGANISM: Bacillus anthracis

<400> SEQUENCE: 103

Met Glu Gly Gln Glu Leu Thr Leu Glu Lys Lys Asp Ser Ile Tyr Leu
1               5                   10                  15

Arg Pro Arg Tyr Pro His Lys Ile Asp Ala Ser Lys Ile Lys Ser Leu
            20                  25                  30

Lys Asp Val Ile Lys Ile Leu Gly Leu Met Asp Ile Arg Leu Asp Asp
        35                  40                  45

Lys Ala Val Ile Gly Leu Glu His Leu Ile Glu Lys Glu Glu Glu
    50                  55                  60


<210> SEQ ID NO 104
<211> LENGTH: 84
<212> TYPE: PRT
<213> ORGANISM: Bacillus anthracis
```

<400> SEQUENCE: 104

Met Gln Val Tyr Cys Ser Glu Cys Asp Lys Ser Tyr Asp Met Gln Pro
1               5                   10                  15

Gln Val Thr Gln Leu Pro Asn Arg Ile Glu Lys Cys Phe Phe Ile Cys
            20                  25                  30

Pro His Cys Asn His Glu His Ile Ala Ala Tyr Val Asn Asp Lys Ile
        35                  40                  45

Arg Lys Tyr Gln Ala Asp Ile Ala Lys Cys His Glu Arg Ile Asn Lys
    50                  55                  60

Lys Asn Leu Ala Ile Glu Asp Glu Met Lys Arg Leu Arg Lys Arg Phe
65                  70                  75                  80

Asp Arg Arg Lys

<210> SEQ ID NO 105
<211> LENGTH: 95
<212> TYPE: PRT
<213> ORGANISM: Bacillus anthracis

<400> SEQUENCE: 105

Leu Lys Arg Arg Lys Asn Lys Met Ala Asn Asn Lys Leu Ile Ile Glu
1               5                   10                  15

Val Thr Ala Asp Thr Thr Glu Ala Leu Glu Gly Ile Lys Glu Val Thr
            20                  25                  30

Glu Ala Ala Asn Glu Cys Ala Asp Ala Leu Asp Lys Leu Glu Lys Ile
        35                  40                  45

Met Asp Lys Phe Thr Asn Arg Ser Asp Thr Val Glu Leu Tyr Cys Glu
    50                  55                  60

Gly Lys Leu Leu Ser Lys Ser Thr Val Asn His Thr Ala Asp Ser Ile
65                  70                  75                  80

Gln Cys Arg Ile Ile Lys Gly Glu Glu Leu Gly Gly Ser Glu Arg
                85                  90                  95

<210> SEQ ID NO 106
<211> LENGTH: 63
<212> TYPE: PRT
<213> ORGANISM: Bacillus anthracis

<400> SEQUENCE: 106

Met Glu Gly Gln Glu Leu Thr Leu Glu Lys Lys Asp Ser Ile Tyr Leu
1               5                   10                  15

Arg Pro Arg Tyr Pro His Lys Ile Asp Ala Ser Lys Ile Lys Ser Leu
            20                  25                  30

Lys Asp Val Ile Lys Ile Leu Gly Leu Met Asp Ile Arg Leu Asp Asp
        35                  40                  45

Lys Ala Val Ile Gly Leu Glu His Leu Ile Glu Lys Glu Glu Glu
    50                  55                  60

<210> SEQ ID NO 107
<211> LENGTH: 127
<212> TYPE: PRT
<213> ORGANISM: Bacillus anthracis

<400> SEQUENCE: 107

Met Lys Lys Pro Leu Arg Pro Cys Cys Glu Phe His Cys Tyr Asn Leu
1               5                   10                  15

Thr Arg Glu Arg Tyr Cys Glu Glu His Arg Tyr Lys Glu Lys Glu Thr
            20                  25                  30

-continued

```
Gln Gln Asp Lys Asn Arg Tyr Tyr Asp Arg Phe Lys Arg Asp Lys Glu
        35                  40                  45

Ser Thr Ala Phe Tyr Arg Ser Lys Ala Trp Glu Arg Leu Arg Glu Gln
    50                  55                  60

Ala Leu Met Arg Asp Lys Gly Leu Cys Leu His Cys Lys Asn Asn Arg
65                  70                  75                  80

Lys Ile Lys Val Ala Asp Met Val Asp His Ile Ile Pro Ile Lys Val
                85                  90                  95

Asp Pro Ser Leu Lys Leu Lys Leu Glu Asn Leu Gln Ser Leu Cys Asn
            100                 105                 110

Pro Cys His Asn Arg Lys Thr Ala Glu Asp Lys Lys Lys Tyr Gly
        115                 120                 125


<210> SEQ ID NO 108
<211> LENGTH: 95
<212> TYPE: PRT
<213> ORGANISM: Bacillus anthracis

<400> SEQUENCE: 108

Leu Lys Arg Arg Lys Asn Lys Met Ala Asn Asn Lys Leu Ile Ile Glu
1               5                   10                  15

Val Thr Ala Asp Thr Thr Glu Ala Leu Glu Gly Ile Lys Glu Val Thr
            20                  25                  30

Glu Ala Ala Asn Glu Cys Ala Asp Ala Leu Asp Lys Leu Glu Lys Ile
        35                  40                  45

Met Asp Lys Phe Thr Asn Arg Ser Asp Thr Val Glu Leu Tyr Cys Glu
    50                  55                  60

Gly Lys Leu Leu Ser Lys Ser Thr Val Asn His Thr Ala Asp Ser Ile
65                  70                  75                  80

Gln Cys Arg Ile Ile Lys Gly Glu Glu Leu Gly Gly Ser Glu Arg
                85                  90                  95


<210> SEQ ID NO 109
<211> LENGTH: 127
<212> TYPE: PRT
<213> ORGANISM: Bacillus anthracis

<400> SEQUENCE: 109

Met Lys Lys Pro Leu Arg Pro Cys Cys Glu Phe His Cys Tyr Asn Leu
1               5                   10                  15

Thr Arg Glu Arg Tyr Cys Glu Glu His Arg Tyr Lys Glu Lys Glu Thr
            20                  25                  30

Gln Gln Asp Lys Asn Arg Tyr Tyr Asp Arg Phe Lys Arg Asp Lys Glu
        35                  40                  45

Ser Thr Ala Phe Tyr Arg Ser Lys Ala Trp Glu Arg Leu Arg Glu Gln
    50                  55                  60

Ala Leu Met Arg Asp Lys Gly Leu Cys Leu His Cys Lys Asn Asn Arg
65                  70                  75                  80

Lys Ile Lys Val Ala Asp Met Val Asp His Ile Ile Pro Ile Lys Val
                85                  90                  95

Asp Pro Ser Leu Lys Leu Lys Leu Glu Asn Leu Gln Ser Leu Cys Asn
            100                 105                 110

Pro Cys His Asn Arg Lys Thr Ala Glu Asp Lys Lys Lys Tyr Gly
        115                 120                 125
```

LYTIC ENZYMES AND SPORE SURFACE ANTIGEN FOR DETECTION AND TREATMENT OF *BACILLUS ANTHRACIS* BACTERIA AND SPORES

This application is the national phase under 35 U.S.C. § 371 of PCT International Application No. PCT/US2005/009928, which has an International filing date of Mar. 23, 2005 and designated the United States of America, which in turn claims priority to U.S. Patent Application Ser. No. 60/555,916, "Lytic Enzymes and Spore Surface Antigen for Detection and Treatment of *Bacillus Anthracis* Bacteria and Spores" (Fischetti, et. al.), filed Mar. 24, 2004 and incorporated herein by reference in its entirety.

TECHNICAL FIELD

The present invention relates to the identification and characterization of environmental bacteriophages infecting *Bacillus anthracis*. Specifically, the invention relates to certain isolated sequences for the gamma (γ)-phage and the W-phage of *B. anthracis*, nucleic acids of each genome, nucleic acids comprising nucleotide sequences of open reading frames (ORF's) of its genome, and polypeptides encoded by the nucleic acids.

BACKGROUND

Anthrax is a disease is believed to be caused by the spore-forming bacterium, *Bacillus anthracis*, a bacterium that is readily found in soil. *B. anthracis* is believed to primarily cause disease in plant-eating animals. Though infrequent, when humans do become infected, they usually acquire the bacterium from contact with infected animals, animal hides or hair, or animal feces. The human disease has a relatively short incubation period (less than a week) and usually progresses rapidly to a fatal outcome.

In humans, anthrax may occur in three different forms: coetaneous anthrax, gastrointestinal anthrax and inhalation anthrax. Coetaneous anthrax, the most common form in humans, is usually acquired when the bacterium, or spores of the bacterium, enter the body through an abrasion or cut on the skin. The bacteria multiply at the site of the abrasion, cause a local edema, and a series of skin lesions—papule, vesicle, pustule and necrotic ulcer—are sequentially produced. Lymph nodes nearby the site are eventually infected by the bacteria and, in cases where the organisms then enter the bloodstream (20% of cases), the disease is often fatal. Gastrointestinal anthrax is caused by eating contaminated meat. Initial symptoms include nausea, vomiting and fever. Later, infected individuals present with abdominal pain, severe diarrhea and vomiting of blood. This type of anthrax is fatal in 25% to 60% of cases. Inhalation anthrax (also called woolsorters' disease) is acquired through inhalation of the bacteria or spores. Initial symptoms are similar to those of a common cold. Symptoms then worsen and these individuals present with high fever, chest pain and breathing problems. The infection normally progresses systemically and produces a hemorrhagic pathology. Inhalation anthrax is fatal in almost 100% of cases.

Coetaneous anthrax is acquired via injured skin or membranes, entry sites where the spore germinate into vegetative cells. Proliferation of vegetative cells results in gelatinous edema. Alternatively, inhalation of the spores results in high fever and chest pain. Both types may be fatal unless the invasive aspect of the infection may be intercepted.

*B. anthracis* is believed to possess two major virulence components. The first virulence component is a polysaccharide capsule which contains poly-D-glutamate polypeptide. The poly-D-glutamate capsule is not itself toxic but plays an important role in protecting the bacterium against anti-bacterial components of serum and phagocytic engulfment. As the *B. anthracis* bacterium multiplies in the host, it produces a secreted toxin which is the second virulence component of the organism. This anthrax toxin mediates symptoms of the disease in humans.

The anthrax toxin is believed to comprise three distinct proteins encoded by the bacterium: protective antigen (PA), lethal factor (LF) and edema factor (EF). PA is the component of the anthrax toxin that is believed to bind to host cells using an unidentified cell-surface receptor. Once it binds to cell surfaces, EF or LF may subsequently interact with the bound PA. The complexes are then internalized by the host cell with significant effects. EF is an adenylate cyclase which causes deregulation of cellular physiology, resulting in edema. LF is a metalloprotease that cleaves specific signal transduction molecules within the cell (MAP kinase isoforms), causing deregulation of said pathways, and cell death. Injection of PA, LF or EF alone, or LF in combination with EF, into experimental animals produces no effects. However, injection of PA plus EF produces edema. Injection of PA plus LF is lethal, as is injection of PA plus EF plus LF.

As an acute, febrile disease of virtually all warm-blooded animals, including man, anthrax can be used in biological weapons (BW). For example, ten grams of anthrax spore may kill as many people as a ton of the chemical warfare agent, sarin. Terrorists have included dry spores in letters. Biological weapons of mass destruction have been developed that contain large quantities of anthrax spores for release over enemy territory. Once released, spores may contaminate a wide geographical area, infecting nearly all susceptible mammals. Due to the spore's resistance to heat and dry conditions, contaminated land may remain a danger for years. In view of the serious threat posed by the disease, effective diagnostic tools are needed to assist in prevention and control of natural and man-made outbreaks. Due to the highly lethal nature of anthrax and BW agents in general, there is great need for the development of sensitive and rapid BW agent detection. Current detection technology for biological warfare agents have traditionally relied on time-consuming laboratory analysis or onset of illness among people exposed to the BW agent.

One promising approach to the detection and treatment of *B. anthracis* is the use of bacteriophage lysins as bacteriolytic agents. Bacteriophages specific for *B. anthracis* and related *B. cereus* bacteria strains may be isolated and used to detect and treat these bacteria. Bacteriophages near *B. anthracis* spores during spore germination may be used to infect and lyse the bacteria. A variety of phage-based bacterial therapies have been reviewed. D. H. Duckworth, P. A. Gulig, "Bacteriophages: Potential treatment for bacterial infections," *BioDrugs,* 16(1), 57-62 (2002). There are various environmental bacteriophages present in soils that may infect and lyse *B. anthracis* under controlled conditions. H. W. Ackermann, et al., "New Bacillus bacteriophage species," *Archives of virology,* 135(3-4), 333-344 (1994); H. W. Ackerman, M. S. Dubrow, *Viruses of prokaryotes: General properties of bacteriophages*, Boca Raton, Fla., CRC Press, Inc. (1989);

A bacterial lysin called PlyG, from bacteriophage-γ of *B. anthraci*, has been shown to lyse vegetative *B. anthracis* cells and is useful in promising methods for treatment of anthrax. R. Schuch, D. Nelson, V. Fischetti, "A bacteriolytic agent that detects and kills *Bacillus anthracis*," *Nature* 418, 884-889 (2002), incorporated herein by reference. A nucleotide sequence encoding PlyG is disclosed in GenBank accession #AF536823 and has a molecular mass of about 27,000. PlyG has been shown to control anthrax disease in mice, and to bind to vegetative cells. However, PlyG has no means to replicate itself in the presence of host bacteria. Methods and composition for the treatment of a variety of bacterial infections using a phage associated lytic enzyme specific for the invasive bacteria and an appropriate carrier for delivering the lytic enzyme into a patient are discussed in the following U.S. patents issued to Fischetti et al.: U.S. Pat. Nos. 5,604,109; 5,985,271; 6,056,954; 6,056,955 6,248,324; 6,254,866; and 6,264,945, all incorporated herein by reference. Effective treatment of 14 of 24 virulent *B. anthracis* strains by phage based methods has been reported in a preliminary study done at Johns Hopkins University Applied Physics Laboratory. Michael Walter, Ph.D., "Efficacy and Durability of *Bacilus anthracis* Bacteriophages Used Against Spores," *Journal of Environmental Health*, July/August 2003, 9-15.

Bacteriophages for *B. anthracis* may be isolated from the environment. For instance, Walter et al. report the isolation of Phages Nk, DB and MH for *B. anthracis* in topsoil. Walter, M H, Baker, D D, "Three *Bacillus anthracis* bacteriophages from topsoil," Curr Microbiol. 2003 July; 47(1): 55-58. Further bacteriophages useful for detection and treatment of *B. anthracis* are reported herein. The W and γ environmental bacteriophages of *B. anthracis* have been identified in topsoil, but the isolation of the polynucleotide and the identification of open reading frames coding for various polypeptides therein were unknown. E. W. McCloy, "Studies of a lysogenic *Bacillus* strain. I. A bacteriophage specific for *Bacillus anthracis," Journal of Hygiene,* 49(1), 114-125 (1951); E. R. Brown, W. B. Cherry, "Specific identification of *Bacillus anthracis* by means of a variant bacteriophage," *Journal of Infectious Diseases,* 96(1), 34-39 (1955).

The direct introduction of bacteriophages into an animal to prevent or fight diseases has certain drawbacks. Specifically, both the bacteria and the phage have to be in the correct and synchronized growth cycles for the phage to attach. Additionally, there are preferably the right number of phages to attach to the bacteria; if there are too many or too few phages, there will be either no attachment or no production of the lysing enzyme. The phage is preferably active enough to be effective. The phages may also be inhibited by many things including bacterial debris from the organism it is going to attack. Further complicating the direct use of a bacteriophage to treat bacterial infections is the possibility of immunological reactions within the subject being treated, potentially rendering the phage non-functional. The ability of bacteriophages to lyse and kill target bacterial may also be decreased by sunlight, UV light, desiccation or other conditions encountered during storage or use of a phage-containing therapeutic agent. Therefore, the potential effectiveness of any given bacteriophage against a target bacteria depends on the conditions under which the phage is deployed against the target bacteria. Studying the structure of phages and their efficacy against target bacteria in various conditions are useful in developing therapeutic methods for treating and preventing disease caused by target bacteria. Investigations of the structure and function of phages may also relate to diagnostic methods for detecting target bacteria and spores, such as those of *B. anthracis*. Many environmental conditions that may alter the effectiveness of a phage, such as phage W and phage-γ, against a *B. anthracis* or related target bacteria. The isolation and analysis of the phage polynucleotide sequences, and associated polypeptide sequences, of these and other phages are needed to relate to effective methods for prevention, treatment and diagnosis of *B. anthracis* bacteria and spores.

SUMMARY

Two bacteriophages of *B. anthracis*, bacteriophage gamma (γ) and bacteriophage W, can be isolated. Applicants have isolated and characterized various bacteriophages active against *B. anthracis*. The γ and W bacteriophages for *B. anthracis*, the nucleic acid sequence of these bacteriophage genomes, portions of the nucleic acid sequence of the bacteriophage genome (e.g., a portion containing an open reading frame), and proteins encoded by the nucleic acid sequences, as well as nucleic acid constructs comprising portions of the nucleic acid sequence of the bacteriophage genome, and host cells comprising such nucleic acid constructs are provided herein.

More particularly, in some embodiments, the invention relates to certain nucleic acids of the genome of bacteriophages γ and W, as well as to the nucleic acids of portions of the genome of bacteriophages γ and W; to isolated nucleic acid molecules containing a nucleotide sequence of an open reading frame (or more than one open reading frame) of the genomes of bacteriophages γ and W; to isolated nucleic acid molecules encoding a polypeptide obtainable from bacteriophages γ and W or an active derivative or fragment of the polypeptide (e.g., a DNA polymerase, such as a DNA polymerase lacking exonuclease domains; a 3'-5' exonuclease, such as a 3'-5' exonuclease lacking DNA polymerase domain; a 5'-3' exonuclease (RNase H); a DNA helicase; or an RNA ligase); to DNA constructs containing the isolated nucleic acid molecule operatively linked to a regulatory sequence; and also to host cells comprising the DNA constructs. The invention further relates to isolated polypeptides encoded by these nucleic acids, as well as active derivatives or fragments of the polypeptides.

In particular embodiments, the present invention relates to an isolated nucleic acid sequences that are at least 60%, 70%, 80%, 90%, 95%, 97%, 98-100% or 100% identical to a polynucleotide sequences encoded by SEQ ID NO:1, SEQ ID NO:2, SEQ ID NO:110, SEQ ID NO:111, SEQ ID NO:112 or SEQ ID NO:113 and to a polynucleotide sequence encoding a polypeptide selected from SEQ ID NO:3-SEQ ID NO:109. In other embodiments, the polynucleotide of the invention is an isolated nucleic acid consisting of the sequence of SEQ ID NO:1 or SEQ ID NO:2, and an open reading frame (ORF) portion therein as identified in Table 1 or Table 2 below. The invention relates to an isolated nucleic acid sequence of SEQ ID NO:1, an open reading frame of SEQ ID NO:1 set forth in Table 1, SEQ ID NO:2, or an open reading frame of SEQ ID NO:2 set forth in Table 2, with up to 5, 10, 20, 30, 40, 50, 60, 80, 100 or more conservative nucleic acid substitutions. Further provided are nucleic acid sequences of SEQ ID NO:110, SEQ ID NO:111, SEQ ID NO:112 or SEQ ID NO:113 with up to 5, 10 or 20 conservative nucleic acid substitutions. The invention also relates to an isolated nucleic acid molecule comprising 5, 10, 20, 30, 40, 50, 60, 70, 80, 90, 100 or more contiguous nucleotides of SEQ ID NO:1 or SEQ ID NO:2. Other embodiments relate to an isolated nucleic acid molecule comprising contiguous nucleotides of an open reading frame from SEQ ID NO:1 or SEQ ID NO:2. Still other embodiments relate to a DNA construct comprising an isolated nucleic acid molecule comprising the nucleotide sequence of an open reading frame SEQ ID NO:1 or SEQ ID NO:2, operatively linked to a regulatory sequence, or the nucleic acid sequences of SEQ ID NO:110, SEQ ID NO:111, SEQ ID NO:112 or SEQ ID NO:113.

The invention further relates to a polypeptide comprising a polypeptide sequence selected from SEQ ID NO:3-SEQ ID NO:109. Some embodiments relate to a purified polypeptide, the amino acid sequence of which comprises a sequence at least 60%, 70%, 80%, 90%, 95%, 97%, 98-100% or 100% identical to a polypeptide sequence selected from SEQ ID NO:3-SEQ ID NO:109. Also provided is an isolated nucleic acid sequence encoding a polypeptide comprising the amino acid sequence set forth in a polypeptide sequence selected from SEQ ID NO:3-SEQ ID NO:109, with up to 5, 10, 20, 30, 40, 50, 60, 80, 100 or more conservative amino acid substitutions. The invention also relates to a purified polypeptide, the amino acid sequence of which consists of a polypeptide sequence selected from SEQ ID NO:3-SEQ ID NO:109. Other embodiments of the invention relate to a purified polypeptide, the amino acid sequence of which is encoded by an open reading frame from SEQ ID NO:1 or SEQ ID NO:2.

The invention relates to polypeptides encoded by SEQ ID NO:1 or SEQ ID NO:2 that are able to infect *B. anthracis* or RSVF1 bacteria. Particular embodiments relate to polypeptide sequences that infect *B. anthracis* or RSVF1 to a greater extent than other *B. cereus* bacteria. For example, some polypeptides of the invention may bind to *B. cereus* bacteria other than *B. anthracis* or RSVF1 at less than 100 plaque forming units/ml (PFU/ml), or even less than 10 PFU/ml, or less than 1 PFU/ml. In one embodiment, the invention relates to polypeptides encoded by SEQ ID NO:1 or SEQ ID NO:2 that are able to specifically bind to *B. anthracis* or RSVF1. The nucleic acid may encode one or more polypeptides that are able to infect *B. anthracis*. The nucleic acid may also encode one or more polypeptides that are able to bind to the surface of *B. anthracis*. The nucleic acid may also encode one or more polypeptides that exhibit fosfomycin resistance. The nucleic acid may encode one or more polypeptides that are spore surface antigens of *B. anthracis.*

In one embodiment, the invention relates to a polypeptide encoded by the ORF 14 portion of SEQ ID NO:1, the polypeptide of SEQ ID NO:29, the polypeptide encoded by the ORF 14 portion of SEQ ID NO:2, or the polypeptide of SEQ ID NO:30, wherein the polypeptide is able to bind to the surface of *B. anthracis*. In another embodiment, the invention relates to a polypeptide encoded by the ORF17 portion of SEQ ID NO:1, the polypeptide of SEQ ID NO:35, the polypeptide encoded by the ORF 17 portion of SEQ ID NO:2, or the polypeptide of SEQ ID NO:36, wherein the polypeptide kills *B. anthracis*. In yet another embodiment, the invention relates to a polypeptide encoded by the ORF 41 portion of SEQ ID NO:1, or the polypeptide of SEQ ID NO:83, wherein the polypeptide exhibits Fosfomycin resistance. In further embodiments, the invention relates to the polypeptide encoded by the ORF 39 portion of SEQ ID NO:2, or the polypeptide of SEQ ID NO:82, wherein the polypeptide is a surface antigen of *B. anthracis.*

Further provided are isolated nucleic acids that hybridize under high stringency conditions to the sequence of SEQ ID NO:1, SEQ ID NO:2, or open reading frame portions thereof as detailed in Table 1 and Table 2. In one embodiment, the invention relates to an isolated nucleic acid that hybridizes under high stringency conditions to a nucleic acid encodes a polypeptide that comprises a polypeptide sequence selected from SEQ ID NO:3-SEQ ID NO:109.

Also provided is an isolated nucleic acid that hybridizes under high stringency conditions to the sequence of the ORF 14 from SEQ ID NO:1, or the ORF 14 from SEQ ID NO:2, wherein said nucleic acid encodes a polypeptide that is able to bind to the surface of *B. anthracis*. Further provided is an isolated nucleic acid that hybridizes under high stringency conditions to the sequence of the ORF 17 from SEQ ID NO:1, or the ORF 17 from SEQ ID NO:2, wherein said nucleic acid encodes a polypeptide that is kills *B. anthracis*. Further provided is an isolated nucleic acid that hybridizes under high stringency conditions to the sequence of the ORF 41 from SEQ ID NO:1, wherein said nucleic acid encodes a polypeptide exhibits Fosfomycin resistance. Also provided is an isolated nucleic acid that hybridizes under high stringency conditions to the sequence of the ORF 39 from SEQ ID NO:2, wherein said nucleic acid is a spore surface antigen of *B. anthracis.*

Further provided are expression vectors comprising the nucleic acid sequence associated with ORF 14 from SEQ ID NO:1, the ORF 14 from SEQ ID NO:2, the ORF 17 from SEQ ID NO:1, the ORF 17 from SEQ ID NO:2, the ORF 41 from SEQ ID NO:1 or the ORE 39 from SEQ ID NO:2, operably associated with a promoter, and associated host cells comprising these vectors. Further provided are methods for preparing a polypeptide, each method comprising the step of culturing the host cell comprising the nucleotide sequence associated with ORF 14 from SEQ ID NO:1, the ORF 14 from SEQ ID NO:2, the ORF 17 from SEQ ID NO:1, the ORF 17 from SEQ ID NO:2, the ORF 41 from SEQ ID NO:1 or the ORF 39 from SEQ ID NO:2, under conditions that permit expression of the polypeptide from the expression vector, and isolating the polypeptide from the host cell. The invention also relates to an isolated nucleic acid comprising a sequence that hybridizes under high stringency conditions to a hybridization probe, the nucleotide sequence of which comprises or consists of ORF 14 from SEQ ID NO:1, the ORF 14 from SEQ ID NO:2, the ORF 17 from SEQ ID NO:1, the ORF 17 from SEQ ID NO:2, the ORF 41 from SEQ ID NO:1 or the ORF 39 from SEQ ID NO:2, or the complements thereof. Further provided is an isolated nucleic acid comprising a sequence that hybridizes under high stringency conditions to a hybridization probe, the nucleotide sequence of which encodes the protein of a polypeptide sequence encoded by the ORF 14 from SEQ ID NO:1, the ORF 14 from SEQ ID NO:2, the ORF 17 from SEQ ID NO:1, the ORF 17 from SEQ ID NO:2, the ORF 41 from SEQ ID NO:1 or the ORF 39 from SEQ ID NO:2, or the nucleotide sequence of which encodes the protein encoded by these ORFs.

Other embodiments of the instant invention include an isolated nucleic acid comprising a sequence that hybridizes under high stringency conditions to a hybridization probe, the nucleotide sequence of which consists of an open reading frame from SEQ ID NO:1 from Table 1, an open reading frame from SEQ ID NO:2 from Table 2, SEQ ID NO:110, SEQ ID NO:111, SEQ ID NO:112 or SEQ ID NO:113 or the complements thereof. The invention also relates to an isolated nucleic acid comprising a sequence that hybridizes under high stringency conditions to a hybridization probe, the nucleotide sequence of which encodes the protein of a polypeptide sequence selected from SEQ ID NO:3-SEQ ID NO:109.

The invention further relates to an expression vector comprising the nucleic acid sequence of SEQ ID NO:1 or SEQ ID NO:2 or an open reading frame thereof as noted in Table 1 or Table 2, operably associated with a promoter, or a host cell comprising said vector. The invention also relates to an isolated nucleic acid comprising a sequence that encodes a protein of a polypeptide sequence selected from SEQ ID NO:3-SEQ ID NO:109, operably associated with a promoter, or a host cell comprising said vector.

The invention also relates to methods for preparing a polypeptide, the method comprising the step of culturing the host cell under conditions that permit expression of the polypeptide from the expression vector, and isolating the polypeptide from the host cell.

The invention also relates to methods of screening for a compound that binds to a polypeptide, the method comprising: providing the nucleic acid of an open reading frame from SEQ ID NO:1 or SEQ ID NO:2, or an isolated nucleic acid comprising a sequence that encodes a protein of a polypeptide sequence selected from SEQ ID NO:3-SEQ ID NO:109, and introducing the nucleic acid into a cell and allowing the cell to produce the polypeptide encoded by the nucleic acid, contacting a test compound with the polypeptide, and determining whether the test compound has bound to the polypeptide.

The invention also relates to a method of screening for a compound that binds to a polypeptide, the method comprising: providing the nucleic acid encoding the polypeptide selected from the group consisting of: SEQ ID NO:3-SEQ ID NO:109, introducing the nucleic acid into a cell and allowing the cell to produce the polypeptide encoded by the nucleic acid, contacting a test compound with the polypeptide, and determining whether the test compound has bound to the polypeptide.

BRIEF DESCRIPTION OF THE DRAWINGS

FIGS. 1A-1B (FIG. 1A, FIG. 1B) show the nucleotide (FIG. 1A; SEQ ID NO:1) and amino acid (FIG. 1B) sequences of *Bacillus anthracis* bacteriophage-γ.

FIGS. 2A-2B show the nucleotide (FIG. 1A; SEQ ID NO:2) and amino acid (FIG. 1B) sequences of *Bacillus anthracis* bacteriophage-W.

DETAILED DESCRIPTION

Figure 3:
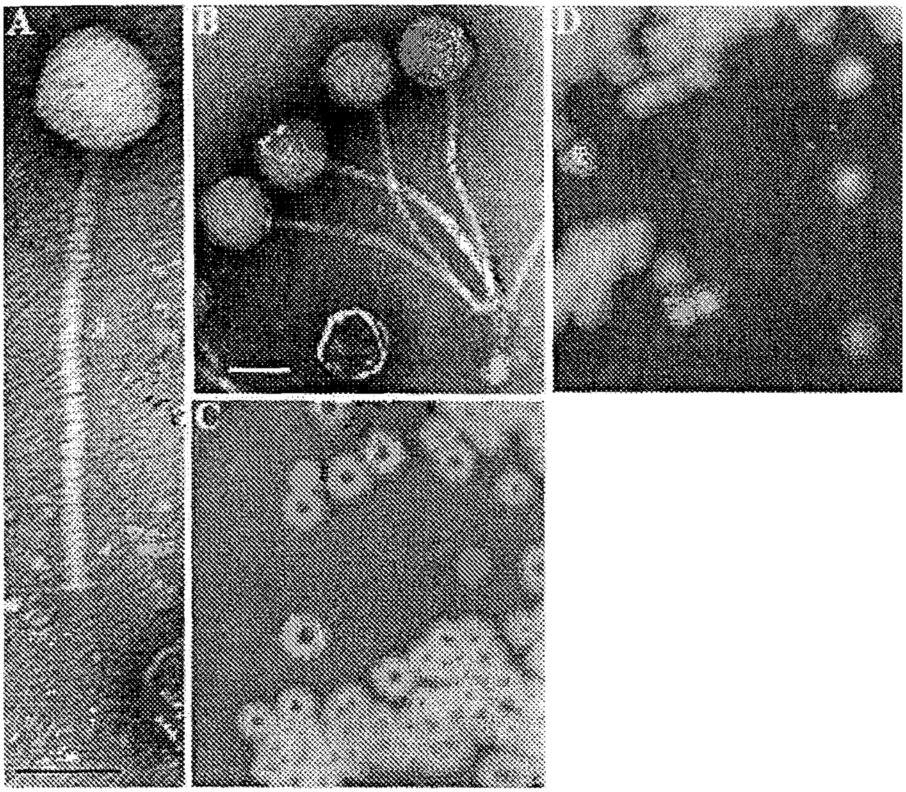
FIG. 3A is an electron microscope view of the page-γ.
FIG. 3B is an electron micrograph of page-γ particles adhered to cellular debris via the tips of the tail fibers.
FIG. 3C is an electron micrograph showing induction of unusual ring-shaped colonies of *B. cereus* strain ATCC 11950 with phage-W in the presence of fosfomyin.
FIG. 3D is an electron micrograph showing absence of ring-shaped colonies of *B. cereus* strain ATCC 11950 with phage-W in the absence of fosfomyin.

The invention relates to the identification and characterization of an environmental bacteriophage infecting both *B. anthracis* and a transition state *B. cereus* strain, and thus establishing a means for genetic exchange between the two. Lysogeny of either organism exerts profound phenotypic changes and with *B. anthracis*, involves the acquisition of *B. cereus*-like features.

A definition of terms used and their applicability to the disclosure are provided as follows:

In this context of the embodiments, the term "lytic enzyme genetically coded for by a bacteriophage" means a polypeptide having at least some lytic activity against the host bacteria. The polypeptide has a sequence that encompasses a native sequence of a lytic enzyme and variants thereof. The polypeptide may be isolated from a variety of sources, such as from phage, or prepared by recombinant or synthetic methods, such as those by Garcia et al. Every polypeptide has two domains. One domain is a choline binding portion at the carboxyl terminal side and the other domain is an amidase activity that acts upon amide bonds in the peptidoglycan at the amino terminal side. Generally speaking, a lytic enzyme according to the disclosure is between 25,000 and 35,000 daltons in molecular weight and comprises a single polypeptide chain; however, this may vary depending on the enzyme chain. The molecular weight most conveniently is determined by assay on denaturing sodium dodecyl sulfate gel electrophoresis and comparison with molecular weight markers.

The term "purified" means that the biological material has been measurably increased in concentration by any purification process, including by not limited to, column chromatography, HPLC, precipitation, electrophoresis, etc., thereby partially, substantially or completely removing impurities such as precursors or other chemicals involved in preparing the material. Hence, material that is homogenous or substantially homogenous (e.g., yields a single protein signal in a separation procedure such as electrophoresis or chromatography) is included within the meanings of isolated and purified. Skilled artisans will appreciated that the amount of purification necessary will depend upon the use of the material. For example, compositions intended for administration to humans ordinarily may be highly purified in accordance with regulatory standards.

"A native sequence phage associated lytic enzyme" is a polypeptide having the same amino acid sequence as an enzyme derived from nature. Such native sequence enzyme may be isolated from nature or may be produced by recombinant or synthetic means. The term "native sequence enzyme" specifically encompasses naturally occurring forms (e.g., alternatively spliced or modified forms) and naturally-occurring variants of the enzyme. In one embodiment of the disclosure, the native sequence enzyme is a mature or full-length polypeptide that is genetically coded for by a gene from a bacteriophage specific for *Bacillus anthracis*. Of course, a number of variants are possible and known, as acknowledged in publications such as Lopez et al., Microbial Drug Resistance 3: 199-211 (1997); Garcia et al., Gene 86: 81-88 (1990); Garcia et al., Proc. Natl. Acad. Sci. USA 85: 914-918 (1988); Garcia et al., Proc. Natl. Acad. Sci. USA 85: 914-918 (1988); Garcia et al., Streptococcal Genetics (J. J. Ferretti and Curtis eds., 1987); Lopez et al., FEMS Microbiol. Lett. 100: 439-448 (1992); Romero et al., J. Bacteriol. 172: 5064-5070 (1990); Ronda et al., Eur. J. Biochem. 164: 621-

624 (1987) and Sanchez et al., Gene 61: 13-19 (1987). The contents of each of these references, particularly the sequence listings and associated text that compares the sequences, including statements about sequence homologies, are specifically incorporated by reference in their entireties.

"A variant sequence phage associated lytic enzyme" means a functionally active lytic enzyme genetically coded for by a bacteriophage specific for *Bacillus anthracis*, as defined below, having at least 50%, 55%, 60%, 65%, 70%, 75%, 80%, 85%, 90%, 95%, 97%, 98%, 99%, or even at least 99.5% sequence identity with the amino acid or polynucleotide sequences shown below, or portions thereof. Of course a skilled artisan readily will recognize portions of this sequence that are associated with functionalities such as binding, and catalyzing a reaction. Polypeptide sequences and nucleic acids that encode these sequences are contemplated by some embodiments that comprise at least 75%, 80%, 85%, 90%, 95%, 97%, 98%, 99% or more of each functional domain or open reading frame from the sequences provided herein. Such portions of the total sequence are very useful for diagnostics as well as therapeutics/prophylaxis. In fact, sequences as short as 5 amino acids long have utility as epitopic markers for the phage. More desirably, larger fragments or regions of protein having a size of at least 8, 9, 10, 12, 15 or 20 amino acids, and homologous sequences to these, have epitopic features and may be used either as small peptides or as sections of larger proteins according to embodiments. Nucleic acids corresponding to these sequences also are contemplated.

Such phage associated lytic enzyme variants include, for instance, lytic enzyme polypeptides wherein one or more amino acid residues are added, or deleted at the N or C terminus of the sequences provided. In an embodiment one or more amino acids are substituted, deleted, and/or added to any position(s) in the sequence, or sequence portion. Ordinarily, a phage associated lytic enzyme will have at least about (e.g. exactly) 50%, 55%, 60%, 65%, 70%, 75%, amino acid sequence identity with native phage associated lytic enzyme sequences, more preferably at least about (e.g. exactly) 80%, 85%, 90%, 95%, 97%, 98%, 99% or 99.5% amino acid sequence identity. In other embodiments a phage associated lytic enzyme variant will have at least about 50% (e.g. exactly 50%), 55%, 60%, 65%, 70%, 75%, 80%, 85%, 90%, 95%, 97%, 98%, 99%, or even at least 99.5% amino acid sequence identity with the sequences provided, or portions thereof.

A polypeptide or amino acid "selected from SEQ ID NO:3-SEQ ID NO: 109" refers to a polypeptide sequence selected from the group consisting of: SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, SEQ ID NO:73, SEQ ID NO:74, SEQ ID NO:75, SEQ ID NO:76, SEQ ID NO:77, SEQ ID NO:78, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, and SEQ ID NO:109.

"Percent amino acid sequence identity" with respect to the phage associated lytic enzyme sequences identified herein is defined as the percentage of amino acid residues in a candidate sequence that are identical with the amino acid residues in the phage associated lytic enzyme sequence, after aligning the sequences in the same reading frame and introducing gaps, if necessary, to achieve the maximum percent sequence identity, and not considering any conservative substitutions as part of the sequence identity. Alignment for purposes of determining percent amino acid sequence identity may be achieved in various ways that are within the skill in the art, such as using publicly available computer software such as blast software. Those skilled in the art may determine appropriate parameters for measuring alignment, including any algorithms needed to achieve maximal alignment over the whole length of the sequences being compared.

In each case, of course conservative amino acid substitutions also may be made simultaneously in determining percent amino acid sequence identity. For example, a 15 amino acid long region of protein may have 50%, 55%, 60%, 65%, 70%, 75%, 80%, 85%, 90%, 95%, 97%, 98%, or 99% sequence homology with a polypeptide sequence selected from SEQ ID NO:3-SEQ ID NO:109, or portions thereof. At the same time, the 15 amino acid long region of the protein may also have up to 0.5%, 1%, 2%, 5%, 10%, 15%, 20%, 30%, 40%, 50%, 65%, 75%, or more amino acids replaced with conservative substitutions. Preferably the region will have fewer than 30%, 20%, 10% or even less conservative substitutions. The "percent amino acid sequence identity" calculation in such cases will be higher than the actual percent sequence identity when conservative amino acid substitutions have been made.

"Percent nucleic acid sequence identity" with respect to the phage associated lytic enzyme sequences identified herein is defined as the percentage of nucleotides in a candidate sequence that are identical with the nucleotides in the phage associated lytic enzyme sequence, after aligning the sequences and introducing gaps, if necessary, to achieve the maximum percent sequence identity. Alignment for purposes of determining percent nucleic acid sequence identity may be achieved in various ways that are within the scope of those skilled in the art, including but not limited to the use of publicly available computer software. Those skilled in the art may determine appropriate parameters for measuring alignment, including any algorithms needed to achieve maximal alignment over the full length of the sequences being compared.

"Polypeptide" refers to a molecule comprised of amino acids which correspond to those encoded by a polynucleotide sequence which is naturally occurring. The polypeptide may include conservative substitutions wherein the naturally occurring amino acid is replaced by one having similar properties, where such conservative substitutions do not alter the function of the polypeptide (see, for example, Lewin "Genes V" Oxford University Press Chapter 1, pp. 9-13 1994).

A "chimeric protein" or "fusion protein" comprises all or (preferably a biologically active) part of a polypeptide of the disclosure operably linked to a heterologous polypeptide. Chimeric proteins or peptides are produced, for example, by combining two or more proteins having two or more active sites. Chimeric protein and peptides may act independently on the same or different molecules, and hence have a potential to treat two or more different bacterial infections at the same time. Chimeric proteins and peptides also are used to treat a bacterial infection by cleaving the cell wall in more than one location.

The term "operably linked" means that the polypeptide of the disclosure and the heterologous polypeptide are fused in-frame. The heterologous polypeptide may be fused to the N-terminus or C-terminus of the polypeptide of the disclosure. Chimeric proteins are produced enzymatically by chemical synthesis, or by recombinant DNA technology. A number of chimeric lytic enzymes have been produced and studied. Gene E-L, a chimeric lysis constructed from bacteriophages phi X174 and MS2 lysis proteins E and L, respectively, was subjected to internal deletions to create a series of new E-L clones with altered lysis or killing properties. The lytic activities of the parental genes E, L, E-L, and the internal truncated forms of E-L were investigated in this study to characterize the different lysis mechanism, based on differences in the architecture of the different membranes spanning domains. Electron microscopy and release of marker enzymes for the cytoplasmic and periplasmic spaces revealed that two different lysis mechanisms may be distinguished depending on penetration of the proteins of either the inner membrane or the inner and outer membranes of the *E. coli*. FEMS Microbiol. Lett. 1998 Jul. 1, 164(1); 159-67 (incorporated herein by reference).

Isolated bacteriophages γ and W may be used in the study of the relationship between the bacteriophages and their host cells (e.g., *B. anthracis*, such as *B. anthracis* species ITI 378). Isolated bacteriophages γ and W may also be used as a vector to deliver nucleic acids to a host cell; that is, the bacteriophage may be modified to deliver nucleic acids comprising a gene from an organism other than the bacteriophage (a "foreign" gene). For example, nucleic acids encoding a polypeptide (e.g., an enzyme or pharmaceutical peptide) may be inserted into the genome of bacteriophages γ and W, using standard techniques. The resultant modified bacteriophage may be then used to infect host cells, and the protein encoded by the foreign nucleic acids may then be produced.

Phage, or bacterial viruses, are major mediators of bacterial genetic diversity. They persist in bacterial populations by stably integrating into the host genome (lysogenic growth as a prophage form) and/or by freely replicating within a host (lytic growth). During such passage the phage genome may acquire, maintain, and transmit "foreign" DNA (obtained from other phage or the bacterial host) which serves to enhance fitness of the host. This foreign DNA may promote bacterial exploitation of animal tissues (resulting from exotoxins, colonization factors, serum resistance proteins, etc.), and it is likely to promote survival in other niches as well. Despite the increasingly well described role for phage in pathogen evolution, their place in the pathogenesis of *B. anthracis* is unclear. Since the *B. anthracis* pool is so genetically uniform, it is unlikely that phage drive the mergence of distinctly pathogenic strains, as is the case for other Gram-positive pathogens like *Streptococcus pyogene* and *Staphylococcus aureus*. The role may rather be related to interactions (or a relationship) between *B. anthracis* and transition state *B. cereus*. Such possibility is based on studies from the 1940's and 50's showing that a lysogenic phage from the soil, called W, and a obligately lytic derivative thereof, called γ, infect both *B. anthracis* and the rare transition state *B. cereus* strains and thus may transmit information between the two. More recent studies suggest that several distinct naturally occurring and laboratory-induced *B. anthracis* phage may also infect certain *B. cereus* strains, which may have represented transition state isolates.

Without being limited by theory, it is believed that *B. anthracis* is a genetically monomorphic variant of the otherwise highly polymorphic *B. cereus* lineage, which also includes *B. cereus* and *B. thuringiensis*. *B. anthracis* isolates recovered from diverse geographical locations or from present and past outbreaks are genetically distinguishable largely by molecular typing schemes that discriminate distinct and stable allelic states based on variations of tandem nucleotide-repeat elements in a few hypervariable loci. Several alternate analyses of genetic polymorphisms (multilocus enzyme electophoretic studies, for example) show a very close phylogenetic relationship between *B. anthracis* and a group of rare *B. cereus* "transition state" strains, possessing both *B. anthracis*- and *B. cereus*-like qualities and that may be more readily recoverable from *B. anthracis* outbreak sites than is bona fide *B. anthracis*. The significance of this relationship to the ecology of anthrax is unclear. Currently, little is known regarding the fate of *B. anthracis* in the environment after host death, although it is held to involve stagnancy in the form of an absolutely dormant spore. Here, we report the identification and characterization of an environmental bacteriophage infecting both *B. anthracis* and a transition state *B. cereus* strain, and thus establishing a means for genetic exchange between the two. Lysogeny of either organism exerts profound phenotypic changes and with *B. anthracis*, involves the acquisition of *B. cereus*-like features.

One embodiment of the invention relates to isolated γ or W bacteriophage. "Isolated" γ or W bacteriophage refers to bacteriophage that has been separated, partially or totally, from its native environment (e.g., separated from *B. anthracis* host cells) ("native bacteriophage"), and also refers to bacteriophage that has been chemically synthesized or recombinantly produced ("recombinant bacteriophage"). A bacteriophage that has been "recombinantly produced" refers to a bacteriophage that has been manufactured using recombinant DNA technology, such as by inserting the bacteriophage genome into an appropriate host cell (e.g., by introducing the genome itself into a host cell, or by incorporating the genome into a vector, which is then introduced into the host cell).

Isolation and Preparation of Bacteriophages

Bacteriophages γ and W may be produced by inoculating appropriate host cells with the bacteriophage. Representative host cells in which the bacteriophage may replicate include *B. anthracis*. The host cells may be cultured in a suitable medium (e.g., medium 162 for Thermus as described by Degryse et al., Arch. Microbiol. 11 7:189-196 (1978), with 1/10 buffer and with 1% NaCl). In addition, the host cells may be cultured under conditions suitable for replication of the bacteriophage. For example, in a preferred embodiment, the host cells may be cultured at a temperature of at least approximately 50° C. In a more preferred embodiment, the host cells may be cultured at a temperature between about 50° C. and about 80° C. The bacteriophage may also be stored in a cell lysate at about 4° C.

Nucleic Acid Sequences

Another embodiment of the invention relates to isolated nucleic acid sequences obtainable from the genome of bacteriophages γ and W.

The nucleic acid molecules of the invention may be "isolated;" as used herein, an "isolated" nucleic acid molecule or nucleotide sequence is intended to mean a nucleic acid molecule or nucleotide sequence which is not flanked by nucleotide sequences which normally (in nature) flank the gene or nucleotide sequence (as in genomic sequences) and/or has been completely or partially purified from other transcribed sequences (e.g., as in an RNA library). For example, an isolated nucleic acid of the invention may be substantially isolated with respect to the complex cellular milieu in which it naturally occurs. In some instances, the isolated material will form part of a composition (for example, a crude extract containing other substances), buffer system or reagent mix. In other circumstance, the material may be purified to essential homogeneity, for example as determined by PAGE or column chromatography such as HPLC. Thus, an isolated nucleic acid molecule or nucleotide sequence may include a nucleic acid molecule or nucleotide sequence which is synthesized chemically or by recombinant means. Therefore, recombinant DNA contained in a vector may be included in the definition of "isolated" as used herein. Also, isolated nucleotide sequences include recombinant DNA molecules in heterologous organisms, as well as partially or substantially purified DNA molecules in solution. In vivo and in vitro RNA transcripts of the DNA molecules of the present invention may be also encompassed by "isolated" nucleotide sequences.

The present invention also relates to nucleotide sequences which may be not necessarily found in nature but that encode the polypeptides described below. Thus, DNA molecules which comprise a sequence which is different from the naturally-occurring nucleotide sequence but which, due to the degeneracy of the genetic code, encode the polypeptides described herein, such as SEQ ID NO:3-SEQ ID NO:109, are also provided. Embodiments of the invention also encompass variations of the nucleotide sequences of the invention, such as those encoding active fragments or active derivatives of the polypeptides as described below. Such variations may be naturally-occurring, or non-naturally-occurring, such as those induced by various mutagens and mutagenic processes. Intended variations include, but are not limited to, addition, deletion and substitution of one or more nucleotides which may result in conservative or non-conservative amino acid changes, including additions and deletions. Preferably, the nucleotide or amino acid variations are silent or conserved; that is, they do not alter the characteristics or activity of the encoded polypeptide.

The invention also relates to fragments of the isolated nucleic acid molecules described herein. The term "fragment" encompasses a portion of a nucleotide sequence described that is from at least about 25 contiguous nucleotides to at least about 50 contiguous nucleotides or longer in length. These fragments may be useful as probes and also as primers. Particularly preferred primers and probes selectively hybridize to the nucleic acid molecule encoding the polypeptides described herein. For example, fragments that encode polypeptides that retain activity, as described below, may be particularly useful.

The invention also relates to nucleic acid molecules that hybridize under high stringency hybridization conditions, such as for selective hybridization, to a nucleotide sequence described herein (e.g., nucleic acid molecules which specifically hybridize to a nucleotide sequence encoding polypeptides described herein, and, optionally, have an activity of the polypeptide). Hybridization probes may be oligonucleotides that may bind in a base-specific manner to a complementary strand of nucleic acid. Suitable probes include polypeptide nucleic acids, as described in (Nielsen et al., Science 254, 1497-1500 (1991)).

These nucleic acid molecules may be detected and/or isolated by specific hybridization (e.g., under high stringency conditions). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 60%, 75%, 85%, 95%). For example, certain high stringency conditions may be used which distinguish perfectly complementary nucleic acids from those of less complementarity.

"High stringency conditions," "moderate stringency conditions" and "low stringency conditions" for nucleic acid hybridizations are explained on pages 2.10.1-2.10.16 and pages 6.3.1-6 in Current Protocols in Molecular Biology (Ausubel, F. M. et al., "Current Protocols in Molecular Biology," John Wiley & Sons, (1998)) the teachings of which are hereby incorporated by reference. The exact conditions which determine the stringency of hybridization depend not only on ionic strength (e.g., 0.2.times.SSC, 0.1.times.SSC), temperature (e.g., room temperature, 42° C., 68° C.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions may be determined empirically.

By varying hybridization conditions from a level of stringency at which no hybridization occurs to a level at which hybridization is first observed, conditions which will allow a given sequence to hybridize (e.g., selectively) with the most similar sequences in the sample may be determined.

In one embodiment, PlyG may be used in the preparation of DNA, for example for hybridization studies. Using PlyG, DNA from *B. anthracis* can be rapidly and more gently extracted because of the specificity of PlyG for particular types of bacteria including *B. anthracis*. Accordingly, in this embodiment, less stringent hybridization conditions may be required to prepare DNA from bacteria that PlyG selectively acts upon than would otherwise be required in the absence of PlyG.

Exemplary conditions are described in Krause, M. H. and S. A. Aaronson, Methods in Enzymology, 200:546-556 (1991). Also, in, Ausubel, et al., "Current Protocols in Molecular Biology," John Wiley & Sons, (1998), which describes the determination of washing conditions for moderate or low stringency conditions. Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in T.sub.m of about 17° C. Using these guidelines, the washing temperature may be determined empirically for high, moderate or low stringency, depending on the level of mismatch sought.

For example, a low stringency wash may comprise washing in a solution containing 0.2.times. SSC/0.1% SDS for 10 min at room temperature; a moderate stringency wash may comprise washing in a prewarmed solution (42° C.) solution containing 0.2. times.SSC/0.1% SDS for 15 min at 42° C.; and a high stringency wash may comprise washing in prewarmed (68° C.) solution containing 0.1.times.SSC/0.1% SDS for 15 min at 68° C. Furthermore, washes may be performed repeatedly or sequentially to obtain a desired result as known in the art.

Equivalent conditions may be determined by varying one or more of the parameters given as an example, as known in the art, while maintaining a similar degree of identity or similarity between the target nucleic acid molecule and the primer or probe used. Hybridizable nucleic acid molecules may be useful as probes and primers, e.g., for diagnostic applications.

Examples of high stringency conditions may be selected from the group consisting of:

(a) 0.015 M sodium chloride/0.0015 M sodium citrate/0.1% sodium dodecyl sulfate at 50° C.;

(b) 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; and (c) 50% formamide, 5×SSC (0.75 M sodium chloride, 0.075 M sodium citrate), 50 mM sodium phosphate (pH 6.8), 0.1% sodium pyrophosphate, 5×Denhardt's solution, sonicated salmon sperm DNA (50 μg/ml), 0.1% sodium dodecyl sulphate, and 10% dextran sulfate at 42° C., with washes at 42° C. in 0.2×SSC (0.75 M sodium chloride, 0.075 M sodium citrate) and 50% formamide at 55° C., followed by a high-stringency wash consisting of 0.1×SSC (0.75 M sodium chloride, 0.075 N sodium citrate) containing EDTA at 55° C.

Such hybridizable nucleotide sequences may be useful as probes and primers for diagnostic applications. As used herein, the term "primer" refers to a single-stranded oligonucleotide which acts as a point of initiation of template-directed DNA synthesis under appropriate conditions (e.g., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer, but typically ranges from 15 to 30 nucleotides. Short primer molecules generally require cooler temperatures to form sufficiently stable hybrid complexes with the template. A primer need not reflect the exact sequence of the template, but are preferably sufficiently complementary to hybridize with a template. The term "primer site" refers to the area of the target DNA to which a primer hybridizes. The term "primer pair" refers to a set of primers including a 5' (upstream) primer that hybridizes with the 5' end of the DNA sequence to be amplified and a 3' (downstream) primer that hybridizes with the complement of the 3' end of the sequence to be amplified.

As described herein, the genome of bacteriophages γ and W have been sequenced. The polynucleotide sequence of bacteriophage γ is set forth in FIG. 1A (SEQ ID NO:1), and corresponding polypeptide sequences for open reading frames of SEQ ID NO:1 are set forth in FIG. 1B. There are approximately 53 open reading frames (ORFs) in the polynucleotide sequence, as set forth in Table 1. The polynucleotide sequence of bacteriophage W is set forth in FIG. 2A (SEQ ID NO:2), and corresponding polypeptide sequences for open reading frames of SEQ ID NO:2 are set forth in FIG. 2B. There are approximately 54 open reading frames (ORFs) in the polynucleotide sequence of bacteriophage W, as set forth in Table 2. Table 1 and Table 2 relate to the locus of each ORF; the number of nucleotides in the ORF; the structure and function of various putative proteins encoded therein; the protein identified by a BLAST search as being the closest match to certain putative proteins; and other information relating to the ORFs.

The invention thus relates to isolated nucleic acid sequence of the genome ("isolated genomic DNA") of the bacteriophages γ and W. The invention also relates to isolated nucleic acid sequence of the genome of bacteriophages γ and W. The invention additionally relates to isolated nucleic acid molecules comprising the nucleotide sequences of each of the ORFs described above or fragments thereof, as well as nucleic acid molecules comprising nucleotide sequences of more than one of the ORFs described above or fragments of more than one of the ORFs. The nucleic acid molecules of the invention may be DNA, or may also be RNA, for example, mRNA. DNA molecules may be double-stranded or single-stranded; single stranded RNA or DNA may be either the coding, or sense, strand or the non-coding, or antisense, strand. Preferably, the nucleic acid molecule comprises at least about 100 nucleotides, or at least one ORF, or more preferably at least about 150 nucleotides, and even more preferably at least about 200 nucleotides. The nucleotide sequence may be only that which encodes at least a fragment of the amino acid sequence of a polypeptide; alternatively, the nucleotide sequence may include at least a fragment of a coding sequence along with additional non-coding sequences such as non-coding 3' and 5' sequences (including regulatory sequences, for example). Certain preferred nucleotide sequences of the invention may consist essentially of one of the ORFs and its flanking sequences. For example, in certain preferred embodiments, the nucleotide sequence comprises one of the following ORFs: ORF 14 of the g-phage (Gp14), ORF 14 of the W-phage (Wp14), and ORF 38 of the W-phage (Wp38).

Bacteriophage Gamma (γ)

Analysis of the γ phage host range in Table 1 demonstrated its specificity for *B. anthracis* and RSVF1. By electron microscopy (FIG. 3A), γ is morphologically similar to members of the *Siphoviridae* family of tailed phages (double-stranded DNA viruses of the order *Caudovirales*) consisting of a DNA-filled isometric, icosahedral head (90 nm in diameter) and a long non-contractile tail (260 nm in length) connected distally to a small plate and a fibrous tail extension (75 nm in length). Phage particles adhered to cellular debris via the tips of the tail fibers (FIG. 3B).

A Fos resistance gene (ORF 41 or "Gp41") is found in γ and appears to be derived from a similar sequence in Ba prophage ϕ4537. This is based on 99% identity at the DNA level between gp39, pg40 and gp41 and sequences in a Ba prophage. The DNA surrounding this region of homology is quite divergent, suggesting the acquisition of the island by γ through recombination with the ϕ4537 prophage. Since there is no obvious homology in W to have supported this insertion, it has likely arisen via a illegitimate mechanism.

Figure 4:
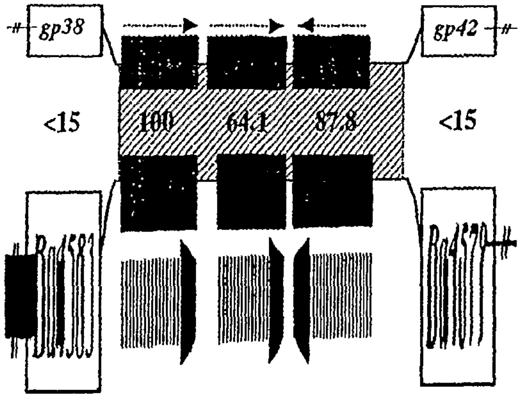
FIG. 4A and FIG. 4B show analysis of the *Bacillus anthracis* genome (FIG. 4A) compared with other *Bacillus* spp. and *Clostridium* (FIG. 4B).
FIG. 4C is a graph showing results from the introduction of the pDG148::pg41 clone into RSVF1 has resulted in a 4-log increase in resistance to the antibiotic fosfomycin.
Figure 4:
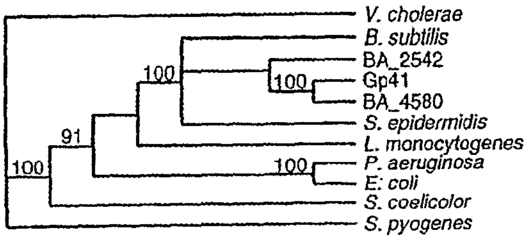
Figure 4:
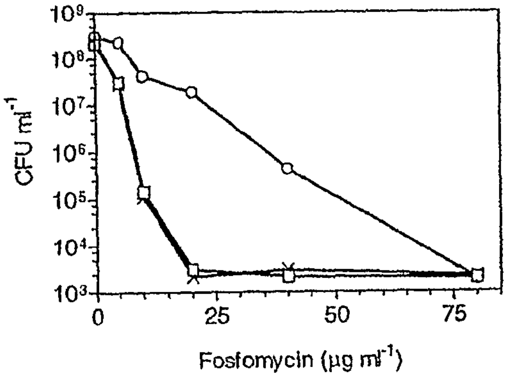

Gp41 encodes a fosfomycin resistance protein, or a glutathione transferase. Analysis of the Ba genome (FIG. 4A) shows 35 such proteins, while other *Bacillus* spp. and *Clostridium* have 10-15 each (FIG. 4B). Only in the Ba genome is a copy prophage encoded and therefore mobile.

We have cloned the Gp41 locus into an IPTG-inducible *Bacillus* protein expression vector (pDG148) and established a system for stably transforming RSVF1. Introduction of the pDG148::pg41 clone into RSVF1 has resulted in a 4-log increase in resistance to the antibiotic fosfomycin (FIG. 4C). The MIC for fosfomycin was 62.5 μg $ml^{-1}$ for RSVF1 and RSVF1/pDG148 and 500 μg $ml^{-1}$ for RSVF1/pDG148::gp41.

TABLE 1

ORF's of Gamma (γ) Bacteriophage of *B. anthracis*

| ORF | Frame | Position | Size | Matches (E value)* | Structure† | Function‡ |
|---|---|---|---|---|---|---|
| 1 | 3 | 54-539 | 18.5 (161) | Orf21 ϕ105 *B. subtilis* (5e–25),<br>Phage terminase, small subunit (1e–6) | c-c domain | DNA packaging |
| 2 | 2 | 536-2233 | 65.1 (565) | Orf22 ϕ105 *B. subtilis* (1e–151),<br>Phage terminase, large subunit (2e–131) | | DNA packaging |
| 3 | 2 | 2249-3547 | 48.8 (432) | Gp3 ϕ3626 *C. perfringens* (e–112)<br>Phage portal protein (9e–53) | | Portal protein |
| 4 | 3 | 3510-4130 | 23.7 (206) | Gp5 ϕ3626 *C. perfringens* (2e–49)<br>Caudovirales prohead protease (9e–29) | c-c domain | Head maturation protease |
| 5 | 2 | 4169-5347 | 44.2 (392) | Orf27 ϕ105 *B. subtilis* (4e–95)<br>Phage capsid family (7e–72) | c-c domains | Major head protein |
| 6 | 1 | 5365-5655 | 11.0 (96) | Gp7 ϕ3626 *C. perfringens* (2e–3)<br>Phage QLRG family (1e–7) | | |
| 7 | 3 | 5652-5975 | 12.1 (107) | BA_4559 *B. anthracis* (6e–5)<br>Bacteriophage head-tail adaptor (4e–9) | Pyrophosphatase domain | Putative head-tail adaptor |
| 8 | 1 | 5968-6408 | 16.2 (146) | BA_4558 *B. anthracis* (2e–16)<br>CRPp0301 (2e–5) | | Uncharacterized protein |
| 9 | 3 | 6405-6764 | 13.9 (119) | BA_4557 *B. anthracis* (4e–15)<br>CRPp0346 (5e–8) | | Uncharacterized protein |
| 10 | 3 | 6765-7373 | 22.9 (202) | Chte_p_1640 *C. thermocellum* (9e–29)<br>CRPp0161 (6e–11) | c-c domain | Major tail protein |
| 11 | 1 | 7423-7740 | 11.8 (105) | BA_4555 *B. anthracis* (2e–3) | | |
| 12 | 3 | 7770-7946 | 7.0 (58) | | | |
| 13 | 1 | 7963-11814 | 139.4 (1283) | BA_4552-BA_4554 *B. anthracis* (>6e–25),<br>CRPp0381 (4e–40) | c-c domains | Tail protein |
| 14 | 3 | 11829-13319 | 56.8 (496) | BA_4550 *B. anthracis* (e–153),<br>CRPp0325 (2e–4) | c-c domain<br>Pyridoxal-phosphate binding domain | Tail component |
| 15 | 2 | 13316-17311 | 149.8 (1331) | BA_4578-BA_4579 *B. anthracis* (>5e–20),<br>CRPp0329 (2e–36) | c-c domains | Similar to myosin heavy chain |
| 16 | 1 | 17350-17775 | 15.0 (141) | BA_4545 *B. anthracis* (9e–57),<br>Phage–related holin (3e–28) | 3 TM domains | Holin, host lysis |
| 17 | 3 | 17775-18476 | 26.3 (233) | BA_4545 *B. anthracis* (1e–112)<br>Cell wall amidase (2e–43) | | Lysin, host lysis |
| 18 | –1 | 19031-18534 | 18.0 (165) | | c-c domain,<br>1 TM domain | May be a lipoprotein |
| 19 | –3 | 19230-19018 | 8.3 (70) | BA_4541 *B. anthracis* (4e–13)<br>Helix-turn-helix XRe–family (1e–4) | HTH domain only | |
| 20 | 1 | 19414-19722 | 12.3 (102) | BA_4540 *B. anthracis* (2e–40) | | |
| 21 | 3 | 19719-19901 | 6.7 (60) | BA_4539 *B. anthracis* (3e–12) | 2 TM domains | |
| 22 | 3 | 19911-21200 | 49.3 (414) | BA_4538 *B. anthracis* (e–168)<br>FtsK/SpoIIIE family: C- term. (1e–15) | c-c domain, P-loop<br>(ATP/GTP binding) | DNA translocation?<br>Integration? |
| 23 | 1 | 21178-21759 | 25.2 (175) | BC1920 *B. cereus* (2e–61) | c-c domain | |
| 24 | –3 | 22029-21793 | 8.6 (78) | BC1914 *B. cereus* (5e–18) | | |
| 25 | 2 | 21863-22090 | 8.4 (75) | | 2 TM domains | |
| 26 | 1 | 22297-23160 | 33.3 (287) | BC4930 *B. cereus* (6e–11) | c-c domain | lysogeny? |
| 27 | 1 | 23236-24681 | 56.4 (481) | Chte1631 *C. thermocellum* (2e–30)<br>PinR, Site–specific reombinases (4e–20) | c-c domains | Integrase |
| 28 | –1 | 24812-24684 | 4.8 (39) | Helix-turn-helix XRe–family (0.01) | HTH domain fragment | Fragment of CI-like repressor? |
| 29 | 3 | 24972-25199 | 8.8 (75) | BC2559 *B. cereus* (7e–5)<br>Helix-turn-helix, Cro and CI (0.008) | HTH domain | Cro-like DNA binding role? |
| 30 | 3 | 25212-25397 | 7.2 (61) | BA_4542 *B. antrhacis* (7e–5) | | |
| 31 | 1 | 25642-26457 | 31.0 (271) | Orf6 *L. lactis* ϕbIL285 (2e–12),<br>CRPp0355 (6e–17) | c-c domain | Anti-repressor |
| 32 | 1 | 26524-27177 | 25.7 (217) | Orf16 *L. lactis* ϕbIL312 (4e–12) | | |
| 33 | 3 | 27306-28253 | 37.1 (315) | Orf11 *L. lactis* ϕrlt (1e–18)<br>DnaA phage analogs | c-c domain<br>AT-rich repeats | Phage replication; Origin of replication |
| 34 | 3 | 28269-29180 | 34.9 (303) | DnaC DNA replication protein (3e–10)<br>Ntp *Lactobacillus* ϕgle (6e–29) | c-c domain, P-loop<br>(ATP-GTP binding) | Phage replication |
| 35 | 3 | 29199-29432 | 9.2 (77) | | | |
| 36 | 1 | 29425-30171 | 28.1 (248) | BA_4585 *B. anthracis* (6e–41)<br>FliA family of sigma factors (1e–20) | | Transcriptional effects |
| 37 | 3 | 30168-30644 | 19.0 (158) | | | |
| 38 | 2 | 30704-31246 | 21.1 (180) | BA_5241 *B. anthracis* (2e–20) | | |
| 39 | 1 | 31270-31500 | 8.8 (76) | BA_4582 *B. anthracis* (1e–20) | 2 TM domains<br>(signal sequence) | Membrane protein |
| 40 | 2 | 31607-32077 | 18.1 (156) | BA_4581 *B. anthracis* (2e–47) | | |
| 41 | –1 | 32124-32513 | 15.5 (129) | BA_4580 *B. anthracis* (2e–58)<br>Glyoxalase resistance protein (1e–7) | | Fosfomycin resistance |
| 42 | 3 | 32994-33164 | 6.5 (56) | | | |

TABLE 1-continued

ORF's of Gamma (γ) Bacteriophage of *B. anthracis*

| ORF | Frame | Position | Size | Matches (E value)* | Structure† | Function‡ |
|---|---|---|---|---|---|---|
| 43 | 2 | 33353-33658 | 11.9 (101) | | c-c domain | |
| 44 | 3 | 33651-33890 | 9.3 (79) | | | |
| 45 | 1 | 34327-34734 | 16.0 (135) | BC3700 *B. cereus* (1e−39) | c-c domains | |
| 46 | 3 | 34854-35078 | 8.5 (74) | | c-c domains | |
| 47 | 3 | 35085-35306 | 8.2 (73) | | | 30% identity to C-term. half of hamster IL-6 |
| 48 | 1 | 35311-35715 | 15.6 (134) | | | |
| 49 | 3 | 35820-36011 | 7.2 (63) | | | |
| 50 | 1 | 36031-36285 | 10.2 (84) | | c-c domains | |
| 51 | 1 | 36484-36675 | 7.3 (63) | | | |
| 52 | 2 | 36656-36943 | 10.6 (95) | BA_4569 *B. anthracis* (5e−4) | c-c domains | |
| 53 | 1 | 36943-37326 | 15.5 (128) | Gp50 ϕ3626 *C. perfringens* (6e−13)<br>MerA restriction endonuclease (2e−5) | | endonuclease |

*No entry indicates no significant homologies based on a protein-protein BLAST search. First line indicates the protein name, organism of origin, and BLAST E value for most significant hit. Second line indicates, if detected, the pfam conserved domain and E value or the cluster of related viral proteins (CRP) designation and E value.
†Indicates a significant protein structure or motif detected by bioinformatics analysis. Abbreviations are used: c-c domain/s, indicating the significant likelihood of one or more coiled-coil domains; TM, for transmembrane domain; and HTH, for helix-turn-helix.
‡Indicates putative function based on homologies detected with proteins of known function.

Bacteriophage W

We also isolated the parental lysogenic phage, W. As part of a study of resistance to fosfomycin in *B. cereus* strains tested, ATCC 11950 produced unusual ring-shaped colonies when plated in the presence of fosfomyin (FIG. 3C), but not in the absence (FIG. 3D). The central clearing zone was found to be enriched for intact phage W particles, thus suggesting that the fosfomycin may have induced the phage from older colony members, which constitute the central portion of a colony. Much like γ, phage W infected both *B. anthracis* and RSVF 1, and not other *B. cereus* or *B. thuringiensis* strains. Phage W was also morphologically identical to γ, confirming their close genetic relationship.

TABLE 2

ORF's of W-Bacteriophage of *B. anthracis*.

| Wp | Frame | Position | Size | Matches (E value)* | Structure† | Function‡ |
|---|---|---|---|---|---|---|
| 1 | 3 | 54-539 | 18.5 (161) | Orf21 ϕ105 *B. subtilis* (5e−25),<br>Phage terminase, small subunit (1e−6) | c-c domain | Terminase, small subunit |
| 2 | 2 | 536-2233 | 65.1 (565) | Orf22 ϕ105 *B. subtilis* (1e−151),<br>Phage terminase, large subunit (2e−131) | | Terminase |
| 3 | 2 | 2249-3547 | 48.8 (432) | Gp3 ϕ3626 *C. perfringens* (e−112)<br>Phage portal protein (9e−53) | | Portal protein |
| 4 | 3 | 3510-4130 | 23.7 (206) | Gp5 ϕ3626 *C. perfringens* (2e−49)<br>Caudovirales prohead protease (9e−29) | c-c domain | Head maturation protease |
| 5 | 2 | 4169-5347 | 44.2 (392) | Orf27 ϕ105 *B. subtilis* (4e−95)<br>Phage capsid family (7e−72) | c-c domains | Major head protein |
| 6 | 1 | 5365-5655 | 11.0 (96) | Gp7 ϕ3626 *C. perfringens* (2e−3)<br>Phage QLRG family (1e−7) | | |
| 7 | 3 | 5652-5975 | 12.1 (107) | BA_4559 *B. anthracis* (6e−5)<br>Bacteriophage head-tail adaptor (4e−9) | Pyrophosphatase domain | Putative head-tail adaptor |
| 8 | 1 | 5968-6408 | 16.2 (146) | BA_4558 *B. anthracis* (2e−16)<br>CRPp0301 (2e−5) | s | Uncharacterized protein |
| 9 | 3 | 6405-6764 | 13.9 (119) | BA_4557 *B. anthracis* (4e−15)<br>CRPp0346 (5e−8) | | Uncharacterized protein |
| 10 | 3 | 6765-7373 | 22.9 (202) | Chte_p_1640 *C. thermocellum* (9e−29)<br>CRPp0161 (6e−11) | c-c domain | Major tail protein |
| 11 | 1 | 7423-7740 | 11.8 (105) | BA_4555 *B. anthracis* (2e−3) | | |
| 12 | 3 | 7770-7946 | 7.0 (58) | | | |
| 13 | 1 | 7963-11814 | 139.4 (1283) | BA_4552-BA_4554 *B. anthracis* (>6e−25),<br>CRPp0381 (4e−40) | c-c domains | Tail protein |
| 14 | 3 | 11829-13319 | 56.8 (496) | BA_4550 *B. anthracis* (e−153),<br>CRPp0325 (2e−4) | c-c domain,<br>Pyridoxal-phosphate binding domain | Putative tail component protein |
| 15 | 2 | 13316-17311 | 149.8 (1331) | BA_4578-BA_4579 *B. anthracis* (>5e−20),<br>CRPp0329 (2e−36) | c-c domains | Similar to myosin heavy chain |
| 16 | 1 | 17350-17775 | 15.0 (141) | BA_4545 *B. anthracis* (9e−57),<br>Phage−related holin (3e−28) | 3 TM domains | Holin |
| 17 | 3 | 17775-18476 | 26.3 (233) | BA_4545 *B. anthracis* (1e−112)<br>Cell wall amidase (2e−43) | | Lysin |
| 18 | −1 | 19031-18534 | 18.0 (165) | | c-c domain,<br>1 TM domain | May be a lipoprotein |

TABLE 2-continued

ORF's of W-Bacteriophage of *B. anthracis.*

| Wp | Frame | Position | Size | Matches (E value)* | Structure† | Function‡ |
|---|---|---|---|---|---|---|
| 19 | −3 | 19230-19018 | 8.3 (70) | BA_4541 *B. anthracis* (4e−13)<br>Helix-turn-helix XRe-family (1e−4) | HTH domain only | |
| 20 | 1 | 19414-19722 | 12.3 (102) | BA_4540 *B. anthracis* (2e−40) | | |
| 21 | 3 | 19719-19901 | 6.7 (60) | BA_4539 *B. anthracis* (3e−12) | 2 TM domains | |
| 22 | 3 | 19911-21200 | 49.3 (414) | BA_4538 *B. anthracis* (e−168)<br>FtsK/SpoIIIE family: C-term. (1e−15) | c-c domain, P-loop (ATP/GTP binding) | DNA translocation? Integration? |
| 23 | 1 | 21178-21759 | 25.2 (175) | BC1920 *B. cereus* (2e−61) | c-c domain | |
| 24 | −3 | 22029-21793 | 8.6 (78) | BC1914 *B. cereus* (5e−18) | | |
| 25 | 2 | 21863-22090 | 8.4 (75) | | 2 TM domains | |
| 26 | 2 | 22325-23188 | 33.3 (287) | BC4930 *B. cereus* (6e−11) | c-c domain | Transcriptional effects? |
| 27 | 2 | 23264-24709 | 56.4 (481) | Chte1631 *C. thermocellum* (2e−30)<br>PinR, Site-specific recombinases (4e−20) | c-c domains | Integrase |
| 28 | 2 | 24812-26146 | 51.2 (444) | Orf4 *B. thuringiensis* pAW63 plasmid (3e−6) | | Absent from γ |
| 28.1 | −3 | 26488-26844 | 13.6 (115) | BC2558 *B. cereus* (1e−11)<br>Helix-turn-helix Cro and CI family (2e−7) | c-c domain | CI-like DNA binding role? Absent from γ |
| 29 | 1 | 27004-27231 | 8.8 (75) | BC2559 *B. cereus* (7e−5)<br>Helix-turn-helix Cro and CI family (0.008) | HTH domain | Cro-like DNA binding role? |
| 30 | 1 | 27244-27429 | 7.2 (61) | BA_4542 *B. antrhacis* (7e−5) | | |
| 31 | 2 | 27674-28489 | 31.0 (271) | Orf6 *L. lactis* ϕbIL285 (2e−12),<br>CRPp0355 (6e−17) | c-c domain | Anti-repressor |
| 32 | 2 | 28556-29209 | 25.7 (217) | Orf16 *L. lactis* ϕbIL312 (4e−12) | | |
| 33 | 1 | 29338-30285 | 37.1 (315) | DnaA phage analogs<br>Orf11 *L. lactis* ϕrlt (1e−18) | c-c domain<br>AT-rich repeats | Phage replication;<br>Origin of replication |
| 34 | 1 | 30301-31212 | 34.9 (303) | DnaC DNA replication protein (3e−10)<br>Ntp *Lactobacillus* ϕgle (6e−29) | c-c domain; P-loop (ATP-GTP binding) | Phage replication |
| 35 | 1 | 31231-31464 | 9.2 (77) | | | |
| 36 | 2 | 31457-32203 | 28.1 (248) | BA_4585 *B. anthracis* (6e−41)<br>FliA family of sigma factors (1e−20) | | Transcriptional effects |
| 37 | 1 | 32200-32676 | 19.0 (158) | | | |
| 38 | 3 | 32736-33278 | 21.1 (180) | BA_5241 *B. anthracis* (2e−20) | | |
| 39 | 1 | 33514-34446 | 28.7 (310) | Bcol14-2 *B. thuringiensis* pTX14-2 plasmid (6e−83) | 4 collagen-like triple helix repeats | Spore surface antigen |
| 40 | 3 | 34440-34931 | 16.8 (163) | BC4769 *B. cereus* (2e−26) C.-term half of collagen triple helix repeat protein | 4 TM domains | |
| 41 | −2 | 35903-35379 | 21.2 (191) | CTC01899 *C. tetani* (2e−54)<br>Mannose-6-phosphate isomerase (5e−19) | | Nutrient acquisition or a role in surface carbohydrate structure |
| 42 | 1 | 36490-36660 | 6.5 (56) | | | |
| 43 | 3 | 36849-37154 | 11.9 (101) | | c-c domain | |
| 44 | 1 | 37147-37386 | 9.3 (79) | | | |
| 45 | 2 | 37823-38230 | 16.0 (135) | BC3700 *B. cereus* (1e−39) | c-c domains | |
| 46 | 1 | 38350-38574 | 8.5 (74) | | c-c domains | |
| 47 | 1 | 38581-38802 | 8.2 (73) | | | 30% identity to C-term. half of hamster IL-6 |
| 48 | 2 | 38807-39211 | 15.6 (134) | | | |
| 49 | 1 | 39316-39507 | 7.25 (63) | | | |
| 50 | 2 | 39527-39781 | 10.25 (84) | | c-c domains | |
| 51 | 2 | 39980-40171 | 7.35 (63) | | | |
| 52 | 3 | 40152-40439 | 10.65 (95) | BA_4569 *B. anthracis* (5e−4) | c-c domains | |
| 53 | 2 | 40439-40822 | 15.5 (128) | Gp50 Θ3626 *C. perfringens* (6e−13)<br>McrA restriction endonuclease (2e−5) | | endonuclease |

*No entry indicates no significant homologies based on a protein-protein BLAST search. First line indicates the protein name, organism of origin, and BLAST E value for most significant hit. Second line indicates, if detected, the pfam conserved domain and E value or the cluster of related viral proteins (CRP) designation and E value.

†Indicates a significant protein structure or motif detected by bioinformatics analysis. Abbreviations are used: c-c domain/s, indicating the significant likelihood of one or more coiled-coil domains; TM, for transmembrane domain; and HTH, for helix-turn-helix.

‡Indicates putative function based on homologies detected with proteins of known function.

Polynucleotide Sequence Comparison

Similar Features of γ and W Bacteriophage Sequences

Figure 5:
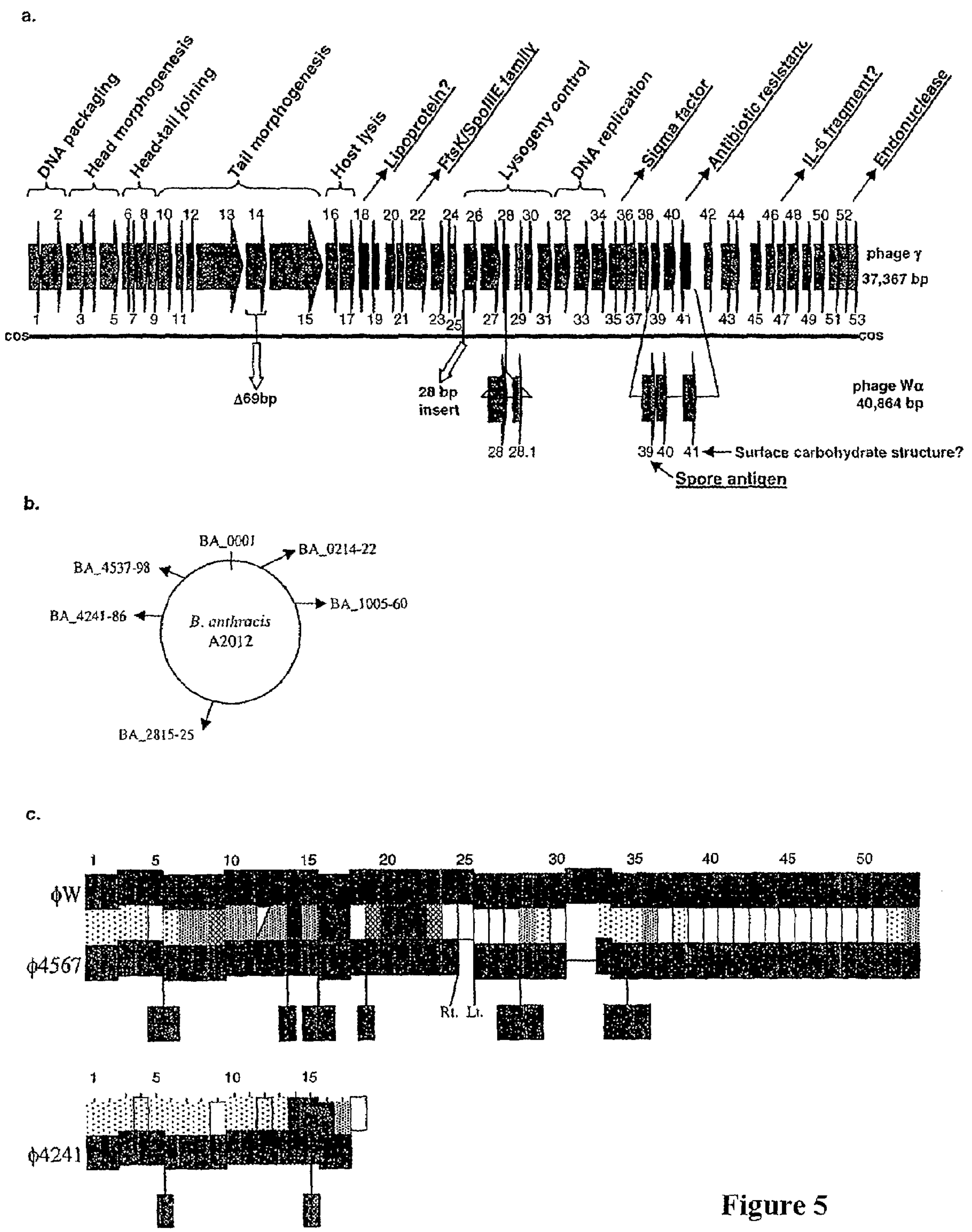
FIG. 5A shows a comparison of the genomic sequences of both γ and W by pair wise comparison.
FIG. 5B is a schematic of the *Bacillus anthracis* genome.
FIG. 5C is a schematic showing an alignment of the W phage.

The genomic sequences of both γ and W were determined and shown by pairwise comparison to be 100% identical with exceptions at four loci (FIG. 5A). The G_C contents of γ and W were 35.1% and 35.3%, respectively, similar to that of the *B. anthracis* genome (36.4%). Complementary 9 bp 5'-single-stranded cohesive ends (cos sites) flanked both phage. The γ phage encoded 53 ORFs over 37,367 bp, while the parental W phage had 54 ORFs within its 40,864 bp genome.

A common feature of the lambdoid genomes is a genetic mosaicism that results from rampant recombination and the horizontal transfer of functional gene modules (discrete transcriptional units containing one or more genes) among related phage genomes infecting, perhaps, a disparate range of bacterial organisms. As such, the genomes appear as a 'pasting' of modules from different sources, encoding part or all of each of the basic phage functions, including capsid building, host lysis, lysogeny, and replication. The architecture of the γ and W genomes is consistent with this model. The virion structural and host lysis proteins of γ and W (ORFs 1-17), are the most well conserved components, similar in both sequence and gene order to phage elements encoded by phages ϕ3626 of *Clostridium perfringens,* ϕ105 of *B. subtilis* or ϕ4537 and ϕ4241 prophages deduced from the *B. anthracis* genome (FIG. 5B). The lysogeny genes (ORFs 26-30) are divergent, showing homology for phage elements of *B. cereus, C. thermocellum, Lactococcus lactis* and a plasmid gene of *Bacillus* spp. The replication module (ORFs 31-34) is primarily similar to replication elements from phage of *L. lactis* and lactobacilli. In this manner, the functional genes of γ and W are indeed an assembled mosaic. A high proportion of genes (61 and 62% for the W and γ genomes, respectively) are similar to phage proteins from $Gram^+$ spore forming bacteria. Twenty-one of these genes are similar to elements of *B. anthracis* ϕ4537, and within this group, eight genes are found nowhere else. Alignment of the W phage and with the complete ϕ4537 genome and the late genes of ϕ4241 are presented (FIG. 5C) to illustrate the extent of this homology and the likelihood that W (and thus γ) arose from a common precursor of these phage. This divergence was likely not recent owing to the notable difference between the W and ϕ4537 genomes seen in FIG. 5C, and the presence of twelve largely unlinked γ and W loci are novel genes unrelated to known phage and host proteins. One feature of the γ and W genomes is the presence of 8 loci between the Orf17 amidase and the lysogenic module (starting at Orf26), which are similar only to *B. anthracis* and *B. cereus* phage. Notably in *Streptococcal* phage, this position often encodes genes not for phage function, but for lysogenic conversion of the host. This region in γ and W notably encodes two host membrane proteins and a 1242 bp gene homologous to the 5' half of the bacterial host cell division protein FtsK. The presence of an FtsK homolog in *B. anthracis* and transition strains may relate to the notable chain-like morphology of these organisms. Downstream of the replication module is another notable *B. anthracis* phage-specific host factor, Orf35, encoding a homolog of the sporulation sigma factor sigma F. Sigma F directs the RNA polymerase holoenzyme to a specific set of gene promoters within the developing spore of *Bacillus* spp. The presence of such a regulatory factor in W phage suggest that lysogeny may be accompanied by alterations in host gene expression.

Features of Which Differ Between γ and W Bacteriophage Sequences

Differences between γ and W, were observed with respect to the phage and to the host. Four changes have occurred in γ (compared to W) in the 50 years since its isolation and use as a diagnostic phage for *B. anthracis*. Without being bound by theory, it is believed that two alterations in the lysogeny module relate to the conversion of γ from a lysogenic to a lytic phage. It is further believed that a set of alterations with a single tail fiber gene explains the reported alteration in host specificity (ability of γ to infect encapsulated *B. anthracis*) and defines the gene which is essentially the basis for the widespread use of γ as a diagnostic tool. The last alternation is believed to be particularly significant, and involves the replacement of a three gene island in W with an alternate three gene island in γ.

Changes in the Lysogeny Module

Changes in the gamma lysogeny module (ORFs 26-32) may explain the derivation of gamma from W. The lysogeny region is a known hotspot for recombination in several phage, including W. The decision between lytic and lysogenic growth is often influenced by a genetic switch region encoding two divergently transcribed small DNA binding repressor proteins, which represent functional homologs of the well studied CI and Cro proteins of L phage. In phage W, the CI and Cro-like functions are likely encoded by wp28.1 and wp29, with Wp28.1 (CI-like) required for repressing the lytic proliferation genes and promoting lysogeny and Wp29 (Cro-like) required for repressing expression of the lysogeny module and promotin lytic growth. In the gamma phage, the lytic-only variant of W, both Wp28.1 and the adjacent gene Wp28 have been lost as part of a 2003 bp deletion that fused the 5' third of Wp28.1 to a short peptide sequence between Wp27 and Wp28, creating Gp28, a presumed gene fragment encoding only a partial heli-turn-helix DNA binding motf. In addition to this, there is a 28 bp deletion in an intergenic region between ORFs25 and 26, which is immediately adjacent to the phage attachment (att) site, which is required for insertion of the phage into the host genome during the establishment of the lysogenic state. Without being limited to theory, it is believed that the gamma bacteriophage has developed as a lytic variant through two separate deletion events at sites required for lysogenic functions.

Changes in the Orf14 Tail Fiber Gene

We sought to identify γ encoded genes that specify the interaction with the surface of *B. anthracis*. Elements which are the basis of diagnostic tools and also key to the phage infection cycle. Two likely candidates observed in genome—PlyG (lysine known to bind Ba, however it has same sequence in both γ and W) and Orf14 (putative tail fiber, which has undergone major change in gamma compared to W). We investigated the ability of each to bind Ba and RSVF1 using GFP protein fusions.

At least 69 missense mutations have occurred in γ ORF14 (referred to as Gp14) since its isolation from W 50 years ago. The resultant proteins differ by 24 amino acid residues (92% identity), likely affecting structural changes in the binding domain need for improved infection of a *B. anthracis* host. The gene appears to have arisen specifically in the Ba phage through insertion of a novel binding module into a tail fiber found in many bacillus phage.

Three Gene Island in W Phage Polynucleotide Sequence

The W phage as a 2824 bp three gene island (ORFs 39-41) encoding a putative spore surface antigen, a transmembrane domain that may be expressed with the surface antigen as part of a translational frameshift mechanism, and an enzyme (often associated with pathogenicity islands) which is a mannose-6-phosphate isomerse. The spore antigen appears to be similar, but not identical to, fibrous appendages that are found on the surface of spores, are the dominant surface antigen of spores, and are likely involved in the initial infection process of *Bacillus anthracis*. The mannose-6-phosphate isomerase is often considered a horizontally transferred virulence associated gene involved in generating alterations in surface carbohydrate structure in $Gram^-$ bacteria. This three gene island appears to encode proteins not required directly for the phage lifecycle, but are rather of use to the host (lysogenic conversion genes). The gamma phage has lost this island probably due to recombination with a three gene segment in *B. anthracis* ϕ4567. This 1360 bp segment (replacing the 2824 bp W island) is 99% identical to sequence in γ. This island encodes two proteins found only in Ba phage, and also a Fosfomycin resistance gene. The Fos gene (Gp41) is similar to this family of proteins, which act as glutathione S transferases. Similar genes are found in most bacteria, however, only in Ba is it phage encoded. Most soil bacteria examined (*Clostridium* spp., *Bacillus subtilis, Bacillus cereus*, have about 10-15 glutathione S transferase-like genes, while *B. anthracis* has almost 40.

Other Polynucleotide Sequences

The invention also relates to nucleotide sequences which have a substantial identity with the nucleotide sequences described herein; particularly preferred are nucleotide sequences which have at least about 10%, preferably at least about 20%, more preferably at least about 30%, more preferably at least about 40%, even more preferably at least about 50%, yet more preferably at least about 70%, still more preferably at least about 80%, and even more preferably at least about 90% identity, or 95% identity or more, with nucleotide sequences described herein. Particularly preferred in this instance are nucleotide sequences encoding polypeptides having an activity of a polypeptide described herein. For example, in one embodiment, the nucleotide sequence encodes a DNA polymerase, 3'-5' exonuclease, 5'-3' exonuclease (RNase H), DNA helicase, or RNA ligase, as described below. In a preferred embodiment, the nucleotide encodes a DNA polymerase lacking exonuclease domains, or a 3'-5' exonuclease lacking DNA polymerase domain, as described below.

To determine the percent identity of two nucleotide sequences, the sequences are aligned for optimal comparison purposes (e.g., gaps may be introduced in the sequence of a first nucleotide sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=# of identical positions/total # of positions.times. 100).

The determination of percent identity between two sequences may be accomplished using a mathematical algorithm. A preferred, non-limiting example of a mathematical algorithm utilized for the comparison of two sequences is the algorithm of Karlin et al., Proc. Natl. Acad. Sci. USA, 90:5873-5877 (1993). Such an algorithm is incorporated into the NBLAST program which may be used to identify sequences having the desired identity to nucleotide sequences of the invention. To obtain gapped alignments for comparison purposes, Gapped BLAST may be utilized as described in Altschul et al., Nucleic Acids Res, 25:3389-3402 (1997). When utilizing BLAST and Gapped BLAST programs, the default parameters of the respective programs (e.g., NBLAST) may be used. See the programs provided by National Center for Biotechnology Information, National Library of Medicine, National Institutes of Health. In one embodiment, parameters for sequence comparison may be set at W=12. Parameters may also be varied (e.g., W=5 or W=20). The value "W" determines how many continuous nucleotides are preferably identical for the program to identify two sequences as containing regions of identity.

One skilled in the art will recognize that the DNA mutagenesis techniques described here may produce a wide variety of DNA molecules that code for a bacteriophage lysin specific for *Bacillus anthracis* yet that maintain the essential characteristics of the lytic protein. Newly derived proteins may also be selected in order to obtain variations on the characteristic of the lytic protein, as will be more fully described below. Such derivatives include those with variations in amino acid sequence including minor deletions, additions and substitutions.

While the site for introducing an amino acid sequence variation is predetermined, the mutation per se does not need to be predetermined. For example, in order to optimize the performance of a mutation at a given site, random mutagenesis may be conducted at the target codon or region and the expressed protein variants screened for the optimal combination of desired activity. Techniques for making substitution mutations at predetermined sites in DNA having a known sequence as described above are well known.

Amino acid substitutions are typically of single residues; insertions usually will be on the order of about from 1 to 10 amino acid residues; and deletions will range about from 1 to 30 residues. Deletions or insertions may be in single form, but preferably are made in adjacent pairs, i.e., a deletion of 2 residues or insertion of 2 residues. Substitutions, deletions, insertions or any combination thereof may be combined to arrive at a final construct. Obviously, the mutations that are made in the DNA encoding the protein preferably does not place the sequence out of reading frame and preferably will not create complementary regions that could produce secondary mRNA structure (EP 75,444A).

Substitutional variants are those in which at least one residue in the amino acid sequence has been removed and a different residue inserted in its place. Such substitutions may be made in accordance with the following Table 3 when it is desired to finely modulate the characteristics of the protein. Table 3 shows amino acids which may be substituted for an original amino acid in a protein and which are regarded as conservative substitutions.

TABLE 3

| Original Residue | Conservative Substitutions |
|---|---|
| Ala | ser |
| Arg | lys |
| Asn | gln, his |
| Asp | glu |
| Cys | ser |
| Gln | asn |
| Glu | asp |
| Gly | pro |
| His | asn; gln |
| Ile | leu, val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than in Table 3, i.e., selecting residues that differ more significantly in their effect on maintaining: (a) the structure of the polypeptide backbone in the area of the substitution, for example, as a sheet or helical conformation; (b) the charge or hydrophobicity of the molecule at the target site; or (c) the bulk of the side chain. The substitutions which in general are expected to produce the greatest changes in protein properties will be those in which: (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histadyl, is substituted for (or by) an electronegative residue, e.g., glutamyl or aspartyl; or (d) a residue having a bulky side chain, e.g., phenylalanine, is substituted for (or by) one not having a side chain, e.g., glycine.

The effects of these amino acid substitutions or deletions or additions may be assessed for derivatives of the lytic protein by analyzing the ability of the derivative proteins to complement the sensitivity to DNA cross-linking agents exhibited by phages in infected bacteria hosts. These assays may be performed by transfecting DNA molecules encoding the derivative proteins into the bacteria as described above.

Having herein provided nucleotide sequences that code for lytic enzyme genetically coded for by a bacteriophage specific for *Bacillus anthracis* and fragments of that enzyme, correspondingly provided are the complementary DNA strands of the cDNA molecule and DNA molecules which hybridize under stringent conditions to the lytic enzyme cDNA molecule or its complementary strand. Such hybridizing molecules include DNA molecules differing only by minor sequence changes, including nucleotide substitutions, deletions and additions. Also contemplated by this disclosure are isolated oligonucleotides comprising at least a segment of the cDNA molecule or its complementary strand, such as oligonucleotides which may be employed as effective DNA hybridization probes or primers useful in the polymerase chain reaction. Hybridizing DNA molecules and variants on the lytic enzyme cDNA may readily be created by standard molecular biology techniques.

The detection of specific DNA mutations may be achieved by methods such as hybridization using specific oligonucleotides (Wallace et al. (1986). Cold Spring Harbor Symp. Quant. Biol. 51:257-261), direct DNA sequencing (Church and Gilbert (1988). Proc. Natl. Acad. Sci. USA 81:1991-1995), the use of restriction enzymes (Flavell et al. (1978). Cell 15:25), discrimination on the basis of electrophoretic mobility in gels with denaturing reagent (Myers and Maniatis (1986). Cold Spring Harbor Symp. Quant. Biol. 51:275-284), RNase protection (Myers et al. (1985). Science 230:1242), chemical cleavage (Cotton et al. (1985). Proc. Natl. Acad. Sci. USA 85:4397-4401) (incorporated herein by reference), and the ligase-mediated detection procedure (Landegren et al., 1988).

Expression Vectors

The invention also relates to expression vectors containing a nucleic acid sequence encoding a polypeptide described herein (or an active derivative or fragment thereof), operably linked to at least one regulatory sequence. Many expression vectors are commercially available, and other suitable vectors may be readily prepared by the skilled artisan. “Operably linked” is intended to mean that the nucleotide sequence is linked to a regulatory sequence in a manner which allows expression of the nucleic acid sequence. Regulatory sequences are art-recognized and are selected to produce the polypeptide or active derivative or fragment thereof The term “regulatory sequence” includes promoters, enhancers, and other expression control elements which are described in Goeddel, Gene Expression Technology: Methods in Enzymology 185, Academic Press, San Diego, Calif. (1990). For example, the native regulatory sequences or regulatory sequences native to bacteriophages γ and W may be employed. It should be understood that the design of the expression vector may depend on such factors as the choice of the host cell to be transformed and/or the type of polypeptide desired to be expressed. For instance, the polypeptides of the present invention may be produced by ligating the cloned gene, or a portion thereof, into a vector suitable for expression in an appropriate host cell (see, for example, Broach, et al., Experimental Manipulation of Gene Expression, ed. M. Inouye (Academic Press, 1983) p. 83; Molecular Cloning: A Laboratory Manual, 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance. Thus, prokaryotic and eukaryotic host cells transformed by the described expression vectors are also provided by this invention. The host cells may be transformed by the described vectors by various methods (e.g., electroporation, transfection using calcium chloride, rubidium chloride, calcium phosphate, DEAE-dextran, or other substances; microprojectile bombardment; lipofection, infection where the vector is an infectious agent such as a retroviral genome, and other methods), depending on the type of cellular host. The nucleic acid molecules of the present invention may be produced, for example, by replication in such a host cell, as described above. Alternatively, the nucleic acid molecules may also be produced by chemical synthesis.

Probes

The isolated nucleic acid molecules and vectors of the invention are useful in the manufacture of the encoded polypeptide, as probes for isolating homologous sequences (e.g., from other bacteriophage species), as well as for detecting the presence of the bacteriophage in a culture of host cells.

The nucleotide sequences of the nucleic acid molecules described herein (e.g., a nucleic acid molecule comprising any of the open reading frames shown in Table 1 or Table 2 may be amplified by methods known in the art. For example, this may be accomplished by e.g., PCR. See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202.

Other suitable amplification methods include the ligase chain reaction (LCR) (see Wu and Wallace, Genomics 4, 560 (1989), Landegren et al., Science 241, 1077 (1988), transcription amplification (Kwoh et al., Proc. Natl. Acad. Sci. USA 86, 1173 (1989)), and self-sustained sequence replication (Guatelli et al., Proc. Nat Acad. Sci. USA, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively.

The amplified DNA may be radiolabelled and used as a probe for screening a library or other suitable vector to identify homologous nucleotide sequences. Corresponding clones may be isolated, DNA may be obtained following in vivo excision, and the cloned insert may be sequenced in either or both orientations by art recognized methods, to identify the correct reading frame encoding a protein of the appropriate molecular weight. For example, the direct analysis of the nucleotide sequence of homologous nucleic acid molecules of the present invention may be accomplished using either the dideoxy chain termination method or the Maxam Gilbert method (see Sambrook et al., Molecular Cloning, A Laboratory Manual (2nd Ed., CSHP, New York 1989); Zyskind et al., Recombinant DNA Laboratory Manual, (Acad. Press, 1988)). Using these or similar methods, the protein(s) and the DNA encoding the protein may be isolated, sequenced and further characterized.

Polypeptides

The invention additionally relates to isolated polypeptides obtainable from the bacteriophages γ and W. The term, “polypeptide,” as used herein, includes proteins, enzymes, peptides, and gene products encoded by nucleic acids described herein. In one embodiment, the invention relates to the polypeptides encoded by the ORFs as described above in Table 1 and Table 2. The invention relates to polypeptide sequences for the γ-phage and other polypeptides that may hybridize to the polypeptide sequences of the invention, including those of FIG. 2B. The invention further relates to polypeptide sequences for the W-phage, such as those in FIG. 4B, and other polypeptides that may hybridize to these sequences. Also provided in the present invention are polypeptide sequences for each ORF in Table 1 and Table 2. The invention relates to polypeptides encoding Gp 14 (ORF 14 of g-phage), Wp14 (ORF 14 of W-phage), and Wp38 (ORF 38 of W-phage). Further provided are polynucleotide sequences that hybridize to polypeptide sequences of FIG. 2B and FIG. 4B.

Also included in the invention are polypeptides which are at least about 60, 70, 80, 90, and 95% identical (i.e., polypeptides which have substantial sequence identity) to the polypeptides described herein. However, polypeptides exhibiting lower levels of identity are also useful, particular if they exhibit high, e.g., at least about 90%, identity over one or more particular domains of the polypeptide. For example, polypeptides sharing high degrees of identity over domains necessary for particular activities, such as binding or enzymatic activity, are included herein. Thus, polypeptides which are at least about 10%, preferably at least about 20%, more preferably at least about 30%, more preferably at least about 40%, even more preferably at least about 50%, yet more preferably at least about 60%, still more preferably at least about 70%, yet more preferably at least about 80%, still more preferably at least about 90%, yet more preferably at least about 95%, still more preferably at least about 80% and even more preferably at least about 97% identity to the polypeptides of the invention, including SEQ ID NO:3 through SEQ ID NO:109, are encompassed by the invention.

Polypeptides described herein may be isolated from naturally-occurring sources (e.g., isolated from host cells infected with bacteriophages γ and W). Alternatively, the polypeptides may be chemically synthesized or recombinantly produced. For example, PCR primers may be designed to amplify the ORFs from the start codon to stop codon. The primers may contain suitable restriction sites for an efficient cloning into a suitable expression vector. The PCR product may be digested with the appropriate restriction enzyme and ligated between the corresponding restriction sites in the vector (the same restriction sites, or restriction sites producing the same cohesive ends or blunt end restriction sites).

Polypeptides of the present invention may be used as a molecular weight marker on SDS-PAGE gels or on molecular sieve gel filtration columns using art-recognized methods. They are particularly useful for molecular weight markers for analysis of proteins from thermophilic organisms, as they will behave similarly (e.g., they will not denature as proteins from mesophilic organisms would).

The polypeptides of the present invention may be isolated or purified (e.g., to homogeneity) from cell culture (e.g., from culture of host cells infected with bacteriophages γ and W) by a variety of processes. These include, but are not limited to, anion or cation exchange chromatography, ethanol precipitation, affinity chromatography and high performance liquid chromatography (HPLC). The particular method used will depend upon the properties of the polypeptide; appropriate methods will be readily apparent to those skilled in the art. For example, with respect to protein or polypeptide identification, bands identified by gel analysis may be isolated and purified by HPLC, and the resulting purified protein may be sequenced. Alternatively, the purified protein may be enzymatically digested by methods known in the art to produce polypeptide fragments which may be sequenced. The sequencing may be performed, for example, by the methods of Wilm et al. (Nature 379(6564):466-469 (1996)). The protein may be isolated by conventional means of protein biochemistry and purification to obtain a substantially pure product, i.e., 80, 95 or 99% free of cell component contaminants, as described in Jacoby, Methods in Enzymology Volume 104, Academic Press, New York (1984); Scopes, Protein Purification, Principles and Practice, 2nd Edition, Springer-Verlag, New York (1987); and Deutscher (ed), Guide to Protein Purification, Methods in Enzymology, Vol. 182 (1990).

For example, representative proteins expected to be encoded by genes of bacteriophages γ and W include the following: DNA topoisomerase; exonuclease (e.g., 3'-5' exonuclease, 5'-3' exonuclease (RNase H)); helicase; enzymes related to DNA or RNA synthesis (e.g., dCTPase, dUTPase, dCDPase, dUDPase, GTPase, dGTPase, ATPase, dATPase); transposase; reverse transcriptase; polymerase (e.g., DNA polymerase, RNA polymerase); DNA polymerase accessory protein; DNA packaging protein; DNA topoisomerase; RNA polymerase binding protein; RNA polymerase sigma factor; site-specific RNase inhibitor of protease; recombinant protein; alpha-glucosyltransferase; mobility nuclease; endonuclease (e.g., endonuclease II, endonuclease V, endonuclease VII); inhibitor of Lon protease; thymidine kinase; site-specific RNase; N-glycosidase; endolysin; lysozyme; dNMP kinase; DNA ligase; deoxyribonucleotide-3'-phosphatase; ssDNA binding protein; dsDNA binding protein; and RNA ligase.

The polypeptides of the invention may be partially or substantially purified (e.g., purified to homogeneity), and/or are substantially free of other polypeptides. According to the invention, the amino acid sequence of the polypeptide may be that of the naturally-occurring polypeptide or may comprise alterations therein. Polypeptides comprising alterations are referred to herein as "derivatives" of the native polypeptide. Such alterations include conservative or non-conservative amino acid substitutions, additions and deletions of one or more amino acids; however, such alterations should preserve at least one activity of the polypeptide, i.e., the altered or mutant polypeptide should be an active derivative of the naturally-occurring polypeptide. For example, the mutation(s) may preferably preserve the three dimensional configuration of the binding site of the native polypeptide, or may preferably preserve the activity of the polypeptide (e.g., if the polypeptide is a DNA polymerase, any mutations preferably preserve the ability of the enzyme to catalyze combination of nucleotide triphosphates to form a nucleic acid strand complementary to a nucleic acid template strand). The presence or absence of activity or activities of the polypeptide may be determined by various standard functional assays including, but not limited to, assays for binding activity or enzymatic activity.

Additionally included in the invention are active fragments of the polypeptides described herein, as well as fragments of the active derivatives described above. An "active fragment," as referred to herein, is a portion of polypeptide (or a portion of an active derivative) that retains the polypeptide's activity, as described above.

Homologous proteins and nucleic acids may be prepared that share functionality with such small proteins and/or nucleic acids (or protein and/or nucleic acid regions of larger molecules) as will be appreciated by a skilled artisan. Such small molecules and short regions of larger molecules, that may be homologous specifically are intended as embodiments. Preferably the homology of such valuable regions is at least 50%, 65%, 75%, 85%, and more preferably at least 90%, 95%, 97%, 98%, or at least 99% compared to the polypeptides encoded by a polypeptide sequence selected from SEQ ID NO:3-SEQ ID NO:109. These percent homology values do not include alterations due to conservative amino acid substitutions.

Of course, an epitope as described herein may be used to generate an antibody and also may be used to detect binding to molecules that recognize the lysin protein. Another embodiment is a molecule such as an antibody or other specific binder that may be created through use of an epitope such as by regular immunization or by a phase display approach where an epitope may be used to screen a library if potential binders. Such molecules recognize one or more epitopes of lysin protein or a nucleic acid that encodes lysin protein. An antibody that recognizes an epitope may be a monoclonal antibody, a humanized antibody, or a portion of an antibody protein. Desirably the molecule that recognizes an epitope has a specific binding for that epitope which is at least 10 times as strong as the molecule has for serum albumin. Specific binding may be measured as affinity (Km). More desirably the specific binding is at least $10^2$, $10^3$, $10^4$, $10^5$, $10^6$, $10^7$, $10^8$, or even higher than that for serum albumin under the same conditions.

In a desirable embodiment the antibody or antibody fragment is in a form useful for detecting the presence of the lysin protein. A variety of forms and methods for their synthesis are known as will be appreciated by a skilled artisan. The antibody may be conjugated (covalently complexed) with a reporter molecule or atom such as a fluor, an enzyme that creates an optical signal, a chemilumiphore, a microparticle, or a radioactive atom. The antibody or antibody fragment may be synthesized in vivo, after immunization of an animal, for example, The antibody or antibody fragment may be synthesized via cell culture after genetic recombination. The antibody or antibody fragment may be prepared by a combination of cell synthesis and chemical modification.

Biologically active portions of a protein or peptide fragment of the embodiments, as described herein, include polypeptides comprising amino acid sequences sufficiently identical to or derived from the amino acid sequence of the phage protein of the disclosure, which include fewer amino acids than the full length protein of the phage protein and exhibit at least one activity of the corresponding full-length protein. Typically, biologically active portions comprise a domain or motif with at least one activity of the corresponding protein. A biologically active portion of a protein or protein fragment of the disclosure may be a polypeptide which is, for example, 10, 25, 50, 100 less or more amino acids in length. Moreover, other biologically active portions, in which other regions of the protein are deleted, or added may be prepared by recombinant techniques and evaluated for one or more of the functional activities of the native form of a polypeptide of the embodiments.

Appropriate amino acid alterations may be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes may also be found in Bowie et al. (Science 247:1306-1310(1990)). For example, conservative amino acid replacements may be those that take place within a family of amino acids that are related in their side chains. Genetically encoded amino acids are generally divided into four families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan and tyrosine are sometimes classified jointly as aromatic amino acids. For example, it is reasonable to expect that an isolated replacement of a leucine with an isoleucine or valine, an aspartate with a glutamate, a threonine with a serine or a similar conservative replacement of an amino acid with a structurally related amino acid will not have a major effect on activity or functionality.

Fusion Proteins

The polypeptides of the invention may also be fusion polypeptides comprising all or a portion (e.g., an active fragment) of the native bacteriophages γ and W polypeptide amino acid sequence fused to an additional component, with optional linker sequences. Additional components, such as radioisotopes and antigenic tags, may be selected to assist in the isolation or purification of the polypeptide or to extend the half life of the polypeptide; for example, a hexahistidine tag would permit ready purification by nickel chromatography. The fusion protein may contain, e.g., a glutathione-S-transferase (GST), thioredoxin (TRX) or maltose binding protein (MBP) component to facilitate purification; kits for expression and purification of such fusion proteins are commercially available. One example of a useful fusion protein is a GST fusion protein in which the polypeptide of the disclosure is fused to the C-terminus of a GST sequence. The polypeptides of the invention may also be tagged with an epitope and subsequently purified using antibody specific to the epitope using art recognized methods. Additionally, all or a portion of the polypeptide may be fused to carrier molecules, such as immunoglobulins, for many purposes, including increasing the valency of protein binding sites. For example, the polypeptide or a portion thereof may be linked to the Fc portion of an immunoglobulin; for example, such a fusion could be to the Fc portion of an IgG molecule to create a bivalent form of the protein.

Additionally, the nucleotide sequence(s) may be fused to a marker sequence, for example, a sequence which encodes a polypeptide to assist in isolation or purification of the polypeptide. Representative sequences include, but are not limited to, those that encode a glutathione-S-transferase (GST) fusion protein. In one embodiment, the nucleotide sequence contains a single ORF in its entirety (e.g., encoding a polypeptide, as described below); or contains a nucleotide sequence encoding an active derivative or active fragment of the polypeptide; or encodes a polypeptide which has substantial sequence identity to the polypeptides described herein. In a preferred embodiment, the nucleic acid encodes a polymerase (e.g., DNA polymerase); DNA polymerase accessory protein; dsDNA binding protein; deoxyriboncleotide-3-phosphatase; DNA topoisomerase; DNA helicase; an exonuclease (e.g., 3'-5' exonuclease, 5'-3' exonuclease (RNase H)); RNA ligase; site-specific RNase inhibitor of protease; endonuclease; exonuclease; mobility nuclease; reverse transcriptase; single-stranded binding protein; endolysin; lysozyme; helicase; alpha-glucosyltransferase; or thymidine kinase, as described herein. In a particularly preferred embodiment, the nucleic acid encodes a DNA polymerase, 3'-5' exonuclease, 5'-3 exonuclease (RNase H), DNA helicase or RNA ligase. In another particularly preferred embodiment, the nucleic acid encodes a DNA polymerase that lacks exonuclease domains, or a 3'-5' exonuclease that lacks DNA polymerase domain, as described below.

Another embodiment discloses an immunoglobulin fusion protein in which all or part of a polypeptide of the disclosure is fused to sequences derived from a member of the immunoglobulin protein family. An immunoglobulin fusion protein may be incorporated into a pharmaceutical composition and administered to a subject to inhibit an interaction between a ligand (soluble or membrane-bound) and a protein on the surface of a cell (receptor), to thereby suppress signal transduction in vivo. The immunoglobulin fusion protein may alter bioavailability of a cognate ligand of a polypeptide of the disclosure. Inhibition of ligand/receptor interaction may be useful therapeutically, both for treating bacterial-associated diseases and disorders for modulating (i.e. promoting or inhibiting) cell survival. Moreover, an immunoglobulin fusion protein of the disclosure may be used as an immunogen to produce antibodies directed against a polypeptide of the disclosure in a subject, to purify ligands and in screening assays to identify molecules which inhibit the interaction of receptors with ligands. Chimeric and fusion proteins and peptides of the disclosure may be produced by standard recombinant DNA techniques.

The acts of methods of the present invention may be done in any order, and may have other intervening steps or acts unless otherwise indicated.

It is intended that the foregoing detailed description be regarded as illustrative rather than limiting. The following claims, including all equivalents, that are intended to define the spirit and scope of this invention. Therefore, the embodiment of any figure and features thereof may be combined with the embodiments depicted in other figures. Other features known in the art and not inconsistent with the structure and function of the present invention may be added to the embodiments.

The recitations of “embodiments,” “one embodiment,” “some embodiments,” “other embodiments,” “illustrative embodiments,” “selected embodiments,” “certain embodiments,” and “another embodiment” herein are synonymous. All of these recitations refer to illustrative embodiments and are not exclusive of each other or of other embodiments not recited herein. The invention also relates to embodiments that comprise combinations of one or more of the illustrative embodiments described above.

All references cited herein are hereby incorporated into this disclosure in their entirety.

The following Examples are offered for the purpose of illustrating the present invention and are not to be construed to limit the scope of this invention. The teachings of all references cited are hereby incorporated herein by reference in their entirety.

EXAMPLES

Example 1

Isolation of Polynucleotides of γ and W Bacteriophages

The *B. anthracis* strain used in this study lacks the pXO1 and pXO2 virulence plasmids (Δsterne), while the *B. cereus* strain used, RSVF1, is an American Type Culture Collection (ATCC) reference strain that is largely genetically indistinct from *B. anthracis* and transition state *B. cereus*. Initially, we determined whether RSVF1 represents a transition strain (or derivative thereof, as it is a laboratory passaged strain) by looking for *B. anthracis* features either shared by or lacking in the transition strains. Like *B. anthracis*, RSVF1 was nonmotile, sensitive to the γ lysine, grew in chains, was virulent in mice, and encoded the csa operon (products of which modify *B. anthracis* surface carbohydrate), the Ba813 locus (diagnostic marker for *B. anthracis* and transition state *B. cereus*), and a specific 12 base pair tandem repeat array within vrrA (characteristic of certain *B. anthracis* isolates). Unlike *B. anthracis*, but like transition *B. cereus*, RSVF1 lacked pXO1 and pXO2, and had a functional P1cR transcriptional regulator (inactive in *B. anthracis* owing to a single nonsense mutation.). Prophage content differed as well, based on findings that a) PCR analyses of several distinct *B. anthracis* prophage genes yielded no amplification products with RSVF1, and b) long-range repetitive PCR using primers specific for a phage attachment site detects gross genetic polymorphisms between *B. anthracis* and transition state *B. cereus*. RSVF1 does, therefore, represent transition state *B. cereus*, largely distinguished from *B. anthracis* by the absence of plasmid and phage elements.

The γ phage was isolated as variant of W that had a more *B. anthracis*-specific host range (though still infecting transition state *B. cereus*) and, unlike W, infected both encapsulated and unencapsulated bacilli. As such, γ became an important tool for rapid confirmatory clinical diagnosis of *B. anthracis* still in widespread use.

A majority of the γ phage genome (–95%) was sequenced by Genome Therapeutics Corporation (Waltham, Mass.) using a library of 3.0-3.5 kb fragments as templates. This analysis was performed using ABI dye terminator chemistry on automated MegaBace 1000 (Amersham) machines. Base calls and quality scores were determined using the PHRED program (Ewing and Green, 1998 Genome Res. 8:186-194) and reads were assembled by using PHRAP with default program parameters and quality scores. Closure of numerous gaps and determination of the phage termini were accomplished at The Rockefeller University using a primer walking method and purified γDNA as template. At The Rockefeller University samples were thermocycled in an ABI GeneAmp PCR System 9600/9700 and the purified extension products were electrophoresed on an ABI Prism 3700 DNA Analyzer. Sequence data was assembled into a completed contig using the SeqMan program (DNASTAR software package). Putative OREs were determined by both ORE Finder available through the NCBI and GeneMark approach of gene prediction. The BLAST algorithms, available through NCBI, were used for similarity searches of putative ORFs.

The W phage genome was sequenced completely at The Rockefeller University using a primer walking method. Primer construction was completely based on the γ phage genomic sequence. Sequence was assembled, annotated and analyzed in the same manner used for the γ genome.

Example 2

Binding of GFP Fusion Proteins

Figure 6:
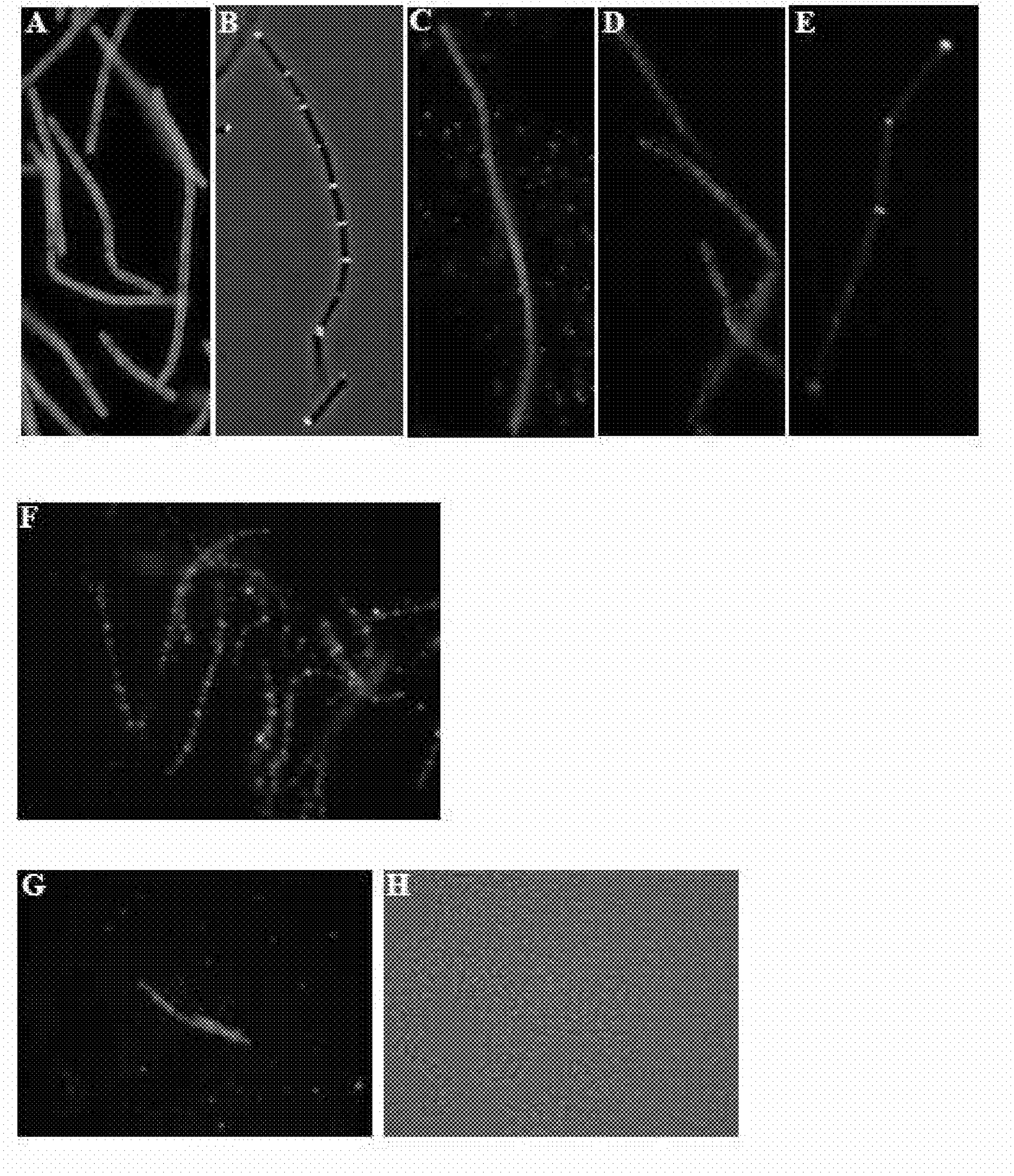
FIG. 6A is a micrograph showing GFP-PlyG—binding of *Bacillus anthracis* in a whole cell manner.
FIG. 6B is a micrograph showing GFP-PlyG—binding of RSVF1 at only a polar positions.
FIG. 6C is a micrograph showing GFP-PlyG—binding of rare RSVF1 derivatives that bind in a whole cell fashion.
FIG. 6D is a micrograph showing GFP-Gp14—whole cell binding with *Bacillus anthracis*.
FIG. 6E is a micrograph showing GFP-Gp14—polar cell binding with *Bacillus anthracis*.
FIG. 6F is a micrograph showing *Bacillus anthracis* lysogenized with W becomes polar.
FIG. 6G and FIG. 6H are micrographs showing fluorescence of GFP-PlyG binding to *Bacillus anthracis*.

GFP-PlyG—binds *Bacillus anthracis* (“Ba”) in a whole cell manner (FIG. 6A), RSVF1 only a polar positions (FIG. 6B). Rare RSVF1 derivatives bind whole cell (FIG. 6C).

GFP-Gp14—whole cell binding with Ba (FIG. 6D) and polar with RSVF 1 (FIG. 6E). Ba lysogenized with W is now polar (FIG. 6F). Indicates that phage affect alteration in surface distribution of receptor, likely carbonhydrate. This is a major change in *B. anthracis* phenotype associated with W phage infection. Either directly affects carbohydrate structure (W does encode a gene involved in sugar conversion to mannose, a known component of the Ba carbohydrate) or indirectly via a transcriptional regulatory factor.

GFP-PlyG binding (or presumably Gp14) may be used as a diagnostic tool . . . shows that when Ba is diluted 10,000 fold in a culture of *B. cereus* 10987, it is still readily identifiable by fluorescence (FIG. 6G, FIG. 6H). The speed of this binding (seconds) and difficulty in washing it away (can stand up to >5 washes in PBS) suggests that GFP-PlyG may be used as a part of a Ba diagnostic method.

Example 3

Effects of Ivsogeny with W on RSVF1 and *B. anthracis*

Figure 7:
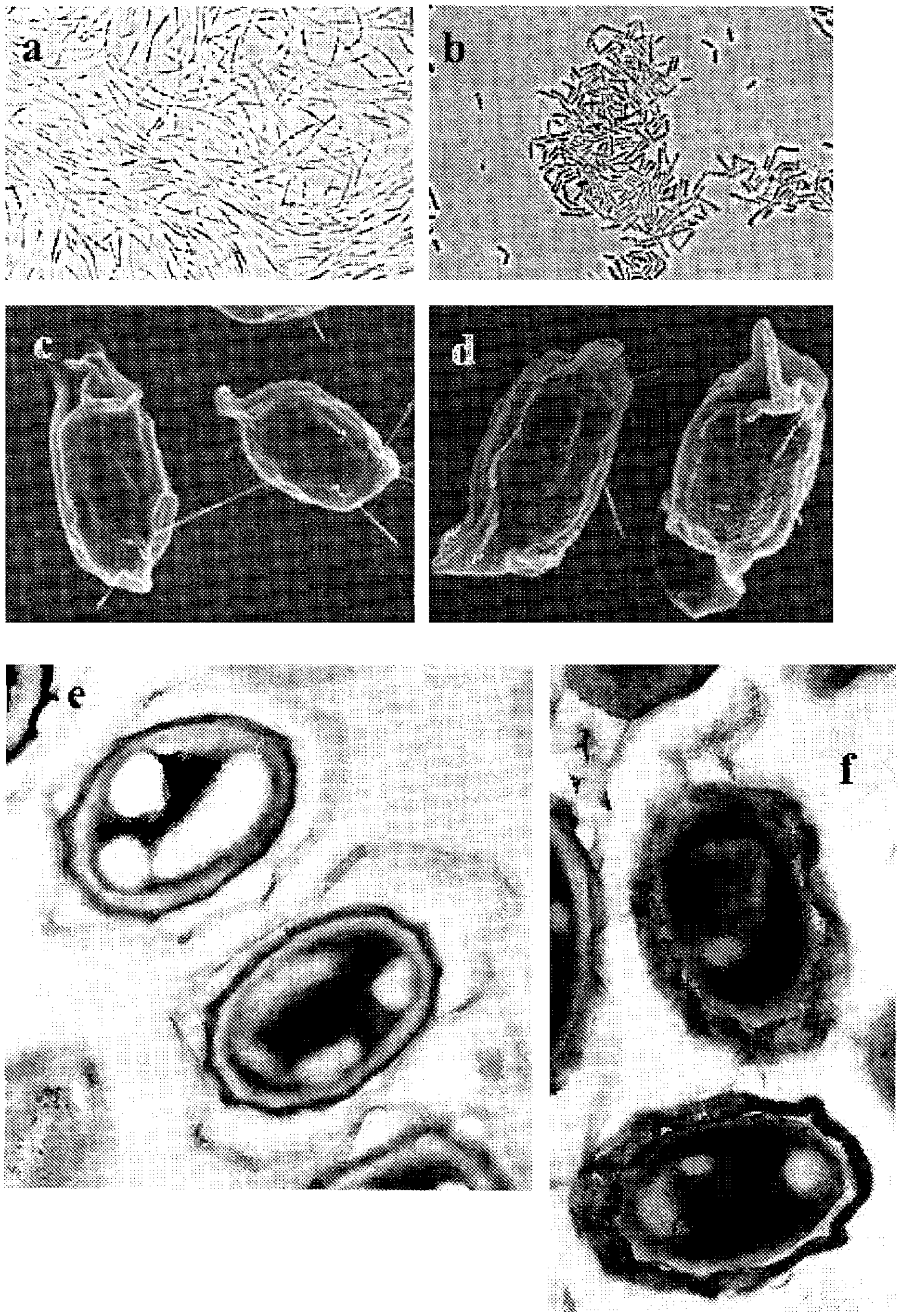
FIG. 7A and FIG. 7B are micrographs showing the effects of lysogeny with W on RSVF1 and *B. anthracis* showing rod shape formation.
FIG. 7C, FIG. 7D, FIG. 7E, and FIG. 7F are electron micrographs showing spore appearance by SEM under various conditions as described below.

Effect on RSVF1:

No alteration in % sporulation, hemolysis, extracellular lipase or protease secretion, motility or colony morphology. Did notice two main changes, however. 1) The strain no longer grows as a filamentous form, but as a rod shape (FIG. 7A, FIG. 7B). 2) the spore structure is altered. The spore has a more mottled or textured appearance by SEM (compared to parental non-lysogen) (FIG. 7C, FIG. 7D). By negative staining TEM, there is no difference in exosporial structure or surface components. There is however, a change in the coat structure. The coat is more osmiophillic and consist on multiple darkened outer layers, with surface knob-like extensions or striations (FIG. 7E, FIG. 7F).

Effect on *B. anthracis:*

No alteration in % sporulation, motility, colony morphology or shape. However, the strain is now alpha hemolytic. Infection has activated a cryptic hemolysin. Transcriptional activators in the W phage are likely responsible. A hallmark of Ba is it lack of hemolysis, despite having hemolysin. The lysogen definitely now has hemolytic activity on plates. A quantitative analysis was performed based on a technique described by Mignot et al. 2001 (Mol Microbiol 42:1189) in which the lysogen had 64 units of activity and the parental strain (no phage) had 0 units. The lysogen is also weakly but definitely activated for extracellular protease and lipase activity on plates. These features are all more Bc like. An entire regulon of extracellular activities is encoded in both Ba and Bc, however, they are only expressed in Bc (repressed in Ba) due to a point mutation in a transcriptional regulator PlcR in Ba. What we see here is the weak activation of this Bc-like regulon in Ba. Either a phage transcriptional regulator is doing this, or the phage integration is activating some downstream regulator.

Example 4

Gp14 ORF Used with Primers

The entire gp14 ORF was PCR amplified with primers flanking the 1.5 kb locus, using purified γ phage genomic DNA as template. The primers used were as follows:

```
                                    (SEQ ID NO:110)
5' ACAGATATCTTGGGGAAACTTAGTTTTACTT 3'

                                    (SEQ ID NO:111)
5' CCCAAGCTTTCATCTATATCTCTCCCTATAACTGA 3'
```

The EcoRV and HindIII 'sticky ends" were used to clone the 1.5 kb amplification product at the 3' end of gfpmut2 (GenBank nucleotide accession number AF302837) in plasmid pBAD24::gfp digested with SmaI and HindIII. The reference for pBAD24 is Guzman et al., 1995 J. Bacteriol. 177: 4121-4130. The reference for the gfpmut2 is Cormack et al., 1996 Gene 173:33-38. The cloning described above yields a gfpmut2-gp14 translational fusion. The gfpmut2-gp14 construct was excised with EcoRI-HindIII and cloned into the EcoRI-HindIII sites of the vector pBAD/His (Invitrogen). This creates an in frame His tagged fusion, which was subsequently purified by affinity chromatography. The purified His-GFP-Gp14 fusion protein was used to label both *B. cereus* 4342 and *B. anthracis* Δsterne. Exponential phase bacteria growing in BHI media were washed with PBS and concentrated 10 fold and fixed in a 3% formalin in PBS solution for 20 minutes at room temperature. A 100 μl aliquot was then incubated with 100 μl of the GFP fusion protein for 5 minutes at 4C. The cells were washed with PBS, mounted in SlowFade (Molecular Probes, Inc.), and examined by fluorescence microscopy.

The His-GFP-PlyG fusion protein was constructed, purified, and analyzed in the exact same manner, with the exception that the plyG ORF was amplified with the following primers:

```
                                    (SEQ ID NO:112)
5' gaagatatcatgttcagtaatggaaatcca 3'

                                    (SEQ ID NO:113)
5' accaagcttttatttaacttcataccaccaac 3'
```

Prophetic Example 5

Use of Wp38 as a Means to Deliver Antigens to the *B. anthracis* Spore Surface

This may be used for vaccine delivery of an anthrax antigen delivered to the surface of an anthrax spore resulting in a vaccine that may protect against both vegetative anthrax and its spores. Wp38 is encoded in the W phage and is similar to a family of spore surface proteins encoded within the *B. anthracis* and *B. cereus* genomes. It is likely expressed from a sporulation-specific promoter and is integrated into the spore exosporium facing the extracellular environment. Since it is not essential for spore formation and resistance properties, we may modify the wp38 sequence, through fusions to exogenous proteins, thereby effecting delivery of the exogenous proteins to the spore surface.

Prophetic Example 6

Use of the W Lysogenic Phage as a Means to Deliver Novel DNA Sequences to the *B. anthracis* Genome, and to Express Those Sequences Since the W phage genome is stably maintained in *B. anthracis*, we may genetically modify the phage (ie, insert genes of interest) and allow the recombinant phage to infect and be maintained within the bacterium. If the inserted gene is cloned downstream of an inducible promoter also engineered into the W phage, then an expression system is established. We may thus express foreign genes of interest within *B. anthracis*. Expression may be induced either during vegetative growth or during sporulation. With the addition of signal peptide-encoding sequences to the foreign gene, their protein products may be directed to the vegetative cell surface, or into the bacterial supernatant.

Prophetic Example 7

Use of the W or Gamma Phases as Tools for Intact Phage Therapy

Even though we are not involved in phage therapy, those interested could use these phage in their application. Highly purified phage stocks may be used either alone, or in combinations with other *B. anthracis*-specific phage to kill and clear *B. anthracis* during systemic anthrax infections. This therapy may be performed alone or in conjunction with antibiotic and/or anti-toxin treatment. The phage stocks may also be used to kill or clear *B. anthracis* from contaminated environmental surfaces or from production facilities.

Example 8

Use of the Gamma or W Phage Tail Protein (Gp14 and Wp14, Respectively) as a Tool to Detect *B. anthracis* in Environmental or Clinical Samples as a Diagnostic Gp14 fusion with GFP has been constructed and shown to specifically bind the surface of *B. anthracis* and relate to a detectable fluorescent signal. This binding is rapid, requiring incubation of the fusion protein and bacteria for only 1 minute. This binding is specific, as it may be used to readily detect a fluorescing *B. anthracis* rod among a background of non *B. anthracis* bacilli, where the *B. anthracis* is diluted 1:10,000.

Example 9

Study of the Specificity of Phage for *B. anthracis* and Strength of γ-Phage The gamma phage was isolated from *Bacillus anthracis* and was obtained from Hans W. Ackermann (Laval University, Quebec, Canada). Phage susceptibilities were initially tested by adding 10 ml of high titer gamma aliquots to fresh lawns of strains indicated in Table 1; clearance after 16 h growth indicated susceptibility. A high titer phage stock containing $2.2\times10^{10}$ plaque forming units (pfu) $ml^{-1}$ was prepared using RSVF1 by a previously described method (Loeffler, J. M., Nelson, D. & Fischetti, V. A. Rapid killing of *Streptococcus pneumoniae* with a bacteriophage cell wall hydrolase. Science 294, 2170-2 (2001) ). A pfu is a single phage that forms a small clearing zone, or plaque, after successive rounds of infection, growth, and release on lawns of susceptible bacteria. The RSVF1-derived phage stock was used in titer determinations.

To study the specificity and strength of the gamma phage and the resulting lytic enzyme, different strains of Bacillus were prepared. Most strains were grown at 30° C. in Luria broth (LB) or brain-heart infusion broth (BHI), supplemented with 1.5% agar when needed. Analyses involving *E. coli* XL1-Blue (Stratagene) were performed at 37° C., while *B. stearothermophilis* was handled at 55° C. Strain RSVF1 is a streptomycin resistant derivative of *B. cereus* reference strain ATCC 4342. Despite the similarities between RSVF1 and *Bacillus anthracis*, important genotypic differences exist, and RSVF1 is not a misidentified *Bacillus anthracis* stain (Pannucci, J., Okinaka, R. T., Sabin, R. & Kuske, C. R. *Bacillus anthracis* pXO1 plasmid sequence conservation among closely related bacterial species. J Bacteriol 184, 134-41 (2002); Helgason, E., Caugant, D. A., Olsen, I. & Kolsto, A. B. Genetic structure of population of *Bacillus cereus* and *B. thuringiensis* isolates associated with periodontitis and other human infections. J Clin Microbiol 38, 1615-22 (2000); Ticknor, L. O. et al. Fluorescent Amplified Fragment Length Polymorphism Analysis of Norwegian *Bacillus cereus* and *Bacillus thuringiensis* Soil Isolates. Appl Environ Microbiol 67, 4863-73 (2001)). Analysis of the vrrA locus of RSVF1 was performed as described (Jackson, P. J. et al. Characterization of the variable-number tandem repeats in vrrA from different *Bacillus anthracis* isolates. Appl Environ Microbiol 63, 1400-5 (1997).). *Bacillus anthracis* manipulations were provided by Leonard W. Mayer (Centers for Disease Control, Atlanta, Ga.) and Abraham L. Turetsky (Aberdeen Proving Grounds, Aberdeen, Md.). These bacterial strains were then exposed to gamma phage.

Example 10

Studies with the Lysin Produced by the γ-Phage

It was found that RSVF1 was sensitive to infection by γ-phage, and exhibited matt colony morphology, a filamentous structure, and repetitive sequences in the hypervariable vrrA locus which are all characteristic of *Bacillus anthracis*. The lytic activity of PlyG (the gamma lysin produced by gamma phage) was examined by exposing a panel of the indicated liquid bacterial cultures to either PlyG (20 units) or phosphate buffer. The fold killing represents the decrease in bacterial viability determined 15 minutes post-lysing compared to the buffer treatment. The "Bc" and "Bt" prefixes indicate strains as either *B. cereus* or *B. thuringiensis*, respectively. RSVF1 has no virulence plasmids, but is nonetheless highly related to *Bacillus anthracis* and a suitable gamma phage host.

A phenotypic screen was used to identify gamma phage proteins that lyse RSVF1 "from without." An induced gamma phage expression library in an *E. coli* background was permeabilized and overlaid with a RSVF1 lawn. gamma genomic DNA was isolated using the 1 Maxi kit of Qiagen Inc. 5 mg aliquots of gamma DNA were partially digested with Tsp509I and cloned fragments ranging from 0.5-3.0 kb into the EcoRI site of the arabinose-inducible expression vector pBAD24. The resulting expression library was then transformed into *E. coli* XL1-Blue and screened for lysin activity on glass LB plates containing 100 mg $ml^{-1}$ ampicillin and 0.25% arabinose. The induced library was permeabilized with chloroform vapors and overlaid with exponential phase RSVF1 in 0.75% LB agar. After a 24 h incubation, distinct clearing, or lytic, zones were identified over library members. Corresponding plasmid DNA was prepared and sequenced. DNA sequence analysis and manipulations required the BLASTP (NCBI), ORF finder (NCBI), and SeqMan 5.0 (Dnastar Inc.) programs.

One of the pBAD24:plyG constructs recovered in the library search and encoding only the plyG ORF was used as a source of recombinant PlyG. Expression was induced with 0.25% L-arabinose in an overnight LB culture supplemented with ampicillin 100 mg $ml^{-1}$. Cells were washed, resuspended in 50 mM Tris, pH 8.0, and lysed with chloroform added to a concentration of 16.6%. Cellular debris and chloroform were removed by centrifugation, yielding the crude PlyG supernatant. The cationic nature of PlyG enabled it to pass through a HiTrap Q Sepharose XL column (Amersham Biosciences), which bound to most contaminants. The enzyme was further purified by application to a Mono S HR 5/5 column (Amersham Biosciences) and elution in a linear gradient containing 1 M NaCl. Active fractions were pooled and purity was assessed by gel electrophoresis and chromatography on a Superose 12 column (Amersham Biosciences) equilibrated with gel filtration standards (Bio-Rad).

Clones that yielded lytic zones all contained a 702 bp gamma ORF encoding a product homologous to lysins called N-acetylmuramoyl-L-alanine amidases. TP21 and f105 indicate *B. cereus* and *B. subtilis* phage amidases, respectively. Cw1A and ClyA are encoded in the *B. cereus* and *B. subtillis* genomes, respectively. The dark shading represents sequence identity and the lighter shading represents similarity. Homology is restricted to their catalytic NH2-terminal halves, and absent in the lysin-specific COOH-terminal binding domains. Recombinant gamma lysin (called PlyG, for phage lysin gamma) was purified to homogeneity by column chromatography using Coomassie Blue-stained, SDS-Page of purified PlyG. The molecular mass was estimated based on the positions of Kaleidoscope (Bio-Rad) standards that are not shown. The N-terminal sequence of this band corresponds to the predicted PlyG sequence. Gel filtration confirmed a predicted size of ~27 kDa, and suggests that PlyG acts as a monomer and is not proteolytically processed.

Example 11

In Vitro Lysin Activity

Activity was examined in several ways. A Spectramax Plus 384 spectrophotometer (Molecular Devices) was used to follow the drop in $OD_{650}$ of logarithmic phase RSVF1 incubated for 15 min at 37° C. with serial dilutions of purified PlyG. Enzyme activity in units $ml^{-1}$ was then determined as described (Nelson, D., Loomis, L. & Fischetti, V. A., Prevention and elimination of upper respiratory colonization of mice by group A streptococci by using a bacteriophage lytic enzyme. Proc Natl Acad Sci USA 98, 4107-12 (2001)). It was estimated that 1 unit of enzyme corresponded to 1 mg of PlyG. A crude measure of lysin specificity was performed in which 10 ml drops of purified PlyG (0.5 units) were applied to fresh lawns derived from the indicated strains. After overnight incubation, the appearance of clearing zones was used to assess activity. A liquid killing assay was also used, in which 1.0 ml of logarithmic phase cells (~$1.0\times10^8$ cells) was treated with the indicated amounts of PlyG for 15 min at 37° C.; at the indicated time points, samples were removed, washed to remove lysin, and plated for enumeration. As a measure of PlyG-directed lysis, ATP released from dying cells was indirectly measured in a reaction containing a luciferin/luciferase reagent and a microluminometer (PROFILE-1 reagent kit and model 3550i luminometer, New Horizons Diagnostics Corp.) according to the manufacturers protocol. In brief, vegetative cells of the indicated strains were immobilized on 0.45 uM filters at the base of a 0.4 ml reaction chamber. The immobilized cells were washed twice with somatic cell releasing agent to remove impurities and 0.1 ml of PlyG in phosphate buffer was added for 2 min. 0.05 ml of the luciferin/luciferase reagent provided with the kit was added and immediately assayed at room temperature for 10 sec. All samples were tested five times. The relative light units released by RSVF1 were consistently ten to twenty percent of its total releasable light (as determined using a strong detergent mixture provided with the kit).

RSVF1 was as sensitive to PlyG killing as a set of *Bacillus anthracis* isolates from America, Europe, Asia and Africa (13). *B. cereus* 10987, a rare strain closely related to *Bacillus anthracis*, was slightly susceptible to PlyG, while all other strains examined were resistant. Helgason, E. et al. *Bacillus anthracis, Bacillus cereus*, and *Bacillus thuringiensis*—one species on the basis of genetic evidence. Appl Environ Microbiol 66, 2627-30 (2000). A more sensitive test of PlyG-mediated killing was evaluated in buffer containing ~$5.0\times10^7$ bacteria and treated with 20 units of PlyG for 15 min. RSVF1 was reduced >$1.6\times10^7$-fold, while ATCC 10987 was reduced ~100 fold. Other strains examined were largely resistant, even after a three-hour incubation. PlyG may clearly direct a potent and specific lethal action to the *Bacillus anthracis* cluster, exhibiting a substrate specificity that closely matches the gamma phage host range. Moreover, the capsulated state of several *Bacillus anthracis* strains examined, indicated that capsule does not block access of PlyG to the cell wall.

It was found that PlyG, like most lysins, is a very active enzyme. The addition of 2 units of PlyG to $1.0\times10^4$ RSVF1 caused an immediate release of intracellular ATP (measured as light emitted by firefly luciferin/luciferase), which is consistent with a rapid lytic effect. This effect was specific for RSVF1, and was not observed in other isolates tested, therefore suggesting that the ATP release assay is a strong diagnostic tool for g-sensitive bacilli. In a separate kinetic analysis of RSVF1 killing, it found that as little as 2 units of PlyG effected a $1.7\times10^4$-fold decrease in viability within 20 sec, and sterilization at 2 min. Here the time course of RSVF1 killing in cultures was treated with buffer (r) or 1 unit of PlyG™. These values are shown as colony forming units per ml of culture determined at each time point The corresponding $OD_{600}$ determined for the PlyG-treated sample (i) is shown. The loss of culture optical density lagged behind the loss in viability, implying that killing by PlyG does not necessarily require extensive cell wall degradation.

Example 12

Microscopy

To visually examine the lytic effect phase contrast microscopy of PlyG-treated RSVF1 was used. It was found that the normally filamentous RSVF1 rapidly converts to short rod- and minicell-like forms 30 sec after exposure; nearly complete loss of cytoplasmic material occurs by 15 min, leaving “ghost” cells. Transmission electron microscopy of the rod forms reveals the cytoplasmic membrane bulging from regions of localized cell wall hydrolysis. These structures are usually apparent at polar and septal positions, and rupture to yield a ghost-like form.

Example 13

In Vivo Lysin Activity

The lytic effect of PlyG suggested it could be used to kill g-sensitive bacteria in a mouse model of infection. Four- to eight-week old BALB/c female were purchased from Charles River Laboratories and housed at the Laboratory Animal Research Center at The Rockefeller University. Mouse infections were performed as a variation of a previously described procedure. Log phase RSVF1 grown in BHI medium, was pelleted and washed twice in 50 mM $K\cdot PO_4$ buffer (pH 7.4). Aliquots of ~$1.0\times10^6$ cells in buffer were injected intraperitoneally (i.p.) into mice in 0.1 ml doses. After 15 min, 0.5 ml of either buffer alone or PlyG in buffer were injected into the peritoneal cavity. Injections of PlyG alone (no bacteria) were also performed to assess toxicity. Mice were monitored for up to 3-4 days, at which time all surviving mice had recovered a normal and unremarkable appearance.

The i.p. injection of some *B. cereus* isolates may induce a rapidly fatal illness similar to experimental anthrax. The injection of ~$1.0\times10^6$ RSVF1 cells into BALB/c mice, killed all subjects in five hours or less. More specifically, mice were injected i.p. with ~$1.0\times10^6$ RSVF1 cfu and treated after 15 min with either phosphate buffer (n=15), 50 U PlyG (n=17), or 150 U PlyG (n=9). As an additional control, mice that were not challenged with bacteria were injected with 50 U PlyG (n=5). The experiment was terminated at 72 hours. Administration of either 50 U or 150 U to the infected mice was significantly protective compared to the buffer control (P<0.0001). The median survival time for the buffer treated mice was 2 hours. At death, many mice exhibited severe edema at the inoculation site, and hemorrhaging through the eyes and mouth. When PlyG (50 units) was injected i.p. 15 min post-infection, a pronounced therapeutic effect was observed: thirteen of nineteen mice fully recovered, while the remainder survived six to twenty-one hours. When 150 units of PlyG were used, a similar rate of recovery was observed. No toxicity was detected with either the i.p. or i.v. injection of PlyG alone. PlyG does, therefore, rapidly kill g-sensitive bacteria in an infected animal.

The ability of PlyG to degrade germinating spores was examined next. Spores were prepared as described in Mazas, M., Martinez, S., Lopez, M., Alvarez, A. B. & Martin, R. Thermal inactivation of Bacillus cereus spores affected by the solutes used to control water activity of the heating medium. Int J Food Microbiol 53, 61-7 (1999). Samples containing 95-99% refractile endospores, as determined by phase contrast microscopy, were stored at 4° C. in water. For spore killing experiments, 0.2 ml aliquots of ~$2.0\times10^8$ spores were heat activated at 65° C. for 5 min. Samples were pelleted and suspended in 1.0 ml tryptic soy broth (TSB, Difco) containing 100 mM L-alanine (to induce germination) for 5 min at 37° C. The cells were then treated with 1.0 ml of PlyG (10 units) for 5 min at 37° C. and plated for enumeration. TSB with L-alanine is a potent inducer of germination for each spore type, converting >99% of each spore type used to heat sensitive forms within 15 min. In the presence of D-alanine, germination frequency was reduced to <10%.

Example 14

Spore Detection

For spore detection, the spore killing protocol was modified for use with a microluminometer (model 3550i, New Horizons Diagnostics Corp.). Essentially, 0.1 ml of heat-activated spores (65° C., 5 min) were immobilized on a 0.45 mM filter in the 0.4 ml reaction tube. The immobilized spores were washed twice with somatic cell releasing agent and treated with 0.15 ml TSB with 100 mM L-alanine for 5 min at room temperature. Samples were then washed and treated with 0.15 ml PlyG (2 units) for 5 min at room temperature. 50 ml of a luciferin/luciferase reagent was added for the indicated length of time and a quantitative measure of the resulting light, given as relative light units, was displayed by the luminometer. In the dormant state, the spore's peptidoglycan, or cortex, is protected from lysozymes and amidases by a proteinaceous coat. However, within 10 min of inducing germination, coat porosity increases as it begins to degrade; it was reasoned that subjacent peptidoglycan may be rendered susceptible to PlyG.

To evaluate this, spores were prepared from RSVF1, closely related *B. cereus* (ATCC 14579) and *B. thuringiensis* (ATCC 33679) strains, and *B. subtilis*. Aliquots of ~108 heat activated spores were induced to germinate for 5 min and then treated with PlyG (10 units) for 5 minutes. Resulting spore viability was compared to that of spores treated with D-alanine, a germination inhibitor. While all D-alanine-treated spore samples were PlyG-resistant, only RSVF1 was sensitive after germination in the presence of L-alanine, showing a dramatic decrease in viability of log10 3.9. A sporocidal action, therefore, occurs rapidly after the induction of germination, when PlyG may likely access the cortex. In light of the thickness of the cortex, the rapid PlyG effect suggests a subtle alteration impairing spore outgrowth, rather than a massive degradative action.

The ability of PlyG to kill germinating spores was exploited to develop a rapid and specific system for detecting g-sensitive spores using a hand-held luminometer. Spores were immobilized or placed on filters or in cuvettes (in a solution) and incubated in at least one 5 min round with at least one germinant and PlyG (2 units). The temperature at which the incubation took place was from room temperature to 60 degrees Centigrade. The spores could be incubated first in germinant and then in PlyG or with the germinant and PlyG together. The phage associated lytic enzyme does not have to be PlyG but are preferably specific for the spore being tested. The release of ATP from degrading spores was then measured as a light "flash" emitted in the presence of a luciferin/luciferase reagent. ATP released from PlyG-treated germinating spores was assessed in the presence of luciferin/luciferase. 2.5×103 RSVF1 spores were induced to germinate with L-alanine and treated with 2 units of PlyG. The PlyG-mediated flash was measured. Germinating spores of Bc 14579, Bt33679, and *B. subtilis* showed no activity, demonstrating the expected recognition specificity of PlyG. Not surprisingly, when spore preparations were mixed, only the combination containing RSVF1 yielded a light signal Samples containing $2.5\times10^3$ spores of Bc 14579, Bt 33679, and *B. subtilis* with (RSVF+mix) or without (RSVF1−mix) RSVF1 were induced to germinate in L-alanine. The intensity of luminescence after PlyG treatment (2 units) was measured. The sensitivity of our system was examined using samples containing as few as ~100 spores. Rather than an immediate light flash, an RSVF1 signal was observed after 60 min incubation in the presence of PlyG and the luciferin/luciferase reagent. This signal is consistent with a low-level "glow," and is consistent with the low levels of ATP likely being released. No glow was detected in the presence of other germinating spore types, and is, therefore, specific to the g-sensitive spores. This sensitivity, combined with the specificity, rapidness, and highly portable nature of our detection method, suggests applications in monitoring both domestic and battlefield use of Bacillus anthracis as a biological weapon. This technique may be used to identify the presence of spores from other bacterial species using bacteriophage lysins specific for those species.

The phage associated enzyme used to lyse the *Bacillus anthracis* spores may be a lytic enzyme, chimeric lytic enzymes, shuffled lytic enzymes, and combinations thereof The phage associated lytic enzyme, and its altered forms, may be the PLY gamma enzyme, or another phage associated lytic enzyme specific for *Bacillus anthracis.*

A holin protein may also be used to assist in the lysing of the germinating spores. The holin protein may be unaltered, chimeric, shuffled, or may be combinations, thereof.

The nature of the luminometer that may be used for the detection of ATP, and its method of use is found and described in U.S. Pat. No. 6,395,504 (herein incorporated by reference).

Example 15

Mutagenesis and Screening for Resistance

Spontaneous lysin resistance was initially examined as described (Loeffler, et al.) by repeated exposure to PlyG at low concentrations on agar plates or to increasing concentrations in liquid assays. No resistance was detected.

To determine if spontaneous resistance was at all possible, chemically mutagenized cells were examined. Log phase RSVF1 was treated for 4 hours with methanesulfonic acid ethyl ester (EMS) at a concentration of 150 mM, resulting in 90% killing. The cells were then washed with BHI and grown 3 h (three cell doublings) prior to freezing at −70° C. The efficiency of mutagenesis was estimated by the frequency of mutations giving resistance to 150 mg $ml^{-1}$ streptomycin ($strep^R$) or to 3.5 mg $ml^{-1}$ novobiocin ($nov^R$). The spontaneous frequencies in non-mutagenized cultures were $2.4\times10^9$ for $strep^R$ and $4.0\times10^{10}$ for $strep^R$; for EMS treated RSVF1 the frequencies were $2.1\times10^{-6}$ for $strep^R$ and $4.3\times10^{-6}$ for $strep^R$. For screening, frozen mutagenized cells were then thawed, washed in BHI, and grown for 30 min at 30° C. One milliliter aliquots (~$1.0\times10^8$ cells) were incubated with PlyG for 30 min at 37° C., washed, and either plated or incubated overnight in BHI. Colonies arising from the plated cells were picked and evaluated for resistance to 20 units of PlyG in the spectrophotometric lysin assay. For the overnight BHI cultures, log phase cells were established and ultimately treated again with PlyG as before; this was repeated for 4 successive days. In one set of experiments, 20 units of PlyG was used for each treatment, while in another 0.05 units was used and followed by serial 10-fold higher doses on following days. Bacteria were plated after each treatment, and later examined for resistance to 20 units of PlyG in the spectrophotometric lysin assay. No resistance was detected.

We claim:

1. An isolated polypeptide comprising the amino acid sequence of SEQ ID NO:29.

2. The isolated polypeptide of claim 1, where the isolated polypeptide consists of the amino acid sequence of SEQ ID NO:29 that binds to *B. anthracis* bacteria.

3. The isolated polypeptide of claim 1, where the isolated peptide consists of the amino acid sequence of SEQ ID NO:29.

4. The isolated polypeptide of claim 1, where the isolated polypeptide is a fusion protein further comprising a heterologous polypeptide.

5. The isolated polypeptide of claim 1, where the isolated polypeptide further comprises a detectable reporter molecule or atom.

6. The isolated polypeptide of claim 5, where the reporter molecule or atom is selected from the group consisting of: a fluorescent molecule, an enzyme that creates an optical signal, a chemilumiphore, a microparticle and a radioactive atom.

7. The isolated polypeptide of claim 1, where the isolated polypeptide is a fusion protein comprising a green fluorescent protein (GFP) and the amino acid.

8. The isolated polypeptide of claim 7, where the fusion protein binds to *B. anthracis* in the presence of a culture of *B. anthracis* and *B. cereus* comprising a concentration of *B. cereus* ATCC-4342 that is up to 10.000-fold greater than the concentration of *B. anthracis*.

9. The isolated polypeptide of claim 1, where the isolated polypeptide comprises a pyridoxal-phosphate binding domain.

10. A composition comprising an isolated polypeptide, the isolated polypeptide comprising an amino acid sequence encoded by the open reading frame 14 of the polynucleotide sequence at positions 11,829-13,319 of SEQ ID NO:1, where the polypeptide binds to *B. anthracis* bacteria.

11. The composition of claim 10, where the isolated polypeptide is a fusion protein further comprising a heterologous polypeptide.

12. The composition of claim 10, where the isolated polypeptide further comprises a detectable reporter molecule or atom.

13. The composition of claim 12, where the reporter molecule or atom is selected from the group consisting of: a fluorescent molecule, an enzyme that creates an optical signal, a chemilumiphore, a microparticle and a radioactive atom.

14. The composition of claim 10, where the isolated polypeptide is a fusion protein comprising a green fluorescent protein (GFP) and the amino acid.

15. The composition of claim 10, where the polypeptide comprises a pyridoxal-phosphate binding domain.

* * * * *